US008993261B2

(12) United States Patent
Goodman et al.

(10) Patent No.: US 8,993,261 B2
(45) Date of Patent: *Mar. 31, 2015

(54) ANTIBODIES FOR THE DETECTION OF INTEGRIN COMPLEXES IN FFPE MATERIAL

(71) Applicant: Merck Patent Gesellschaft mit beschrankter Haftung, Darmstadt (DE)

(72) Inventors: Simon Goodman, Griesheim (DE); Claudia Wilm, Darmstadt (DE); Francesc Mitjans, Igualada (ES)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/838,405

(22) Filed: Mar. 15, 2013

(65) Prior Publication Data
US 2013/0203079 A1 Aug. 8, 2013

Related U.S. Application Data

(62) Division of application No. 13/390,791, filed as application No. PCT/EP2010/004313 on Jul. 15, 2010, now Pat. No. 8,420,348.

(30) Foreign Application Priority Data

Aug. 19, 2009 (EP) .................................... 09010666

(51) Int. Cl.
| | | |
|---|---|---|
| G01N 1/30 | (2006.01) |
| G01N 33/53 | (2006.01) |
| C12N 5/00 | (2006.01) |
| C12P 21/06 | (2006.01) |
| C12P 21/04 | (2006.01) |
| C07H 21/04 | (2006.01) |
| C07K 16/00 | (2006.01) |
| C07K 16/28 | (2006.01) |
| G01N 33/566 | (2006.01) |

(52) U.S. Cl.
CPC ............ *C07K 16/2839* (2013.01); *C07K 16/00* (2013.01); *G01N 33/566* (2013.01); *G01N 2333/70546* (2013.01)
USPC .......... 435/40.5; 435/7.1; 435/325; 435/69.1; 435/70.21; 536/23.53; 530/387.1; 530/388.1

(58) Field of Classification Search
CPC .................... A61K 2300/00; A61K 39/39558; A61K 2039/505; A61K 38/1709; C07K 14/705; C07K 2317/92; C07K 16/00; C07K 16/18; C07K 16/2842; C07K 16/2848; C07K 16/2839; C07K 14/47
See application file for complete search history.

(56) References Cited

U.S. PATENT DOCUMENTS

| | | | |
|---|---|---|---|
| 7,163,681 B2 * | 1/2007 | Giles-Komar et al. .... 424/144.1 |
| 7,452,677 B2 | 11/2008 | Lundgren-Akerlund |
| 7,465,449 B2 | 12/2008 | Violette et al. |
| 7,820,155 B2 | 10/2010 | Way et al. |
| 2004/0001835 A1 | 1/2004 | Woessner et al. |
| 2004/0048312 A1 | 3/2004 | Li et al. |
| 2005/0255102 A1 | 11/2005 | Violette et al. |
| 2007/0178098 A1 | 8/2007 | Way et al. |
| 2009/0148459 A1 | 6/2009 | Woessner et al. |
| 2009/0186036 A1 | 7/2009 | Violette et al. |
| 2010/0254977 A1 | 10/2010 | Goodman et al. |
| 2011/0038877 A1 | 2/2011 | Way et al. |

FOREIGN PATENT DOCUMENTS

| | | |
|---|---|---|
| WO | WO 89/05155 | 6/1989 |
| WO | WO 2004/007530 | 1/2004 |
| WO | WO 2009/010290 | 1/2009 |

OTHER PUBLICATIONS

Hii, L.L., et al., "Endometrial vascular and glandular expression of integrin alpha(v)beta(3) in women with and without endometriosis," Human Reproduction (Apr. 1998) vol. 13, No. 4, pp. 1030-1035, European Society for Human Reproduction and Embryology, Oxford, England; cited in the International Search Report issued in corresponding PCT/EP2010/004313 on Mar. 18, 2011.

Laurens, N., et al., "Single and combined effects of alpha(v)beta(3)- and alpha5beta1-integrins on capillary tube formation in a human fibrinous matrix," Angiogenesis (May 6, 2009) vol. 12, No. 3, pp. 275-285, Springer; cited in the International Search Report issued in corresponding PCT/EP2010/004313 on Mar. 18, 2011.

Singh, B., et al., "Vascular expression of the alpha(v)beta(3)-integrin in lung and other organs," American Journal of Physiology. Lung Cellular and Molecular Physiology (Jan. 2000) vol. 278, No. 1, pp. L217-L226, the American Physiological Society; cited in the International Search Report issued in corresponding PCT/EP2010/004313 on Mar. 18, 2011.

Mitjans, F., et al., "In vivo therapy of malignant melanoma by means of antagonists of alpha v integrins," International Journal of Cancer, (Sep. 1, 2000) vol. 87, No. 5, pp. 716-723, Wiley-Liss, Inc.; cited in the International Search Report issued in corresponding PCT/EP2010/004313 on Mar. 18, 2011.

(Continued)

*Primary Examiner* — Shulamith H Shafer
(74) *Attorney, Agent, or Firm* — Millen, White, Zelano & Branigan, P.C.

(57) ABSTRACT

The invention relates to antibodies that are capable to bind the extracellular domain of integrin. Another object of the invention concerns the use of said antibodies for detecting integrins in archival formalin fixed paraffin embedded (FFPE) tissue. The invention also relates to methods for preparing monoclonal rabbit antibodies, wherein the immunogen is an insect expression culture-derived recombinant extracellular integrin domain, and another method for screening anti-integrin antibodies that discriminate between closest integrin homologues and that are especially suited for immunohistochemistry in FFPE material.

21 Claims, 41 Drawing Sheets

(56) References Cited

OTHER PUBLICATIONS

Mitjans, F., et al., "An anti-alpha v-integrin antibody that blocks integrin function inhibits the development of a human melanoma in nude mice," Journal of Cell Science (Aug. 1995) vol. 108, pp. 2825-2838, The Company of Biologists Limited, Great Britain; cited in the International Search Report issued in corresponding PCT/EP2010/004313 on Mar. 18, 2011.

Unknown, "Product data sheet of anti-integrin alpha v antibody Mouse mAb (272-17E6) and corresponding safety data sheet dated May 29, 2003," E. Merck Chemicals (May 29, 2003) Retrieved from the Internet: URL: http://www.merckmillipore.com/usa/lifb-1-mouse-mab-272-1736/EMD_BIO-407286/p_JR6b.s1LruAAAAEWZmEfVhTm, the whole document; cited in the International Search Report issued in corresponding PCT/EP2010/004313 on Mar. 18, 2011.

Koopman, L.A., et al., "Antibody-Mediated Blockade of Integrin alpha v beta 6 Inhibits Tumor Progression in vivo by a Transforming Growth Factor-beta-Regulated Mechanism," Cancer Research (Jan. 15, 2008), vol. 6, No. 2, pp. 561-570, American Association for Cancer Research; cited in the International Search Report issued in corresponding PCT/EP2010/004313 on Mar. 18, 2011.

Database Geneseq [Online], "Human integrin beta3 subunit 1JV2 (chain B) mature protein," (Jun. 16, 2004) retrieved from EBI accession No. GSP:ADM99600 Data accession No. ADM99600, one page; cited in the International Search Report issued in corresponding PCT/EP2010/004313 on Mar. 18, 2011.

Xiong, Jian-Ping, et al., "Purification, Analysis, and Crystal Structure of Integrins," Methods in Enzymology (Jan. 1, 2007) vol. 426, pp. 307-336, Academic Press Inc., San Diego, CA, US; cited in the International Search Report issued in corresponding PCT/EP2010/004313 on Mar. 18, 2011.

Mehta, R. J., et al., "Transmembrane-truncated alpha v beta 3 integrin retains high affinity for ligand binding: evidence for an "inside-out" suppressor?" The Biochemical Journal (Mar. 1, 1998) vol. 330, pp. 861-869; cited in the International Search Report issued in corresponding PCT/EP2010/004313 on Mar. 18, 2011.

Unknown, "Product data sheet of anti-integrin alpha v antibody: sc-9969" Santa Cruz Biotechnology catalogue (2004), retrieved from the internet: URL:http://datasheets.scbt.com/sc-9969.pdf, retrieved on Oct. 11, 2010, one page; cited in the International Search Report issued in corresponding PCT/EP2010/004313 on Mar. 18, 2011.

Zoppi, N., et al., "The FN 13 peptide inhibits human tumor cells invasion through the modulation of alphavbeta3 integrins organization and the inactivation of ILK pathway," Biochemica et Biophysica Acta. (2007) vol. 1773, No. 6, pp. 747-763, Elsevier Science Publishers, Amsterdam, NL; cited in the International Search Report issued in corresponding PCT/EP2010/004313 on Mar. 18, 2011.

International Search Report issued in corresponding PCT/EP2010/004313 on Mar. 18, 2011.

* cited by examiner

M21 xenograft avb3_E3531-227-3 avb3_E3531-229-3

CAX08, overview ion is a divisional application of U.S. Ser. No. 13/390,791, filed Feb. 16, 2012, which is a U.S. National Stage under §371 of PCT/EP2010/004313, filed Jul. 15, 2010, the disclosures in which are incorporated by reference herein in their entirety.

ANTIBODIES FOR THE DETECTION OF INTEGRIN COMPLEXES IN FFPE MATERIAL

This application is a divisional application of U.S. Ser. No. 13/390,791, filed Feb. 16, 2012, which is a U.S. National Stage under §371 of PCT/EP2010/004313, filed Jul. 15, 2010, the disclosures in which are incorporated by reference herein in their entirety.

The invention relates to antibodies that are capable to bind the extracellular domain of integrin. Another object of the invention concerns the use of said antibodies for detecting integrins in archival formalin fixed paraffin embedded (FFPE) tissue. The invention also relates to methods for preparing monoclonal rabbit antibodies, wherein the immunogen is an insect expression culture-derived recombinant extracellular integrin domain, and another method for screening anti-integrin antibodies that discriminate between closest integrin homologues and that are especially suited for immunohistochemistry in FFPE material.

Integrins are a family of cell adhesion molecules composed of two non-covalently associated chains. The complex multi-domain structure of integrins is sensitive to subtle modulation. Integrins are regulated at many levels, including translation and transcription, post-translational glycosylation, cell surface delivery, cell surface activation by intracellular prompts and cell surface activation by extracellular prompts. Both alpha and beta chains are class I transmembrane proteins, which transverse the membrane and integrate extracellular matrix with intracellular compartment, thus providing a pathway for the signals that ultimately lead to control of adhesion, proliferation, survival, migration and invasion.

Integrins are therapeutic targets in much human pathology. For example in cancer, alpha-v series integrins ($\alpha v \beta 1$, $\alpha v \beta 3$, $\alpha v \beta 5$, $\alpha v \beta 6$ and $\alpha v \beta 8$) are variously implicated in angiogenesis, protecting tumor cells from chemo- and radiotherapy, tumor survival and local immune suppression. $\alpha 5 \beta 1$ and $\alpha 4 \beta 1$ are also implicated in angiogenesis, while $\alpha 2 \beta 1$ and $\alpha 6 \beta 4$ have been implicated in tumor proliferation. $\alpha v \beta 3$ over-expression correlates with the invasive phase of human melanoma, and both $\alpha v \beta 3$ and $\alpha v \beta 5$ are specifically up-regulated in tumor-invasive endothelium, where they appear to regulate the functions of angiogenic growth factors on the endothelial surface. The precise expression pattern of the integrins is highly variable both between and within a given class of tumors and reflects the functional biology. Hence, they are also biomarkers of tumor status, and the expression pattern is prognostic for outcome and can define therapeutic opportunities.

The monoclonal antibody DI-17E6 directed against the $\alpha v$-integrin chain, and cilengitide, a cyclized RGD-containing pentapeptide, that inhibits integrins $\alpha v \beta 33$ and $\alpha v \beta 5$ are in clinical development. However, the full therapeutic potential of therapies targeting integrins has yet to be attained, in part because there is a remarkably incomplete picture of the integrin expression patterns in pathological conditions. Pathological characterization of integrin distribution has relied on studies on fresh frozen tissues. The live cell-to-cryostaining linkage is well established, and frozen tissues are excellent substrates for integrin staining, but their level of preservation and the ultra-structural fealty are much lower than that routine in FFPE material. This can critically affect the interpretations of staining in complex tissue. Furthermore, routine clinical practice, and generally and commercially available tissue banks, provides FFPE material: obtaining frozen clinical material is a logistic and often a clinical-cultural challenge, or simply an impossibility when dealing with certain tumors and with rare and precious clinical samples.

It is due to the conflicting needs of classical histology and of the integrins' structure that unequivocal integrin detection in FFPE material is prevented in prior art. Histology needs excellent and robust morphological preservation of tissue structures, involving an extensive cross linking, infiltration and stabilization of soft hydrophilic tissues by hydrophobic insolubilizing reagents, such as formaldehyde solution, graded alcohols and paraffin wax, optionally along with heat impact. It is known that fixation and embedding, especially as practiced in clinical histology laboratories can conceal or even destroy epitopes. The non-native conditions result in integrins that are rather not extracted or degraded, but mainly occluded. The conformationally active obligate integrin heterodimers are sensitive to such conformational change, and they cannot readily be recovered from occlusion as it occurs during FFPE procedures.

Since the chemistries involved in tissue fixation and embedding affect integrin structure seriously, the defining available monoclonal antibodies used by skilled artisans in the field do not reliably recognize integrins after FFPE processing. Antibodies that recognize integrin cytoplasmic domains are necessarily restricted to single integrin chains, leading to ambiguous staining patterns in FFPE material since they do not report the distribution of intact integrin heterodimers. Furthermore, such antibodies, being directed against short peptide epitopes, tend to be conformation independent, which leads to the detection of single chains or degradation products, and a lower specificity and affinity than antibodies which would detect intact integrin complexes.

Several mouse monoclonal antibodies, such as mouse monoclonal anti-integrin $\alpha v \beta 3$ antibody LM609, detect $\alpha v \beta 3$ and $\alpha v \beta 5$ integrins using FACS or frozen tissue, however, they do not show significant or reproducible labeling of their epitopes in FFPE material. The deficiencies of murine monoclonals in their restricted epitope recognition and low affinity are widely recognized. The distribution patterns seen when such antibodies are used on FFPE material diverge from the patterns observed in fresh-frozen cryo-sectioned material; while these latter expression profiles closely match those of viable cells isolated from such tissues. FFPE staining with such antibodies must be viewed as of dubious provenance, and a technology on antigen retrieval has to grow up to recover such determinants from FFPE material.

At present, no monoclonal antibody is available that robustly recognizes the $\alpha v \beta 3$ or $\alpha v \beta 5$ extracellular epitopes in FFPE tissue, allowing the characterization of integrins in the FFPE patient tumor tissue. The end result of this situation is that decades of pathological specimens cannot be analyzed for the integrin expression profiles that might reveal patient populations who could benefit from therapies that target integrins. In the emerging therapeutic landscape, such a deficit can mean that effective therapeutics may tragically never reach the needy.

Therefore, the technical problem forming the basis of the present invention is to provide antibodies, which allow the reliable and unequivocal detection of integrin complexes in FFPE material, especially in routine FFPE tumor biopsies. It is another problem to provide a method for screening anti-integrin antibodies, which exhibit an effective discriminatory behavior between integrin homologues during immunohistochemistry in FFPE material.

The present invention solves the first problem by providing an antibody comprising one or more light chains and/or heavy chains, each of the chains comprising one or more complementarity determining regions (CDRs) of rabbit origin and optionally framework regions (FRs) in variable regions of the light ($V_L$) and/or heavy ($V_H$) chains, wherein the antibody has the capacity to bind an extracellular or intracellular domain of integrin. In other words, the antibody comprises at least one light chain variable region ($V_L$) and/or at least one heavy chain variable region ($V_H$), each of the regions comprising at least one complementarity determining region (CDR) of rabbit origin and optionally one or more framework regions (FRs), wherein the antibody has the capacity to bind an extracellular or intracellular domain of integrin.

In more detail, the present invention solves the first problem by providing a monoclonal rabbit antibody, or a fragment thereof, against both integrin with insect-derived glycosylation pattern and integrin with any other eukaryotic glycosylation pattern, wherein the antibody or the fragment thereof comprises at least a light chain variable region ($V_L$) and a heavy chain variable region ($V_H$), wherein the antibody has antigen binding specificity for a non-occluded epitope of an extracellular integrin domain, extracellular integrin chain domain or intracellular integrin chain domain, and wherein the antibody is able to bind to intact heterodimers of integrin in formalin fixed paraffin embedded (FFPE) material and in an isolated form in ELISA and/or in a native state on viable cells with the substantially same specificity.

It has been surprisingly demonstrated by the inventors that FFPE-capable antibodies can readily be generated by using the extracellular or intracellular domain of integrins or integrin chains as immunogen in rabbits. Best results are obtained with the intact domain, which can be favorably recombinantly expressed. In particular, the extracellular heterodimeric integrin domains have been proven to be effective immunogens if prepared in insect cells. The provision of the truncated integrin immunogens according to the invention significantly enhances the accessibility of epitopes and results in antibodies of exquisite sensitivity and specificity to the antigen. The monoclonal rabbit antibodies bind the antigen selectively, but independently from the glycosylation pattern. Even though the active antibodies of the invention are raised against insect-derived recombinant proteins, they are multi-functional in terms of antigenic glycosylation pattern and hence, they are considered as suitable for the recognition of an insect-derived recombinant antigen, but without being limited to this pattern. The antibodies of the invention are well suited to recognize the extracellular domain of a specific integrin or parts thereof of any eukaryotic glycosylation pattern. It shall be understood that the glycosylation patterns are not mixed up, but derived from a distinct eukaryotic cell or organism, respectively. In doing so, the generated antibodies are especially capable of recognizing the target structure within a complex FFPE matrix. The inventors have shown the unexpected suitability of these antibodies for integrin detection in FFPE tissue. The suitability is demonstrated in so far as the resulting antibodies are intensively specific and active on FFPE material. It is an overwhelming effect that integrin complexes in FFPE material can be easily detected by the antibody of the invention. While classical monoclonal antibodies do not work in FFPE material, the antibodies of the invention substantially bind their antigens in FFPE material and on viable cells with the same specificity; the latter is proven without limitations in live cell flow cytometry (e.g. fluorescence-activated cell sorting, briefly FACS). The antibodies of the invention can also substantially bind their antigens in FFPE material and in an isolated form in ELISA with the same specificity; the latter is proven without limitations in standard ELISAs as described in the course of the present specification and detailed in example 3.3. The staining pattern in FFPE tissue achieved herewith is of clear advantage over ambiguous results necessarily obtained from antibodies of prior art.

To date, the compositions of at least 24 integrin complexes have been described. Integrins are a family of cell adhesion molecules composed of two non-covalently associated chains. Both subunits, alpha ($\alpha$) and beta ($\beta$), traverse the membrane and integrate extracellular matrix with intracellular compartment, to deliver those extracellular signals which control cell adhesion, proliferation, migration and invasion. Based on the respective composition, the extracellular and intracellular integrin domains are assigned and known and they can be prepared by conventional processes. Either a domain of natural origin is isolated from a biological sample or the domain is recombinantly expressed and purified thereafter. Particularly, the sample is taken in-vivo from a mammal to be analyzed for integrin distribution pattern. The withdrawal of the sample shall follow good medical practice. Biological samples may be taken from any kind of biological species having an integrin of interest, but the sample is especially taken from a laboratory animal or a human, more preferably a rat, mouse, rabbit or human. The downstream processing of integrin is conducted by any process known in the art and followed by domain splitting and separating the extracellular or intracellular domain. Cell lysis can be performed in suitable, well-known lysis buffers, which may cause an osmotic shock and perforate the cell membrane. The stability of the cell structure can also be destroyed by mechanical forces, such as ball mill, French press, ultrasonic, etc., by enzymatic degradation of cell wall and cell membrane, respectively, and/or by the action of tensides. The integrins may be further purified to remove disturbing substances, or the integrins can be concentrated in the sample. Downstream-processing and/or concentrating are preferably performed by the method of precipitation, dialysis, gel filtration, gel elution or chromatography, such as HPLC or ion exchange chromatography. It is recommended to combine several methods for better yields.

Preferably, the extracellular integrin domain is recombinantly expressed and purified. The DNA encoding the protein sequence can be obtained, amplified, optionally altered or synthesized with techniques known to the skilled artisan. The DNA can be introduced into a vector and transcribed and translated in cells. The domain can be fused with a tag for affinity chromatography, such as Strep-tag, His-tag, GST-tag, Arg-tag or the calmodulin binding protein, or purified using established antibody-affinity purification techniques. A column is loaded with the protein suspension and all components lacking the tag are immediately eluted. After removal of unspecific binders by washing steps, the tag-fused construct is removed from the column. If the tag affects the induction of antibodies, it is cleaved off before immunization.

Several expression systems are state of the art. Interestingly, the titer against the protein elements of the immunogen can be beneficially increased if insect-derived recombinant integrin domains are applied. Insect-derived, recombinant mammalian glycoproteins are incompletely glycosylated, and lack terminal sugar processing and extension, which means that the protein epitopes are highly exposed in comparison to non-recombinant proteins or recombinant proteins of conventional eukaryotic expression. It is preferred, therefore, that the immunogenic integrin domain has an insect-derived glycosylation pattern, preferably the extracellular domain. Moreover, the antigenic properties to elicit or rather increase an immune response can be affected when attaching the antigen to a large carrier, such as a protein or polysaccharide; the carrier may be one which does not elicit an immune response by itself.

It is a preferred embodiment that the integrin domain has a human primary structure, i.e. the amino acid sequence aligns with an human entry in matching databases, such as the accession number of the sequence database Swiss-Prot. The skilled artisan knows such databases of molecular biology in order to extract sequences to be applied herein. In a more preferred embodiment of the present invention, the extracellular integrin domain has a human primary structure and an insect glycosylation pattern.

The inventive antibody denotes a polypeptide encoded by an immunoglobulin gene, or fragments thereof. The antibody comprises at least one light chain and/or at least one heavy chain, preferably at least one light chain and at least one heavy chain, more preferably two light chains and two heavy chains, each of them as defined hereunder. That means, the light chain comprises at least a single CDR, particularly of rabbit origin, in the variable region of said light ($V_L$) chain and optionally at least a single FR in the variable region of said light ($V_L$) chain, preferably at least said CDR and at least said FR. The heavy chain comprises at least a single CDR, particularly of rabbit origin, in the variable region of said heavy ($V_H$) chain and/or at least a single FR in the variable region of said heavy ($V_H$) chain, preferably at least said CDR and at least said FR. Within the antigen-binding portion of an antibody, the CDRs directly interact with the epitope of the antigen while the FRs maintain the tertiary structure of the paratope. In both the light chain and the heavy chain of immunoglobulins, there are three to four framework regions (FR-1 through FR-4) separated respectively by three complementarity determining regions (CDR-1 through CDR-3). The CDRs or hyper-variable regions, in particular the CDR-3 regions, more particularly the heavy chain CDR-3, are largely responsible for antibody affinity and specificity.

In another preferred embodiment of the invention, the light chain variable region ($V_L$) comprises two CDRs, more preferably three CDRs, most preferably together with the same number of FRs or even one FR more. In still another preferred embodiment of the invention, the heavy chain variable region ($V_H$) comprises two CDRs, more preferably three CDRs, most preferably together with the same number of FRs or even one FR more. In another more preferred embodiment, the antibody of the invention comprises the light chain variable region ($V_L$) and the heavy chain variable region ($V_H$), each of the regions comprises two CDRs, most preferably three CDRs, highly preferably together with the same number of FRs or even one FR more.

In other words, the antibody of the invention shall comprise at least that minimum scaffold from a variable region of a single chain, which confers binding capacity to any integrin domain or the extracellular domain in particular, respectively. According to the invention, the antibody can also be present as a number of other well-characterized fragments of an immunoglobulin or even as an intact immunoglobulin provided that the aforementioned minimum scaffold is given. Fragments are preferably selected from the group comprising heavy chain (H), light chain (L), variable regions (V), single chain variable fragment (scFv), $F_{ab}$ fragments consisting of a covalently bound antibody light chain and a portion of the antibody heavy chain ($F_d$), and the like.

The light chain of the antibody can additionally comprise a constant region of the light ($C_L$) chain. Similarly, the heavy chain of the antibody can additionally comprise a constant region of the heavy ($C_H$) chain, or a portion thereof, wherein the portion especially refers to the constant region within the $F_d$ region. The $F_d$ fragment is the major determinant of antibody specificity and retain epitope-binding ability in isolation. The antibody of the invention can also be completed by $F_c$ fragment as effector of the complement cascade, which is not involved in antigen binding. Fragments, such as $F_{ab}$ and $F_c$ fragments, can be produced by cleavage using various peptidases. Furthermore, fragments can be engineered and recombinantly expressed, preferably scFv.

In the scope of the invention, the antibody can be of polyclonal or monoclonal origin. Polyclonal antibodies are usually produced in mammal organisms when an immune response is caused by antigens being strange to the organism and having a molecular weight that exceeds 3.000 g/mol. Preferably, the antibodies of the invention are monoclonals. The great advantages of monoclonal antibodies include an immortal source of reagents, stable antibody properties and precise specificity. Popular techniques for producing monoclonal antibodies, such as the hybridoma technology, are also well-known to the skilled artisan.

Favorable host species for polyclonal and/or monoclonal antibody production comprise rat, goat, rabbit and mouse, more preferably rabbit. The rabbit antibodies, more preferably rabbit monoclonal antibodies (RabMabs), exhibit higher affinity along with a wider range of epitope recognition than mouse monoclonals, while due to divergence in the immune systems, and extended CDRs, stronger responses to epitopes, preferably human epitopes, can be produced compared to murine responses. It shall be understood that chimeric antibodies can be genetically engineered, which CDRs, FRs and/or constant regions are derived from different mammalian sources provided that one or more CDRs have a rabbit source. Accordingly, chimeric antibodies can be obtained by replacing not only the CDR but the whole variable regions of the light and heavy chains of non-rabbit origin. The affinity of the antigen-binding sites can be alternatively influenced by selective exchange of some amino acids within the variable regions.

The basic principal for making monoclonal rabbit antibodies were as for mouse monoclonals. Following the immunization of rabbits, the spleen is taken from those rabbits producing polyclonal serum. The isolated rabbit B cells of the immunized rabbits are fused with a rabbit plasmocytoma cell line to produce stable hybridomas. The hybridoma cells are tested for secretion of antibodies, which are specific for the immunogen, and they can be subsequently cloned. The original establishment of the rabbit hybridomas fusion partner cell line is described by Spieker-Polet et al., PNAS USA 1995, 92(20): 9348-9352. Further developments of the fusion partner cell line are disclosed in U.S. Pat. No. 7,429,487 B2. Still further methods are published in the U.S. application Ser. Nos. 10/705,109; 10/266,387; 10/313,881; 10/350,841 and 11/476,277. The cDNA of inserts encoding the antibody is preferably cloned, sequenced and inserted in an expression vector to allow production of wholly defined antibodies. The skilled artisan knows suitable techniques for the recombinant production of antibodies, such as in the EBNA cell expression system according to Pham et al., Biotech Bioeng 2003, 84(3): 332-342. Said publications are incorporated by reference as a whole in the disclosure of the invention.

The antibody or a fragment thereof is particularly directed against the extracellular domain of integrin $\alpha v\beta 3$, $\alpha v\beta 5$, $\alpha v\beta 6$ or $\alpha v\beta 8$.

In a preferred special embodiment of the present invention, the antibody or a fragment thereof is directed against the extracellular domain of the integrin $\alpha v\beta 3$. Suitable CDRs in $V_L$ comprise amino acid sequences of SEQ ID NO: 81 (CDR-1-$V_L$-$\alpha v\beta 3$), SEQ ID NO: 82 (CDR-2-$V_L$-$\alpha v\beta 3$) and/or SEQ ID NO: 83 (CDR-3-V$_L$-αvβ3), and/or suitable CDRs in V$_H$ comprise amino acid sequences of SEQ ID NO: 84 (CDR-1-V$_H$-αvβ3), SEQ ID NO: 85 (CDR-2-V$_H$-αvβ3) and/or SEQ ID NO: 86 (CDR-3-V$_H$-αvβ3). Preferably, the CDRs in V$_L$ comprise amino acid sequences of SEQ ID NO: 81 (CDR-1-V$_L$-αvβ3), SEQ ID NO: 82 (CDR-2-V$_L$-αvβ3) and SEQ ID NO: 83 (CDR-3-V$_L$-αvβ3), and/or the CDRs in V$_H$ comprise amino acid sequences of SEQ ID NO: 84 (CDR-1-V$_H$-αvβ3), SEQ ID NO: 85 (CDR-2-V$_H$-αvβ3) and SEQ ID NO: 86 (CDR-3-V$_H$-αvβ3). More preferably, the CDRs in V$_L$ comprise amino acid sequences of SEQ ID NO: 81 (CDR-1-V$_L$-αvβ3), SEQ ID NO: 82 (CDR-2-V$_L$-αvβ3) and SEQ ID NO: 83 (CDR-3-V$_L$-αvβ3), and the CDRs in V$_H$ comprise amino acid sequences of SEQ ID NO: 84 (CDR-1-V$_H$-αvβ3), SEQ ID NO: 85 (CDR-2-V$_H$-αvβ3) and SEQ ID NO: 86 (CDR-3-V$_H$-αvβ3).

Yet referring to the context of the anti-αvβ3 antibody, suitable FRs in V$_L$ comprise amino acid sequences of SEQ ID NO: 87 (FR-1-V$_L$-αvβ3), SEQ ID NO: 88 (FR-2-V$_L$-αvβ3) and/or SEQ ID NO: 89 (FR-3-V$_L$-αvβ3), and/or suitable FRs in V$_H$ comprise amino acid sequence of SEQ ID NO: 91 (FR-1-V$_H$-αvβ3), SEQ ID NO: 92 (FR-2-V$_H$-αvβ3), SEQ ID NO: 93 (FR-3-V$_H$-αvβ3) and/or SEQ ID NO: 94 (FR-4-V$_H$-αvβ3). Preferably, the FRs in V$_L$ comprise amino acid sequences of SEQ ID NO: 87 (FR-1-V$_L$-αvβ3), SEQ ID NO: 88 (FR-2-V$_L$-αvβ3) and SEQ ID NO: 89 (FR-3-V$_L$-αvβ3), and/or the FRs in V$_H$ comprise amino acid sequence of SEQ ID NO: 91 (FR-1-V$_H$-αvβ3), SEQ ID NO: 92 (FR-2-V$_H$-αvβ3), SEQ ID NO: 93 (FR-3-V$_H$-αvβ3) and SEQ ID NO: 94 (FR-4-V$_H$-αvβ3). More preferably, the FRs in V$_L$ comprise amino acid sequences of SEQ ID NO: 87 (FR-1-V$_L$-αvβ3), SEQ ID NO: 88 (FR-2-V$_L$-αvβ3) and SEQ ID NO: 89 (FR-3-V$_L$-αvβ3), and the FRs in V$_H$ comprise amino acid sequence of SEQ ID NO: 91 (FR-1-V$_H$-αvβ3), SEQ ID NO: 92 (FR-2-V$_H$-αvβ3), SEQ ID NO: 93 (FR-3-V$_H$-αvβ3) and SEQ ID NO: 94 (FR-4-V$_H$-αvβ3).

It is another combinatorial embodiment in the anti-αvβ3 antibody context, in which suitable CDRs in V$_L$ comprise amino acid sequences of SEQ ID NO: 81 (CDR-1-V$_L$-αvβ3), SEQ ID NO: 82 (CDR-2-V$_L$-αvβ3) and/or SEQ ID NO: 83 (CDR-3-V$_L$-αvβ3), and suitable FRs in V$_L$ comprise amino acid sequences of SEQ ID NO: 87 (FR-1-V$_L$-αvβ3), SEQ ID NO: 88 (FR-2-V$_L$-αvβ3) and/or SEQ ID NO: 89 (FR-3-V$_L$-αvβ3). Preferably, the CDRs in V$_L$ comprise amino acid sequences of SEQ ID NO: 81 (CDR-1-V$_L$-αvβ3), SEQ ID NO: 82 (CDR-2-V$_L$-αvβ3) and SEQ ID NO: 83 (CDR-3-V$_L$-αvβ3), and the FRs in V$_L$ comprise amino acid sequences of SEQ ID NO: 87 (FR-1-V$_L$-αvβ3), SEQ ID NO: 88 (FR-2-V$_L$-αvβ3) and SEQ ID NO: 89 (FR-3-V$_L$-αvβ3).

It is still another combinatorial embodiment in the anti-αvβ3 antibody context, in which suitable CDRs in V$_H$ comprise amino acid sequences of SEQ ID NO: 84 (CDR-1-V$_H$-αvβ3), SEQ ID NO: 85 (CDR-2-V$_H$-αvβ3) and/or SEQ ID NO: 86 (CDR-3-V$_H$-αvβ3), and suitable FRs in V$_H$ comprise amino acid sequence of SEQ ID NO: 91 (FR-1-V$_H$-αvβ3), SEQ ID NO: 92 (FR-2-V$_H$-αvβ3), SEQ ID NO: 93 (FR-3-V$_H$-αvβ3) and/or SEQ ID NO: 94 (FR-4-V$_H$-αvβ3). Preferably, the CDRs in V$_H$ comprise amino acid sequences of SEQ ID NO: 84 (CDR-1-V$_H$-αvβ3), SEQ ID NO: 85 (CDR-2-V$_H$-αvβ3) and SEQ ID NO: 86 (CDR-3-V$_H$-αvβ3), and the FRs in V$_H$ comprise amino acid sequence of SEQ ID NO: 91 (FR-1-V$_H$-αvβ3), SEQ ID NO: 92 (FR-2-V$_H$-αvβ3), SEQ ID NO: 93 (FR-3-V$_H$-αvβ3) and SEQ ID NO: 94 (FR-4-V$_H$-αvβ3).

In another preferred embodiment in the anti-αvβ3 antibody context, V$_L$ comprises an amino acid sequence of SEQ ID NO: 95 (V$_L$-αvβ3) and/or V$_H$ comprises an amino acid sequence of SEQ ID NO: 96 (V$_H$-αvβ3), more preferably V$_L$ consists of an amino acid sequence of SEQ ID NO: 95 (V$_L$-αvβ3) and/or V$_H$ consists of an amino acid sequence of SEQ ID NO: 96 (V$_H$-αvβ3), most preferably the antibody is shaped as anti-αvβ3 scFv.

The anti-αvβ3 antibody can be completed by constant regions of the light (C$_L$) and/or heavy (C$_H$) chain. Preferably, C$_L$ comprises an amino acid sequence of SEQ ID NO: 97 (C$_L$-αvβ3) and/or C$_H$ comprises an amino acid sequence of SEQ ID NO: 98 (C$_H$-αvβ3).

Accordingly, the anti-αvβ3 antibody comprises more preferably light and/or heavy chains, wherein the light chain comprises an amino acid sequence of SEQ ID NO: 99 (L-αvβ3) and/or the heavy chain comprises an amino acid sequence of SEQ ID NO: 100 (H-αvβ3). Most preferably, the light chain consists of an amino acid sequence of SEQ ID NO: 99 (L-αvβ3) and/or the heavy chain consists of an amino acid sequence of SEQ ID NO: 100 (H-αvβ3). In a highly preferred embodiment of the present invention, the light chain consists of an amino acid sequence of SEQ ID NO: 99 (L-αvβ3) and the heavy chain consists of an amino acid sequence of SEQ ID NO: 100 (H-αvβ3).

In another preferred special embodiment of the present invention, the antibody or a fragment thereof is directed against the extracellular domain of the integrin αvβ5. Suitable CDRs in V$_L$ comprise amino acid sequences of SEQ ID NO: 1 (CDR-1-V$_L$-αvβ5), SEQ ID NO: 2 (CDR-2-V$_L$-αvβ5) and/or SEQ ID NO: 3 (CDR-3-V$_L$-αvβ5), and/or suitable CDRs in V$_H$ comprise amino acid sequences of SEQ ID NO: 4 (CDR-1-V$_H$-αvβ5), SEQ ID NO: 5 (CDR-2-V$_H$-αvβ5) and/or SEQ ID NO: 6 (CDR-3-V$_H$-αvβ5). Preferably, the CDRs in V$_L$ comprise amino acid sequences of SEQ ID NO: 1 (CDR-1-V$_L$-αvβ5), SEQ ID NO: 2 (CDR-2-V$_L$-αvβ5) and SEQ ID NO: 3 (CDR-3-V$_L$-αvβ5), and/or the CDRs in V$_H$ comprise amino acid sequences of SEQ ID NO: 4 (CDR-1-V$_H$-αvβ5), SEQ ID NO: 5 (CDR-2-V$_H$-αvβ5) and SEQ ID NO: 6 (CDR-3-V$_H$-αvβ5). More preferably, the CDRs in V$_L$ comprise amino acid sequences of SEQ ID NO: 1 (CDR-1-V$_L$-αvβ5), SEQ ID NO: 2 (CDR-2-V$_L$-αvβ5) and SEQ ID NO: 3 (CDR-3-V$_L$-αvβ5), and the CDRs in V$_H$ comprise amino acid sequences of SEQ ID NO: 4 (CDR-1-V$_H$-αvβ5), SEQ ID NO: 5 (CDR-2-V$_H$-αvβ5) and SEQ ID NO: 6 (CDR-3-V$_H$-αvβ5).

Yet referring to the context of the anti-αvβ5 antibody, suitable FRs in V$_L$ comprise amino acid sequences of SEQ ID NO: 7 (FR-1-V$_L$-αvβ5), SEQ ID NO: 8 (FR-2-V$_L$-αvβ5) and/or SEQ ID NO: 9 (FR-3-V$_L$-αvβ5), and/or suitable FRs in V$_H$ comprise amino acid sequence of SEQ ID NO: 11 (FR-1-V$_H$-αvβ5), SEQ ID NO: 12 (FR-2-V$_H$-αvβ5), SEQ ID NO: 13 (FR-3-V$_H$-αvβ5) and/or SEQ ID NO: 14 (FR-4-V$_H$-αvβ5). Preferably, the FRs in V$_L$ comprise amino acid sequences of SEQ ID NO: 7 (FR-1-V$_L$-αvβ5), SEQ ID NO: 8 (FR-2-V$_L$-αvβ5) and SEQ ID NO: 9 (FR-3-V$_L$-αvβ5), and/or the FRs in V$_H$ comprise amino acid sequence of SEQ ID NO: 11 (FR-1-V$_H$-αvβ5), SEQ ID NO: 12 (FR-2-V$_H$-αvβ5), SEQ ID NO: 13 (FR-3-V$_H$-αvβ5) and SEQ ID NO: 14 (FR-4-V$_H$-αvβ5). More preferably, the FRs in V$_L$ comprise amino acid sequences of SEQ ID NO: 7 (FR-1-V$_L$-αvβ5), SEQ ID NO: 8 (FR-2-V$_L$-αvβ5) and SEQ ID NO: 9 (FR-3-V$_L$-αvβ5), and the FRs in V$_H$ comprise amino acid sequence of SEQ ID NO: 11 (FR-1-V$_H$-αvβ5), SEQ ID NO: 12 (FR-2-V$_H$-αvβ5), SEQ ID NO: 13 (FR-3-V$_H$-αvβ5) and SEQ ID NO: 14 (FR-4-V$_H$-αvβ5).

It is another combinatorial embodiment in the anti-αvβ5 antibody context, in which suitable CDRs in V$_L$ comprise amino acid sequences of SEQ ID NO: 1 (CDR-1-V$_1$-αvβ5), SEQ ID NO: 2 (CDR-2-V$_L$-αvβ5) and/or SEQ ID NO: 3

(CDR-3-$V_L$-αvβ5), and suitable FRs in $V_L$ comprise amino acid sequences of SEQ ID NO: 7 (FR-1-$V_L$-αvβ5), SEQ ID NO: 8 (FR-2-$V_L$-αvβ5) and/or SEQ ID NO: 9 (FR-3-$V_L$-αvβ5). Preferably, the CDRs in $V_L$ comprise amino acid sequences of SEQ ID NO: 1 (CDR-1-$V_L$-αvβ5), SEQ ID NO: 2 (CDR-2-$V_L$-αvβ5) and SEQ ID NO: 3 (CDR-3-$V_L$-αvβ5), and the FRs in $V_L$ comprise amino acid sequences of SEQ ID NO: 7 (FR-1-$V_L$-αvβ5), SEQ ID NO: 8 (FR-2-$V_L$-αvβ5) and SEQ ID NO: 9 (FR-3-$V_L$-αvβ5).

It is still another combinatorial embodiment in the anti-αvβ5 antibody context, in which suitable CDRs in $V_H$ comprise amino acid sequences of SEQ ID NO: 4 (CDR-1-$V_H$-αvβ5), SEQ ID NO: 5 (CDR-2-$V_H$-αvβ5) and/or SEQ ID NO: 6 (CDR-3-$V_H$-αvβ5), and suitable FRs in $V_H$ comprise amino acid sequence of SEQ ID NO: 11 (FR-1-$V_H$-αvβ5), SEQ ID NO: 12 (FR-2-$V_H$-αvβ5), SEQ ID NO: 13 (FR-3-$V_H$-αvβ5) and/or SEQ ID NO: 14 (FR-4-$V_H$-αvβ5). Preferably, the CDRs in $V_H$ comprise amino acid sequences of SEQ ID NO: 4 (CDR-1-$V_H$-αvβ5), SEQ ID NO: 5 (CDR-2-$V_H$-αvβ5) and SEQ ID NO: 6 (CDR-3-$V_H$-αvβ5), and the FRs in $V_H$ comprise amino acid sequence of SEQ ID NO: 11 (FR-1-$V_H$-αvβ5), SEQ ID NO: 12 (FR-2-$V_H$-αvβ5), SEQ ID NO: 13 (FR-3-$V_H$-αvβ5) and SEQ ID NO: 14 (FR-4-$V_H$-αvβ5).

In another preferred embodiment in the anti-αvβ5 antibody context, $V_L$ comprises an amino acid sequence of SEQ ID NO: 15 ($V_L$-αvβ5) and/or $V_H$ comprises an amino acid sequence of SEQ ID NO: 16 ($V_H$-αvβ5), more preferably $V_L$ consists of an amino acid sequence of SEQ ID NO: 15 ($V_L$-αvβ5) and/or $V_H$ consists of an amino acid sequence of SEQ ID NO: 16 ($V_H$-αvβ5), most preferably the antibody is shaped as anti-αvβ5 scFv.

The anti-αvβ5 antibody can be completed by constant regions of the light ($C_L$) and/or heavy ($C_H$) chain. Preferably, $C_L$ comprises an amino acid sequence of SEQ ID NO: 17 ($C_L$-αvβ5) and/or $C_H$ comprises an amino acid sequence of SEQ ID NO: 18 ($C_H$-αvβ5).

Accordingly, the anti-αvβ5 antibody comprises more preferably light and/or heavy chains, wherein the light chain comprises an amino acid sequence of SEQ ID NO: 19 (L-αvβ5) and/or the heavy chain comprises an amino acid sequence of SEQ ID NO: 20 (H-αvβ5). Most preferably, the light chain consists of an amino acid sequence of SEQ ID NO: 19 (L-αvβ5) and/or the heavy chain consists of an amino acid sequence of SEQ ID NO: 20 (H-αvβ5). In a highly preferred embodiment of the present invention, the light chain consists of an amino acid sequence of SEQ ID NO: 19 (L-αvβ5) and the heavy chain consists of an amino acid sequence of SEQ ID NO: 20 (H-αvβ5).

In still another preferred special embodiment of the present invention, the antibody or a fragment thereof is directed against the extracellular domain of the integrin αvβ6. Suitable CDRs in $V_L$ comprise amino acid sequences of SEQ ID NO: 121 (CDR-1-$V_L$-αvβ6), SEQ ID NO: 122 (CDR-2-$V_L$-αvβ6) and/or SEQ ID NO: 123 (CDR-3-$V_L$-αvβ6), and/or suitable CDRs in $V_H$ comprise amino acid sequences of SEQ ID NO: 124 (CDR-1-$V_H$-αvβ6), SEQ ID NO: 125 (CDR-2-$V_H$-αvβ6) and/or SEQ ID NO: 126 (CDR-3-$V_H$-αvβ6). Preferably, the CDRs in $V_L$ comprise amino acid sequences of SEQ ID NO: 121 (CDR-1-$V_L$-αvβ6), SEQ ID NO: 122 (CDR-2-$V_L$-αvβ6) and SEQ ID NO: 123 (CDR-3-$V_L$-αvβ6), and/or the CDRs in $V_H$ comprise amino acid sequences of SEQ ID NO: 124 (CDR-1-$V_H$-αvβ6), SEQ ID NO: 125 (CDR-2-$V_H$-αvβ6) and SEQ ID NO: 126 (CDR-3-$V_H$-αvβ6). More preferably, the CDRs in $V_L$ comprise amino acid sequences of SEQ ID NO: 121 (CDR-1-$V_L$-αvβ6), SEQ ID NO: 122 (CDR-2-$V_L$-αvβ6) and SEQ ID NO: 123 (CDR-3-$V_L$-αvβ6), and the CDRs in $V_H$ comprise amino acid sequences of SEQ ID NO: 124 (CDR-1-$V_H$-αvβ6), SEQ ID NO: 125 (CDR-2-$V_H$-αvβ6) and SEQ ID NO: 126 (CDR-3-$V_H$-αvβ6).

Yet referring to the context of the anti-αvβ6 antibody, suitable FRs in $V_L$ comprise amino acid sequences of SEQ ID NO: 127 (FR-1-$V_L$-αvβ6), SEQ ID NO: 128 (FR-2-$V_L$-αvβ6) and/or SEQ ID NO: 129 (FR-3-$V_L$-αvβ6), and/or suitable FRs in $V_H$ comprise amino acid sequence of SEQ ID NO: 131 (FR-1-$V_H$-αvβ6), SEQ ID NO: 132 (FR-2-$V_H$-αvβ6), SEQ ID NO: 133 (FR-3-$V_H$-αvβ6) and/or SEQ ID NO: 134 (FR-4-$V_H$-αvβ6). Preferably, the FRs in $V_L$ comprise amino acid sequences of SEQ ID NO: 127 (FR-1-$V_L$-αvβ6), SEQ ID NO: 128 (FR-2-$V_L$-αvβ6) and SEQ ID NO: 129 (FR-3-$V_L$-αvβ6), and/or the FRs in $V_H$ comprise amino acid sequence of SEQ ID NO: 131 (FR-1-$V_H$-αvβ6), SEQ ID NO: 132 (FR-2-$V_H$-αvβ6), SEQ ID NO: 133 (FR-3-$V_H$-αvβ6) and SEQ ID NO: 134 (FR-4-$V_H$-αvβ6). More preferably, the FRs in $V_L$ comprise amino acid sequences of SEQ ID NO: 127 (FR-1-$V_L$-αvβ6), SEQ ID NO: 128 (FR-2-$V_L$-αvβ6) and SEQ ID NO: 129 (FR-3-$V_L$-αvβ6), and the FRs in $V_H$ comprise amino acid sequence of SEQ ID NO: 131 (FR-1-$V_H$-αvβ6), SEQ ID NO: 132 (FR-2-$V_H$-αvβ6), SEQ ID NO: 133 (FR-3-$V_H$-αvβ6) and SEQ ID NO: 134 (FR-4-$V_H$-αvβ6).

It is another combinatorial embodiment in the anti-αvβ6 antibody context, in which suitable CDRs in $V_L$ comprise amino acid sequences of SEQ ID NO: 121 (CDR-1-$V_L$-αvβ6), SEQ ID NO: 122 (CDR-2-$V_L$-αvβ6) and/or SEQ ID NO: 123 (CDR-3-$V_L$-αvβ6), and suitable FRs in $V_L$ comprise amino acid sequences of SEQ ID NO: 127 (FR-1-$V_L$-αvβ6), SEQ ID NO: 128 (FR-2-$V_L$-αvβ6) and/or SEQ ID NO: 129 (FR-3-$V_L$-αvβ6). Preferably, the CDRs in $V_L$ comprise amino acid sequences of SEQ ID NO: 121 (CDR-1-$V_L$-αvβ6), SEQ ID NO: 122 (CDR-2-$V_L$-αvβ6) and SEQ ID NO: 123 (CDR-3-$V_L$-αvβ6), and the FRs in $V_L$ comprise amino acid sequences of SEQ ID NO: 127 (FR-1-$V_L$-αvβ6), SEQ ID NO: 128 (FR-2-$V_L$-αvβ6) and SEQ ID NO: 129 (FR-3-$V_L$-αvβ6).

It is still another combinatorial embodiment in the anti-αvβ6 antibody context, in which suitable CDRs in $V_H$ comprise amino acid sequences of SEQ ID NO: 124 (CDR-1-$V_H$-αvβ6), SEQ ID NO: 125 (CDR-2-$V_H$-αvβ6) and/or SEQ ID NO: 126 (CDR-3-$V_H$-αvβ6), and suitable FRs in $V_H$ comprise amino acid sequence of SEQ ID NO: 131 (FR-1-$V_H$-αvβ6), SEQ ID NO: 132 (FR-2-$V_H$-αvβ6), SEQ ID NO: 133 (FR-3-$V_H$-αvβ6) and/or SEQ ID NO: 134 (FR-4-$V_H$-αvβ6). Preferably, the CDRs in $V_H$ comprise amino acid sequences of SEQ ID NO: 124 (CDR-1-$V_H$-αvβ6), SEQ ID NO: 125 (CDR-2-$V_H$-αvβ6) and SEQ ID NO: 126 (CDR-3-$V_H$-αvβ6), and the FRs in $V_H$ comprise amino acid sequence of SEQ ID NO: 131 (FR-1-$V_H$-αvβ6), SEQ ID NO: 132 (FR-2-$V_H$-αvβ6), SEQ ID NO: 133 (FR-3-$V_H$-αvβ6) and SEQ ID NO: 134 (FR-4-$V_H$-αvβ6).

In another preferred embodiment in the anti-αvβ6 antibody context, $V_L$ comprises an amino acid sequence of SEQ ID NO: 135 ($V_L$-αvβ6) and/or $V_H$ comprises an amino acid sequence of SEQ ID NO: 136 ($V_H$-αvβ6), more preferably $V_L$ consists of an amino acid sequence of SEQ ID NO: 135 ($V_L$-αvβ6) and/or $V_H$ consists of an amino acid sequence of SEQ ID NO: 136 ($V_H$-αvβ6), most preferably the antibody is shaped as anti-αvβ6 scFv.

The anti-αvβ6 antibody can be completed by constant regions of the light ($C_L$) and/or heavy ($C_H$) chain. Preferably, $C_L$ comprises an amino acid sequence of SEQ ID NO: 137 ($C_L$-αvβ6) and/or $C_H$ comprises an amino acid sequence of SEQ ID NO: 138 ($C_H$-αvβ6).

Accordingly, the anti-αvβ6 antibody comprises more preferably light and/or heavy chains, wherein the light chain comprises an amino acid sequence of SEQ ID NO: 139 (L-αvβ6) and/or the heavy chain comprises an amino acid sequence of SEQ ID NO: 140 (H-αvβ6). Most preferably, the light chain consists of an amino acid sequence of SEQ ID NO: 139 (L-αvβ6) and/or the heavy chain consists of an amino acid sequence of SEQ ID NO: 140 (H-αvβ6). In a highly preferred embodiment of the present invention, the light chain consists of an amino acid sequence of SEQ ID NO: 139 (L-αvβ6) and the heavy chain consists of an amino acid sequence of SEQ ID NO: 140 (H-αvβ6).

In still another preferred special embodiment of the present invention, the antibody or a fragment thereof is directed against the extracellular domain of the integrin αvβ8. Suitable CDRs in $V_L$ comprise amino acid sequences of SEQ ID NO: 161 (CDR-1-$V_L$-αvβ8), SEQ ID NO: 162 (CDR-2-$V_L$-αvβ8) and/or SEQ ID NO: 163 (CDR-3-$V_L$-αvβ8), and/or suitable CDRs in $V_H$ comprise amino acid sequences of SEQ ID NO: 164 (CDR-1-$V_H$-αvβ8), SEQ ID NO: 165 (CDR-2-$V_H$-αvβ8) and/or SEQ ID NO: 166 (CDR-3-$V_H$-αvβ8). Preferably, the CDRs in $V_L$ comprise amino acid sequences of SEQ ID NO: 161 (CDR-1-$V_L$-αvβ8), SEQ ID NO: 162 (CDR-2-$V_L$-αvβ8) and SEQ ID NO: 163 (CDR-3-$V_L$-αvβ8), and/or the CDRs in $V_H$ comprise amino acid sequences of SEQ ID NO: 164 (CDR-1-$V_H$-αvβ8), SEQ ID NO: 165 (CDR-2-$V_H$-αvβ8) and SEQ ID NO: 166 (CDR-3-$V_H$-αvβ8). More preferably, the CDRs in $V_L$ comprise amino acid sequences of SEQ ID NO: 161 (CDR-1-$V_L$-αvβ8), SEQ ID NO: 162 (CDR-2-$V_L$-αvβ8) and SEQ ID NO: 163 (CDR-3-$V_L$-αvβ8), and the CDRs in $V_H$ comprise amino acid sequences of SEQ ID NO: 164 (CDR-1-$V_H$-αvβ8), SEQ ID NO: 165 (CDR-2-$V_H$-αvβ8) and SEQ ID NO: 166 (CDR-3-$V_H$-αvβ8).

Yet referring to the context of the anti-αvβ8 antibody, suitable FRs in $V_L$ comprise amino acid sequences of SEQ ID NO: 167 (FR-1-$V_L$-αvβ8), SEQ ID NO: 168 (FR-2-$V_L$-αvβ8) and/or SEQ ID NO: 169 (FR-3-$V_L$-αvβ8), and/or suitable FRs in $V_H$ comprise amino acid sequence of SEQ ID NO: 171 (FR-1-$V_H$-αvβ8), SEQ ID NO: 172 (FR-2-$V_H$-αvβ8), SEQ ID NO: 173 (FR-3-$V_H$-αvβ8) and/or SEQ ID NO: 174 (FR-4-$V_H$-αvβ8). Preferably, the FRs in $V_L$ comprise amino acid sequences of SEQ ID NO: 167 (FR-1-$V_L$-αvβ8), SEQ ID NO: 168 (FR-2-$V_L$-αvβ8) and SEQ ID NO: 169 (FR-3-$V_L$-αvβ8), and/or the FRs in $V_H$ comprise amino acid sequence of SEQ ID NO: 171 (FR-1-$V_H$-αvβ8), SEQ ID NO: 172 (FR-2-$V_H$-αvβ8), SEQ ID NO: 173 (FR-3-$V_H$-αvβ8) and SEQ ID NO: 174 (FR-4-$V_H$-αvβ8). More preferably, the FRs in $V_L$ comprise amino acid sequences of SEQ ID NO: 167 (FR-1-$V_L$-αvβ8), SEQ ID NO: 168 (FR-2-$V_L$-αvβ8) and SEQ ID NO: 169 (FR-3-$V_L$-αvβ8), and the FRs in $V_H$ comprise amino acid sequence of SEQ ID NO: 171 (FR-1-$V_H$-αvβ8), SEQ ID NO: 172 (FR-2-$V_H$-αvβ8), SEQ ID NO: 173 (FR-3-$V_H$-αvβ8) and SEQ ID NO: 174 (FR-4-$V_H$-αvβ8).

It is another combinatorial embodiment in the anti-αvβ8 antibody context, in which suitable CDRs in $V_L$ comprise amino acid sequences of SEQ ID NO: 161 (CDR-1-$V_L$-αvβ8), SEQ ID NO: 162 (CDR-2-$V_L$-αvβ8) and/or SEQ ID NO: 163 (CDR-3-$V_L$-αvβ8), and suitable FRs in $V_L$ comprise amino acid sequences of SEQ ID NO: 167 (FR-1-$V_L$-αvβ8), SEQ ID NO: 168 (FR-2-$V_L$-αvβ8) and/or SEQ ID NO: 169 (FR-3-$V_L$-αvβ8). Preferably, the CDRs in $V_L$ comprise amino acid sequences of SEQ ID NO: 161 (CDR-1-$V_L$-αvβ8), SEQ ID NO: 162 (CDR-2-$V_L$-αvβ8) and SEQ ID NO: 163 (CDR-3-$V_L$-αvβ8), and the FRs in $V_1$ comprise amino acid sequences of SEQ ID NO: 167 (FR-1-$V_L$-αvβ8), SEQ ID NO: 168 (FR-2-$V_L$-αvβ8) and SEQ ID NO: 169 (FR-3-$V_L$-αvβ8).

It is still another combinatorial embodiment in the anti-αvβ8 antibody context, in which suitable CDRs in $V_H$ comprise amino acid sequences of SEQ ID NO: 164 (CDR-1-$V_H$-αvβ8), SEQ ID NO: 165 (CDR-2-$V_H$-αvβ8) and/or SEQ ID NO: 166 (CDR-3-$V_H$-αvβ8), and suitable FRs in $V_H$ comprise amino acid sequence of SEQ ID NO: 171 (FR-1-$V_H$-αvβ8), SEQ ID NO: 172 (FR-2-$V_H$-αvβ8), SEQ ID NO: 173 (FR-3-$V_H$-αvβ8) and/or SEQ ID NO: 174 (FR-4-$V_H$-αvβ8). Preferably, the CDRs in $V_H$ comprise amino acid sequences of SEQ ID NO: 164 (CDR-1-$V_H$-αvβ8), SEQ ID NO: 165 (CDR-2-$V_H$-αvβ8) and SEQ ID NO: 166 (CDR-3-$V_H$-αvβ8), and the FRs in $V_H$ comprise amino acid sequence of SEQ ID NO: 171 (FR-1-$V_H$-αvβ8), SEQ ID NO: 172 (FR-2-$V_H$-αvβ8), SEQ ID NO: 173 (FR-3-$V_H$-αvβ8) and SEQ ID NO: 174 (FR-4-$V_H$-αvβ8).

In another preferred embodiment in the anti-αvβ8 antibody context, $V_L$ comprises an amino acid sequence of SEQ ID NO: 175 ($V_L$-αvβ8) and/or $V_H$ comprises an amino acid sequence of SEQ ID NO: 176 ($V_H$-αvβ8), more preferably $V_L$ consists of an amino acid sequence of SEQ ID NO: 175 ($V_L$-αvβ8) and/or $V_H$ consists of an amino acid sequence of SEQ ID NO: 176 ($V_H$-αvβ8), most preferably the antibody is shaped as anti-αvβ8 scFv.

The anti-αvβ8 antibody can be completed by constant regions of the light ($C_L$) and/or heavy ($C_H$) chain. Preferably, $C_L$ comprises an amino acid sequence of SEQ ID NO: 177 ($C_L$-αvβ8) and/or $C_H$ comprises an amino acid sequence of SEQ ID NO: 178 ($C_H$-αvβ8).

Accordingly, the anti-αvβ8 antibody comprises more preferably light and/or heavy chains, wherein the light chain comprises an amino acid sequence of SEQ ID NO: 179 (L-αvβ8) and/or the heavy chain comprises an amino acid sequence of SEQ ID NO: 180 (H-αvβ8). Most preferably, the light chain consists of an amino acid sequence of SEQ ID NO: 179 (L-αvβ8) and/or the heavy chain consists of an amino acid sequence of SEQ ID NO: 180 (H-αvβ8). In a highly preferred embodiment of the present invention, the light chain consists of an amino acid sequence of SEQ ID NO: 179 (L-αvβ8) and the heavy chain consists of an amino acid sequence of SEQ ID NO: 180 (H-αvβ8).

In still another preferred special embodiment of the present invention, the antibody or a fragment thereof is directed against the extracellular domain of the integrin αv. Suitable CDRs in $V_L$ comprise amino acid sequences of SEQ ID NO: 201 (CDR-1-$V_L$-αv), SEQ ID NO: 202 (CDR-2-$V_L$-cv) and/or SEQ ID NO: 203 (CDR-3-$V_L$-αv), and/or suitable CDRs in $V_H$ comprise amino acid sequences of SEQ ID NO: 204 (CDR-1-$V_H$-αv), SEQ ID NO: 205 (CDR-2-$V_H$-αv) and/or SEQ ID NO: 206 (CDR-3-$V_H$-αv). Preferably, the CDRs in $V_L$ comprise amino acid sequences of SEQ ID NO: 201 (CDR-1-$V_L$-αv), SEQ ID NO: 202 (CDR-2-$V_L$-αv) and SEQ ID NO: 203 (CDR-3-$V_L$-αv), and/or the CDRs in $V_H$ comprise amino acid sequences of SEQ ID NO: 204 (CDR-1-$V_H$-αv), SEQ ID NO: 205 (CDR-2-$V_H$-αv) and SEQ ID NO: 206 (CDR-3-$V_H$-αv). More preferably, the CDRs in $V_1$ comprise amino acid sequences of SEQ ID NO: 201 (CDR-1-$V_L$-αv), SEQ ID NO: 202 (CDR-2-$V_L$-αv) and SEQ ID NO: 203 (CDR-3-$V_L$-αsv), and the CDRs in $V_H$ comprise amino acid sequences of SEQ ID NO: 204 (CDR-1-$V_H$-αv), SEQ ID NO: 205 (CDR-2-$V_H$-αv) and SEQ ID NO: 206 (CDR-3-$V_H$-αv).

Yet referring to the context of the anti-αv antibody, suitable FRs in $V_L$ comprise amino acid sequences of SEQ ID NO: 207 (FR-1-$V_L$-αv), SEQ ID NO: 208 (FR-2-$V_L$-αv) and/or SEQ ID NO: 209 (FR-3-$V_L$-αv), and/or suitable FRs in $V_H$ comprise amino acid sequence of SEQ ID NO: 211 (FR-1-$V_H$-αv), SEQ ID NO: 212 (FR-2-$V_H$-αv), SEQ ID NO: 213 (FR-3-$V_H$-αv) and/or SEQ ID NO: 214 (FR-4-$V_H$-αv). Preferably, the FRs in V_L comprise amino acid sequences of SEQ ID NO: 207 (FR-1-V_L-αv), SEQ ID NO: 208 (FR-2-V_L-αv) and SEQ ID NO: 209 (FR-3-V_L-αv), and/or the FRs in V_H comprise amino acid sequence of SEQ ID NO: 211 (FR-1-V_H-αv), SEQ ID NO: 212 (FR-2-V_H-αv), SEQ ID NO: 213 (FR-3-V_H-αv) and SEQ ID NO: 214 (FR-4-V_H-αv). More preferably, the FRs in V_L comprise amino acid sequences of SEQ ID NO: 207 (FR-1-V_L-αv), SEQ ID NO: 208 (FR-2-V_L-αv) and SEQ ID NO: 209 (FR-3-V_L-αv), and the FRs in V_H comprise amino acid sequence of SEQ ID NO: 211 (FR-1-V_H-αv), SEQ ID NO: 212 (FR-2-V_H-αv), SEQ ID NO: 213 (FR-3-V_H-αv) and SEQ ID NO: 214 (FR-4-V_H-αv).

It is another combinatorial embodiment in the anti-αv antibody context, in which suitable CDRs in V_L comprise amino acid sequences of SEQ ID NO: 201 (CDR-1-V_L-αv), SEQ ID NO: 202 (CDR-2-V_L-αv) and/or SEQ ID NO: 203 (CDR-3-V_L-αv), and suitable FRs in V_L comprise amino acid sequences of SEQ ID NO: 207 (FR-1-V_L-αv), SEQ ID NO: 208 (FR-2-V_L-αv) and/or SEQ ID NO: 209 (FR-3-V_L-αv). Preferably, the CDRs in V_L comprise amino acid sequences of SEQ ID NO: 201 (CDR-1-V_L-αv), SEQ ID NO: 202 (CDR-2-V_L-αv) and SEQ ID NO: 203 (CDR-3-V_L-αv), and the FRs in V_L comprise amino acid sequences of SEQ ID NO: 207 (FR-1-V_L-αv), SEQ ID NO: 208 (FR-2-V_L-αv) and SEQ ID NO: 209 (FR-3-V_L-αv).

It is still another combinatorial embodiment in the anti-αv antibody context, in which suitable CDRs in V_H comprise amino acid sequences of SEQ ID NO: 204 (CDR-1-V_H-αv), SEQ ID NO: 205 (CDR-2-V_H-αv) and/or SEQ ID NO: 206 (CDR-3-V_H-αv), and suitable FRs in V_H comprise amino acid sequence of SEQ ID NO: 211 (FR-1-V_H-αv), SEQ ID NO: 212 (FR-2-V_H-αv), SEQ ID NO: 213 (FR-3-V_H-αv) and/or SEQ ID NO: 214 (FR-4-V_H-αv). Preferably, the CDRs in V_H comprise amino acid sequences of SEQ ID NO: 204 (CDR-1-V_H-αv), SEQ ID NO: 205 (CDR-2-V_H-αv) and SEQ ID NO: 206 (CDR-3-V_H-αv), and the FRs in V_H comprise amino acid sequence of SEQ ID NO: 211 (FR-1-V_H-αv), SEQ ID NO: 212 (FR-2-V_H-αv), SEQ ID NO: 213 (FR-3-V_H-αv) and SEQ ID NO: 214 (FR-4-V_H-αv).

In another preferred embodiment in the anti-αv antibody context, V_L comprises an amino acid sequence of SEQ ID NO: 215 (V_L-αv) and/or V_H comprises an amino acid sequence of SEQ ID NO: 216 (V_H-αv), more preferably V_L consists of an amino acid sequence of SEQ ID NO: 215 (V_L-αv) and/or V_H consists of an amino acid sequence of SEQ ID NO: 216 (V_H-αv), most preferably the antibody is shaped as anti-αv scFv.

The anti-αv antibody can be completed by constant regions of the light (C_L) and/or heavy (C_H) chain. Preferably, C_L comprises an amino acid sequence of SEQ ID NO: 217 (C_L-αv) and/or C_H comprises an amino acid sequence of SEQ ID NO: 218 (C_H-αv).

Accordingly, the anti-αv antibody comprises more preferably light and/or heavy chains, wherein the light chain comprises an amino acid sequence of SEQ ID NO: 219 (L-αv) and/or the heavy chain comprises an amino acid sequence of SEQ ID NO: 220 (H-αv). Most preferably, the light chain consists of an amino acid sequence of SEQ ID NO: 219 (L-αv) and/or the heavy chain consists of an amino acid sequence of SEQ ID NO: 220 (H-αv). In a highly preferred embodiment of the present invention, the light chain consists of an amino acid sequence of SEQ ID NO: 219 (L-αv) and the heavy chain consists of an amino acid sequence of SEQ ID NO: 220 (H-αv).

In another embodiment of the present invention, integrin cytoplasmic domains are used as primary immunogen. Said cytoplasmic domains are also referred to as intracellular domains. They are especially expressed as N-terminal fusion proteins. The fusion partner can be varied (e.g. GST, MBP, KLH, etc.) to allow the differential screening described below, or the primary and secondary screens can be excluded, going straight to the tertiary screen on cell line arrays. The conformation of the cytoplasmic domains is less defined than that of the extracellular domains, and it is relatively independent of the paired chain, i.e. an antibody directed against β3, e.g., will recognize β3 associated both with αvβ3 and with αiibβ3. This is effectively a reduction in specificity over antibodies directed against the DTM-αvβ3 complex, which can be screened to obtain antibodies that recognize β3 only when it is in association with αv. Similar considerations apply for antibodies generated against αvβ5. The advantage is, however, that the integrin cytoplasmic domains are entirely conserved across mammalian and hence, broad species cross reactivity can be made.

In particular, the antibody or a fragment thereof is directed against the cytoplasmic domain of the integrin β3 chain. It is an special embodiment of such an anti-β3 antibody, that suitable CDRs in V_L comprise amino acid sequences of SEQ ID NO: 41 (CDR-1-V_L-β3), SEQ ID NO: 42 (CDR-2-V_L-β3) and/or SEQ ID NO: 43 (CDR-3-V_L-β3), and/or suitable CDRs in V_H comprise amino acid sequences of SEQ ID NO: 44 (CDR-1-V_H-β3), SEQ ID NO: 45 (CDR-2-V_H-β3) and/or SEQ ID NO: 46 (CDR-3-V_H-β3). Preferably, the CDRs in V_L comprise amino acid sequences of SEQ ID NO: 41 (CDR-1-V_L-β3), SEQ ID NO: 42 (CDR-2-V_L-β3) and SEQ ID NO: 43 (CDR-3-V_L-β3), and/or the CDRs in V_H comprise amino acid sequences of SEQ ID NO: 44 (CDR-1-V_H-β3), SEQ ID NO: 45 (CDR-2-V_H-β3) and SEQ ID NO: 46 (CDR-3-V_H-β3). More preferably, the CDRs in V_L comprise amino acid sequences of SEQ ID NO: 41 (CDR-1-V_L-β3), SEQ ID NO: 42 (CDR-2-V_L-β3) and SEQ ID NO: 43 (CDR-3-V_L-β3), and the CDRs in V_H comprise amino acid sequences of SEQ ID NO: 44 (CDR-1-V_H-β3), SEQ ID NO: 45 (CDR-2-V_H-β3) and SEQ ID NO: 46 (CDR-3-V_H-β3).

Yet referring to the context of the anti-β3 antibody, suitable FRs in V_L comprise amino acid sequences of SEQ ID NO: 47 (FR-1-V_L-β3), SEQ ID NO: 48 (FR-2-V_L-β3) and/or SEQ ID NO: 49 (FR-3-V_L-β3), and/or suitable FRs in V_H comprise amino acid sequence of SEQ ID NO: 51 (FR-1-V_H-β3), SEQ ID NO: 52 (FR-2-V_H-β3), SEQ ID NO: 53 (FR-3-V_H-β3) and/or SEQ ID NO: 54 (FR-4-V_H-β3). Preferably, the FRs in V_L comprise amino acid sequences of SEQ ID NO: 47 (FR-1-V_L-β3), SEQ ID NO: 48 (FR-2-V_L-β3) and SEQ ID NO: 49 (FR-3-V_L-β3), and/or the FRs in V_H comprise amino acid sequence of SEQ ID NO: 51 (FR-1-V_H-β3), SEQ ID NO: 52 (FR-2-V_H-β3), SEQ ID NO: 53 (FR-3-V_H-β3) and SEQ ID NO: 54 (FR-4-V_H-β3). More preferably, the FRs in V_L comprise amino acid sequences of SEQ ID NO: 47 (FR-1-V_L-β3), SEQ ID NO: 48 (FR-2-V_1-β3) and SEQ ID NO: 49 (FR-3-V_L-β3), and the FRs in V_H comprise amino acid sequence of SEQ ID NO: 51 (FR-1-V_H-β3), SEQ ID NO: 52 (FR-2-V_H-β3), SEQ ID NO: 53 (FR-3-V_H-β3) and SEQ ID NO: 54 (FR-4-V_H-β3).

It is another combinatorial embodiment in the anti-β3 antibody context, in which suitable CDRs in V_L comprise amino acid sequences of SEQ ID NO: 41 (CDR-1-V_L-β3), SEQ ID NO: 42 (CDR-2-V_L-β3) and/or SEQ ID NO: 43 (CDR-3-V_L-β3), and suitable FRs in V_L comprise amino acid sequences of SEQ ID NO: 47 (FR-1-V_L-β3), SEQ ID NO: 48 (FR-2-V_L-β3) and/or SEQ ID NO: 49 (FR-3-V_L-β3). Preferably, the CDRs in V_L comprise amino acid sequences of SEQ ID NO: 41 (CDR-1-V_L-β3), SEQ ID NO: 42 (CDR-2-V_L-β3) and SEQ ID NO: 43 (CDR-3-V_L-β3), and the FRs in V_L comprise amino acid sequences of SEQ ID NO: 47 (FR-1-$V_L$-β3), SEQ ID NO: 48 (FR-2-$V_L$-β3) and SEQ ID NO: 49 (FR-3-$V_L$-β3).

It is still another combinatorial embodiment in the anti-β3 antibody context, in which suitable CDRs in $V_H$ comprise amino acid sequences of SEQ ID NO: 44 (CDR-1-$V_H$-β3), SEQ ID NO: 45 (CDR-2-$V_H$-β3) and/or SEQ ID NO: 46 (CDR-3-$V_H$-β3), and suitable FRs in $V_H$ comprise amino acid sequence of SEQ ID NO: 51 (FR-1-$V_H$-β3), SEQ ID NO: 52 (FR-2-$V_H$-β3), SEQ ID NO: 53 (FR-3-$V_H$-β3) and/or SEQ ID NO: 54 (FR-4-$V_H$-β3). Preferably, the CDRs in $V_H$ comprise amino acid sequences of SEQ ID NO: 44 (CDR-1-$V_H$-β3), SEQ ID NO: 45 (CDR-2-$V_H$-β3) and SEQ ID NO: 46 (CDR-3-$V_H$-β3), and the FRs in $V_H$ comprise amino acid sequence of SEQ ID NO: 51 (FR-1-$V_H$-β3), SEQ ID NO: 52 (FR-2-$V_H$-β3), SEQ ID NO: 53 (FR-3-$V_H$-β3) and SEQ ID NO: 54 (FR-4-$V_H$-β3).

In another preferred embodiment in the anti-β3 antibody context, $V_L$ comprises an amino acid sequence of SEQ ID NO: 55 ($V_L$-β3) and/or $V_H$ comprises an amino acid sequence of SEQ ID NO: 56 ($V_H$-β3), more preferably $V_L$ consists of an amino acid sequence of SEQ ID NO: 55 ($V_L$-β3) and/or $V_H$ consists of an amino acid sequence of SEQ ID NO: 56 ($V_H$-β3), most preferably the antibody is shaped as anti-β3 scFv.

The anti-β3 antibody can be completed by constant regions of the light ($C_L$) and/or heavy ($C_H$) chain. Preferably, $C_L$ comprises an amino acid sequence of SEQ ID NO: 57 ($C_L$-β3) and/or $C_H$ comprises an amino acid sequence of SEQ ID NO: 58 ($C_H$-β3).

Accordingly, the anti-β3 antibody comprises more preferably light and/or heavy chains, wherein the light chain comprises an amino acid sequence of SEQ ID NO: 59 (L-β3) and/or the heavy chain comprises an amino acid sequence of SEQ ID NO: 60 (H-β3). Most preferably, the light chain consists of an amino acid sequence of SEQ ID NO: 59 (L-β3) and/or the heavy chain consists of an amino acid sequence of SEQ ID NO: 60 (H-β3). In a highly preferred embodiment of the present invention, the light chain consists of an amino acid sequence of SEQ ID NO: 59 (L-β3) and the heavy chain consists of an amino acid sequence of SEQ ID NO: 60 (H-β3).

It shall be understood that the combinations of CDRs, FRs, $V_L$, $V_H$, C, L and/or H are not exhausted as detailed hereunder, but said components can be combined in any other manner. Each combination shall be regarded to read upon the scope of the present invention provided that the resulting antibody or fragment thereof recognizes an extracellular domain of integrin.

It shall also be understood that variants, mutants, parts of said amino acid sequences or homologous sequences having the same function are included in the scope of definition as well as protection. The degree of alteration between the original sequence and its derivatives is inevitably limited by the requirement of antigen recognition within the structural context, particularly in FFPE material. A couple of methods are known to the skilled artisan to generate equivalent peptides and proteins, i.e. amino acid sequences that are analogous in function to those of the inventive teaching by realizing the benefits of the invention to a large extent. Therefore, the invention also contains the alterations as listed herein. Variants of the amino acid sequences underlying the antibody of the invention can arise from modifications (e.g. alkylation, arylation or acetylation of at least a single amino acid), incorporation of enantiomers, addition of at least a single amino acid and/or fusion with another peptide or a protein. Possible mutations comprise deletion, Insertion, substitution, translocation and/or inversion. Parts of the amino acid sequences and antibodies, respectively, relate to a restriction to those regions that are sufficient for the expression of a specific function. The parts of the antibody can be very small due to the characterization of the paratope, for instance, which also binds to an antigen as to the extracellular integrin domain. In the meaning of the invention, it is to be clearly distinguished between parts of any size and homologous sequences; the homology of the latter is related to the entire sequence. Preferably, the homology between an original sequence and its derivatives having the same features amounts to at least 80%, more preferably at least 95%, most preferably at least 98%. Similarly, the homology is to be considered if the aforementioned part of any size is altered to a variant or mutant. The present teaching if solving the problem of the invention covers all peptide derivatives, which are developed on the basis of the present ingredients by such procedures.

Moreover, several techniques are described in prior art to generate non-homologous peptides with the same function. Herein, non-homologous peptides denote amino acid sequences having less homology compared to the preferred amounts of homology above. For example, it is possible to replace a single amino acid or multiple amino acids without adversely affecting the activity with respect to accomplishing the object of the present invention. For replacement of such amino acids, reference is made to appropriate standard textbooks of biochemistry and genetics. As well-known to those skilled in the art, some amino acids have analogous physicochemical properties and hence, these amino acids can be advantageously replaced by each other. These include the amino acid groups (a) glycine, alanine, valine, leucine and isoleucine, (b) serine and threonine, (c) asparagine and glutamine, (d) aspartic acid and glutamic acid, (e) lysine and arginine, and (f) phenylalanine, tyrosine and tryptophan. Amino acids within one and the same group (a) to (f) can be replaced among one another. Further alterations are possible in accordance with the teaching of Schneider et al., PNAS 1998, 95: 12179-12184; WO 1999/62933 and/or WO 2002/38592, describing one way of generating functionally analogous amino acid sequences. The references are hereby incorporated in the disclosure of the invention. All amino acid sequences, sequence parts or structures comprising sequences, which are designed by using the cited methods and starting from any amino acid sequence of the invention, are considered as sequences in the meaning of the invention, and they shall be included in the teaching according to the invention, provided they accomplish the object of the invention.

Object of the invention is also a polynucleotide encoding the antibody according to the invention, or a fragment thereof. The term "polynucleotide" refers to a natural or synthetic polymer of single or double-stranded DNA or RNA alternatively including synthetic, non-natural or modified nucleotides, which can be incorporated in DNA or RNA polymers. Each nucleotide consists of a sugar moiety, a phosphate moiety, and either a purine or pyrimidine residue. The nucleic acids can be optionally modified as phosphorothioate DNA, locked nucleic acid (LNA), peptide nucleic acid (PNA) or spiegelmer. The term "polynucleotide encoding" refers to that part of a gene which enciphers a protein, a polypeptide or a part thereof. The regulatory sequences and/or elements controlling the initiation or termination of transcription are excluded. The coding sequence and/or the regulatory element can normally be found in cells, in which case it is referred to as autologous one or endogenic one, or it cannot be located in cells, in which case it is referred to as heterologous one. The term "gene" denotes a DNA sequence encoding a specific protein and regulatory elements controlling the expression of said DNA sequence. A heterologous gene may also be composed of autologous elements arranged in an order and/or orientation, which is normally not found in that cell, the gene is transferred into. A heterologous gene can be derived completely or partially from any source known in the art, including a bacterial or viral genome or episome, eukaryotic nuclear or plasmid DNA, cDNA, or chemically synthesized DNA. The structural gene may form a continuous coding region, or it may comprise one or more introns bordered by suitable splice junctions. The structural gene can consist of segments derived from various naturally occurring or synthetic sources.

In a preferred embodiment of the present invention, the polynucleotide encoding the antibodies of the invention comprises one or more nucleic acid sequences selected from the group of SEQ ID NOs: 21 to 29 and 31 to 40, SEQ ID NOs: 61 to 69 and 71 to 80, SEQ ID NOs: 101 to 109 and 111 to 120, SEQ ID NOs: 141 to 149 and 151 to 160, SEQ ID NOs: 181 to 189 and 191 to 200, and SEQ ID NOs: 221 to 229 and 231 to 240. The prior teaching of the present specification concerning the antibody and specific amino acid sequences thereof is considered as valid and applicable without restrictions to the polynucleotide and specific nucleic acid sequences if expedient.

Another object of the invention concerns a vector comprising the antibody-encoding polynucleotide according to the invention as described above. The term "vector" denotes a recombinant DNA construct which can be a plasmid, a virus, an autonomously replicating sequence, a phage, or a nucleotide sequence, which is linear or circular, consisting of single or double-stranded DNA or RNA, wherein a number of nucleotide sequences are inked or recombined to form a unique construction, and which is capable of introducing a promoter fragment and a DNA sequence of a selected gene product in sense or antisense orientation into a cell, together with suitable non-translated 3' sequences.

It is preferred that a plasmid comprises the antibody-encoding polynucleotide of the invention, particularly to clone and express recombinant genes of the inventive antibody or a fragment thereof. In the meaning of the invention, plasmids are genetic elements which are stable inherited without being part of the chromosome of their host cell. They may comprise DNA or RNA, and they can be both linear and circular. Plasmids encode molecules ensuring their replication and stable inheritance during cell replication. The starting plasmids disclosed in the present specification are either commercially available, accessible to the public, or can be constructed from available plasmids by routine use of well-known, published methods. Many plasmids and other cloning and expression vectors, which can be used according to the invention, are well-known and easily available to the skilled artisan. Furthermore, a person skilled in the art can easily construct any number of other plasmids suitable for the use in this invention.

The vector shall be suitable for introduction into host cells. Accordingly, a host cell comprising the vector with the antibody-encoding polynucleotide is still another object of the invention. The present invention preferably relates to isolated prokaryotic or eukaryotic cells, but it shall also cover cell cultures, tissues, organs, and the like, and even organisms, which comprise the host cell of the invention, including an above-described vector. The term "host cell" denotes a cell that has been genetically modified by the transfer of a chimeric, heterologous or autologous nucleic acid sequence or derivatives thereof still including said sequence. These cells are also referred to as transgenic cells. Where an autologous nucleic acid sequence is transferred, the number of copies of this sequence in the host cell is higher than that of the naturally occurring sequences.

The invention also relates to a recombinant immunogen consisting of an extracellular integrin domain with insect-derived glycosylation pattern. The extracellular domain is preferably coupled as delta-trans membrane (DTM) form. Said immunogen of the invention is able to provoke an adaptive immune response if injected on its own in a mammalian species of choice, including rabbit. More preferably, the immunogen of the invention has an amino acid sequence of SEQ ID NOs: 10, 90, 130, 170 or 210, or variants, mutants, parts of the amino acid sequence or at least 95% homologous sequences having the same function. Object of the invention is also a polynucleotide encoding said immunogens of the invention. In a preferred embodiment, the immunogen-encoding polynucleotide has a nucleotide sequence of SEQ ID NOs: 30, 110, 150, 190 or 230, or variants, mutants, parts of the amino acid sequence or at least 95% homologous sequences having the same function. Another object of the invention concerns a vector comprising the immunogen-encoding polynucleotide according to the invention. Still another object is a host cell comprising the vector with the immunogen-encoding polynucleotide according to the invention. It shall be understood that the host species is included in the present scope of protection according to the present invention. The prior teaching of the present specification concerning the antibodies, or variants, mutants, parts of sequences or homologous sequences thereof, antibody-encoding polynucleotides, or vectors, host cells and the like, is valid and applicable without restrictions to the immunogen for raising said or other antibodies, if appropriate.

The invention also relates to a method for preparing rabbit antibodies comprising the steps of: (a) recombinantly expressing an extracellular integrin domain or a fragment thereof in insect cells; (b) purifying the expressed extracellular domain; (c) immunizing a rabbit with the purified extracellular domain; (d) taking polyclonal antiserum comprising polyclonal antibodies from the rabbit; and optionally (e) preparing monoclonal antibodies.

Preferably, the method for preparing monoclonal antibodies comprises the following steps: (a) recombinantly expressing an extracellular integrin domain in insect cells; (b) purifying the expressed extracellular integrin domain; (c) immunizing a rabbit with the purified extracellular integrin domain; (d) taking polyclonal antiserum comprising polyclonal antibodies from the rabbit; and (e) preparing the monoclonal antibodies. More preferably, the method refers to the preparation of said monoclonal antibodies of the invention as described in detail above.

The protein expression of step (a) is a matter of routine for the skilled artisan who has access to several appropriate insect cells, insect cell lines and ways for transfecting them. For example, the BTI-Tn5B1-4 (High Five) insect cell line infected with a recombinant baculovirus has gained widespread use within baculovirus/insect cell expression system because many secreted recombinant proteins are produced at considerably higher rates than in *Spodoptera frugiperda* derived cell lines, such as Sf9. To optimize the yield of the extracellular integrin domain from the baculovirus/insect cell expression system, experiments can be easily performed with suspension adapted cultures of High Five cells to investigate the effects of the state of the host cell, multiplicity of infection, cell density at the time of infection and supplementation of the medium with nutrients and oxygen. Such procedures are state of the art and published, e.g. by Vallazza & Petri, Cytotechnology 1999, 29: 85-92, or Mehta et al., Biochem J 1998, 330: 861-869.

The prior teaching concerning antibody or immunogen alterations is considered to be valid and applicable without restrictions to altered immunogens of step (a) if expedient. As obvious to the skilled artisan, the present invention shall not be construed to be limited to the full-length extracellular domains of integrin. Physiological or artificial fragments of the extracellular domains, secondary modifications of the extracellular domains, species-dependent alterations as well as allelic variants of the extracellular domains are also encompassed by the present invention. In this regard, an "allelic variant" is understood to represent the gene product of one of two or more different forms of a gene or DNA sequence that can exist at a genetic single locus. Artificial fragments preferably encompass a peptide produced synthetically or by recombinant techniques, which at least comprises the epitopes of diagnostic interest.

If expressed in insect cells according to step (e), the extracellular integrin domain has a defective abherant glycosylation pattern that differs from the glycosylation pattern on mature mammalian cells. As the integrins are extensively glycosylated, i.e. more than 10% by mass, this means that the insect protein is more divergent from rabbit native integrins produced in mammalian systems. The insect-derived immunogen leads to a greatly enhanced immunogenicity and stronger antibody response to the protein elements of said immunogen.

The protein purification, mammal immunization and serum extraction of steps (b) to (d) follow well known techniques and good laboratory practice, such as described in the course of the specification and examples. Sera of step (d) are subsequently tested for the presence of polyclonals, and the detected antibodies are screened for antigen recognition. Suitable tests and screens are available to those skilled in the art.

Optionally, the antibody preparation is continued to the species of mono-specific, identical antibodies, i.e. monoclonals of step (e). Monoclonal antibodies are typically made by fusing myeloma cells with the spleen cells from the mammal that has been immunized according to step (c). A selective HAT medium containing hypoxanthine, aminopterin and thymidine is particularly used in which only fused cells can grown. The so-called hybridomas are then diluted and clones are grown from single parent cells on microtiter wells. The antibodies secreted by the different clones are tested for their ability to bind to the antigen of the extracellular integrin domain. Accordingly, the antibodies of the invention are especially prepared by the method hereunder.

It goes without saying that antibodies may be similarly prepared by said method of the invention by using an intracellular integrin domain. The method shall apply mutatis mutandis.

Object of the invention are also the antibodies obtained by immunization of a rabbit with an extracellular or cytoplasmic domain of integrin recombinantly expressed in insect cells. As the immunogen of the invention can be used for raising antibodies, the invention particularly relates to monoclonal antibodies obtained by immunizing a rabbit with the immunogen and/or polynucleotide, each according to the invention, taking polyclonal antiserum with polyclonal antibodies and preparing the monoclonal antibodies. The prior teaching of the present specification concerning the immunogen and the method for preparing rabbit antibodies shall be considered as valid and applicable without restrictions to the antibody product as produced by this process, as appropriate.

Although the most productive and stable clone can be grown in culture medium to a high volume, the monoclonal of choice is preferably expressed in a recombinant fashion. It requires cDNA cloning of the antibody encoding inserts, sequencing and inserting in expression vectors to allow production of wholly defined antibodies. Subsequently, the invention also relates to a method for manufacturing a recombinant monoclonal antibody or a fragment thereof comprising the steps of (a) introducing vector(s), which comprises nucleic acid sequence(s) of SEQ ID NOs: 21 to 29 and 31 to 40, SEQ ID NOs: 61 to 69 and 71 to 80, SEQ ID NOs: 101 to 109 and 111 to 120, SEQ ID NOs: 141 to 149 and 151 to 160, SEQ ID NOs: 181 to 189 and 191 to 200, and/or SEQ ID NOs: 221 to 229 and 231 to 240 into a host cell, (b) cultivating the host cell in a culture medium, thereby expressing the encoded antibody or fragment thereof, and (c) purifying the expressed antibody or fragment thereof.

The vector can be introduced by any method of the art, such as transformation, transfection or transduction. It shall be understood that prokaryotic cells, including bacteria and archaea, are particularly transformed, such as *Escherichia* species or *Bacillus* species, whereas eukaryotic cells are particularly transfected, such as CHO, HeLa, and the like. The three domain systems can also be transducted by viral vehicles. The vector can comprise either one or more nucleic acid sequences encoding the monoclonal antibody or a fragment thereof.

In still another preferred embodiment of step (a), the vector(s) to be introduced comprise(s) the nucleic acid sequences of SEQ ID NO: 115 ($V_L$-αvβ3) and/or SEQ ID NO: 116 ($V_H$-αvβ3). In a more preferred embodiment of step (a), the vector(s) to be introduced comprise(s) the nucleic acid sequences of SEQ ID NO: 119 (L-αvβ3) and/or SEQ ID NO: 120 (H-αvβ3).

In a preferred embodiment of step (a), the vector(s) to be introduced comprise(s) the nucleic acid sequences of SEQ ID NO: 35 ($V_L$-αvβ5) and/or SEQ ID NO: 36 ($V_H$-αvβ5). In a more preferred embodiment of step (a), the vector(s) to be introduced comprise(s) the nucleic acid sequences of SEQ ID NO: 39 (L-αvβ5) and/or SEQ ID NO: 40 (H-αvβ5).

In a preferred embodiment of step (a), the vector(s) to be introduced comprise(s) the nucleic acid sequences of SEQ ID NO: 155 ($V_L$-αvβ6) and/or SEQ ID NO: 156 ($V_H$-αvβ6). In a more preferred embodiment of step (a), the vector(s) to be introduced comprise(s) the nucleic acid sequences of SEQ ID NO: 159 (L-αvβ6) and/or SEQ ID NO: 160 (H-αvβ6).

In a preferred embodiment of step (a), the vector(s) to be introduced comprise(s) the nucleic acid sequences of SEQ ID NO: 195 ($V_L$-αvβ8) and/or SEQ ID NO: 196 ($V_H$-αvβ8). In a more preferred embodiment of step (a), the vector(s) to be introduced comprise(s) the nucleic acid sequences of SEQ ID NO: 199 (L-αvβ8) and/or SEQ ID NO: 200 (H-αvβ8).

In a preferred embodiment of step (a), the vector(s) to be introduced comprise(s) the nucleic acid sequences of SEQ ID NO: 235 ($V_L$-αv) and/or SEQ ID NO: 236 ($V_H$-αv). In a more preferred embodiment of step (a), the vector(s) to be introduced comprise(s) the nucleic acid sequences of SEQ ID NO: 239 (L-αv) and/or SEQ ID NO: 240 (H-αv).

In another preferred embodiment of step (a), the vector(s) to be introduced comprise(s) the nucleic acid sequences of SEQ ID NO: 75 ($V_L$-β3) and/or SEQ ID NO: 76 ($V_H$-β3). In a more preferred embodiment of step (a), the vector(s) to be introduced comprise(s) the nucleic acid sequences of SEQ ID NO: 79 (L-133) and/or SEQ ID NO: 80 (H-β3).

In a preferred aspect that the invention relates a method for manufacturing a recombinant monoclonal antibody comprising a light chain variable region ($V_L$) and a heavy chain variable region ($V_H$) with the steps of: (a) Introducing one or more vectors comprising nucleic acid sequences of (i) SEQ ID NO: 115 ($V_L$-αvβ3) and SEQ ID NO: 116 ($V_H$-αvβ3), (ii) SEQ ID NO: 35 ($V_L$-αvβ5) and SEQ ID NO: 36 ($V_H$-αvβ5), (iii) SEQ ID NO: 155 ($V_L$-αvβ6) and SEQ ID NO: 156

($V_H$-αvβ6), (iv) SEQ ID NO: 195 ($V_L$-αvβ8) and SEQ ID NO: 196 ($V_H$-αvβ8), or (v) SEQ ID NO: 235 ($V_L$-αv) and SEQ ID NO: 236 ($V_H$-αv) into a host cell, (b) cultivating the host cell in a culture medium, thereby expressing the encoded antibody, and (c) purifying the expressed antibody. It shall be understood that several vectors are favorably different by bearing only a single sequence of said SEQ ID NOs above. It is preferred in step (a) to introduce two vectors, each of them bearing one sequence of said SEQ ID NOs above.

Moreover, the prior teaching of the present specification concerning the antibody, amino acid sequences and alterations thereof, polynucleotides encoding the same as well as the preparation of rabbit antibodies is considered as valid and applicable without restrictions to the manufacture of recombinant monoclonals if expedient.

It is still another object to use the antibody of the invention, or a fragment thereof, for the detection of integrins in formalin fixed paraffin embedded (FFPE) material. To date, there are no classical monoclonal antibodies directed to integrins and specifically and reliably reacting with the complexes in FFPE material. Only the antibodies of the invention, particularly rabbit monoclonals, have such a high affinity and specificity, which allows the detection of non-occluded epitopes of integrins. The terms "non-occluded" and "exposed", which are interchangeably used herein, are taken to mean the molecular confirmation of an antigen in which the epitopes can be recognized by an antibody. Hence, the same staining pattern is observed if comparing the antibodies of the invention on FFPE material with murine monoclonals on frozen material. Moreover the substantially same staining pattern is observed if comparing the antibodies of the invention on FFPE material and isolated integrin forms in ELISA and/or the native integrin state on viable cells, preferably if comparing the antibodies of the invention on FFPE material and on viable cells.

In a preferred embodiment of the invention, the FFPE material is a tissue. FFPE tissue is a piece of tissue which is first separated from a specimen animal by dissection or biopsy. Then, this tissue is fixed in order to prevent it from decaying or degeneration and to examine it clearly under a microscope for histological, pathological or cytological studies. Fixation is the process by which the tissue is immobilized, killed and preserved for the purpose of staining and viewing it under a microscope. Post-fixation processing makes tissue permeable to staining reagents and cross-links its macromolecules so that they are stabilized and locked in position. Many fixatives are used for this purpose for example, Bouine solution, formalin or liquid nitrogen. This fixed tissue is then embedded in the wax to allow it to be cut into thin sections and be stained with hematoxylin and eosin stain. After that, microtoming is done by cutting fine sections to study stain with antibodies under microscope.

In a more preferred embodiment of the invention, the FFPE tissue is a tumor tissue, most preferably human tumor tissue. The tumor is particularly selected from the group of tumors of the squamous epithelium, bladder, stomach, kidneys, head, neck, oesophagus, cervix, thyroid, intestine, liver, brain, prostate, urogenital tract, lymphatic system, stomach, larynx and/or lung. The tumor is furthermore particularly selected from the group of lung adenocarcinoma, small-cell lung carcinomas, pancreatic cancer, glioblastomas, colon carcinoma and breast carcinoma. In addition, preference is given to a tumor of the blood and immune system, more particularly for a tumor selected from the group of acute myeloid leukemia, chronic myeloid leukemia, acute lymphatic leukemia and/or chronic lymphatic leukemia. Such tumors can also be designated as cancers in the meaning of the invention.

The antibody of the invention is incubated with the FFPE material for integrin detection. The term "incubation" denotes the contacting of the FFPE material with the antibody of the invention for a distinct period, which depends on the kind of material, antibody and/or antigen. The incubation process also depends on various other parameters, e.g. the sensitivity of detection, which optimization follows routine procedures known to those skilled in the art. Adding chemical solutions and/or applying physical procedures, e.g. impact of heat, can improve the accessibility of the target structures in the sample. Specific incubation products are formed as result of the incubation.

Suitable tests for the detection of formed antibody/antigen complexes are known to those skilled in the art or can be easily designed as a matter of routine. Many different types of assays are known, examples of which are set forth below. Although the assay according to the invention may be any assay suitable to detect and/or quantify integrin expression, the latter is preferably determined by means of substances specifically interacting with the primary antibody of the invention.

The term "specific substances" as used herein comprises molecules with high affinity to the anti-integrin antibody of the invention in order to ensure a reliable binding. The substances are preferably specific to parts of the antibody, e.g. constant regions, particularly rabbit constant regions, more particularly an $F_c$ fragment, if any. There are a distinct number of specific antibodies against rabbit antibodies existing. Parts represent a restriction to those regions which are sufficient for the expression of a specific function, i.e. the provision of a structural determinant for recognition. In the context of the present invention, the term "recognition"—without being limited thereto—relates to any type of interaction between the specific substances and the target antibody, particularly covalent or non-covalent binding or association, such as a covalent bond, hydrophobic/hydrophilic interactions, van der Waals forces, ion pairs, hydrogen bonds, ligand-receptor interactions, interactions between epitope and antibody binding site, nucleotide base pairing, and the like. Such association may also encompass the presence of other molecules such as peptides, proteins or other nucleotide sequences.

The specific substances are composed of biological and/or chemical structures capable to interact with the target molecule in such a manner that makes a recognition, binding and interaction possible. In particular, the substances are selected from the group of proteins, peptides, nucleic acids, carbohydrates, polymers and small molecules having a molecular weight between 50 and 1.000 Da, preferably proteins and nucleic acids. The specific substances express a sufficient sensitivity and specificity in order to ensure a reliable detection. A specific substance has at least an affinity of $10^{-7}$ M for the anti-Integrin antibody. The specific substance has preferably an affinity of $10^{-8}$ M or even more preferred of $10^{-9}$ M for its target molecule. As the skilled artisan will appreciate, the term specific is used to indicate that other biomolecules present in the sample do not significantly bind to the substance specific for anti-integrin antibody. Preferably, the level of binding to a biomolecule other than the target molecule results in a binding affinity of only 10% of the affinity of the target molecule, more preferably only 5% or less. Most preferably, the substances are mono-specific in order to guarantee an exclusive and directed interaction with the chosen primary anti-integrin antibody of the invention. A highly preferred specific substance will fulfill both the above minimum criteria for affinity as well as for specificity.

The proteins or peptides are preferably selected from the group consisting of antibodies, cytokines, lipocalins, receptors, lectins, avidins, lipoproteins, glycoproteins, oligopeptides, peptide ligands and peptide hormones. More preferably, antibodies are used as specific substance. The nucleic acids are preferably single or double stranded DNA or RNA, primers, antisense oligonucleotides, ribozymes, DNA enzymes, aptamers and/or siRNA, or parts thereof. More preferred nucleic acid probes are aptamers, most preferably RNA aptamers since the 2'-hydroxyl group available in RNA promotes a couple of intra- and intermolecular contacts. Aptamers can be synthesized using standard phosphoramidite chemistry. In addition, RNA aptamers having more than approximately 30 nucleotides can be favorably synthesized in large amounts by in-vitro transcription. Selection, synthesis, and purification of aptamers are well-known to those skilled in the art.

The specific substances can be labeled; in doing so the labeling depends on the inherent features of specific substances and specific incubation products to be monitored, as well as the detection method to be applied, i.e. the required sensitivity, ease of conjugation, stability requirements, and available instrumentation and disposal provisions. A labeling method is not particularly limited as long as a label is easily detected. A "labeled specific substance" is one that is bound, either covalently through a linker or a chemical bond, or non-covalently through ionic, van der Waals, electrostatic, hydrophobic interactions or hydrogen bonds, to a label such that the presence of the anti-integrin antibody of the invention may be detected by detecting the presence of the label.

Specific immunological binding of an antibody to a protein can be detected directly or indirectly. Hereunder, the antibody-to-protein pair shall be understood to include either the primary antibody of the invention directed to integrin or a secondary antibody directed to the primary anti-integrin antibody. Preferred examples of suitable detection methods according to the present invention are luminescence, particularly fluorescence, furthermore VIS coloring and/or radioactive emission.

Luminescence concerns the emission of light as a result of chemiluminescence, bioluminescence or photoluminescence. Chemiluminescence involves the emission of visible light as a result of a chemical reaction, whereas bioluminescence requires the activity of luciferase. The presently preferred photoluminescence, which is also known as fluorescence stimulation, is caused by the absorption of photons, preferably provided by radiation, which is released again as photon with a shift in wavelength of 30 to 50 nm and within a period of approximately $10^{-8}$ seconds. The instruments for fluorescence detection include, but are not limited to typical benchtop fluorometers, fluorescence multi-well plate readers, fiber optic fluorometers, fluorescence microscopes and microchips/microfluidics systems coupled with fluorescence detection.

VIS coloring denotes the visualization of any achromatic substance in order to be visible to the naked eye. Preferably, the intensity of coloring is measured by a photometer.

Radioactive radiation of isotopes is measured by scintillation. The process of liquid scintillation involves the detection of beta decay within a sample via capture of beta emissions in a system of organic solvents and solutes referred to as the scintillation cocktail. The beta decay electron emitted by radioactive isotopes such as $^3H$, $^{14}C$, $^{32}P$, $^{33}P$ and $^{35}S$ in the sample excites the solvent molecule, which in turn transfers the energy to the solute. The energy emission of the solute (the light photon) is converted into an electrical signal by a photo-multiplier tube within a scintillation counter. The cocktail must also act as a solubilizing agent keeping a uniform suspension of the sample. Gamma ray photons often arise as a result of other decay processes (series decay) to rid the newly formed nucleus of excess energy. They have no mass and produce little if any direct ionization by collision along their path. Gamma photons are absorbed for detection and quantization by one or more of three mechanisms: the Compton effect, the photoelectric effect and pair production. A favorable gamma decay isotope of the present invention is $^{125}I$.

Direct labels include fluorescent or luminescent tags, metals, dyes, radionuclides, and the like, attached to the antibody. An antibody labeled with iodine-125 ($^{125}I$) can be used. A chemiluminescence assay using a chemiluminescent antibody specific for the protein is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine.

Indirect labels include various enzymes well known in the art, such as horseradish peroxidase (HRP), alkaline phosphatase (AP), β-galactosidase, urease and the like. The covalent linkage of an anti-integrin antibody to an enzyme may be performed by different methods, such as the coupling with glutaraldehyde. Both, the enzyme and the antibody are interlinked with glutaraldehyde via free amino groups, and the by-products of networked enzymes and antibodies are removed. In another method, the enzyme is coupled to the antibody via sugar residues if it is a glycoprotein, such as peroxidase. The enzyme is oxidized by sodium periodate and directly interlinked with amino groups of the antibody. Other enzyme containing carbohydrates can also be coupled to the antibody in this manner. Enzyme coupling may also be performed by interlinking the amino groups of the antibody with free thiol groups of an enzyme, such as β-galactosidase, using a heterobifunctional linker, such as succinimidyl 6-(N-maleimido) hexanoate. The horseradish-peroxidase detection system can be used, for example, with the chromogenic substrate tetramethylbenzidine (TMB), which yields a soluble product in the presence of hydrogen peroxide that is detectable at 450 nm. The alkaline phosphatase detection system can be used with the chromogenic substrate p-nitrophenyl phosphate, for example, which yields a soluble product readily detectable at 405 nm. Similarly, the β-galactosidase detection system can be used with the chromogenic substrate o-nitrophenyl-β-D-galactopyranoxide (ONPG), which yields a soluble product detectable at 410 nm. A urease detection system can be used with a substrate, such as urea-bromocresol purple.

In a preferred embodiment of the present invention, the antibodies are labeled with detectable moieties, which include, but are not limited to, radionuclides, fluorescent dyes, e.g. fluorescein, fluorescein isothiocyanate (FITC), Oregon Green™, rhodamine, Texas red, tetrarhodimine isothiocynate (TRITC), Cy3, Cy5, etc., fluorescent markers, e.g. green fluorescent protein (GFP), phycoerythrin, etc., auto-quenched fluorescent compounds that are activated by tumor-associated proteases, enzymes, e.g. luciferase, HRP, AP, etc., nanoparticles, biotin, digoxigenin, and the like.

In another preferred embodiment of the present invention, the nucleic acids are labeled with digoxigenin, biotin, chemiluminescence substances, fluorescence dyes, magnetic beads, metallic beads, colloidal particles, electron-dense reagents, enzymes; all of them are well-known in the art, or radioactive isotopes. Preferred isotopes for labeling nucleic acids in the scope of the invention are $^3H$, $^{14}C$, $^{32}P$, $^{33}P$, $^{35}S$ or $^{125}I$, more preferred $^{32}P$, $^{33}P$ or $^{125}I$.

A variety of immunoassay techniques, including competitive and non-competitive immunoassays, can be used. The term "immunoassay" encompasses techniques including, without limitation, flow cytometry, FACS, enzyme immunoassays (EIA), such as enzyme multiplied immunoassay technique (EMIT), enzyme-linked immunosorbent assay (ELISA), IgM antibody capture ELISA (MAC ELISA) and microparticle enzyme immunoassay (MEIA), furthermore capillary electrophoresis immunoassays (CEIA), radio-immunoassays (RIA), immunoradiometric assays (IRMA), fluorescence polarization immunoassays (FPIA) and chemiluminescence assays (CL). If desired, such immunoassays can be automated. Immunoassays can also be used in conjunction with laser induced fluorescence. Liposome immunoassays, such as flow-injection liposome immunoassays and liposome immunosensors, are also suitable for use in the present invention. In addition, nephelometry assays, in which the formation of protein/antibody complexes results in increased light scatter that is converted to a peak rate signal as a function of the marker concentration, are suitable for use in the methods of the present invention. In a preferred embodiment of the present invention, the incubation products are detected by ELISA, RIA, fluoro immunoassay (FIA) or soluble particle immune assay (SPIA).

Component of ELISAs are enzymes which are bound to one partner of the immunological reaction. The tracer antigen (analyte derivative) of integrin is preferably labeled in the competitive ELISA using a single capture antibody (herein after referred to as primary), whereas the antibody is preferably labeled in the non-competitive ELISA, preferably comprising the precipitation of the antigen-antibody complex by a second antibody (herein after referred to as secondary). Complexes consisting of antigen and two antibodies are also called sandwich complexes. The detection comprises the subsequent enzymatic conversion of a substrate to a product, preferably a colored product, which is recognized by visual coloring, bioluminescence, fluorescence or the measurement of electrical signals (enzyme electrode). Favorable enzymes for labeling in the present invention are known to the skilled artisan, such as peroxidase (e.g. HRP), chloramphenicol acetyl transferase (CAT), green fluorescent protein (GFP), glutathione S-transferase (GST), luciferase, β-galactosidase and AP.

Additionally preferred are radioactive immunoassays utilizing radioactive isotopes which are either incorporated into an immune reagent during synthesis or subsequently coupled to an immune reagent of the assay, preferably to an antibody.

Antibodies, which are favorably labeled with fluorophores, are used in FIAs.

SPIA utilizes the color change of silver particle as result of agglutination. Neither a secondary antibody nor an indicator reaction are required making it particularly useful in the scope of the present invention. Similarly favorably is the latex agglutination test using antibodies which are bound to colored latex particles. However, it requires a strong immobilization of integrin to remove unbound and/or non-specifically bound antigens in previous washing steps.

In general, all methods for detection include intensive washing steps to separate unbound antibodies from the integrin/antibody complex. Furthermore, the experimental procedure of any detection method is well-known to those skilled in the art.

A signal from the direct or indirect label can be analyzed, for example, using a spectrophotometer to detect color from a chromogenic substrate, using a radiation counter to detect radiation, such as a gamma counter for detection of $^{125}$I, or using a fluorometer to detect fluorescence in the presence of light of a certain wavelength. For detection of enzyme-linked antibodies, a quantitative analysis can be made using a spectrophotometer, such as an EMAX Microplate Reader (Molecular Devices; Menlo Park, Calif.) in accordance with the manufacturer's instructions. If desired, the assays of the present Invention can be automated or performed robotically, and the signal from multiple samples can be detected simultaneously.

Optical images viewed and optionally recorded by a camera or other recording device (e.g. a photodiode and data storage device) are optionally further processed in any of the embodiments herein, e.g. by digitizing the image and storing and analyzing the image on a computer. A variety of commercially available peripheral equipment and software is available for digitizing, storing and analyzing a digitized video or digitized optical image. One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g. by fluorescent or dark field microscopic techniques.

In a preferred embodiment of the invention, the rabbit hybridoma clones consisting of the amino acid sequences of SEQ ID NO: 99 (L-αvβ3) and SEQ ID NO: 100 (H-αvβ3), which are generated against DTM-αvβ3 of SEQ ID NO: 90, produce antibodies suitable for FFPE tissue. They bind αvβ3 selectively. In another preferred embodiment of the present invention, the rabbit hybridoma clones consisting of the amino acid sequences of SEQ ID NO: 19 (L-αvβ5) and SEQ ID NO: 20 (H-αvβ5), which are generated against DTM-αvβ5 of SEQ ID NO: 10, produce antibodies suitable for FFPE tissue. They bind αvβ5 selectively. In still another preferred embodiment of the present invention, the rabbit hybridoma clones consisting of the amino acid sequences of SEQ ID NO: 139 (L-αvβ6) and SEQ ID NO: 140 (H-αvβ6), which are generated against DTM-αvβ6 of SEQ ID NO: 130, produce antibodies suitable for FFPE tissue. They bind αvβ6 selectively. In still another preferred embodiment of the present invention, the rabbit hybridoma clones consisting of the amino acid sequences of SEQ ID NO: 179 (L-αvβ8) and SEQ ID NO: 180 (H-αvβ8), which are generated against DTM-αvβ8 of SEQ ID NO: 170, produce antibodies suitable for FFPE tissue. They bind αvβ8 selectively. In still another preferred embodiment of the present invention, the rabbit hybridoma clones consisting of the amino acid sequences of SEQ ID NO: 219 (L-αv) and SEQ ID NO: 220 (H-αv), which are generated against DTM-αv of SEQ ID NO: 210, produce antibodies suitable for FFPE tissue. They bind αv selectively. In still another preferred embodiment of the invention, the rabbit hybridoma clones consisting of the amino acid sequences of SEQ ID NO: 59 (L-β3) and SEQ ID NO: 60 (H-β3), which are generated against the β3 immunogen of SEQ ID NO: 50, produce antibodies suitable for FFPE tissue. They bind β3 selectively. It shall be understood, however, that any alternative sequence or combinations thereof as described in the present specification may be applied for the inventive use. The prior teaching of the present specification concerning the antibodies and amino sequences thereof is considered as valid and applicable without restrictions to the use if expedient.

Further, the invention may be practiced as a kit comprising the antibody, polynucleotide, vector or host cell, each of them according to the present invention, in order to perform the inventive use of detecting integrins in FFPE material. Particularly, the antibodies can be incorporated into a diagnostic detection kit for characterizing the integrin profile, e.g. the av integrin or other integrin expression profiles of tumors or other human pathologies, and especially in archival FFPE material. The kit of the invention may include an article that comprises written instructions or directs the user to written instructions for how to practice the method of the invention. In an embodiment, the kit further comprises a reporter moiety or a reporter apparatus. The prior teaching of the present specification concerning the kit Ingredients and the use thereof is considered as valid and applicable without restrictions to the kit if expedient.

The present invention solves the second problem by teaching a method for screening anti-integrin antibodies, which are capable of discriminating between the respective closest homologues of integrin α-subunit and/or β-subunit and suitable for immunohistochemistry in FFPE material, comprising the steps of: (a) providing a sample of antibodies being capable of binding a selected integrin; (b) aligning integrin sequences to identify the closest homologue of the α-subunit and/or β-subunit of the selected integrin; (c) performing an differential ELISA on native forms of the selected integrin and the closest homologue(s) thereof with the antibody sample, thereby accumulating antibodies against the selected integrin (primary screen); (d) performing another differential ELISA on native forms of the selected integrin and another integrin with the accumulated antibodies of step c), thereby further accumulating antibodies against the selected integrin (secondary screen); (e) performing immunohistochemistry of FFPE cell lines with the accumulated antibodies of step d), wherein at least one cell line is capable of expressing the selected integrin and optionally another cell line is not capable of expressing the selected integrin, thereby further accumulating antibodies against the selected integrin (tertiary screen); (f) performing immunohistochemistry of FFPE cell lines of step e) with the accumulated antibodies of step e), wherein the cell line is grown as xenograft tumor in a mammal, thereby further accumulating antibodies against the selected integrin (quaternary screen); and (g) performing immunohistochemistry of archival FFPE tumors with the accumulated antibodies of step f), thereby further accumulating antibodies against the selected integrin (quinternary screen).

Primary screening is performed by differential ELISA on native, biologically active, un-denatured forms of the immunogens (Mehta et al., 1998, Biochem J 330: 861-869). If the target immunogen is αvβ3, for example, the primary screen is αvβ3 versus αvβ5. That means the primary screen uses a counter-screen on integrin with the closest sequence homology to the primary target. Closest homologue to the β3 chain is β5, while αv is identical in both complexes. In this way the most discriminatory antibodies can be obtained. Similarly, αvβ5 can be screened versus αvβ8. Screens for alpha-chain specific antibodies can follow the same procedure, i.e. αvβ1 could be used as counter screen for a α5β1 specific antibody. The secondary screen looks at a wider set of recombinant integrins in ELISA to confirm further the specificity, e.g. αiibβ3 can be used to confirm specificity for αv complexes rather than β3-chain alone of αvβ3 antibodies, preferably αvβ3 monoclonals. It is preferred in step (d) that the differential screen is performed on native forms of the selected integrin and another closely related integrin with the accumulated antibodies of step (c). The tertiary screen looks at antibody staining in IHC of FFPE cell lines that are biochemically characterized for their integrin expression profiles. The quaternary screen uses FFPE-IHC on the same cell lines grown as xenograft tumors in nude mice. The quintenary screen looks at archival FFPE human tumors. For example, tertiary and quaternary screens are on M21, U87MG and M24 melanomas as positive screen targets. All these lines are known from in house and literature profiling to express αvβ3, while A549 NSCLC, Raji and HT29 are negative screen targets. All these lines are known from in house and literature profiling to not express αvβ3. The quintenary screens are preferably on malignant melanoma and glioblastoma as αvβ3 positive, and NSCLC and CRC as αvβ3 negative human tumors.

In an embodiment of the screening method, any of steps (c) to (g) comprises the further step of detecting the discriminatory capacity and/or specificity of the accumulated antibodies.

In the scope of the present invention, antibodies have been provided for the first time, which allow the validated detection of integrins in FFPE archival patient material, such as tumor biopsies, and also by live cell flow cytometry (FACS). The staining patterns in FACS correspond to the patterns obtained with the relevant monoclonal antibodies know to those skilled in the art (e.g. LM609 for αvβ3; P1F6 for αvβ5). It shows that the antibodies of the invention detect the respective integrins not only in FFPE material, but also in their native state on viable cells. Integrins, particularly αvβ3, αvβ5, αvβ6 or αvβ8 are primary therapeutic targets that could not be reliably visualized in routine FFPE biopsy material before filing this application. The robust antibodies of the invention have the potential to recognize their integrin targets in archival FFPE material in identical staining pattern to the distribution seen by known αvβ3-, αvβ5- or αvβ6-specific monoclonal antibodies on cryo-preserved material, but with the well-known, much higher spatial resolution and quality of morphological preservation typical of FFPE vs. cryo-histology material. Very suitable antibodies are rabbit monoclonals that are not simply originated from another species, but these RabMabs are favorably proven to possess specificity, reproducibility and eternality (i.e. the same reagent and same specificity for ever). RabMabs, which are generated by using αvβ3 or αvβ5 clones, recognize archival αvβ3 or αvβ5 in human tumors in identical staining patterns to cryo-fixed material stained with the classical anti-αvβ3 antibody LM609 or the anti-αvβ5 antibody PIF6. RabMabs, which are generated by using β3-cytoplasmic domains, stain xenograft arrays in pattern corresponding to known αvβ3 expression profile of target cells. Although antibodies produced, and optionally selected by screening in the way revealed hereunder, mainly function on FFPE integrins, they can also be used in ELISA on isolated integrins, for flow cytometry on live cell populations, or even have other standard biochemical applications. The antibodies provide an unusual and valuable validation bridge between the observed human pathologies and the biochemistry of the receptors.

The invention teaches the generation of anti-integrin antibodies by using purified integrin domains, particularly purified integrin extracellular domains, more particularly of human origin. The immunogen of the invention causes high titers of antibodies within short periods of immunization. The high antibody titers are reflected by a high dilution of serum which is obtained after immunization and used in assays. Simultaneously, adverse effects which could be caused by other serum components are largely reduced due to their diluted presence. The titer could be advantageously increased further by insect recombinant immunogen production that generates a divergence in the glycosylation from the endogenous and highly homologous rabbit integrins. The antibodies and derivatives thereof are characterized by a high specificity stability and expression in mammalian expression systems in an industrial production scale, low manufacturing costs and convenient handling. These features form the basis for a reproducible action, wherein the lack of cross-reactivity and adverse effects is included, and for a reliable and safe interaction with their matching integrin structures. As the antibodies can be cloned into expression vectors, they provide an absolutely stable and reproducible source of material for basic research and diagnosis. In addition, the appropriate kit is cost-efficiently produced.

All the references cited herein are incorporated by reference in the disclosure of the invention hereby.

It is to be understood that this invention is not limited to the specific antibodies, particular methods, uses and kits described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "an antibody" includes a single or several different antibodies, whereas reference to "antibodies" shall be applicable mutatis mutandis, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Other microorganisms, cell lines, plasmids, promoters, resistance markers, replication origins, and the like, which are not mentioned in the application, are commercially available. Provided that no other hints in the application are given, they are used as examples only, they are not considered to be essential according to the invention, but they can be replaced by other suitable tools and biological materials. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again if the technical problem of the invention is solved.

EXAMPLE 1

Generation of Immunogens

EXAMPLE 1.1

Figure 1:
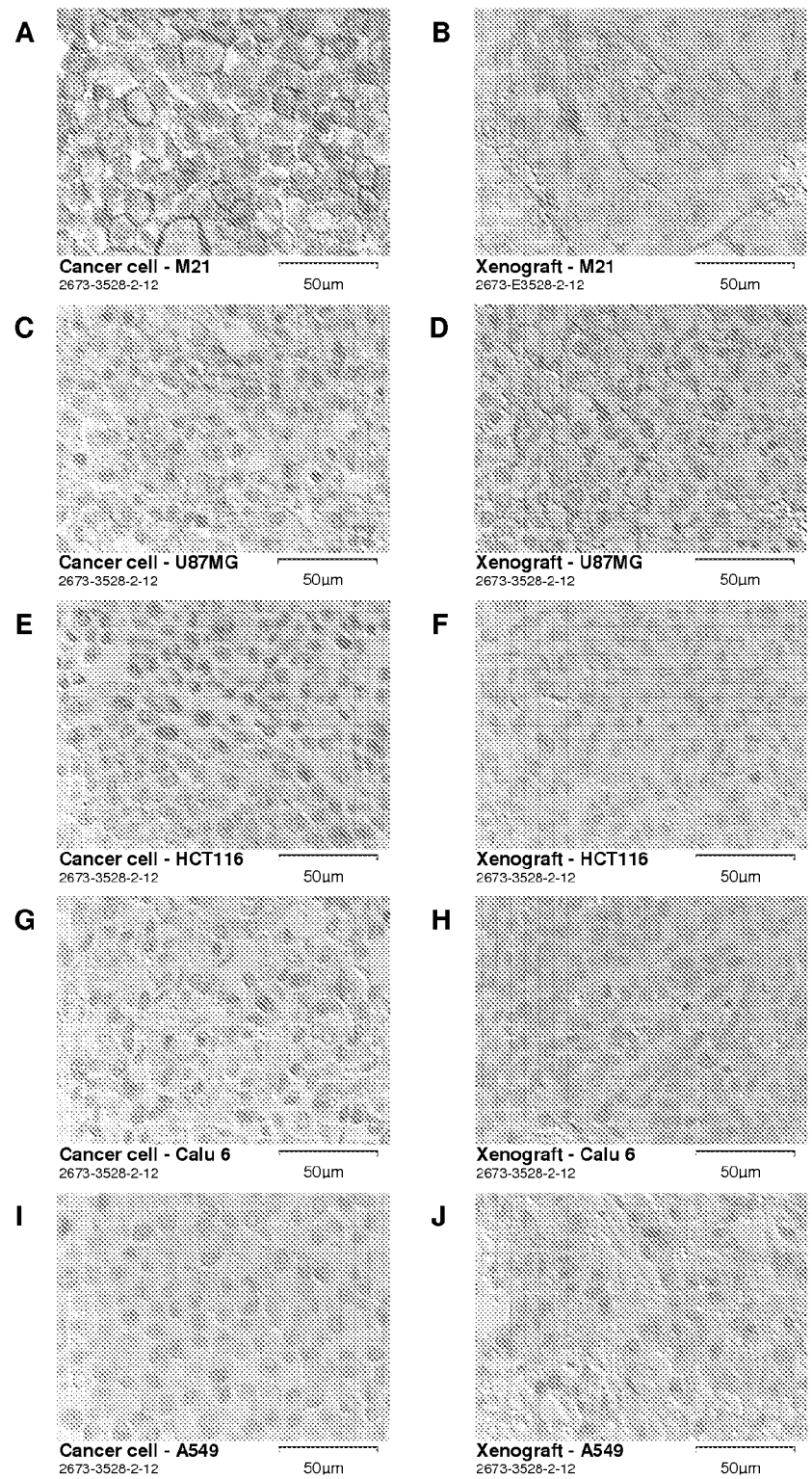
FIG. 1 shows the immunohistochemical staining of FFPE cancer cell lines (left) and xenografts (right) with supernatants of the subclone E3528-2-12 generated against the external domain of $\alpha v \beta 3$.

Generation of extracellular domains αvβ3, αvβ5, αvβ6 and αvβ8v

Recombinant human integrin extracellular domains, αvβ3, αvβ5, αvβ6 and αvβ8, were raised in insect cell lines (Hive Five) using baculovirus infection. The use of the insect line as negative control was apposite. After fermentation, downstream processing comprised the following elements: chromatography on <Mab 14D9> Toyopearl affinity column, dialysis with Spectra/POR dialyze tubing (6-8 kDa for DTM-αvβ3 and DTM-αvβ5; 25 kDa for DTM-αvβ8), concentration with Millipore TFF Labscale having cut off 30 kDa (DTM-αvβ5 and DTM-αvβ8 only), concentration with Amicon Ultra-15 centrifugal filter units having cut off 30 kDa and 0.2 μm filtration with Millex GV (DTM-αvβ3, DTM-αvβ6, DTM-αvβ8 only).

22 mg DTM-αvβ3 were dissolved in buffer of 50 mM Na(CH$_3$COO), 0.2 mM MnCl$_2$, pH 7.4, to give a protein concentration of 2.0 mg/ml. The stock solution was subsequently aliquoted into 22 vials of 500 μl. 10.6 mg DTM-αvβ5 were dissolved in buffer of 50 mM Na(CH$_3$COO), 0.2 mM MnCl$_2$, pH 7.4, to give a protein concentration of 2.36 mg/ml. The stock solution was subsequently aliquoted into 9 vials of 500 μl. 15 mg DTM-αvβ6 were dissolved in buffer of 50 mM Na(CH$_3$COO), 0.2 mM MnCl$_2$, pH 7.4, to give a protein concentration of 2.36 mg/ml. 16.6 mg DTM-αvβ8 were dissolved in buffer of 50 mM Na(CH$_3$COO), 0.2 mM MnCl$_2$, pH 7.4, to give a protein concentration of 2.78 mg/ml.

The aliquots were frozen in liquid nitrogen and stored at −80° C. Analytics was performed by BCA assay and SDS page with Coomassie staining or western blotting pursuant to routine experimental praxis. The following antibodies were used for DTM-αvβ3 detection by western blotting: primary Mab AP3 EMD 330515/CH000, 5 μg/ml, 2 h RT, and secondary gout anti mouse IgG (H+L)×AP, Dianova, 115-055-062, 1:1000, 1 h RT, followed by Precision Step Tractin×AP, BioRad, 161-0382, 1:5000. The following antibodies were used for DTM-αvβ5 detection by western blotting: primary Mab <11D1>-CH004, 2.5 μg/ml, 1 h RT, and secondary goat anti mouse IgG (H+L)×AP, Dianova, 115-055-062, 1:1000, 1 h RT, followed by Precision Step Tractin×AP, BioRad, 161-0382, 1:5000. The following antibodies were used for DTM-αvβ6 detection by western blotting: primary Mab 442-5C4×Biotin <hu-Integrin β6> 330510/CH001, 2 μg/ml, 2 h RT, and secondary anti Biotin×AP, Sigma A-7064, 1:2500, 2 h RT, followed by Precision Step Tractin×AP, BioRad, 161-0380, 1:5000. The following antibodies were used for DTM-αvβ8 detection by western blotting: primary Mab LM 142×Biotin Pool A 269A07H1.G01, 5 μg/ml, 2 h RT, and secondary goat anti mouse IgG (H+L)×AP, Dianova, 115-055-062, 1:1000, 1 h RT, followed by Precision Step Tractin×AP, BioRad, 161-0382, 1:5000, 1 h RT.

The immunogens were characterized as biologically active and specific by their ability to bind their cognate substrates, e.g. vitronectin (αvβ3 and αvβ5) and fibronectin (αvβ3). These preparations were acknowledged as a gold-standard for integrin structural fealty (Mehta et al., Biochem J 1998, 330: 861-869; Xiong et al., Science 2001, 294: 339-345). The recombinant human integrin extracellular domains DTM-αvβ3, DTM-αvβ5, DTM-αvβ6 and DTM-αvβ8 were used as immunogens.

EXAMPLE 1.2

Generation of Cytoplasmic Domain β3

The human β3 integrin cytoplasmic domain, fused to GST was produced in *E. coli* BL21 and purified as a recombinant fusion protein as immunogen. After fermentation, downstream processing comprised the following elements: cell lysis, French press, preparation of inclusion bodies, refolding by dialysis and concentration. 55 mg protein were dissolved in buffer of 0.1 M sodium carbonate, 5 mM DTT, pH 9.5, to give a protein concentration of 1.27 mg/ml. The stock solution was subsequently aliquoted into 2 vials of 10 ml, 4 vials of 5 ml and 4 vials of 1 ml. The aliquots were filtrated (0.2 μm), frozen in liquid nitrogen and stored at −80° C. Analytics was performed by Bradford assay and SDS page with Coomassie staining or western blotting pursuant to routine experimental praxis. The following antibodies were used for 13 detection by western blotting: primary Goat-Anti-GST, Amersham, No. 27-4577-01, 1:5000, 1 h RT, and secondary F(ab')$_2$ Fragment Rabbit-Anti-Goat IgG (H+L)×AP, Dianova, 305-056-045, 1:1000, 1 h RT, followed by Precision Strep Tactin-AP Conjugate, BioRad, Nr. 161-0382, 1:5000.

EXAMPLE 1.3

Generation of gpiibiiia

Full length human gpiibiiia was extracted from outdated human platelets using the octylglucoside as previously detailed (Mitjans et al., J Cell Sci 1995, 108(Pt 8): 2825-38).

EXAMPLE 2

Generation of Antibodies

The generation of rabbit monoclonal antibodies followed a four-step procedure: (A) immunization of rabbits and screening of polyclonal sera, (B) fusion to generate hybridoma cells and screening of supernatants of multiclones, (C) subcloning and screening of supernatants of subclones, and (D) cDNA cloning of the antibody encoding inserts, sequencing and insertion in EBNA expression vectors to allow production of wholly defined antibodies. Rabbit bleeds, hybridoma supernatants and purified antibodies were analyzed in ELISA against immobilized purified immunogens, following standard protocols. Positive clones were retested by differential screen against recombinant extracellular domains of αvβ3, αvβ5 αvβ6 and αvβ8 on delivery, to confirm specificity and activity.

In step (A), several rabbits per immunogen were immunized and the antisera titers were monitored. Prebleeds of all the rabbits gave no signal even at low dilution (1:50) on the FFPE materials, while the primary bleeds (polyclonal sera) prior to fusion already gave clear and unequivocal signals, with strong indications of specificity for cell surface proteins. Three bleeds of each rabbit were delivered, and a single positive rabbit per immunogen was selected for fusion after 8 to 12 weeks.

In step (B), the B cells from the serum positive rabbits were isolated, and the rabbit fusion partner cell line 240E-W were fused to the isolated rabbit B-cells to create rabbit hybridoma cells. 96-well plates were screened for fusion by ELISA. The supernatant for 10 to 100 positive clones were delivered, and 3 multiclones per immunogen were selected after 5 to 6 weeks.

In step (C), hybridomas were cloned and screened to select clones secreting antibodies with appropriate specific antigen recognition, and the antibodies are characterized using a variety of methods (western blotting, IHC, ICC, flow cytometry, etc.). Supernatants of subclones were particularly screened with ELISA for specific antigen recognition. Supernatants of positive tested subclones were frozen and stored at −80° C. until use. Subsequently, the subclone supernatants were screened in the two-step process of Example 3, first on the cancer cell line array and in the second step on xenograft tissue with a cancer cell line array in parallel to verify the first screen.

In step (D), the DNA sequences of the selected antibody clones were excised, cloned into EBNA expression vectors, and sequenced by automated cDNA Sanger dye sequencing. The recombinant antibodies were produced in the EBNA cell expression system according to Pham et al., Biotech Bioeng 2003, 84(3): 332-342, but with the minor modification of using HEK293-6E cells with the pTT5 vector for the transient transfection system. Antibody production was verified by ELISA and IHC. mRNA from hybridoma cells was isolated using TuboCapture Kit (Qiagen) following the manufacturer's suggestion and then reverse transcribed into cDNA using oligo-dT primer. The variable region of heavy chain ($V_H$) was PCR amplified using proprietary primers OYZ64-2 and OYZvh3. The entire light chain (L) was PCR amplified using proprietary primers OYZ62 and OYZ71. The $V_H$ region of PCR fragments was digested using restriction enzyme HindIII and KpnI. The L PCR fragments were digested using HindIII and NotI. All digested product was purified using Qiagen PCR cleaning up kit. After purification, the $V_H$ or L fragment was ligated into the corresponding heavy or light chain proprietary expression vector and transformed into competent cells DH5α (MC Lab). The transformed colonies were picked and inserts were confirmed using the corresponding restriction enzymes (by expected size: approximately 440 bp for $V_H$ and 740 bp for L). Plasmids with inserts of the expected size were sequenced using TT5 for primer. The entire light chain or heavy chain fragment was excised from the corresponding vector with HindIII and NotI and subsequently purified using Qiagen PCR cleaning up kit. Approximately 50 to 100 ng of cDNA inserts were banked.

EXAMPLE 3

Methods for Screening and Characterizing Antibodies

EXAMPLE 3.1

Array Compositions

Twenty seven cancer cell lines and one insect cell line were fixed in phosphate buffered 4% paraformaldehyde, pH 7, over 16 to 24 hours at room temperature, embedded in paraffin and arranged into a 28 cell line paraffin block (CAX05). The integrin cell surface expression profile of several of the cell lines used in the array was previously characterized by flow cytometry, using defined mouse monoclonal antibodies, such as LM609 (Cheresh & Spiro, JBC 1987, 262:17703-17712) and P1F6 (Varner & Cheresh, Important Adv Oncol 1996, 87: 69) directed against the αvβ3 and αvβ5 integrin complexes, respectively (Mitjans et al., J Cell Sci 1995, 108(Pt 8): 2825-38).

CAX05:

| A 431 | squams cancer oes |
|---|---|
| A 549 | lung cancer |
| A2780 ADR | ovarian cancer |
| C 8161 | melanoma |
| Calu 6 | lung adeno |
| Colo 205 | colon cancer |
| DU145 | prostate cancer |
| HCT 116 | colon cancer |
| HT 29 | colon cancer |
| Igrov 1 | ovarian cancer |
| Kyse 30 | squamous cancer |
| Lox | melanoma |
| M21 | melanoma |
| M24-met | melanoma |
| MCF 7 | breast cancer |
| MDA-MB 23 | breast cancer |
| MDA-MB468 | breast cancer |
| MiaPaCa2 | pancreas cancer |
| NCI-H460LC | lung cancer |
| Ovcar-3 | ovarian cancer |
| PC 3 | prostate cancer |
| Raji | BuBVLtt's Lym |
| Sf9 | Insect cell |
| SKOV 3 | ovarian cancer |
| Suit 7 | pancreas cancer |
| SW707 | colon cancer |
| U87MG | glioblastoma |
| WM 164 | melanoma |

Arrays out of different experimental studies (Xeno-08-A; Xeno-08-Mu1) were composed by using xenografts from vehicle treated mice.

Xeno-08-A:

| M21 | mouse |
|---|---|
| U87MG | mouse |
| HCT116 | CD1 nu/nu mouse |
| A549 (human lung carcinoma) | CD1 nu/nu mice |
| Calu 6 | CD1 nu/nu mice |

Xeno-08-Mu1:

A549, HCT116, U87MG, M21, Calu 6, A431, BT474, Colo205, H1975, MDA MB-231, Mes-Sa/Dx5, PC3, SW707, A2780, A2780ADR Sections of 3 µm of the cancer cell line array and the xenograft arrays were mounted on positively charged Super-Frost® Plus slides (Menzel-Glaeser, Braunschweig, Germany) and stored at −80° C. with desiccant.

EXAMPLE 3.2

IHC Procedure

The immunohistochemical staining procedure starting with the deparaffinization of sections was done with the staining instruments Discovery™ or the Discovery® XT (Ventana Medical Systems, Inc., Tucson, USA). After deparaffinization sections were heated for epitope retrieval in Tris-EDTA buffer pH 8 or incubated with protease at 37° C. during 8 (protease 1) or 12 min (protease 2). Endogenous peroxidase was blocked by incubation in 3% hydrogen peroxide (part of OmniMap™ or UltraMap™ Kits, Ventana Medical Systems). After warming the supernatants at room temperature at the day of the first immunohistochemical run, sodium azide was added to a final concentration of 0.01% (w/v), and supernatants were stored at 4° C. One series of supernatants was always stained with the same instrument. Sections were incubated with the supernatants of multiclones and subclones, or recombinantly expressed antibodies (2-10 µg/ml; 100 µl per slide), and then with the appropriated secondary antibody, as are the HRP conjugated polymers of the OmniMap or Ultra-Map Kit, for 16 min at 37° C. Horseradish peroxidase (HRP) catalyzes the 3,3'-diaminobenzidine tetrahydrochloride (DAB)/$H_2O_2$ reaction to produce an insoluble dark brown precipitate that can be visualized. Sections were counterstained with hematoxylin. Slides were washed in tap water, dehydrated, and mounted with glass coverslips in permanent mounting media Entellan® Neu (VWR, Germany). Slides were stored at room temperature, and paraffin blocks were stored at 6° C.

Diagram of Immunohistochemical Staining Procedure:

A. Pre-treatment
  Deparaffinization (temperature: 750 during 8 min, then EZ Prep Buffer at 75° C. during 8 min)
  Cell conditioning (Tris EDTA buffer pH 8, time: 48 min; temperature: 95° C.) or
  Protease conditioning (protease 1: 0.5 U/ml, or protease 2: 0.1 U/ml; time: 8 or 12 min; temperature: 37° C.)

B. Detection
  Primary antibody (volume: 100 µl; time: 32 min; temperature: 37° C.)
  Secondary antibody (OmniMap or UltraMap conjugated with HRP; volume: 100 µl; time: 16 min; temperature: 37° C.
  Detection (ChromoMap DAB)
  Counterstain (Hematoxylin II; time: 8 min)
  Post-counterstain (Bluing Reagent)
  Slide cleaning Cell line arrays were scanned with the automated microscope Ariol SL-50 at X20 (scale x/y: 1 pixel=0.38×0.38 µm²). A circular region (input region area) of 0.1 mm² was set in each tissue spot. The brown color of the positive immunohistochemical labeling was quantified with the help of the image analysis software of the Ariol SL-50 by setting thresholds for "color", "hue", and "saturation". The positive area in the input region area was the fraction of brown labeled tissue. The intensity of positive area was the mean grey value of brown color measured in 3 black and white images photographed with a red, a blue and a green filter. Grey values range from 0 (black) to white (255). Expression was calculated according to positive area fraction*(255-intensity). Data were displayed with Spotfire® DecisionSite™ (version 9.0, Spotfire Inc.).

EXAMPLE 3.3

ELISA Protocol

Recombinant integrins (1 µg/ml) were coated on microtiter plates by adsorption (4% C; 16 h) from coating buffer (150 mM NaCl; 1 mM $CaCl_2$; 1 mM $MgCl_2$; 10 µM $MnCl_2$; 50 mM Tris-Cl; pH 7.5). The plates were washed (wash buffer: 0.5% BSA; 0.05% Tween 20 in PBS), blocked (1 h; 4° C.; 5% BSA in PBS), and incubated with primary antibodies serially diluted in wash buffer (1 h; 37° C.). After washing, secondary detection antibody (goat-anti-rabbit HRP; 1:5000) was added (1 h; 37° C.), followed by washing and detection using tetramethyl-benzidine (100 µg/ml) in citrate-phosphate buffer (pH 5.0), development with sulphuric acid, and reading against a reagent blank at 450 nm. Results were expressed following subtraction of the blank values which were typically <5% of positive control values.

EXAMPLE 3.4

FACS Analysis

Cells in log growth were harvested using trypsin (0.5 µg/ml)/EDTA (0.2 µg/ml), washed in FACS buffer (PBS plus 0.9 mM CaCl$_2$; 0.5 mM MgCl$_2$; 0.5% w/v BSA), and incubated with anti-integrin antibodies (60 min; 4° C.; 10 μg/ml in FACS buffer). After washing, the cells were stained with Alexa-488 labeled antirabbit IgG (Invitrogen), or goat anti-mouse IgG FITC (Becton-Dikinson) (30 min; 4° C.), washed and re-suspended in FACS buffer (500 μl/tube). Cells were analyzed on a FACScan (Becton-Dickinson) and the mean intensity fluorescence (MIF) was normalized to the MIF of the negative control (cells stained with PI and secondary labeled antibody, without primary antibody).

EXAMPLE 3.5

Evaluation and Statistics

The IC$_{50}$ for antibody binding in ELISA was determined from triplicate data points by nonlinear curve fitting in the graphic software package Graphpad Prism (Ver 5.0: GraphPad Software, Inc. LaJolla Calif.). Flow cytometry was analyzed using the BD Facs-scan program (CellQuest MacOS 8.6).

EXAMPLE 4

Characterization of Anti-αvβ3 Clones and Anti-αvβ3-Antibodies

EXAMPLE 4.1

Characterization of E3528-2-7, E3528-2-11 and E3528-2-12

The supernatants from 24 subclones obtained from multiclones 2 and 63 of rabbit E3528 were screened undiluted on the FFPE cell line array of cancer cell lines CAX05. Cytoplasmic signals without clear membrane profile were excluded as non-integrin specific. Subclones of the multiclone 2 exhibit a plasma membrane staining (FIG. 1). The selectivity of the subclones regarding certain cell types was compared with the mouse monoclonal IgG, clone 20H9. Clone 20H9 is an anti-13 chain antibody (Mitjans et al., J Cell Sci 1995, 108(Pt 8): 2825-38), that cross reacts in FFPE, however with a low binding affinity. The positive subclones were tested in a second run on the xenograft array Xeno-08-A to confirm cross-reactivity on tumor tissue (Table 1).

TABLE 1

Clones to extracellular αvβ3 domain. The staining intensity was graded from – (negative) to +++ (strong).

| Clone ID | Cancer cell line array (CAX05) | Xenograft array (Xeno-08-A) |
|---|---|---|
| MRK-1a-E3528-2 multiclone | M21+++, U87MG++, HCT116–, Calu 6–, A549–, SUIT 7–, WM164+, HT29–, MDA-MB231– | M21+–, U87MG–, HCT116–, Calu 6–, A549– |
| MRK-1a-E3528-2 subclones | clones 2-2 to 2-12 were positive | M21+, U87MG–, HCT116–, Calu 6–, A549– |

Figure 2:
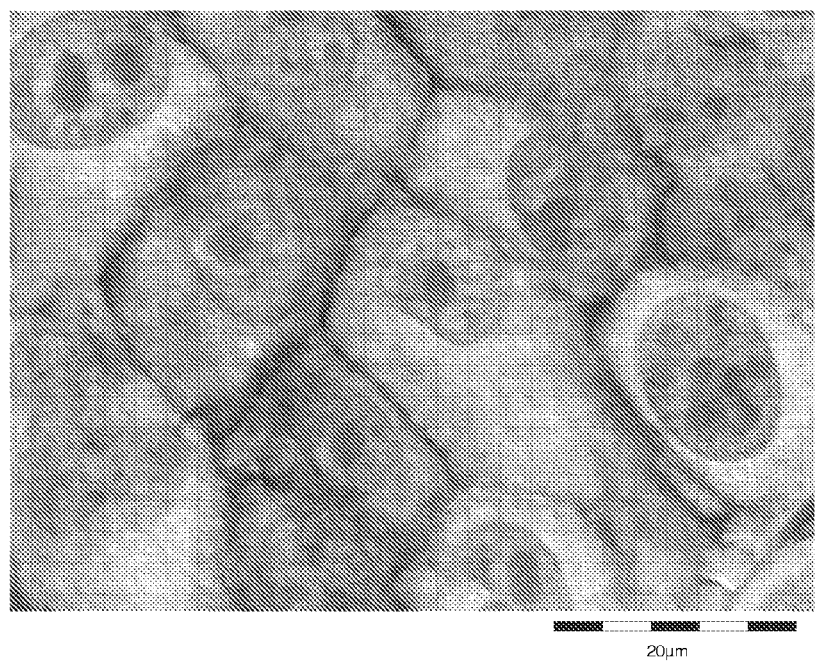
FIG. 2 shows the plasma membrane staining of M21 cells in xenografts with the purified anti-$\alpha v \beta 3$ integrin antibody clone E3528-2-7.
Figure 3:
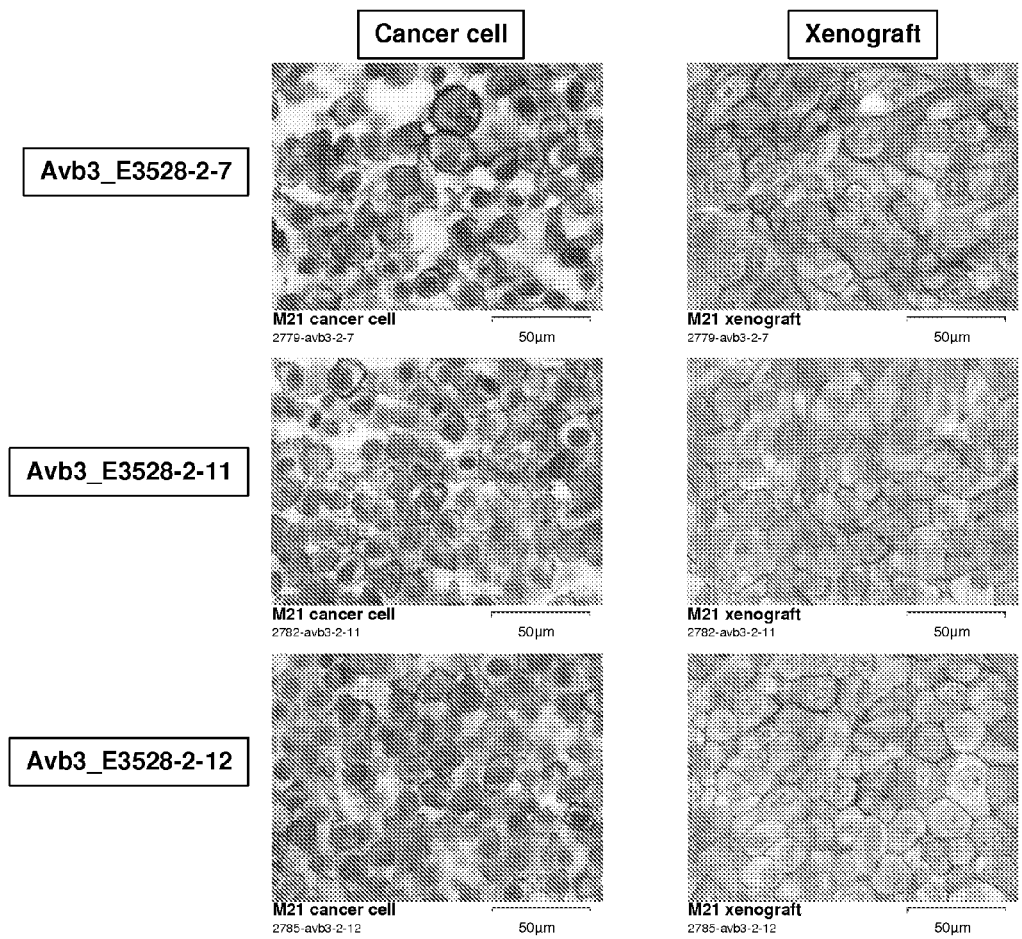
FIG. 3 shows the immunohistochemical staining of the cancer cell line M21 (left) and the M21 xenograft (right) with the purified anti-$\alpha v \beta 3$ integrin antibodies E3528-2-7, E3528-2-11 and E3528-2-12.

Three subclones, 2-7, 2-11 and 2-12, were selected as final clones, based on staining intensity, selectivity regarding known αvβ3 integrin positive cells and quality of plasma membrane staining. The three anti-αvβ3 clones exhibited similar staining characteristics, showing distinct plasma membrane staining (FIG. 2). In the xenograft array Xeno-08-Mu1, M21 xenografts were the only positive ones (FIG. 3).

Figure 4:
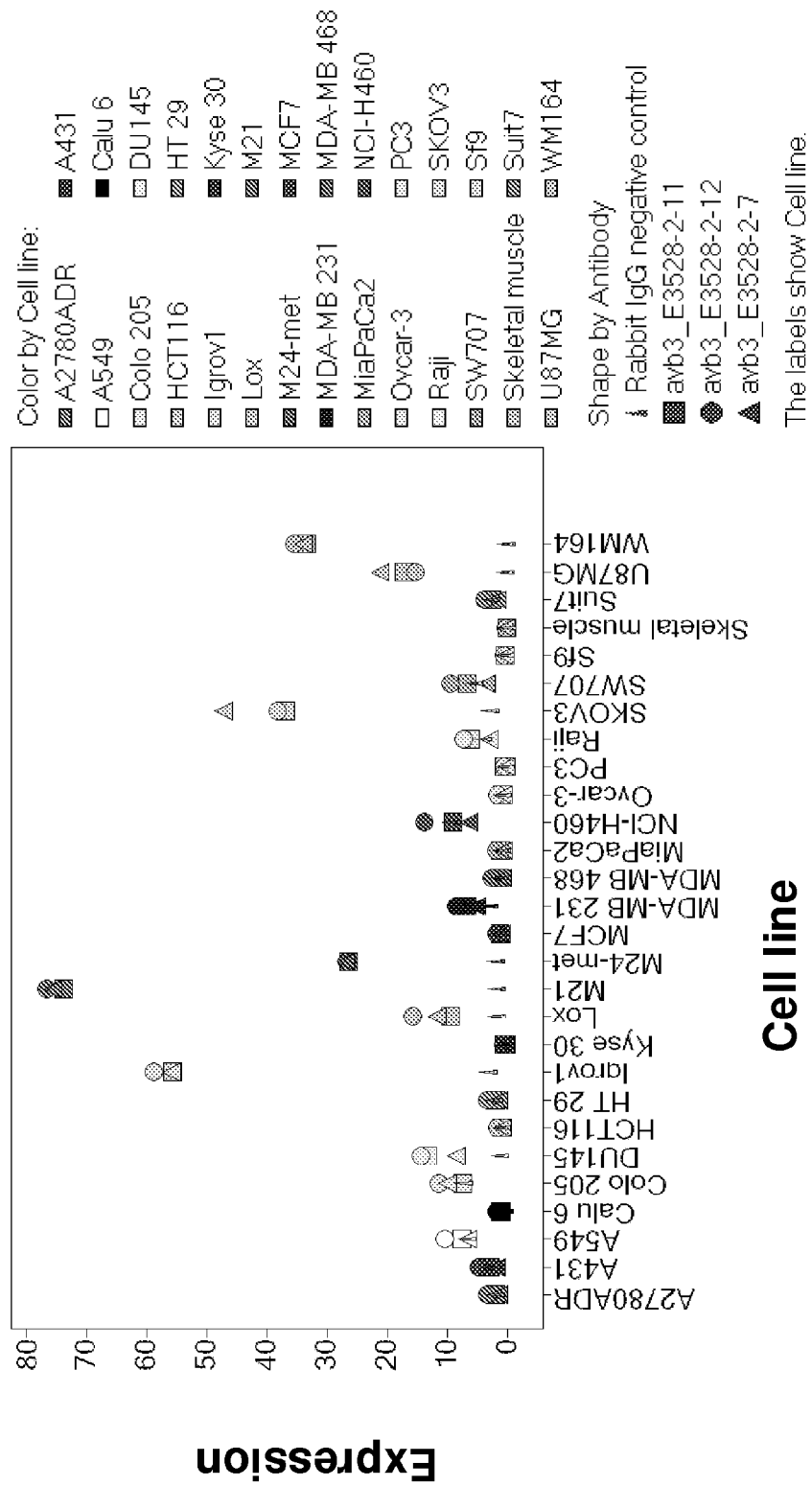
FIG. 4 shows the analysis of immunohistochemical staining with the anti-$\alpha v \beta 3$ antibodies E3528-2-7, E3528-2-11 and E3528-2-12 with the help of image analysis (Ariol SL-50) and graphical representation with Spotfire.
Figure 5:
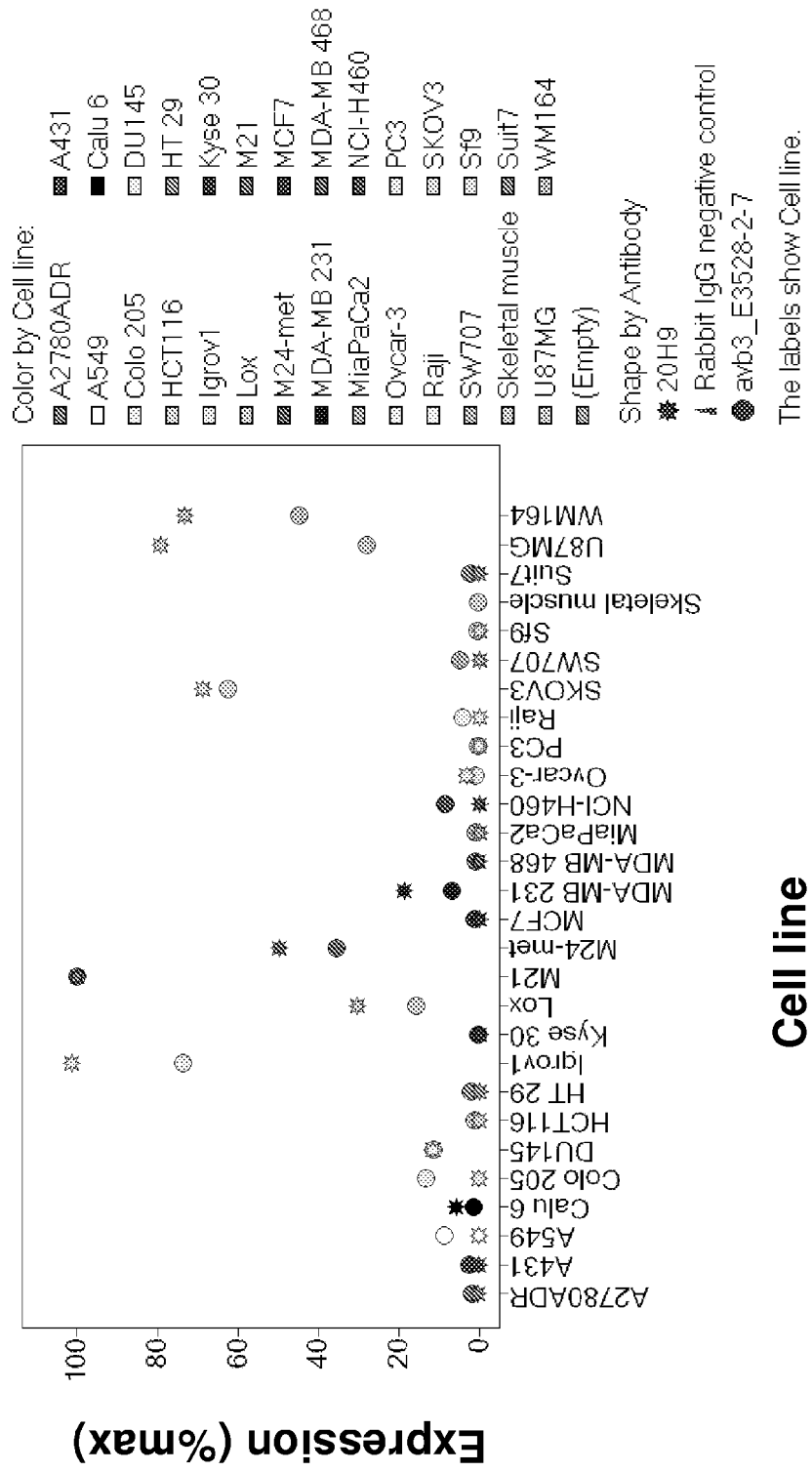
FIG. 5 shows the analysis of immunohistochemical staining with the antibody $\alpha v \beta 3\_E3528$-2-7 and the mouse monoclonal antibody 20H9 with the help of image analysis (Ariol SL-50). Clone 20H9 is directed against the $\beta 3$-integrin chain. The "Expression (% max)" is normalized to the expression of M21.

The subclones were negative in a range of carcinomas including A549 and HCT116, known not to express αvβ3 (Table 2), and in the anchorage independent Raji-T-cell lymphoma. These data were in agreement with a αvβ3-integrin epitope of the antibodies. The selectivity and intensity of staining with the three antibodies on the cancer cell line array was nearly identical (FIG. 4). The selectivity of staining of the three antibodies was compared with the monoclonal anti-β3 integrin antibody clone 20H9 (FIG. 5, shown for clone E3528-2-7). Regarding cell selectivity the three clones showed similar characteristics to the clone 20H9, indicating that the epitope of the three antibodies was a αvβ3 epitope. High expression of αvβ3 in M21 cell lines was shown previously by FACS analysis with clone LM609 (Table 2; Mitjans et al., Int J Cancer 2000, 87(5): 716-723).

TABLE 2

FACS analysis and anti-αvβ3 immunohistochemistry of several cancer cell lines.

| Cancer cell line | FACS αvβ3 (MF/mean background) | FACS % cells | FACS αvβ3 × % cells | IHC αvβ3_E3528-2-7 on CAX08 (Expression) |
|---|---|---|---|---|
| HCT116 | 0.96 | 0.2 | 0.2 | 0.9 |
| KYSE-30 | 0.98 | 0.52 | 0.5 | 0.3 |
| M21 | 1.55 | 91.8 | 142.3 | 75.6 |
| A549 | 0.63 | 1.2 | 0.8 | 6.7 |
| NCI-H460 | 0.79 | 0.0 | 0.0 | 6.5 |
| Calu-6 | 1.5 | 3.6 | 5.4 | 1.1 |

EXAMPLE 4.2

Characterization of E3531-227 and E3531-229

Similarly to Example 4.1, the subclone 227-3 was obtained following a second fusion run of B-lymphocytes of rabbit E3531. The supernatants from 18 subclones obtained from multiclones 227 and 229 were screened undiluted on the FFPE cell line array of cancer cell lines CAX05. Cytoplasmic signals without clear membrane profile were excluded as non-integrin specific. Subclones of both multiclones exhibited a good plasma membrane staining. The selectivity of the subclones regarding certain cell types was compared with the mouse monoclonal IgG, clone 20H9. The positive subclones were tested in a second run on the xenograft array Xeno-08-A to confirm cross-reactivity on tumor tissue. Six subclones, E3531-227-2, -227-3, 227-6, -229-3, 229-9 and -229-11 were selected as final clones, based on staining intensity, selectivity regarding known αvβ3 integrin positive cells, and quality of plasma membrane staining.

Figure 6:
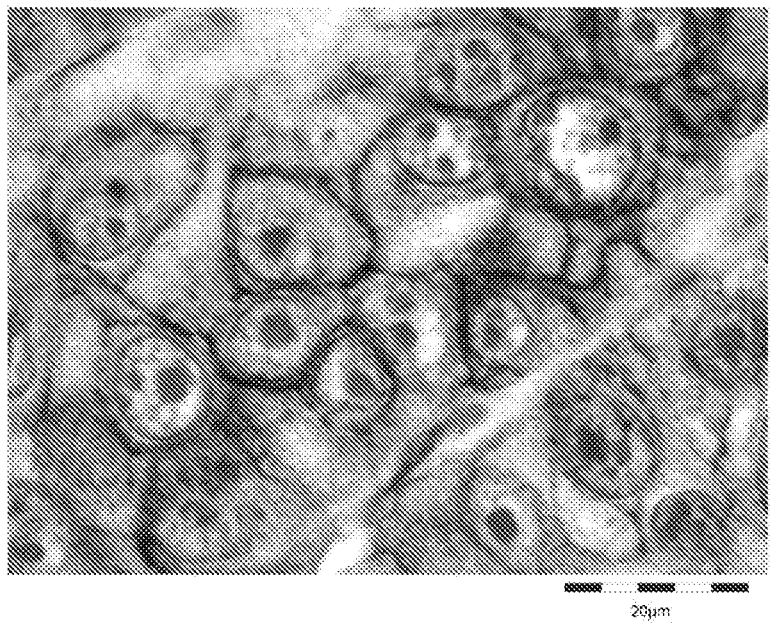
FIG. 6 shows the plasma membrane staining of M21 cells in xenografts with the purified anti-$\alpha v \beta 3$ integrin antibodies E3531-227-3 and E3531-229-3.
Figure 6:
Figure 7:
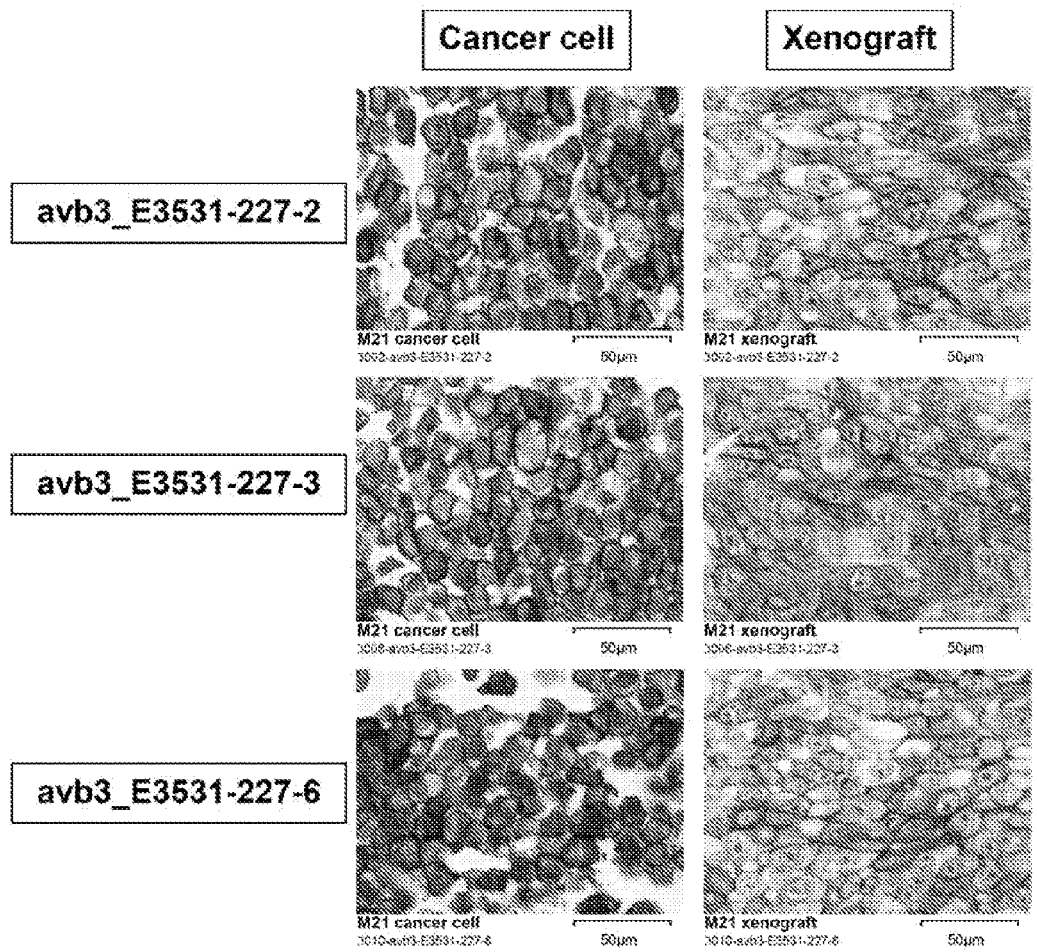
FIG. 7 shows the immunohistochemical staining of the cancer cell line M21 (left) and the M21 xenograft (right) with the purified anti-$\alpha v \beta 3$ integrin antibodies of multiclone 227 (E3531-227-3, E3531-227-3 and E3531-227-6).
Figure 8A:
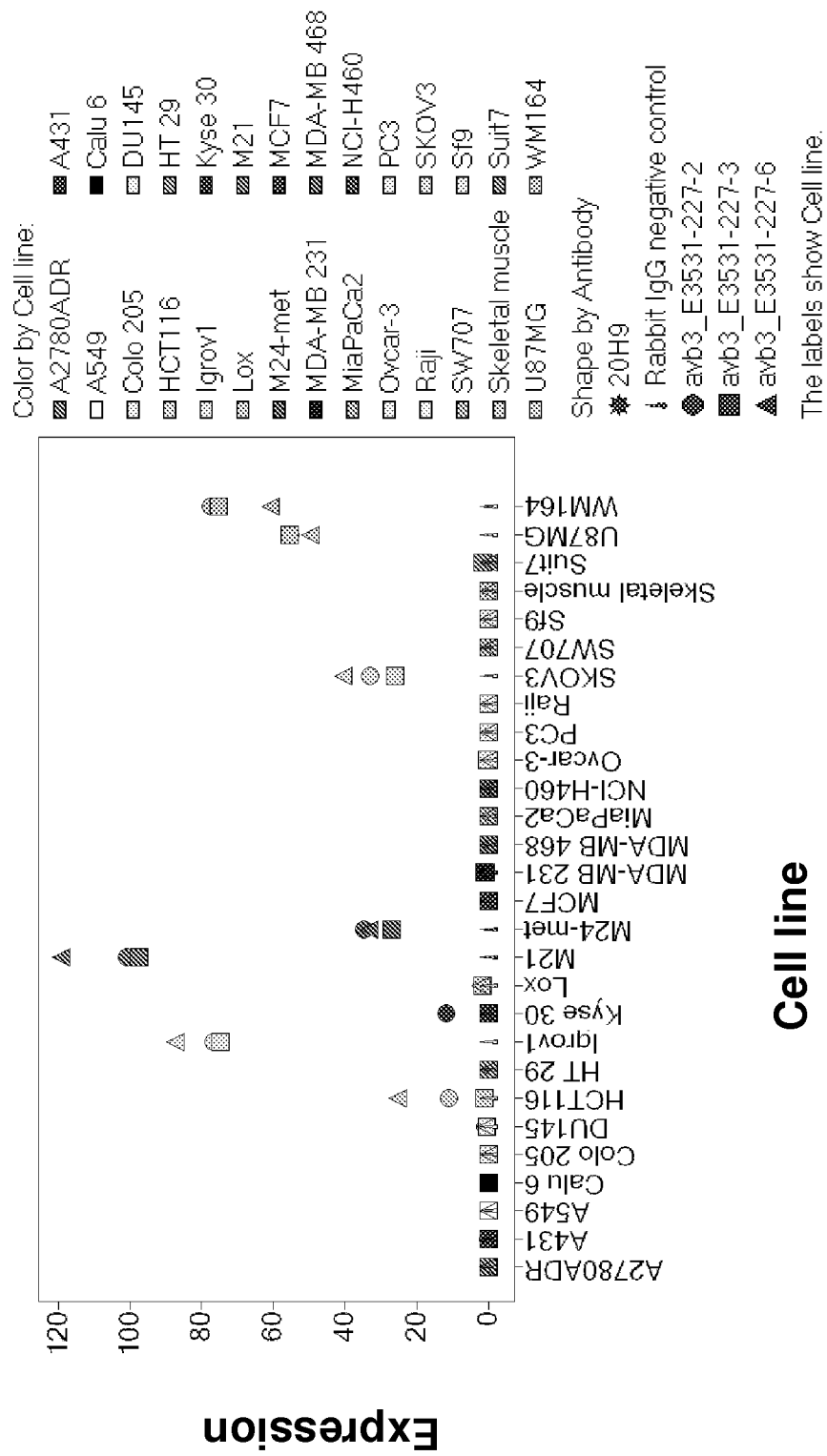
FIGS. 8A and B show the analysis of immunohistochemical staining with the anti-$\alpha v \beta 3$ antibodies of the clones E3531-227 (above) and in comparison to the mouse monoclonal anti-$\beta 3$ antibody 20H9 (below), calculated as % of the expression in M21 cells. Expression was analyzed with the help of image analysis (Ariol SL-50).
Figure 8B:
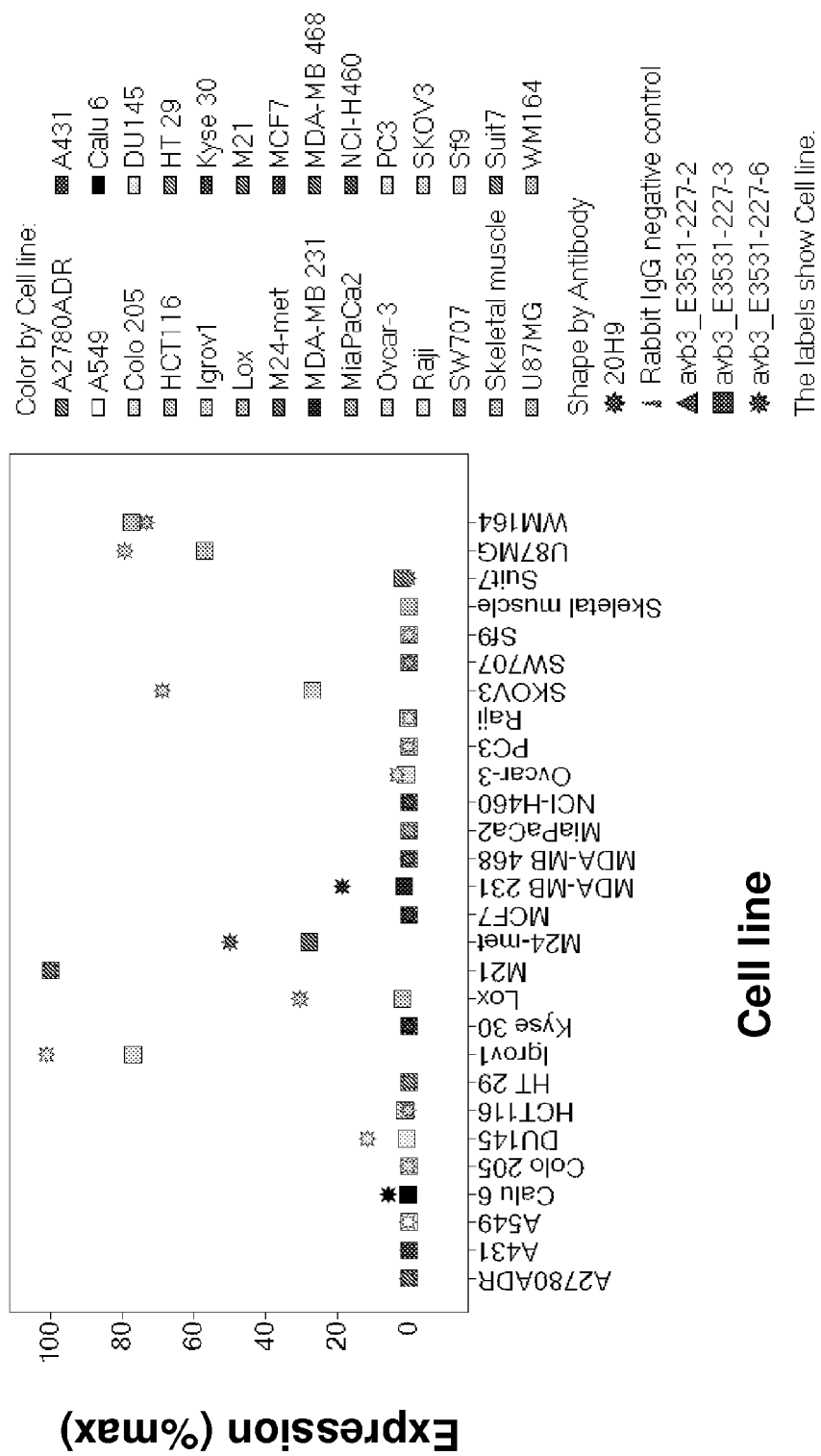

The selected final clones were cultured and the antibodies purified. The six anti-αvβ3 clones exhibited similar staining characteristics, showing distinct plasma membrane staining (FIG. 6). In the xenograft array Xeno-08-Mu1, M21 xenografts were the only positive ones (FIG. 7). U87MG were negative. The selectivity of staining with the three antibodies E3531-227-2, E3531-227-3 and E3531-227-6 on the cancer cell line array CAX08 was nearly identical (FIGS. 8A and B). The selectivity of staining of the anti-αvb3 antibodies was compared with the monoclonal anti-β3 integrin antibody clone 20H9, shown for clone E3531-227-3 (FIGS. 8A and B). Regarding cell selectivity, the clones showed similar characteristics to the clone 20H9, indicating that the epitope of the six antibodies was an αvβ3 epitope. High expression of αvβ3 in M21 cell lines was shown previously by FACS analysis with clone LM609 (Table 3; Mitjans et al., Int J Cancer 2000, 87(5): 716-723). The clones E3531-227-3 and E3531-229-3 producing the highest IgG amount were sequenced and showed identical sequences (cf. below).

TABLE 3

FACS analysis and anti-β3 immunohistochemistry of several cancer cell lines.

| Cancer cell line | FACS αvβ3 (MIF/mean background) | FACS % cells | FACS αvβ3 × % cells | IHC αvβ3_E3531-227-3 on CAX08 (Expression) |
|---|---|---|---|---|
| HCT116 | 0.96 | 0.2 | 0.2 | 1.17 |
| KYSE-30 | 0.98 | 0.52 | 0.5 | 0.00 |
| M21 | 1.55 | 91.8 | 142.3 | 97.4 |
| A549 | 0.63 | 1.2 | 0.8 | 0.02 |
| NCI-H460 | 0.79 | 0.0 | 0.0 | 0.01 |
| Calu-6 | 1.5 | 3.6 | 5.4 | 0.12 |

The staining characteristics of the six clones E3531-227-2, -227-3, 227-6, -229-3, 229-9 and -229-11, as are "plasma membrane staining" and high signal in M21 cells, were in agreement with an αvβ3-integrin epitope of the antibodies. The antibodies detected αvb3-integrin in formaldehyde-fixed paraffin-embedded tissue. EM22703 was further developed. It reacts equally well on intact aiibβ3 ($IC_5$ was the same in ELISA), indicating that it was detecting the β3 chain in complex with both partners. This reflected the power of the monoclonal antibody to detect exactly what it was screened against. In practice, the cross reactivity should not prove a serious disadvantage to detecting αvβ3 in situ: αiibβ3 is expressed solely on the macrophage/megakaryocytic blood borne lineages, and rarely expected to be seen in the intra-tissue locations characteristic of αvβ3.

EXAMPLE 5

Characterization of Anti-αvβ5 Clones and Anti-αvβ5-Antibodies

Figure 9:
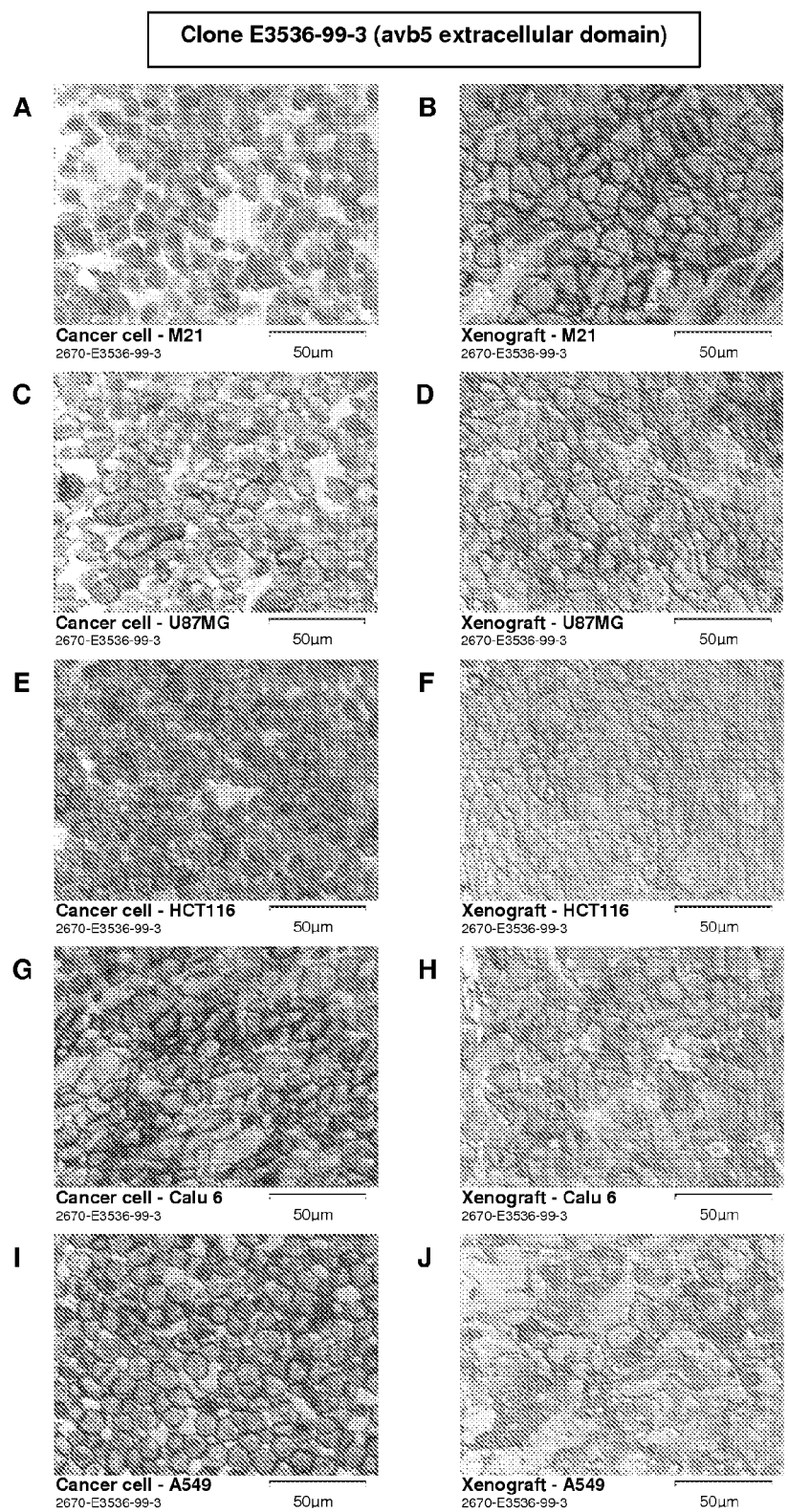
FIG. 9 shows the immunohistochemical staining of FFPE cancer cell lines (left) and xenografts (right) with supernatants of the subclone E3536-99-3 generated against the external domain of $\alpha v \beta 5$.
Figure 10:
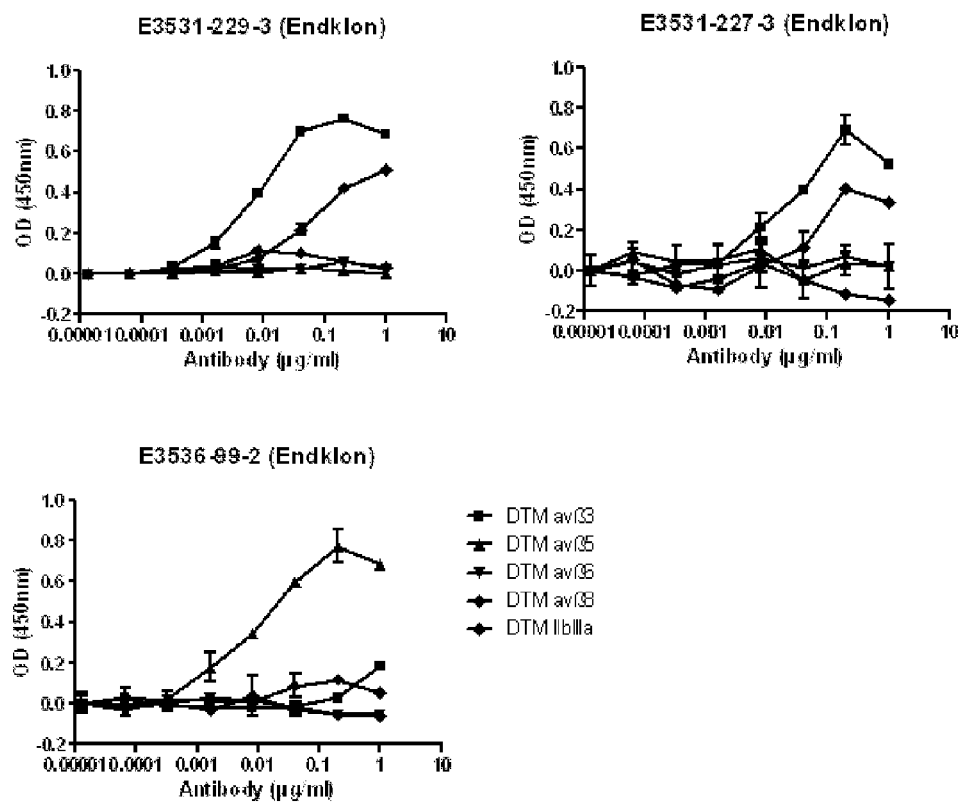
FIG. 10 shows the ELISA profile of purified monoclonal hybridoma antibodies E3531-227-3, E3531-229-3 and E3536-99-2 against recombinant human extracellular domains of integrin $\alpha v \beta 3$ and $\alpha v \beta 5$ and full length purified platelet gpiibiiia.

The supernatants from 27 subclones obtained from multiclones 13, 40 and 99 of rabbit E3536 were screened undiluted on the FFPE cell line array of cancer cell lines CAX05. Three subclones, 99-1, 99-2 and 99-3, exhibited a plasma membrane staining (FIG. 9). They hybridoma supernatants were highly specific for αvβ5 over αvβ3 (a factor of >100 in apparent Kd), with $EC_{50}$ on the immunogen of 50 pM (FIG. 10). The positive subclones were tested on the xenograft array to confirm cross-reactivity on tumor tissue (FIG. 9, right column). Cell lines showed different degrees of αvβ5 expression if grown in culture compared to xenograft tissue.

TABLE 4

Clones to extracellar αvβ5 domain. The staining intensity was graded from − (negative) to +++ (strong).

| Clone ID | Cancer cell line array (CAX05) | Xenograft array (Xeno-08-A) |
|---|---|---|
| MRK-1c-E3536-99 multiclone | HT29+++, WM164−, M21++, U87MG++, HCT116+++, Calu 6++, A549+++, Suit 7+++, MDA-MB231++, Kyse30++, NCI-H460+++ | M21++, U87MG++, HCT116++, Calu 6++, A549+ |
| MRK-1C-E3536-99 subclones | clones 99-1, 99-2 and 99-3 were positive; plasma membrane was labeled | M21++, U87MG++, HCT116+, Calu 6+, A549+ |

Figure 11:
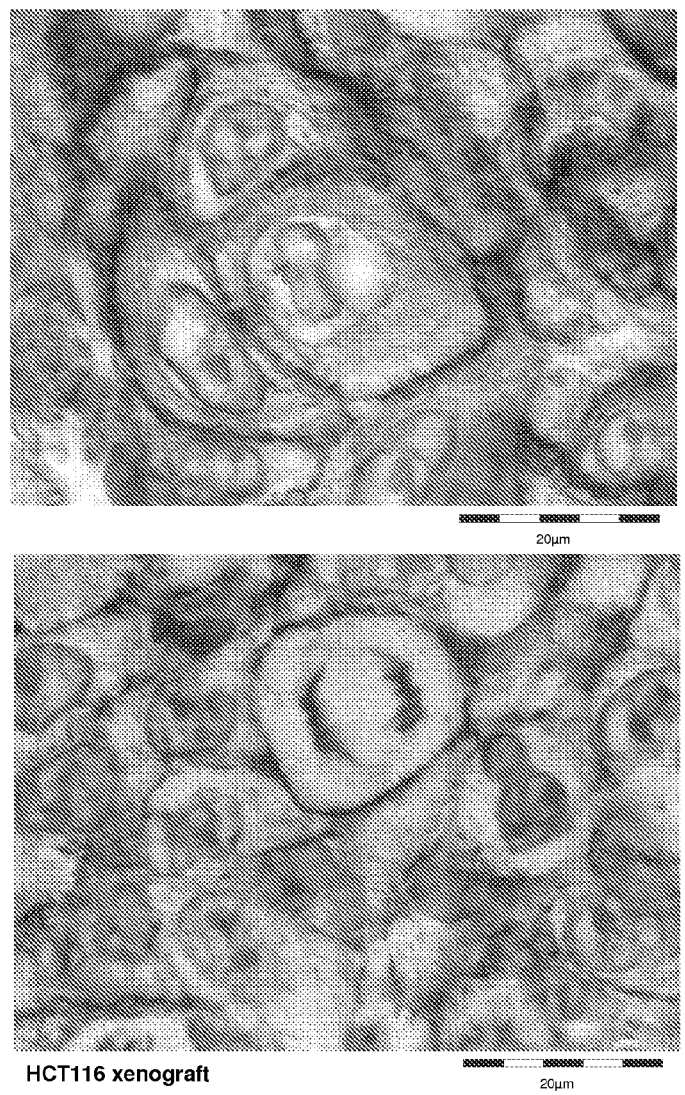
FIG. 11 shows the plasma membrane staining of A431 and HCT116 cells in xenografts with the purified anti-$\alpha v \beta 5$ integrin antibody clone E3536-99-3.
Figure 12:
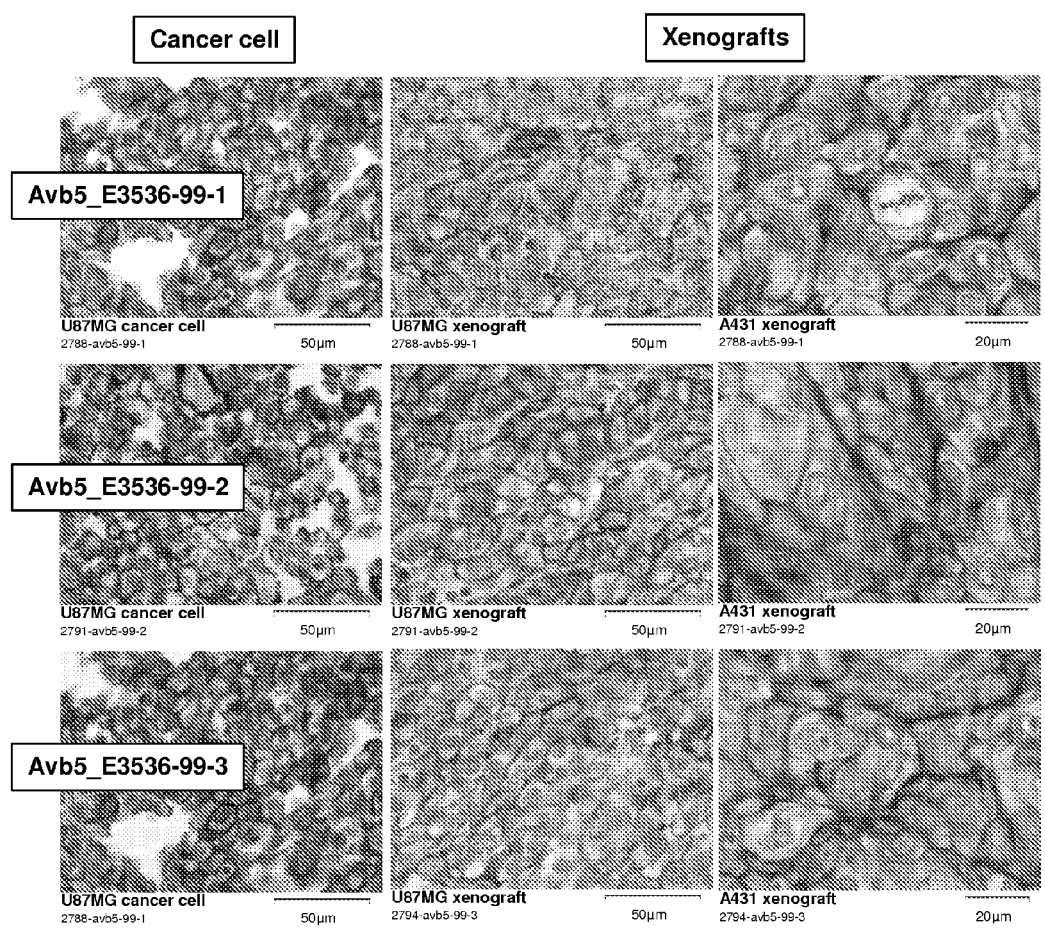
FIG. 12 shows the immunohistochemical staining of the cancer cell line U87MG (left) and the U87MG and A431 xenografts with the purified anti-$\alpha v \beta 5$ integrin antibodies E3536-99-1, E3536-99-2 and E3536-99-3.
Figure 13:
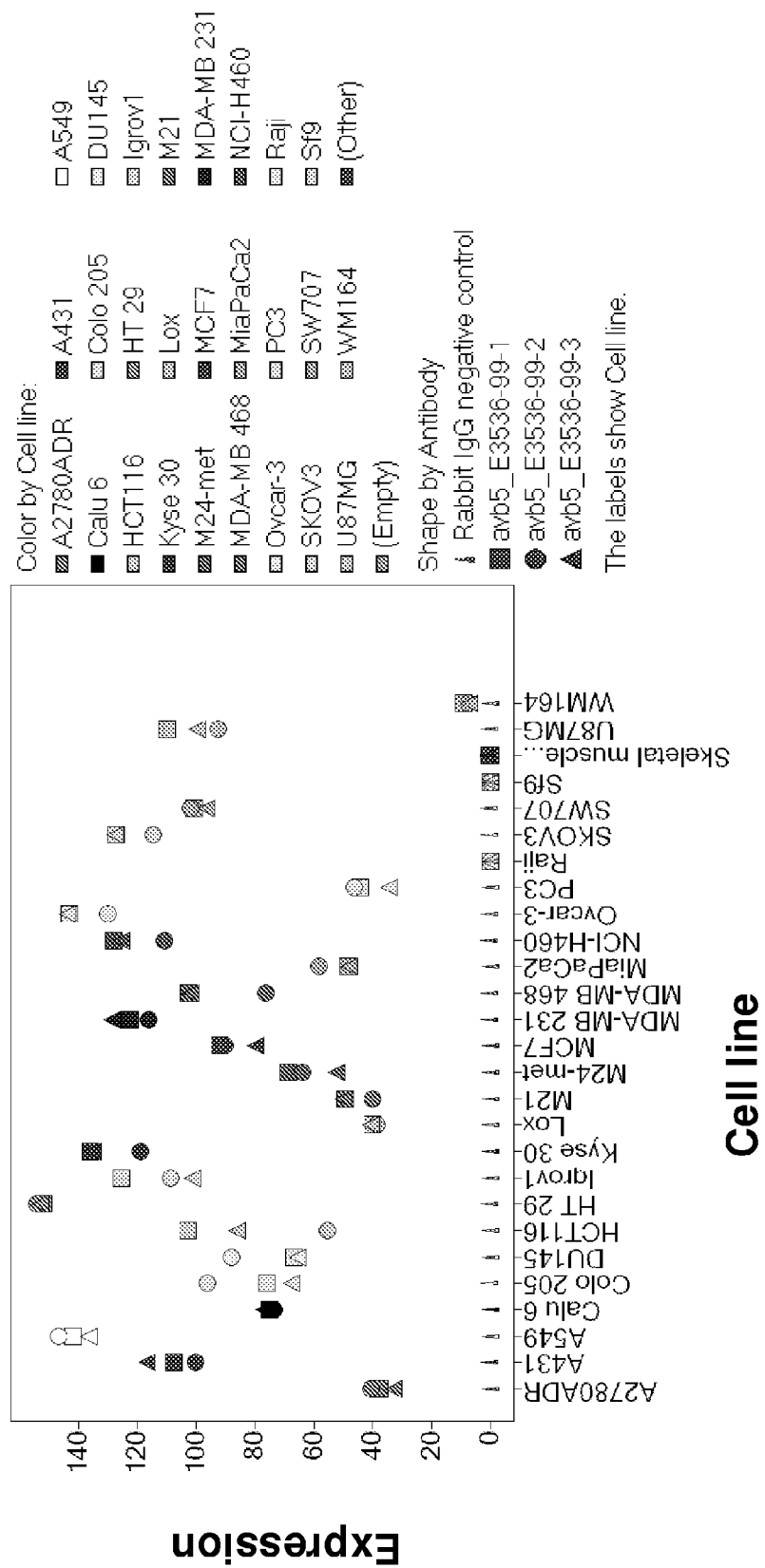
FIG. 13 shows the analysis of immunohistochemical staining with the anti-$\alpha v \beta 5$ antibodies E3536-99-1, E3536-99-2 and E3536-99-3 with the help of image analysis (Ariol SL-50) and graphical representation with Spotfire.

Three subclones, 99-1, 99-2, and 99-3, were selected as final clones based on staining intensity, selectivity regarding known αvβ5 integrin positive cells and quality of plasma membrane staining (Table 4). The three anti-αvβ5 clones labeled the plasma membrane (FIG. 11). In the xenograft array Xeno-08-Mu1, several xenografts were positive, especially A431 (FIG. 12). The three anti-αvβ5 clones, E3536-99-1, -99-2, and -99-3, exhibited very similar staining characteristics regarding cell selectivity and staining intensity measured with image analysis (FIG. 13). Cell lines that showed a high αvβ5_E3536-99-1 (or -99-2, or -99-3) signal (i.e. HT-29, HCT116, Kyse 30, A549 and NCI-H460) exhibited high αvβ5 expression analyzed by FACS with the clone P1F6 (Kemperman et al., Exp Cell Res 1997, 234(1): 156-164; Mitjans et al., Int J Cancer 2000, 87(5): 716-723). The M21 cell line exhibited a low signal with immunohistochemistry and a corresponding low signal by FACS analysis (Table 5). Raji lymphoma cells, that were αv negative, showed no signal on the cancer cell line array with immunohistochemistry.

TABLE 5

FACS analysis and anti-αvβ5 immunohistochemistry of several cancer cell lines.

| Cancer cell line | FACS αvβ5 (MIF/mean background) | FACS % cells | FACS αvβ5 × % cells | IHC αvβ5_E3536-99-1 on CAX08 (Expression) |
|---|---|---|---|---|
| HCT116 | 6.21 | 72.5 | 450.2 | 103.0 |
| KYSE-30 | 7.16 | 80.39 | 575.6 | 136.0 |
| M21 | 0.84 | 39.1 | 32.8 | 50.0 |
| A549 | 1.69 | 97.0 | 163.9 | 142.0 |
| NCI-H460 | 1.67 | 78.0 | 130.3 | 128.0 |
| Calu-6 | 5.2 | 74.4 | 386.9 | 75.0 |

The subclone characteristics matched FACS and biochemical data for the distribution of αvβ5 integrin and supported subclones 99 as reacting with a αvβ5-Integrin epitope. Clones 99 were derived from a unique hybridoma cell, as revealed by cDNA sequencing (cf. below).

EXAMPLE 6

Characterization of Anti-αvβ6 Clones and Anti-αvβ6-Antibodies

Figure 14:
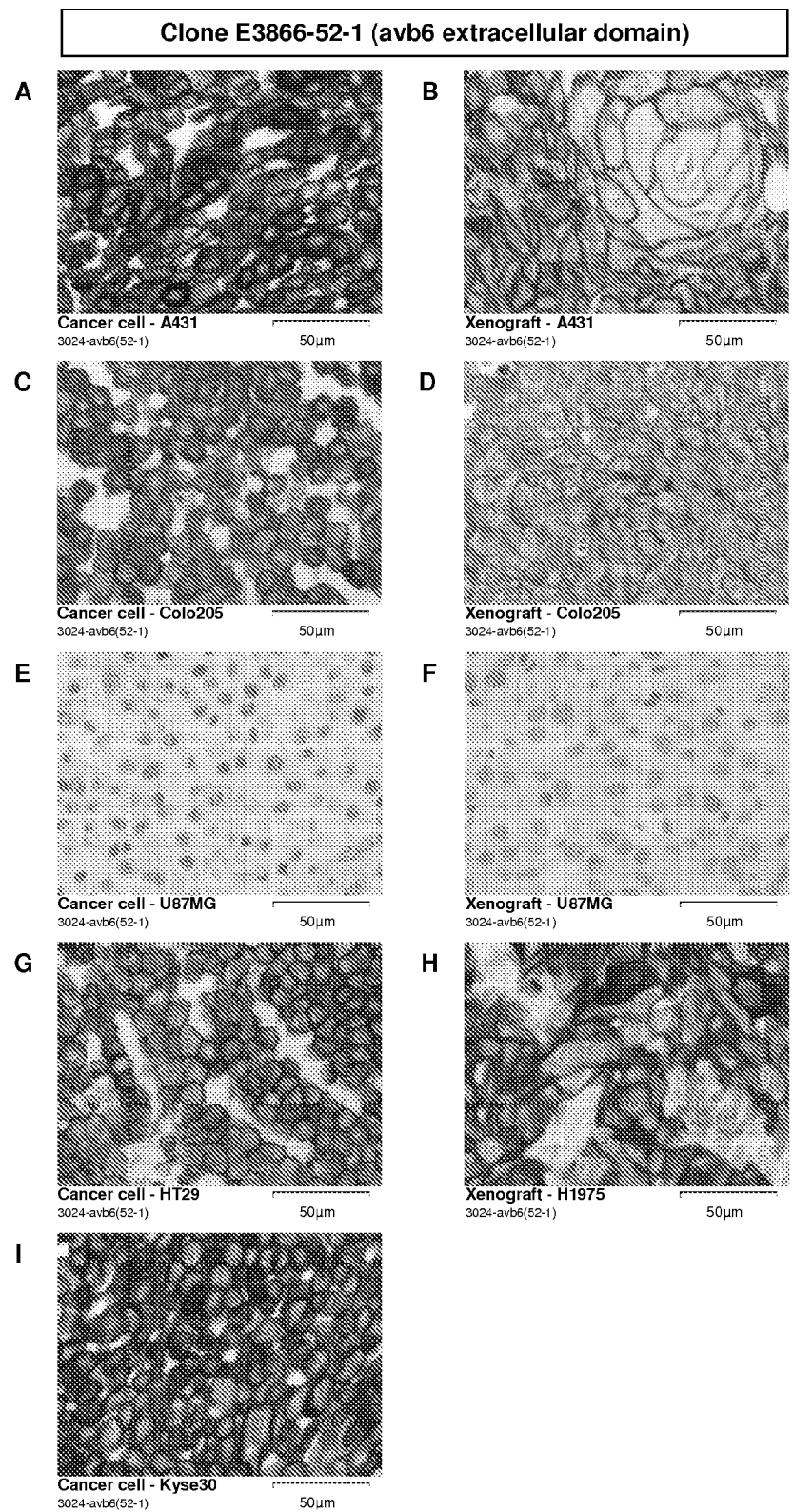
FIG. 14 shows the immunohistochemical staining of FFPE cancer cell lines (left) and xenografts (right) with supernatants of the subclone E3866-52-1.

The supernatants from 33 subclones obtained from these multiclones were screened undiluted on the FFPE cell line array of cancer cell lines CAX08. Cytoplasmic signals without clear membrane profile were excluded as non-integrin specific. Many subclone supernatants tested on the cancer cell lines were positive after heat as well as after protease pretreatment. Subclones of the multiclones 52 (FIG. 14), 106 and 118 showed a good plasma membrane staining. The positive subclones were tested in a second run on the xenograft array Xeno-08-Mu1 to confirm cross-reactivity on tumor tissue. Protease pre-treatment resulted in a higher signal for the subclones of 52 and 106. Therefore, these subclone supernatants were tested on protease pretreated xenografts only. The different subclones of the multiclone 52 were identical in their staining selectivity and specificity. The clone 106-1 was negative in SW707 in contrast to the subclones of the multiclones 52 and 118 (Table 6).

TABLE 6

Subclone supernatants to extracellular αvβ6 domain. The staining intensity was graded from
from − (negative) to +++ (strong) as well as from 0 (negative) to 3 (strong).

| Tissue Pretreatment Clone ID | Plasma-membrane | Cystoplasm | Comment |
|---|---|---|---|
| *Cancer cell lines (CAX08)* | | | |
| *Protease 0.1 units/ml 12 min* | | | |
| 52-1 | 3 | 0 | Kyse30+++, A431+++, MDA-MB468+++, Colo205++, HT29++, SW707+ |
| 52-2 | 3 | 0 | Kyse30+++, A431+++, MDA-MB468+++, Colo205++, HT29++, SW707+ |
| 52-3 | 3 | 0 | Kyse30+++, A431+++, MDA-MB468+++, Colo205++, HT29++, SW707+ |
| 52-4 | 3 | 0 | Kyse30+++, A431+++, MDA-MB468+++, Colo205++, HT29++, SW707+ |
| 52-5 | 3 | 0 | Kyse30+++, A431+++, MDA-MB468+++, Colo205++, HT29++, SW707+ |
| 52-6 | 3 | 0 | Kyse30+++, A431+++, MDA-MB468+++, Colo205++, HT29++, SW707+ |
| 52-7 | 3 | 0 | Kyse30+++, A431+++, MDA-MB468+++, Colo205++, HT29++, SW707+ |
| 52-8 | 3 | 0 | Kyse30+++, A431+++, MDA-MB468+++, Colo205++, HT29++, SW707+ |
| 52-9 | 3 | 0 | Kyse30+++, A431+++, MDA-MB468+++, Colo205++, HT29++, SW707+ |
| 52-10 | 2 | 0 | Kyse30++, A431++, MDA-MB468++, Colo205+, HT29+, SW707+ |
| 52-11 | 2 | 0 | Kyse30++, A431++, MDA-MB468++, Colo205+, HT29+, SW707+ |
| 52-12 | 2 | 0 | Kyse30++, A431++, MDA-MB468++, Colo205+, HT29+, SW707+ |
| 106-1 | 3 | 1 | Kyse30+++, A431+++, MDA-MB468+++, Colo205++, HT29++, SW707− |
| 118-1 | 3 | 0 | Kyse30++, A431++, MDA-MB468++, Colo205++, HT29++, SW707− |
| *Xenografts (Xeno-08-Mu1)* | | | |
| *Protease 0.1 units/ml 12 min* | | | |
| 52-1 | 3 | 1 | H1975+++, A431+++, Colo205++, SW707− |
| 52-2 | 3 | 1 | H1975+++, A431+++, Colo205++, SW707− |
| 52-3 | 3 | 1 | H1975+++, A431+++, Colo205++, SW707− |
| 52-4 | 3 | 1 | H1975+++, A431+++, Colo205++, SW707− |
| 52-6 | 3 | 1 | H1975+++, A431+++, Colo205++, SW707− |
| 52-8 | 3 | 1 | H1975+++, A431+++, Colo205++, SW707− |
| 52-9 | 3 | 1 | H1975+++, A431+++, Colo205++, SW707− |
| 106-1 | 1 | 0-1 | H1975+, A431+ |
| 118-1 | 3 | 0 | A431+++, H1975+++, Col205+, protease pre-treatment was better |

In xenograft tissue, the non small cell lung cancer cell line (NSCLC) H1975 showed the highest staining intensity (FIG. 14H). On the cancer cell line array, the two squamous cell carcinomas Kyse30 (FIG. 14I) and A431 (FIG. 14A), and on the xenograft array the A431 xenografts (FIG. 14B) showed a high signal. The cell lines with high staining intensity on the cancer cell line array were HT29 (FIG. 14G), MDA-MB468, Colo205 and A431. This corresponded to high β6 integrin mRNA of these cell lines. The selectivity and specificity of the subclone supernatants of the multiclones 52, 106 and 118 were in agreement with a αvβ6 epitope recognized by the antibodies. Nine subclones, 52-1, 52-2, 52-3, 52-4, 52-6, 52-8, 52-9, 106-1 and 118-1 were selected as final clones, based on staining intensity, selectivity regarding known αvβ6 integrin positive cells and quality of plasma membrane staining (Table 6). Of subclones with identical stainings, the ones with the highest IgG concentration were selected as final clones.

Figure 15A:
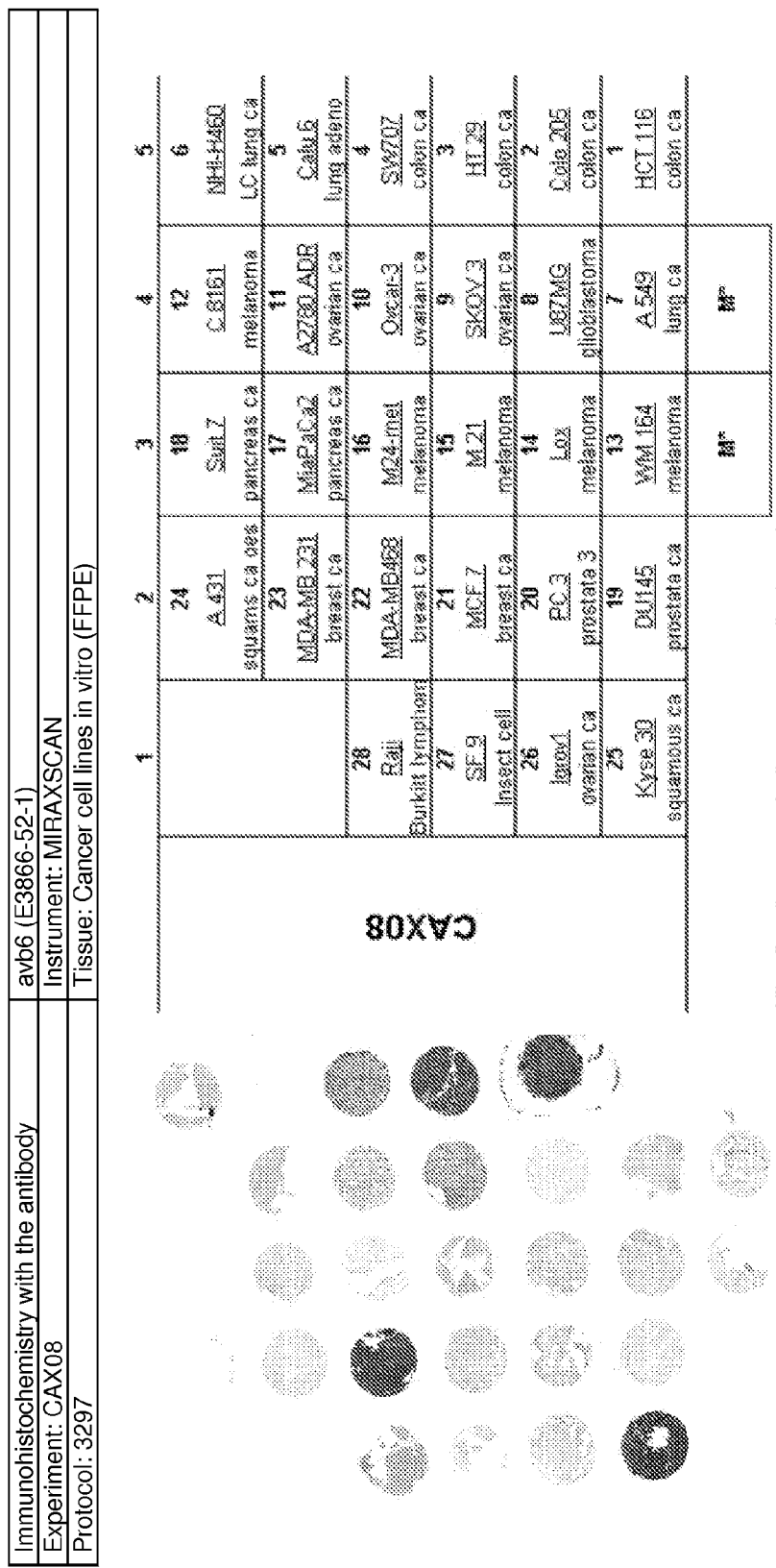
FIGS. 15A and B show the immunohistochemical staining of FFPE cancer cell lines with the purified antibody of subclone E3866-52-1.
Figure 15B:
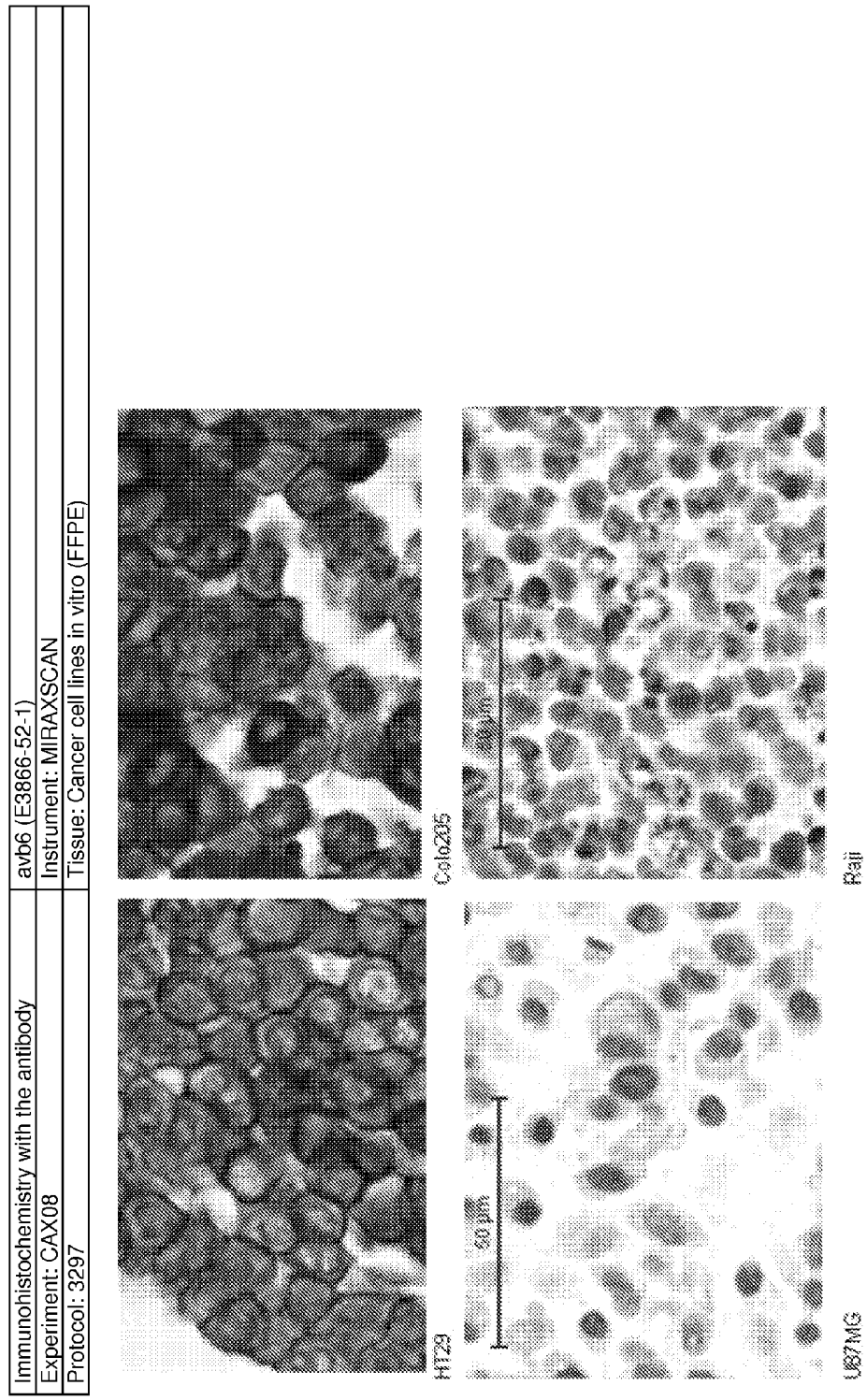
Figure 16:
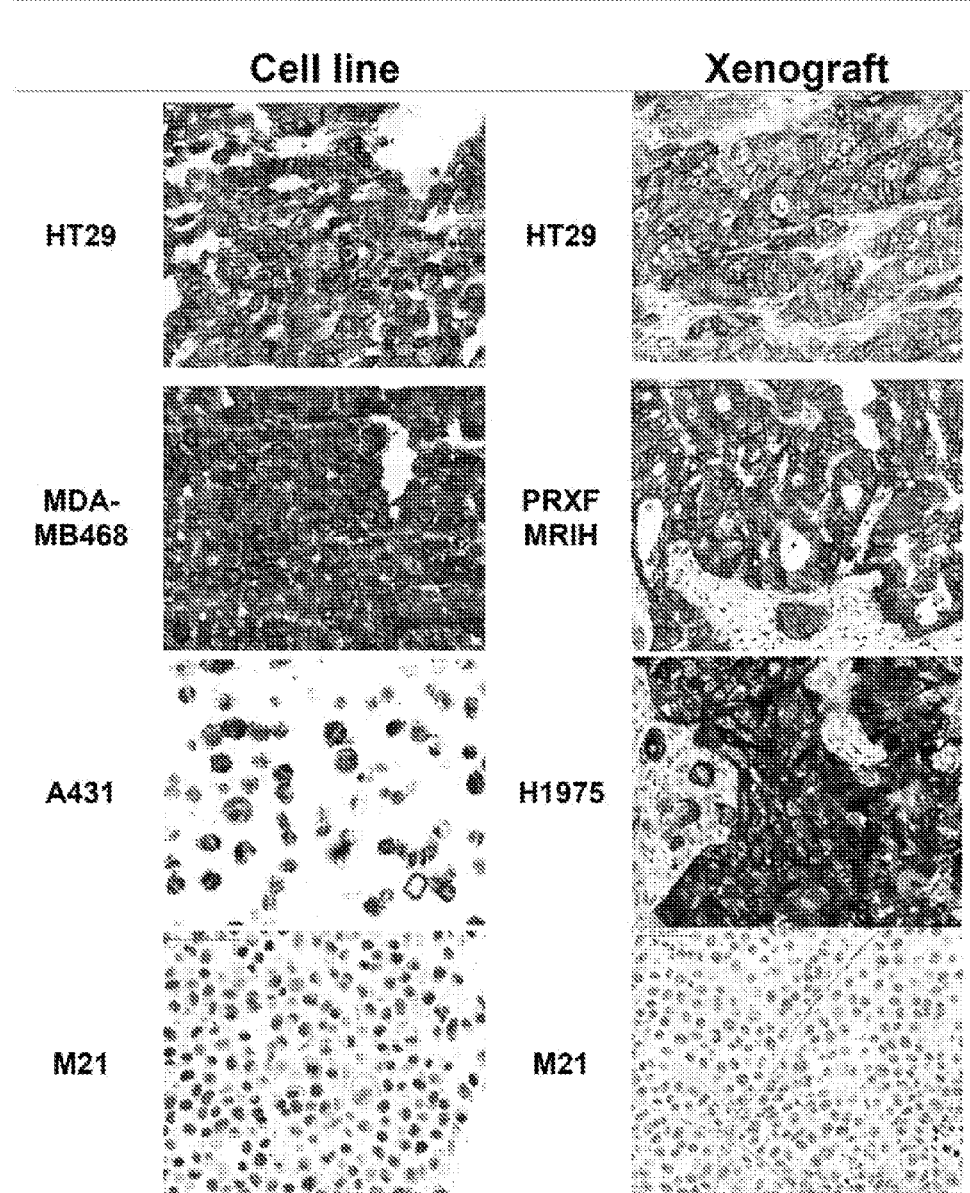
FIG. 16 shows the immunohistochemical staining of cancer cell lines and xenografts with the recombinant anti-$\alpha v \beta 6$ integrin antibody.
Figure 17:
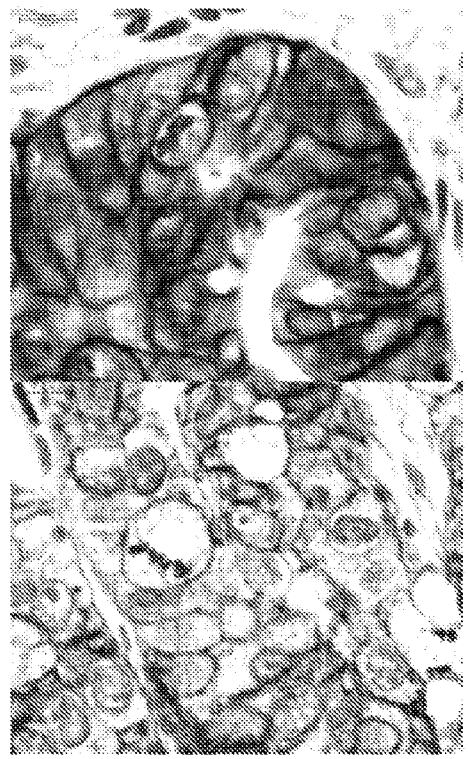
FIG. 17 shows the plasma membrane staining of prostata carcinoma cells (above) and HT29 colon carcinoma cells in xenografts with the recombinant anti-$\alpha v \beta 6$ integrin antibody.
Figure 18:
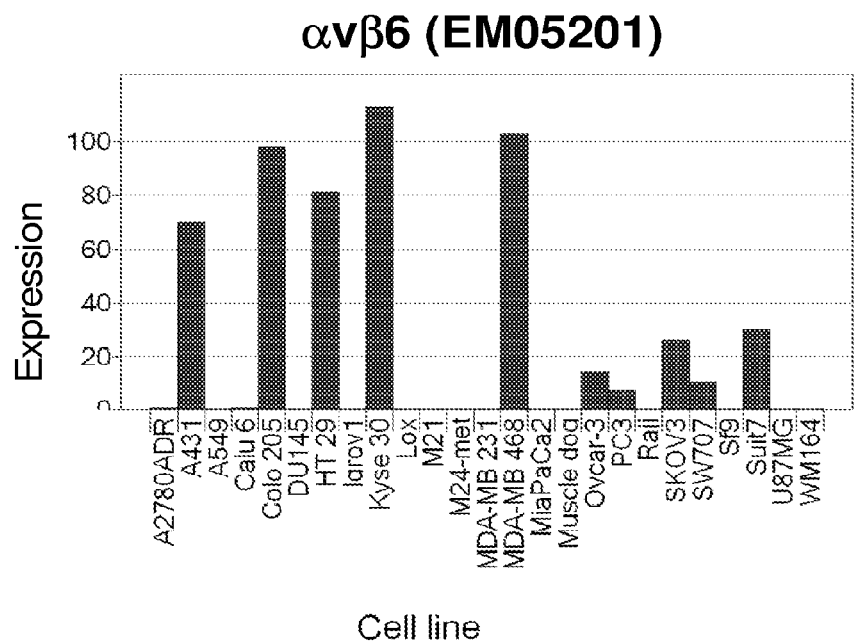
FIG. 18 shows the analysis of immunohistochemical staining (run 3421) with the anti-$\alpha v \beta 6$ antibody with the help of image analysis (Ariol SL-50).
Figure 19:
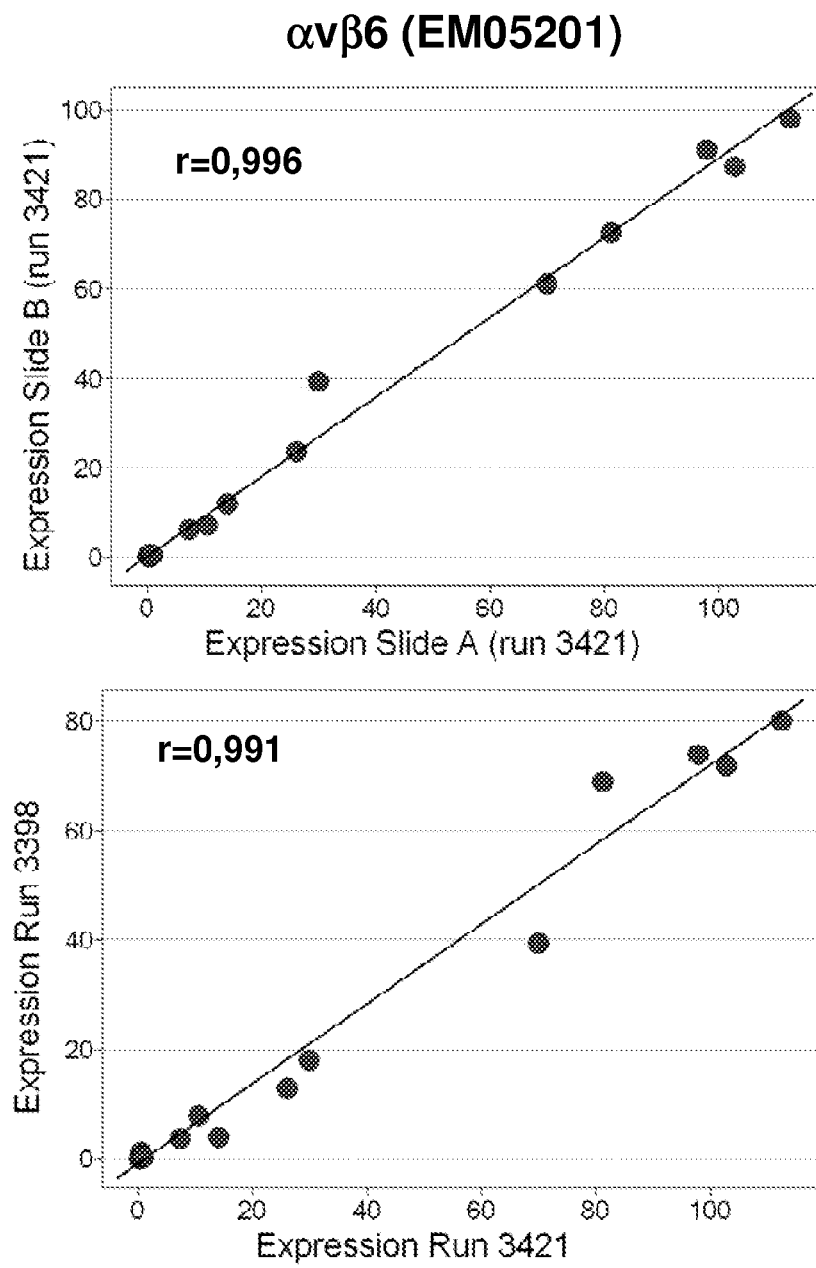
FIG. 19 shows the slide-to-slide and run-to-run reproducibility with the anti-$\alpha v \beta 6$ recombinant antibody.

The clone with the highest IgG concentration, clone E3866-52-1, was cultured and the antibody purified according to standard protocols. Activity of the antibody was shown by IHC on the cancer cell line array (FIGS. 15A and B). With the recombinant antibody, several slides of the cancer cell line array and xenografts were stained (FIG. 16). In xenografts of HT29 colon cancer, H1975 lung carcinoma and a patient prostata tumor explant PRXF MRIH (Oncotest GmbH, Freiburg) the anti-αvβ6 recombinant antibody showed a pronounced signal, whereas a M21 melanoma xenograft with no β6 mRNA expression, was negative (FIG. 16). The anti-αvβ6 recombinant antibody showed a clear staining of the plasma membrane (FIG. 17). The signal on the cancer cell line array was quantified with the help of image analysis (FIG. 18). The cell lines with high antibody staining signal, as were HT29, Colo205 or MDA-MB468, corresponded to the cell lines with high mRNA levels of the β6 integrin mRNA. The recombinant anti-αvβ6 antibody showed high slide-to-slide (r=0.996) and run-to-run reproducibility (r=0.991, FIG. 19) using automatized staining procedures.

The rabbit IgG recombinant antibody αvβ6 (EM05201) generated against an αvβ6-integrin peptide was suitable for FFPE tissue. The ELISA specificities and staining characteristics of the recombinant antibody αvβ6 (EM05201), as were "plasma membrane staining" and high signal in cell lines expressing high β6 integrin mRNA, were in agreement with an αvβ6-integrin epitope of the antibody.

EXAMPLE 7

Characterization of Anti-αvβ8 Clones and Anti-αvβ8-Antibodies

Figure 20:
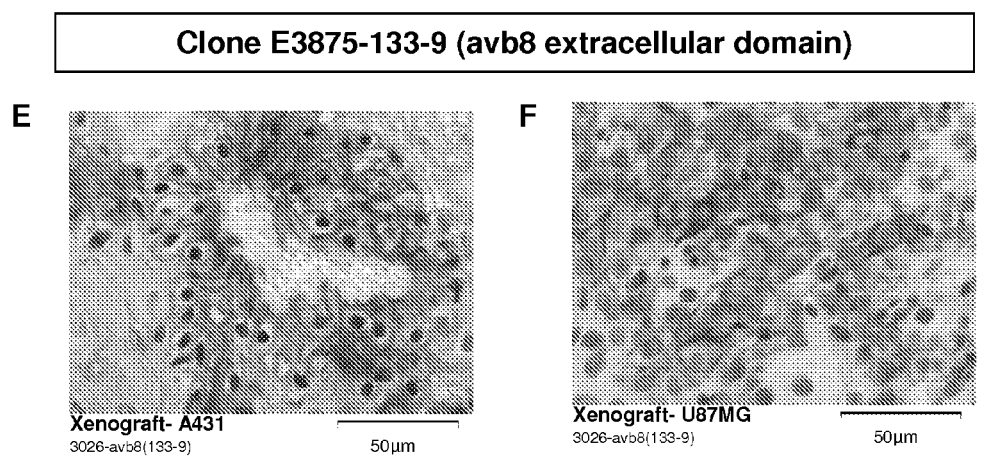
FIG. 20 shows the immunohistochemical staining of FFPE cancer cell lines and xenografts with supernatants of the anti-$\alpha v \beta 8$ subclone 133-9.

The supernatants from 36 subclones obtained from these multiclones were screened undiluted on the FFPE cell line array of cancer cell lines CAX08. All 36 subclones showed a membrane signal, none was excluded due to non-integrin specific cytoplasmic staining. Many subclone supernatants tested on the cancer cell lines were positive after heat as well as after protease pre-treatment. For each multiclone, the four subclones with the highest IgG concentrations were selected for further testing on the xenograft array Xeno-08-Mu1 to confirm cross-reactivity on tumor tissue (FIG. 20). Protease pre-treatment resulted in a higher signal for the subclones. The subclones of the multiclone 6 were negative on the xenografts. The cell lines with high staining intensity on the cancer cell line array, as were Ovcar-3, M24met, MDA-MB 468 and A431 showed the highest mRNA expression of the β8 integrin (Table 7). The subclones 40-4, 40-10, 40-11, 133-5, 133-8 and 133-9 were selected as final clones, based on selectivity regarding known 138 mRNA expression and quality of plasma membrane staining. Of subclones with identical stainings, the ones with the highest IgG concentration were selected as final clones.

TABLE 7

Subclone supernatants to extracellular αvβ8 domain. The staining intensity was graded from from − (negative) to +++ (strong) as well as from 0 (negative) to 4 (very strong).

| Tissue Pre-treatment Clone ID | Plasma-membrane | Cystoplasm | Comment |
|---|---|---|---|
| Cancer cell lines (CAX08) Protease 0.1 units/ml 12 min | | | |
| 6-1 | 3 | 0 | Ovcar3+++ and Scov3++ at contact zones |
| 6-5 | 3 | 0 | Ovcar3+++ and Scov3++ at contact zones |
| 6-8 | 3 | 0 | Ovcar3+++ and Scov3++ at contact zones |
| 6-12 | 3 | 0 | Ovcar3+++ and Scov3++ at contact zones |
| 40-4 | 3 | 0 | Ovcar3+++ and Scov3++ at contact zones |
| 40-9 | 3 | 0 | Ovcar3+++ and Scov3++ at contact zones |
| 40-10 | 3 | 0 | Ovcar3+++ and Scov3++ at contact zones |
| 40-11 | 3 | 0 | Ovcar3+++ and Scov3++ at contact zones |
| 133-5 | 4 | 0 | Ovcar3+++ and Scov3++ at contact zones, A431++, MDA-MB468+++, M24-met+++, Scov3++, Igrov1+++, PC3++, Kyse30++ |
| 133-8 | 4 | 0 | Ovcar3+++ and Scov3++ at contact zones, A431++, MDA-MB468+++, M24-met+++, Scov3++, Igrov1+++, PC3++, Kyse30++ |
| 133-9 | 4 | 0 | Ovcar3+++ and Scov3++ at contact zones, A431++, MDA-MB468+++, M24-met+++, Scov3++, Igrov1+++, PC3++, Kyse30++ |
| 133-12 | 4 | 0 | Ovcar3+++ and Scov3++ at contact zones, A431++, MDA-MB468+++, M24-met+++, Scov3++, Igrov1+++, PC3++, Kyse30++ |
| Xenografts (Xeno-08-Mu1) Protease 0.1 units/ml 12 min | | | |
| 6-1 | 0 | 0 | strong on Ovcar3 in vitro, negative on xenografts |
| 6-5 | 0 | 0 | strong on Ovcar3 in vitro, negative on xenografts |
| 6-8 | 0 | 0 | strong on Ovcar3 in vitro, negative on xenografts |
| 6-12 | 0 | 0 | strong on Ovcar3 in vitro, negative on xenografts |
| 40-4 | 0 | 0 | strong on Ovcar3 in vitro, negative on xenografts |
| 40-9 | 0 | 0 | strong on Ovcar3 in vitro, negative on xenografts |
| 40-10 | 0 | 0 | strong on Ovcar3 in vitro, negative on xenografts |
| 40-11 | 0 | 0 | strong on Ovcar3 in vitro, negative on xenografts |
| 133-5 | 3 | 0 | U87MG++, A431++ |
| 133-8 | 3 | 0 | U87MG++, A431++ |
| 133-9 | 3 | 0 | U87MG++, A431++ |
| 133-12 | 3 | 0 | U87MG++, A431++ |

Figure 21A:
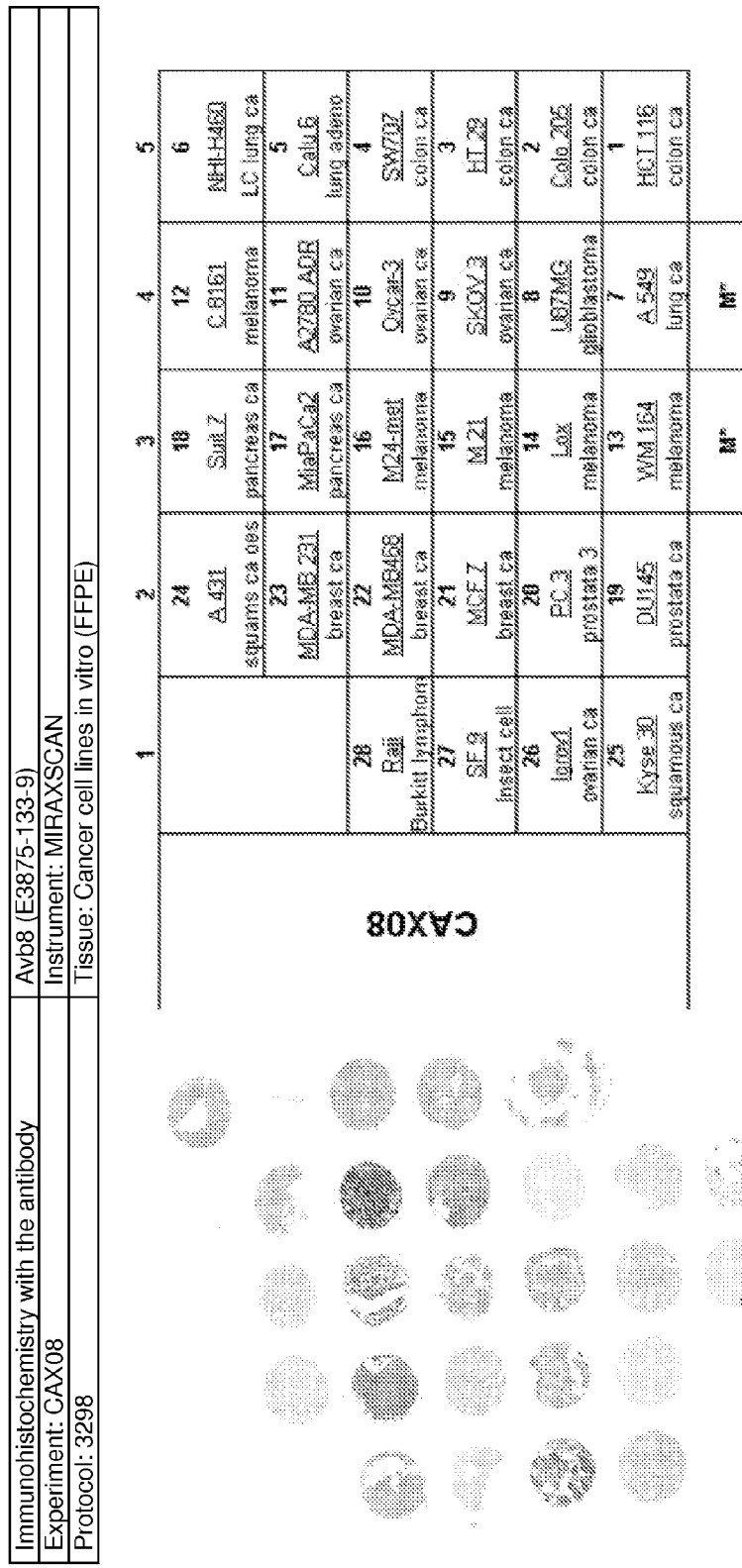
FIGS. 21A and B show the immunohistochemical staining of FFPE cancer cell lines with the purified antibody of anti-$\alpha v \beta 8$ subclone E3875-133-9.
Figure 21B:
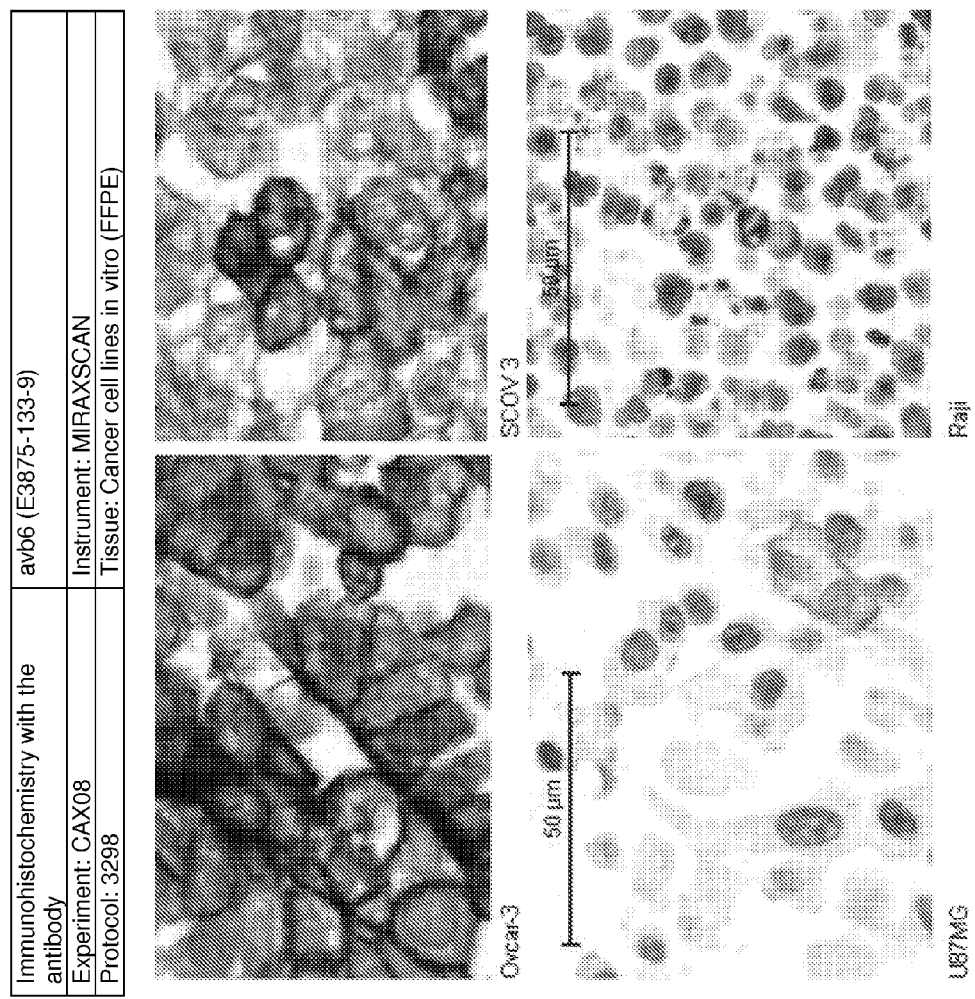

The clone with the highest IgG concentration, clone E3875-133-9, was cultured and the antibody purified according to standard protocols. Activity of the antibody was shown by IHC on the cancer cell line array (FIGS. 21A and B).

Figure 22:
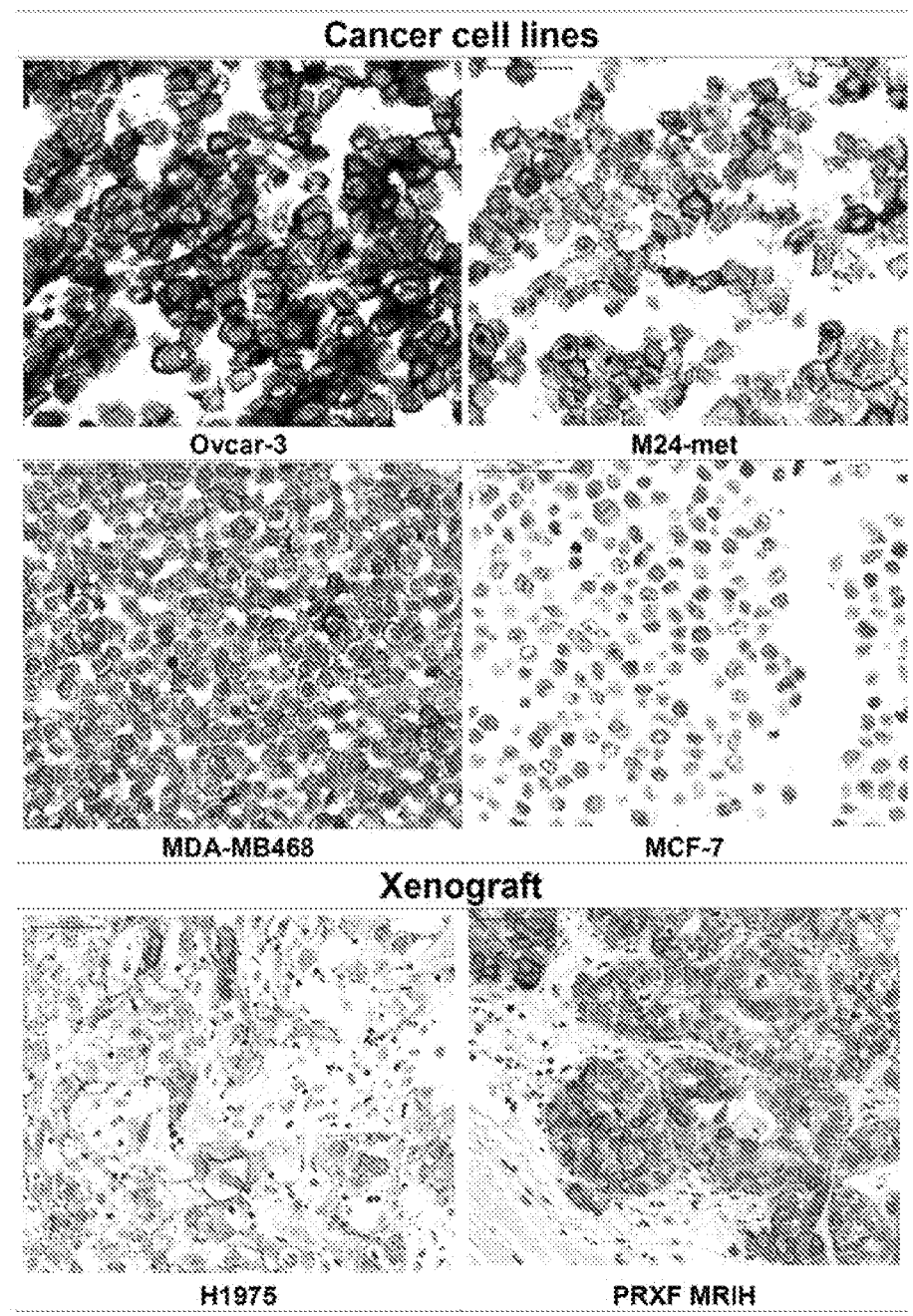
FIG. 22 shows the immunohistochemical staining of cancer cell lines and xenografts with the recombinant anti-αvβ8 integrin antibody EM13309.
Figure 23:
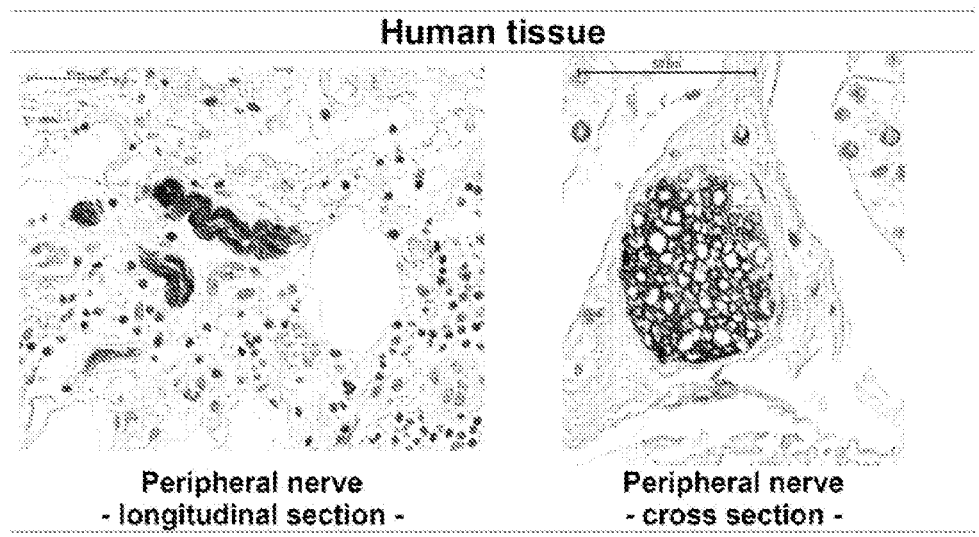
FIG. 23 shows the immunohistochemical staining of human tissue with the recombinant anti-αvβ8 integrin antibody EM13309.
Figure 24:
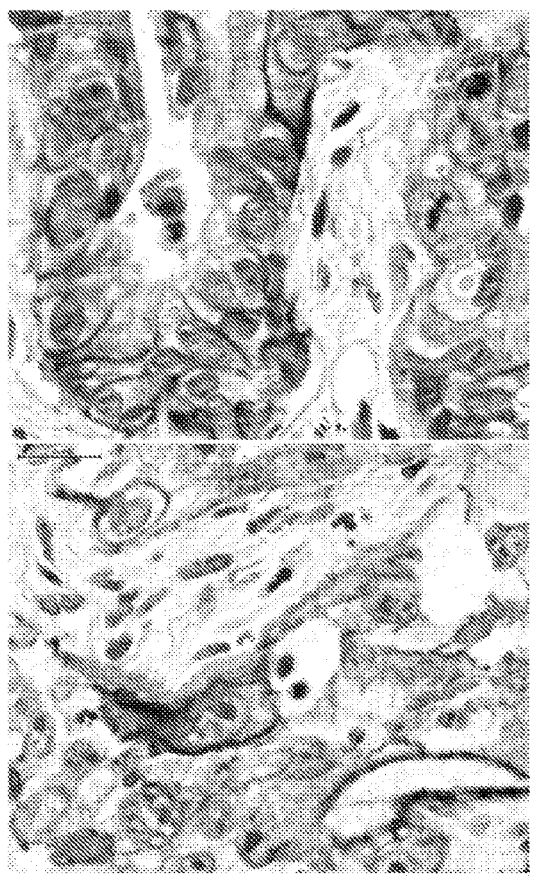
FIG. 24 shows the plasma membrane staining of prostata carcinoma cells (above) and H1975 lung carcinoma cells in xenografts with the recombinant anti-αvβ8 integrin antibody.
Figure 25:
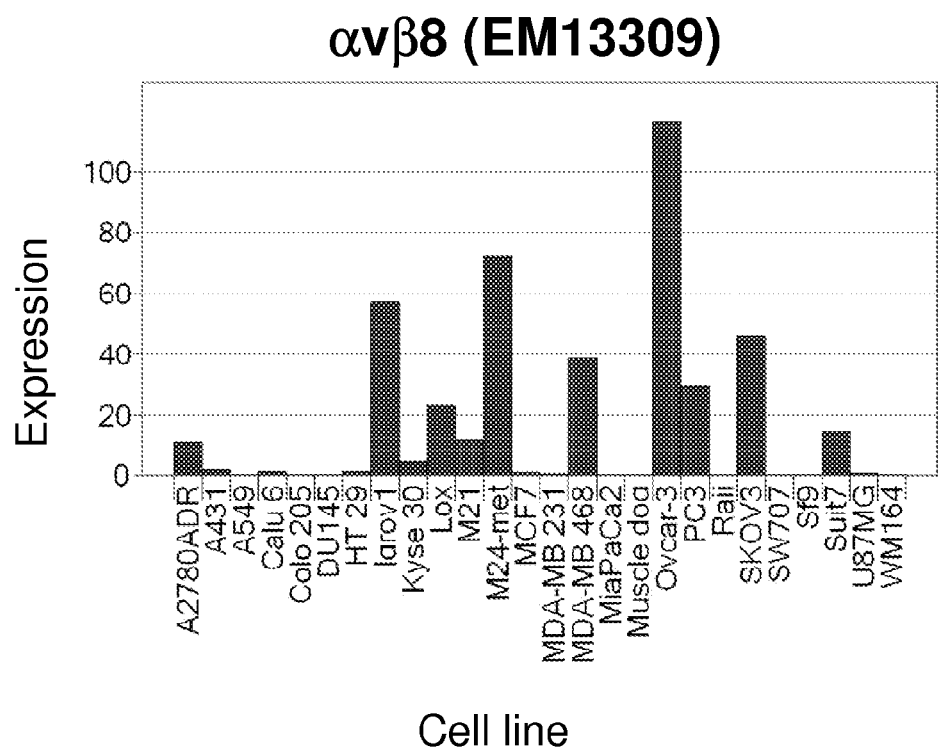
FIG. 25 shows the analysis of immunohistochemical staining (run 3422) with the anti-αvβ8 antibody EM13309 with the help of image analysis (Ariol SL-50).
Figure 26:
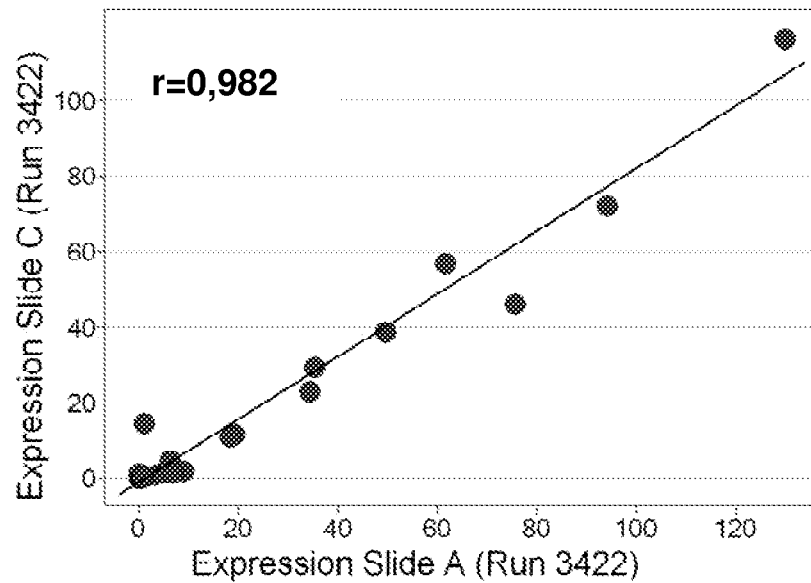
FIG. 26 shows the slide-to-slide and run-to-run reproducibility with the anti-αvβ8 recombinant antibody EM13309.
Figure 26:
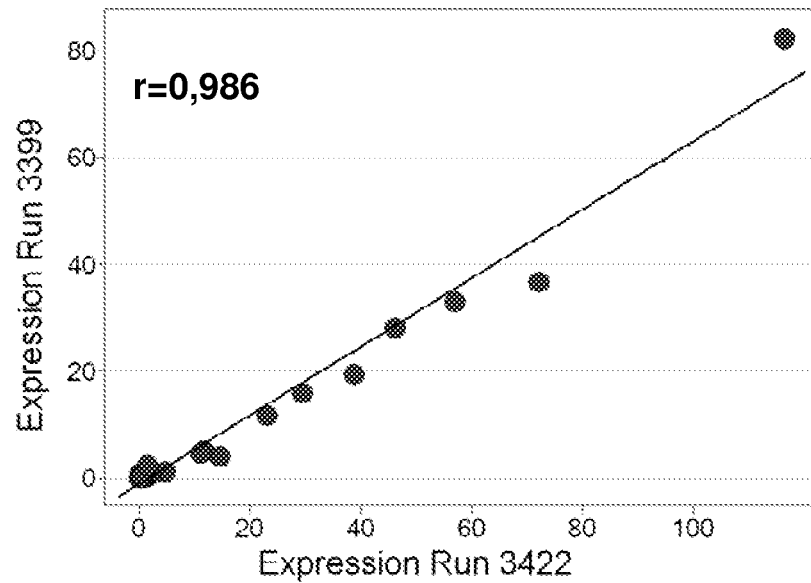

With the recombinant antibody, several slides of the cancer cell line arrays, xenografts, and an array out of normal human tissue were stained. The cancer cell lines Ovcar-3 (ovarian carcinoma), M24-met (melanoma) and MDA-MB468 (breast carcinoma), all expressing 138 mRNA, were positive, whereas MCF-7 cells (breast carcinoma) without P8 mRNA, were negative (FIG. 22). From these cell lines, no xenografts were available. In H1975 lung carcinoma xenografts and stronger in the prostata tumor explant PRXF MRIH (Oncotest GmbH, Freiburg) xenografts the anti-αvβ38 recombinant antibody showed some signal (FIG. 22). The strongest signal was observed in human peripheral nerves (FIG. 23). The anti-αvβ8 recombinant antibody showed a clear staining of the plasma membrane (FIG. 24). The signal on the cancer cell line array was quantified with the help of image analysis (FIG. 25). The cell lines with high antibody staining signal, as were Ovcar-3, M24-met, and MDA-MB468, corresponded to the cell lines with high mRNA levels of the β8 integrin mRNA. The recombinant anti-αvβ8 antibody showed high slide-to-slide (r=0.982) and run-to-run reproducibility (r=0.986, FIG. 26).

The rabbit IgG recombinant antibody αvβ8 (EM13309) generated against a αvβ8-integrin peptide was suitable for FFPE tissue. The ELISA specificities and staining characteristics of the recombinant antibody αvβ8 (EM13309) as are "plasma membrane staining", high signal in cell lines expressing high 18 integrin mRNA, and strong labeling of myelinated peripheral nerves were in agreement with a αvβ8-integrin epitope of the antibody.

EXAMPLE 8

Characterization of Anti-αv Clones and Anti-αv-Antibodies

Figure 27:
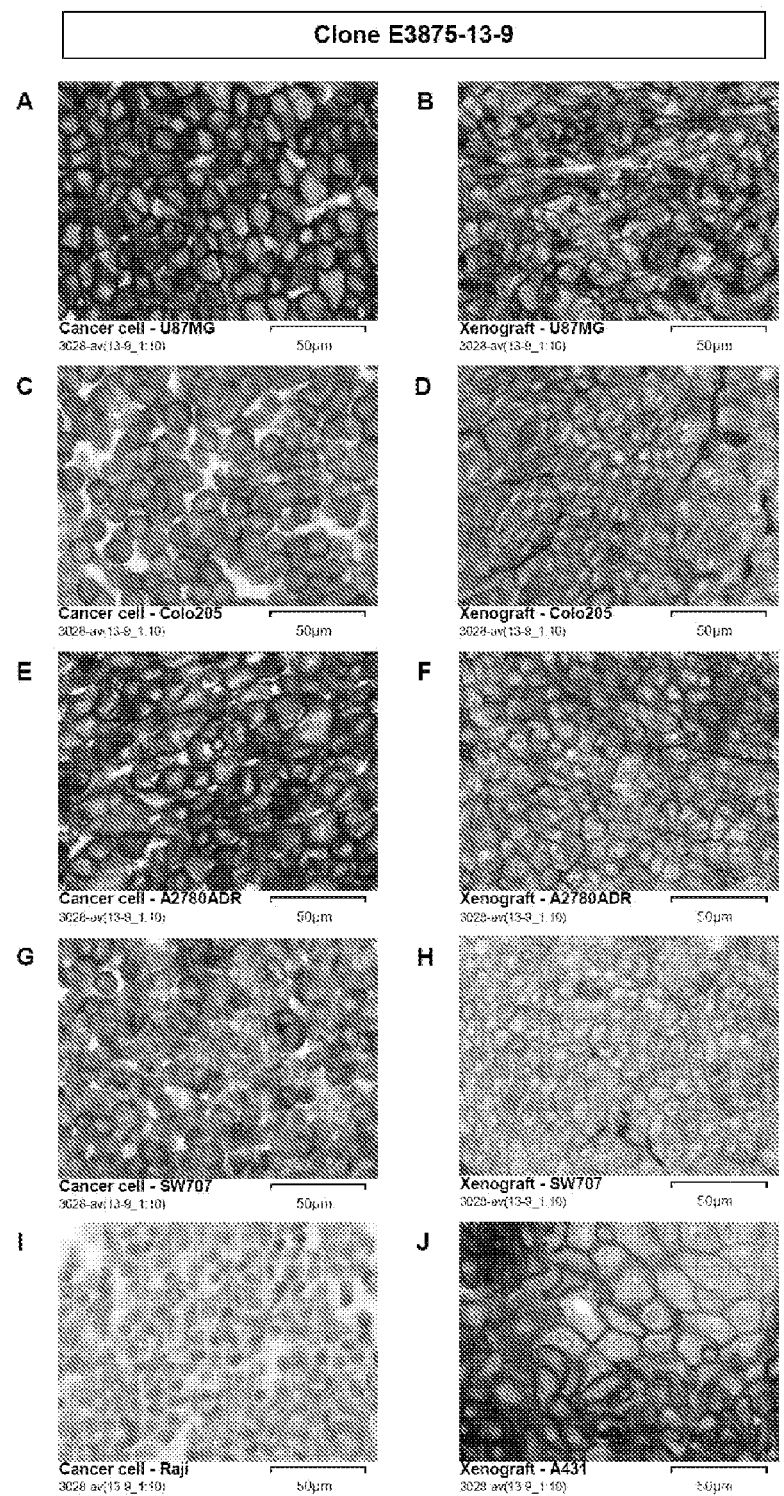
FIG. 27 shows the immunohistochemical staining of FFPE cancer cell lines and xenografts with supernatants of the anti-αv subclone E3875-13-9.

The previously selected multiclones that bind to αvβ6 as well as to αvβ8 were the multiclones E3866-68 and E3875-13. The supernatants from 24 subclones obtained from these multiclones were screened undiluted on the FFPE cell line array of cancer cell lines CAX08. All 24 subclones showed a high plasma membrane signal, however also some cytoplasmic signal (FIG. 27). Nine subclones, 5 of the multiclone E3875-13 and 4 of the multiclone E3866-68, were selected for testing on xenograft tissue to confirm cross-reactivity on tumor tissue. Because of a very high signal, supernatants of clones 13-3, 13-9 and 68-7 were diluted 1:5 and 1:10. The diluted supernatants 13-3- and 13-9 stained all cells on the cancer cell line array except Raji lymphoma cells and the Sf9 insect cell. The xenografts show high plasma membrane signal, and also some cytoplasmic staining (FIG. 27). After 1:5 dilution the subclone 68-7 did not stain MiaPaca2, a cell line that was positive with the subclone 13-3. The epitope of the subclones of the multiclone E3688-68 might be different from E3875-13. The subclones E3875-13-3 and -13-9 were selected as final clones, based on their highest IgG concentration (Table 8).

Figure 29:
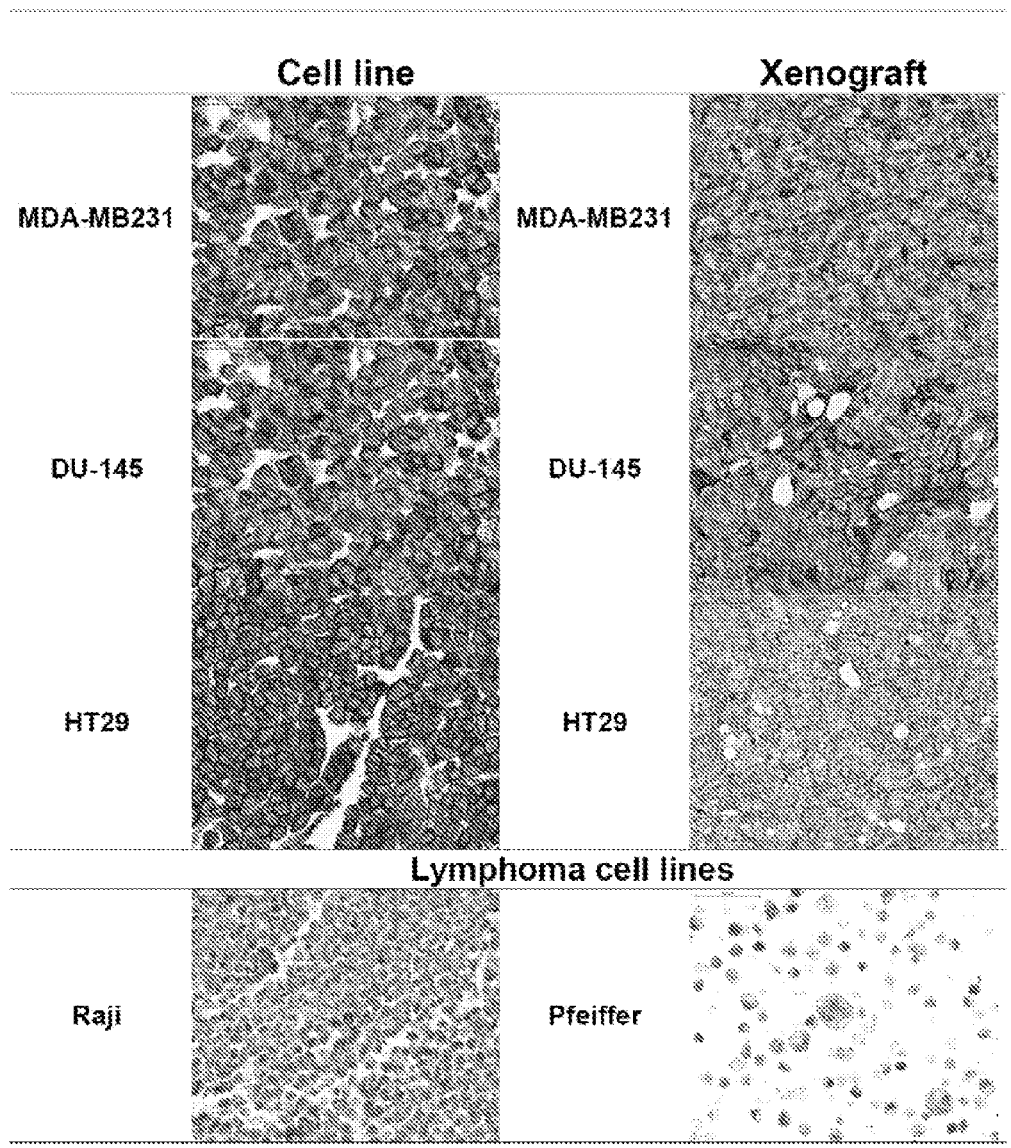
FIG. 29 shows the immunohistochemical staining of cancer cell lines and xenografts with the recombinant anti-αv antibody EM01309.
Figure 30:
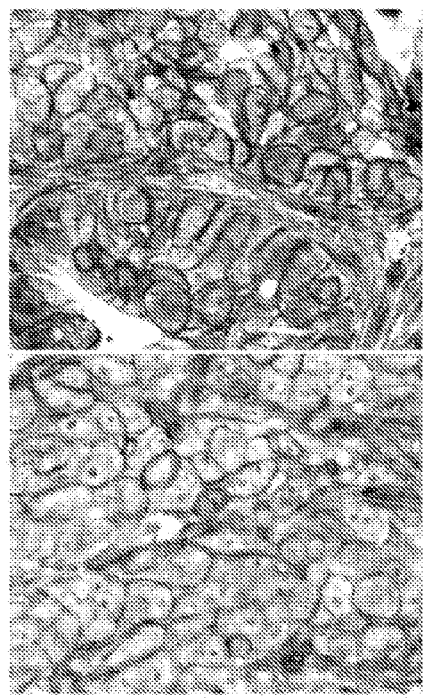
FIG. 30 shows the plasma membrane staining of DU-145 (above) and HT29 cells in xenografts with the recombinant anti-αv antibody EM01309.
Figure 31:
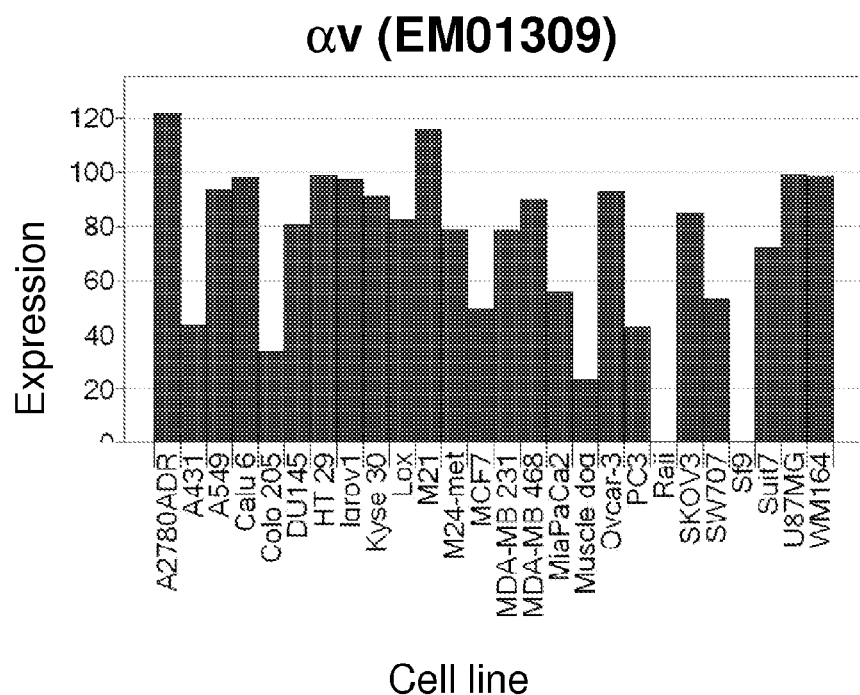
FIG. 31 shows the analysis of immunohistochemical staining with the recombinant anti-αv antibody EM01309 with the help of image analysis (Ariol SL-50).

With the recombinant antibody, several slides of the cancer cell line arrays and xenograft arrays were stained (FIG. 29). In cancer cell lines as well as in xenografts the anti-αv recombinant antibody showed a pronounced signal. Negative are lymphoma cell lines, like Raji and Pfeiffer lymphoma that do not express αv-integrin mRNA. The anti-αv recombinant antibody showed a clear staining of the plasma membrane (FIG. 30). The signal on the cancer cell line array was quantified with the help of image analysis (FIG. 31). The recom-

TABLE 8

Subclone supernatants to extracellular αv domain. The staining intensity was graded from from − (negative) to +++ (strong) as well as from 0 (negative) to 3 (strong).

| Tissue Pre-treatment Clone ID | Plasma-membrane | Cystoplasm | Comment |
|---|---|---|---|
| Cancer cell lines (CAX08) Heat in Tris EDTA pH 8 | | | |
| 2b-E3875-13-3 | 3 | 1 | high plasma membrane and Golgi, some cytoplasmic |
| 2b-E3875-13-5 | 3 | 1 | high plasma membrane and Golgi, some cytoplasmic |
| 2b-E3875-13-6 | 3 | 1 | high plasma membrane and Golgi, some cytoplasmic |
| 2b-E3875-13-7 | 3 | 1 | high plasma membrane and Golgi, some cytoplasmic |
| 2b-E3875-13-9 | 3 | 1 | high plasma membrane and Golgi, some cytoplasmic |
| 2a-E3866-68-4 | 3 | 2 | high plasma membrane, Golgi also positive, not clean, some cytoplasmic |
| 2a-E3866-68-5 | 3 | 2 | high plasma membrane, Golgi also positive, not clean, some cytoplasmic |
| 2a-E3866-68-7 | 3 | 2 | high plasma membrane, Golgi also positive, not clean, some cytoplasmic |
| 2a-E3866-68-9 | 3 | 2 | high plasma membrane, Golgi also positive, not clean, some cytoplasmic |
| Xenografts (Xeno-08-Mu1) Heat in Tris EDTA pH 8 | | | |
| 2b-E3875-13-3 | 3 | 2 | 1:5 and 1:10 dilution tested, high plasma membrane and Golgi, also still some cytoplasm, better staining of A431 than 68-clone |
| 2b-E3875-13-5 | 3 | 2 | high plasma membrane and Golgi, also cytoplasm probably due to very high signal, better staining of A431 than 68-clone |
| 2b-E3875-13-6 | 3 | 2 | high plasma membrane and Golgi, also cytoplasm probably due to very high signal, better staining of A431 than 68-clone |
| 2b-E3875-13-7 | 3 | 2 | high plasma membrane and Golgi, also cytoplasm probably due to very high signal, better staining of A431 than 68-clone |
| 2b-E3875-13-9 | | | 1:5 and 1:10 dilution tested, high plasma membrane and Golgi, also still some cytoplasm, better staining of A431 than 638-clone |
| 2a-E3866-68-4 | 3 | 1 | high plasma membrane staining and Golgi, several cells also cytoplasm, might be due to high concentration |
| 2a-E3866-68-5 | 3 | 1 | high plasma membrane staining and Golgi, several cells also cytoplasm, might be due to high concentration |
| 2a-E3866-68-7 | 3 | 1 | high plasma membrane staining and Golgi, several cells also cytoplasm, might be due to high concentration, with 1:5 and 1:10 dilution MlaPaCa2 negative |
| 2a-E3866-68-9 | 3 | 1 | high plasma membrane staining and Golgi, several cells also cytoplasm, might be due to high concentration |

Figure 28A:
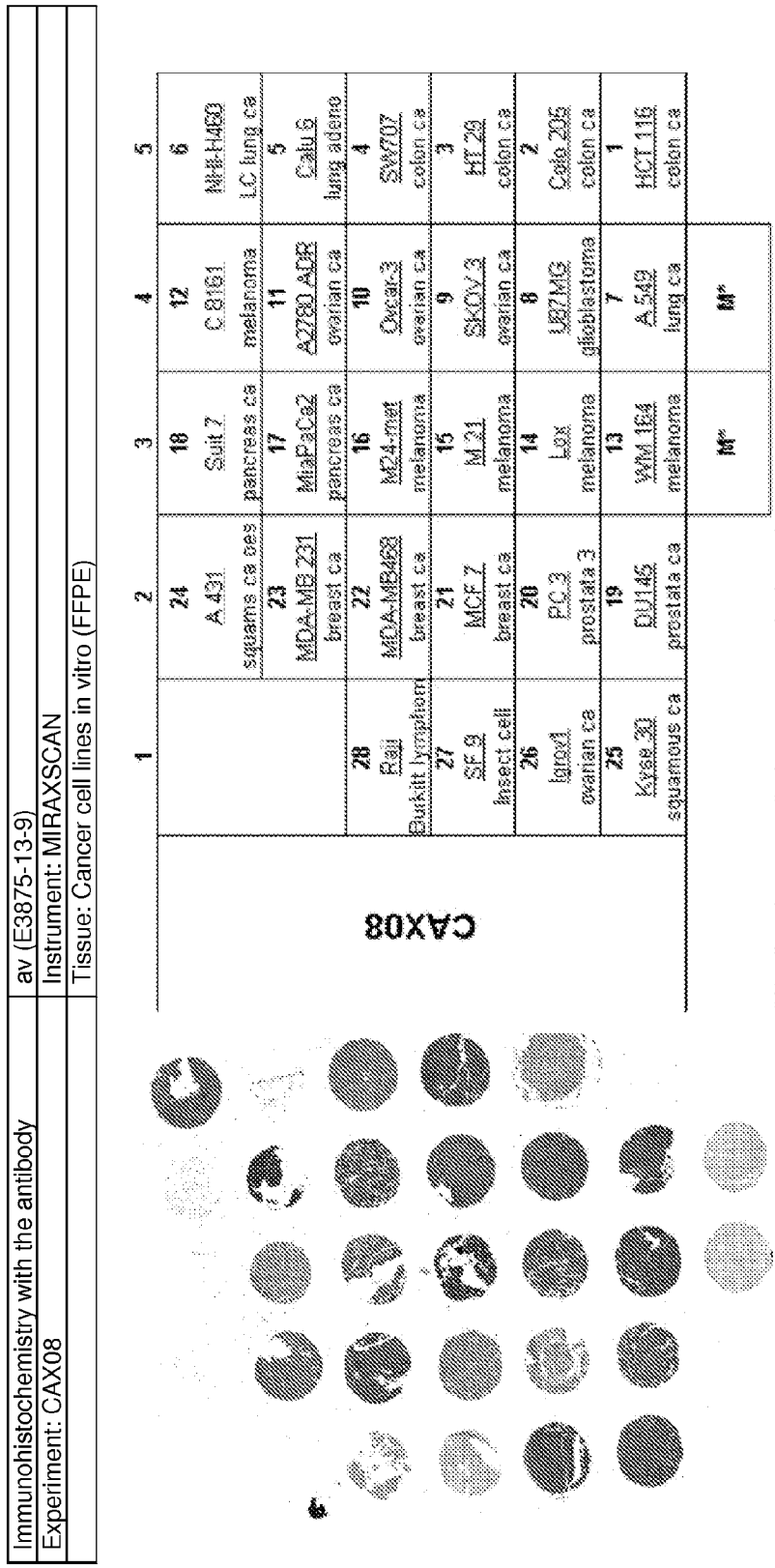
FIGS. 28A and B show the immunohistochemical staining of FFPE cancer cell lines with the purified anti-αv antibody of subclone E3875-13-9.
Figure 28B:
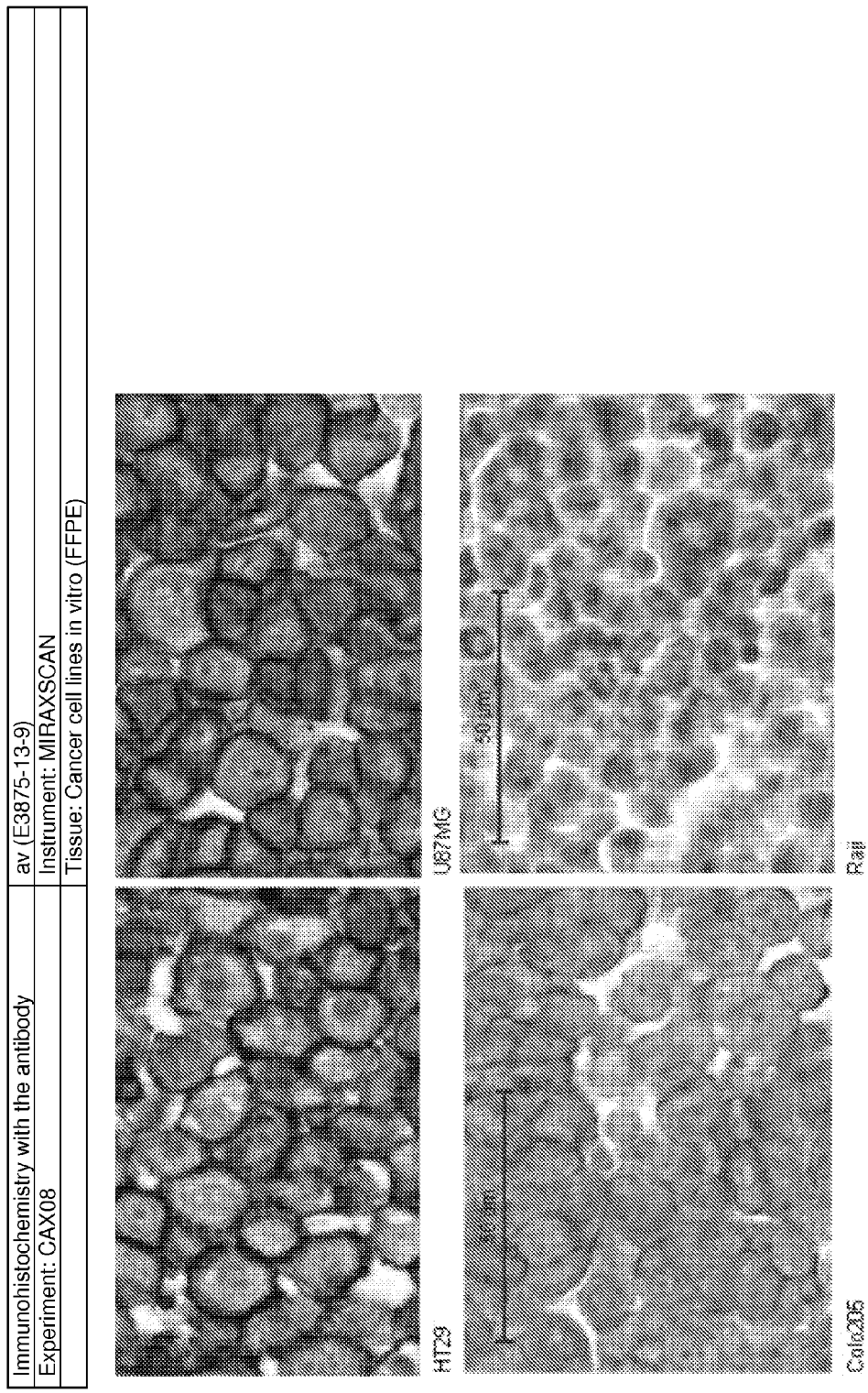
Figure 32:
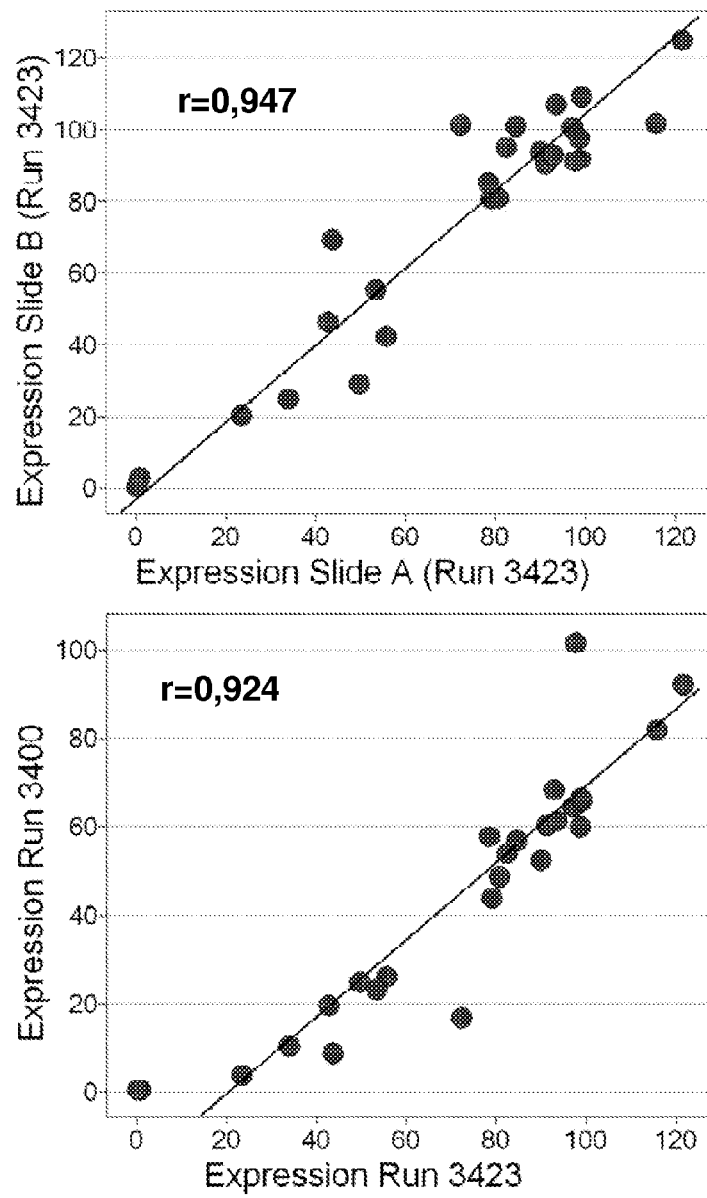
FIG. 32 shows the slide-to-slide and run-to-run reproducibility with the anti-αv recombinant antibody EM01309.

The clone with the highest IgG concentration, clone E3875-13-9, was cultured and the antibody purified according to standard protocols (Protein G Sepharose, HiLoad Superdex 200 pg). Activity of the antibody was shown by IHC on the cancer cell line array (FIGS. 28A and B).

binant anti-αv antibody showed slide-to-slide (r=0.947) and run-to-run reproducibility (r=0.924, FIG. 32).

The rabbit IgG recombinant antibody αv (EM01309) generated against the αvβ8-integrin peptide was suitable for FFPE tissue. The ELISA specificities and staining characteristics of the recombinant antibody αv (EM01309), as were "plasma membrane staining", high signal in cell lines expressing αv-integrin mRNA, and no signal in lymphoma cell lines not expressing αv-integrin were in agreement with the αv-chain epitope of the antibody.

EXAMPLE 9

Characterization of Anti-β3 Cytoplasmic Domain Integrin Clones and Anti-β3-Cytoplasmic Domain Integrin Antibodies The supernatants from 24 subclones obtained from multiclones 2 and 67 were screened undiluted on the FFPE cell line array of cancer cell lines CAX05. Cytoplasmic signals without clear membrane profile were excluded as non-integrin specific. Subclones of the multiclone 2 exhibited a good plasma membrane staining. The selectivity of the subclones regarding certain cell types was compared with the mouse monoclonal IgG, clone 20H9. The positive subclones were tested in a second run on the xenograft array Xeno-08-A to confirm cross-reactivity on tumor tissue. Three subclones, 2-4, 2-10 and 2-12, were selected as final clones, based on staining intensity, selectivity regarding known αvβ3 integrin positive cells, and quality of plasma membrane staining (Table 9).

Figure 33:
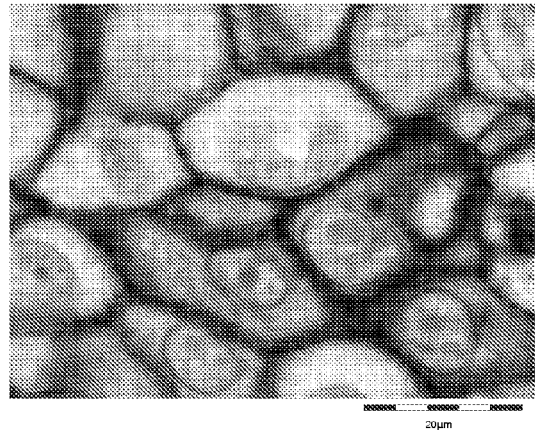
FIG. 33 shows the plasma membrane staining of M21 cells in xenografts with the purified anti-β3 integrin antibody clone E3592-2-12.
Figure 34:
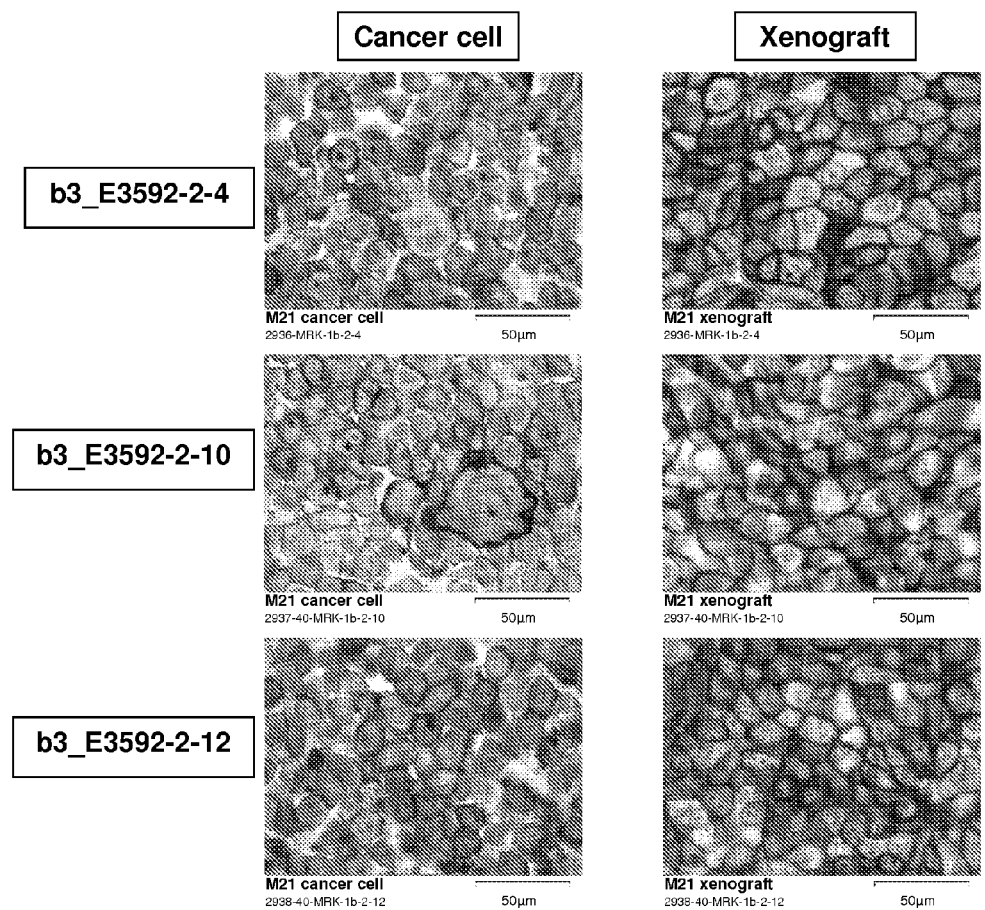
FIG. 34 shows the immunohistochemical staining of the cancer cell line M21 (left) and the M21 xenograft (right) with the purified anti-β3 integrin antibodies E3592-2-4, E3592-2-10 and E3592-2-12.
Figure 35:
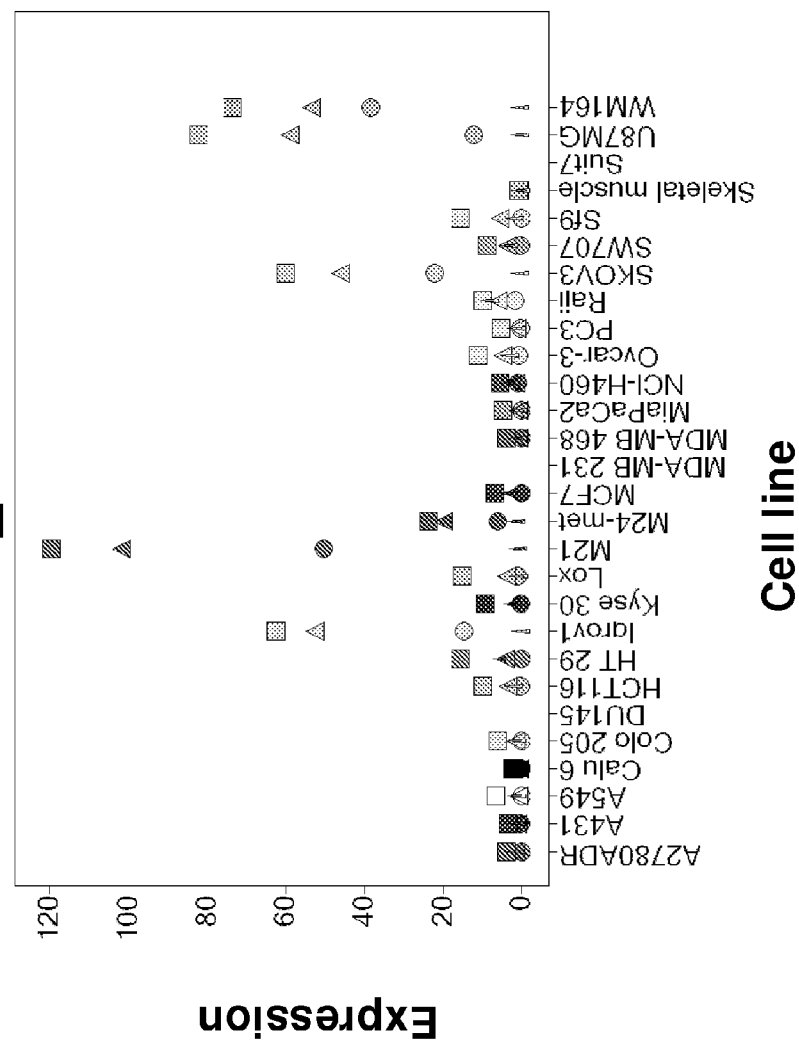
FIG. 35 shows the analysis of immunohistochemical staining with the anti-β3 antibodies E3592-2-4, E3592-2-10 and E3592-2-12 with the help of image analysis (Ariol SL-50) and graphical representation with Spotfire.
Figure 36:
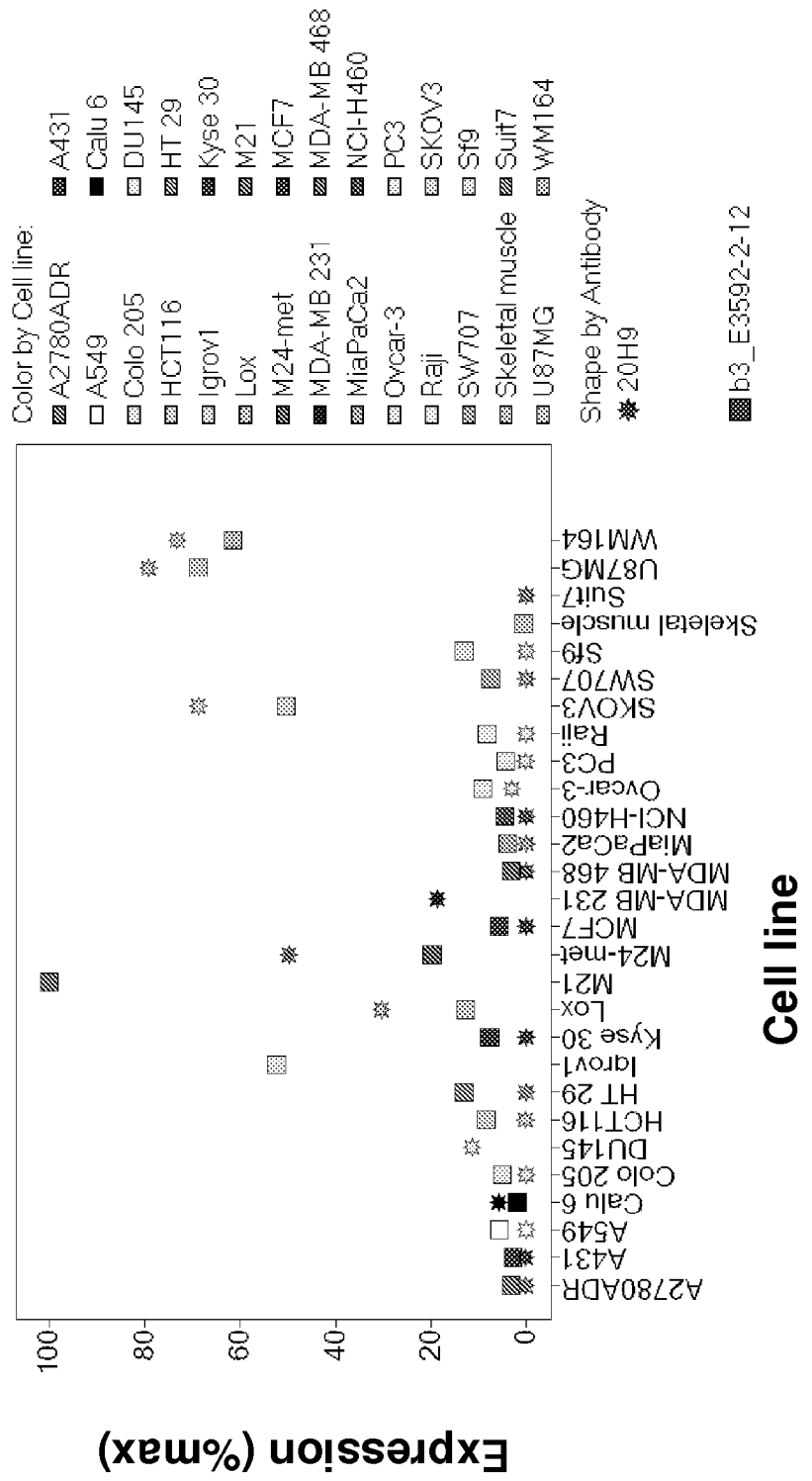
FIG. 36 shows the analysis of immunohistochemical staining with the antibody β3_E3592-2-12 and the mouse monoclonal antibody 20H9 with the help of image analysis (Ariol SL-50). Clone 20H9 is directed against the β3-integrin chain. The "Expression (% max)" is normalized to the expression of M21.

The selected final clones were cultured and the antibodies purified. The three anti-β3 clones, E3592-2-4, -2-10, and -2-12, exhibited similar staining characteristics, showing distinct plasma membrane staining (FIG. 33). In the xenograft array Xeno-08-Mu1, M21 xenografts were positive (FIG. 34). U87MG were negative. The selectivity of staining with the three antibodies on the cancer cell line array CAX08 was nearly identical (FIG. 35). The intensity of staining varied and was strongest for clone E3592-2-12. The selectivity of staining of the three antibodies was compared with the monoclonal anti-β3 exo-domain integrin antibody clone 20H9, shown for clone E3592-2-12 (FIG. 36). Regarding cell selectivity, the three clones showed similar characteristics to the clone 20H9, indicating that the epitope of the three antibodies was a β3 epitope. High expression of αvβ3 in M21 cell lines was shown previously by FACS analysis with clone LM609 (Table 10; Mitjans et al., Int J Cancer 2000, 87(5): 716-723).

TABLE 10

FACS analysis and anti-β3 immunohistochemistry of several cancer cell lines.

| Cancer cell line | FACS αvβ3 (MIF/mean background) | FACS % cells | FACS αvβ3 × % cells | IHC β3_E3592-2-12 on CAX08 (Expression) |
|---|---|---|---|---|
| HCT116 | 0.96 | 0.2 | 0.2 | 10.1 |
| KYSE-30 | 0.98 | 0.52 | 0.5 | 9.2 |

TABLE 9

Subclones to intracellular β3 domain. The staining intensity was graded from − (negative) to +++ (strong) as well as 1 (low), 2 (medium), 3 (high).

| | CAX05 | | | Xeno-08-A | | |
|---|---|---|---|---|---|---|
| Tissue Clone ID | Plasma-membrane | Cytoplasm | Comment | Plasma-membrane | Cytoplasm | Comment |
| 2-1 | 3 | 0 | M21 + Golgi, avb3 specific | | | |
| 2-2 | 3 | 0 | M21 + Golgi, avb3 specific | | | |
| 2-3 | 1 | 0 | M21 + Golgi, avb3 specific | | | |
| 2-4 | 3 | 0 | M21 + Goigi, avb3 specific | 3 | 0 | + Golgi, M21 +++, U87MG+ |
| 2-5 | 1 | 0 | M21 + Golgi, avb3 specific | | | |
| 2-6 | 1 | 0 | M21 + Golgi, avb3 specific | | | |
| 2-7 | 1 | 0 | M21 + Golgi, avb3 specific | | | |
| 2-8 | 3 | 0 | M21 + Golgi, avb3 specific | | | |
| 2-9 | 1 | 0 | M21 + Golgi, avb3 specific | | | |
| 2-10 | 3 | 0 | M21 + Golgi, avb3 specific | 3 | 0 | + Golgi, M21 +++, U87MG+ |
| 2-11 | 1 | 0 | M21 + Golgi, avb3 specific | | | |
| 2-12 | 3 | 0 | M21 + Golgi, avb3 specific | 3 | 0 | + Golgi, M21 +++, U87MG+ |
| 67-1 | 0 | 0 | | | | |
| 67-2 | 0 | 0 | | | | |
| 67-3 | 0 | 0 | | | | |
| 67-4 | | | | | | |
| 67-5 | 1 | 2 | similar to 67-7 | | | |
| 67-6 | | | | | | |
| 67-7 | 1 | 2 | WM164+++, M21 ++, U87MG+, however predominantly cytoplasmic diffuse and precipitation in many other cells | | | |
| 67-8 | 0 | 0 | | | | |
| 67-9 | 1 | 2 | similar to 67-7 | | | |
| 67-10 | 1 | 2 | similar to 67-7 | | | |
| 67-11 | 0 | 0 | | | | |
| 67-12 | 0 | 0 | | | | |

TABLE 10-continued

FACS analysis and anti-β3 immunohistochemistry of several cancer cell lines.

| Cancer cell line | FACS αvβ3 (MIF/mean background) | FACS % cells | FACS αvβ3 × % cells | IHC β3_E3592-2-12 on CAX08 (Expression) |
|---|---|---|---|---|
| M21 | 1.55 | 91.8 | 142.3 | 119.6 |
| A549 | 0.63 | 1.2 | 0.8 | 6.7 |
| NCI-H460 | 0.79 | 0.0 | 0.0 | 1.5 |
| Calu-6 | 1.5 | 3.6 | 5.4 | 2.4 |

The staining characteristics of the three clones E3592-2-4, -2-10, and -2-12, as were "plasma membrane staining" and high signal in M21, were in agreement with an β3-integrin epitope of the antibodies. The rabbit hybridoma clones E3592-2-4 2-10, and -2-12 generated against β3-integrin peptide produced antibodies suitable for FFPE tissue. Their epitope recognition was in agreement with their binding β3 cytoplasmic domain epitope. The antibody chains from the clone producing the most strongly staining antibody, E3592-2-12, was cDNA cloned and the antibody encoding regions were multiply sequenced (cf. below).

EXAMPLE 10

Sequencing and Sequence Listing

Several clones were assessed by cDNA sequencing (Table 11). The information recorded in computer readable form is identical to the written sequence listing.

TABLE 11

Sequenced clones.

| Clone ID | Recombinant antibody identifier | Specificity | Example | SEQ ID NOs |
|---|---|---|---|---|
| E3531-227-3 | EM22703 | anti-αvβ3 | 4.2 | 81-120 except 90, 110 |
| E3531-229-3 | EM22703 | anti-αvβ3 | 4.2 | 81-120 except 90, 110 |
| E3536-99-1 | — | anti-αvβ5 | 5 | 1-40 except 10, 30 |
| E3536-99-2 | EM09902 | anti-αvβ5 | 5 | 1-40 except 10, 30 |
| E3536-99-3 | — | anti-αvβ5 | 5 | 1-40 except 10, 30 |
| E3592-2-12 | EM00212 | anti-β3 | 9 | 41-80 except 50, 70 |
| E3866-052-1 | EM05201 | anti-αvβ6 | 6 | 121-160 except 130, 150 |
| E3875-0133-9 | EM13309 | anti-αvβ8 | 7 | 161-200 except 170, 190 |
| E3875-013-9 | EM01309 | anti-αv | 8 | 201-240 except 210, 230 |

Three primary sequencing runs on each heavy and light chain from the clones were assembled into contigs using Lasergene software (DNAstar Inc.) and analyzed using ClustalW multiple alignment tools. Clones E3531-227-3 and -229-3 had identical heavy and light chain sequences, confirming monoclonality of the antibody population. Clones E3536-99-1, -99-2 and -99-3 had identical heavy and light chain sequences, confirming monoclonality of the antibody population.

EXAMPLE 11

Recombinant RabMabs are Specific for their Ligands by ELISA

Figure 37:
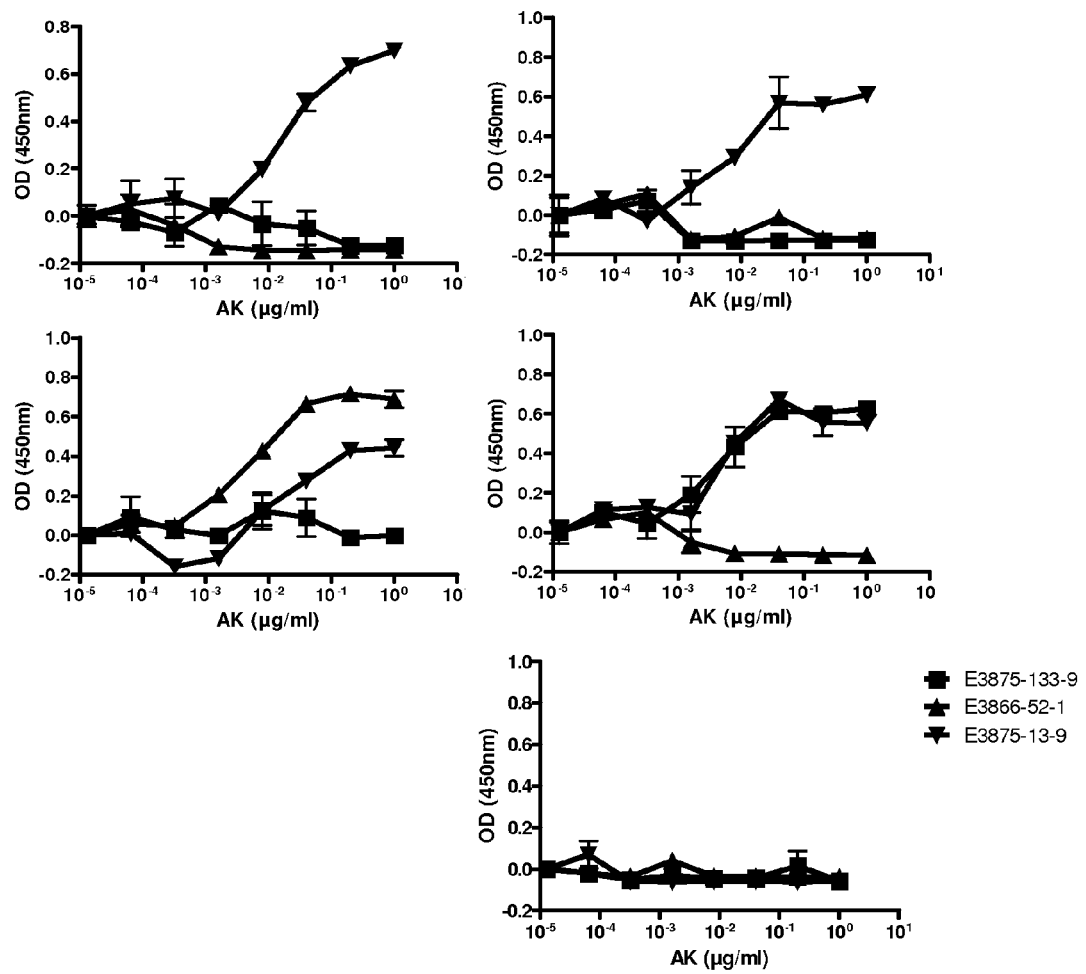
FIG. 37 shows the ELISA profile of purified monoclonal hybridoma antibodies E3875-133-9, E3866-052-1 and E3875-013-9 from rabbit anti-integrin against recombinant human αv-integrin extracellular domains and full length purified platelet gpiibiiia.
Figure 38:
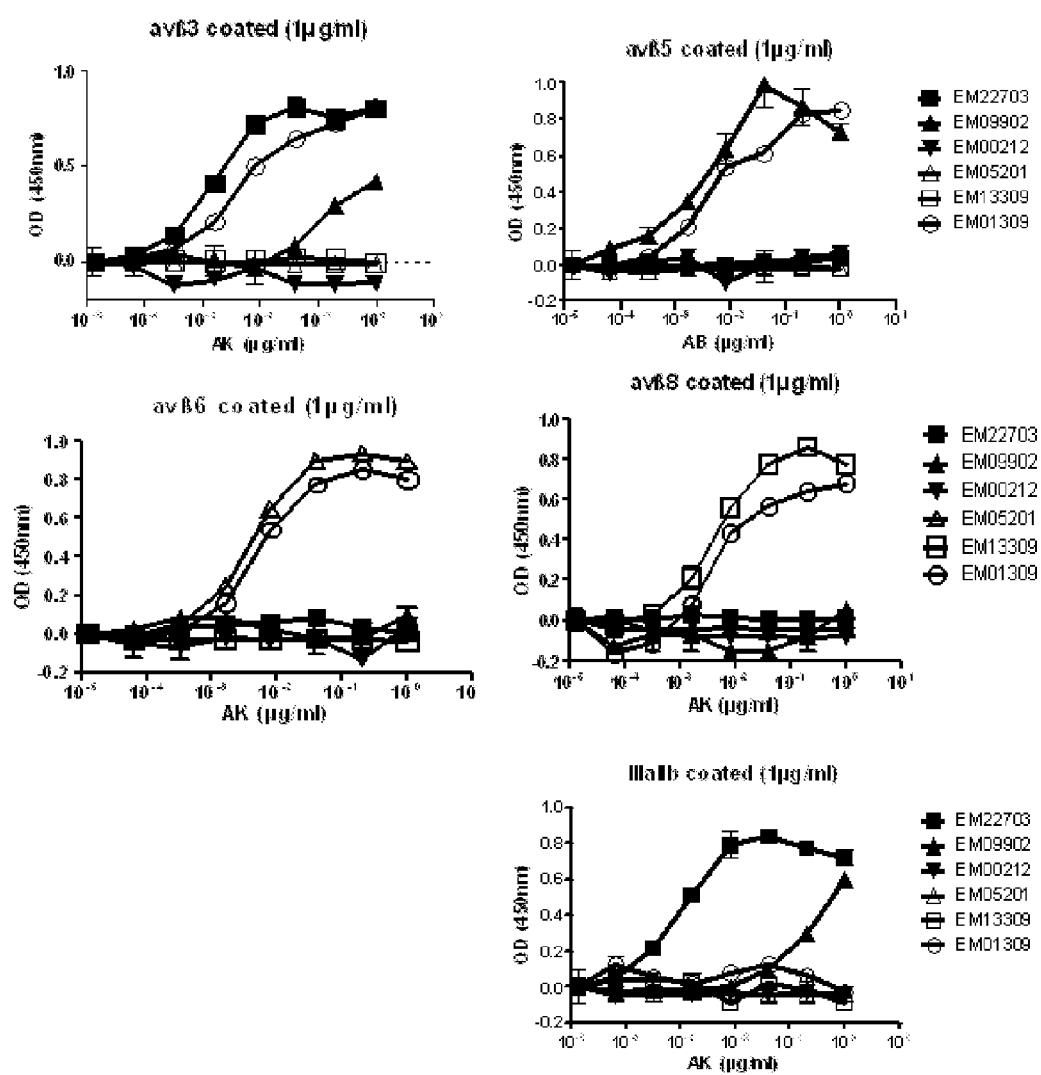
FIG. 38 shows the ELISA profile of EBNA-recombinant rabbit anti-integrin monoclonal antibodies EM22703, EM09902, EM00212, EM05201, EM13309 and EM01309 against recombinant human αv-integrin extracellular domains and full length purified platelet gpiibiiia.

In standard ELISA conditions wits 1 μg/ml coated integrin on the plate, the antibodies were essentially mono-specific for their immunogens, as defined to better than 4 logs of concentrations, and did not cross react significantly with the most closely related integrin chains (FIGS. 10, 37, 38), with the exception of EM09902 that showed a cross-reactivity ($IC_{50}$~100 fold lower) with both gpiibiiia and αvβ3, so apparently recognized a related epitope on both the β5 and β3 chains of the complexes. It should not seriously affect FFPE usage, as the expression of αvβ5 is more prevalent than αvβ3 and the signal from EM09902 is extremely strong in IHC. The specificities of the other recombinant antibodies were indistinguishable in ELISA and in IHC staining from the hybridoma supernatants and antibodies derived from them (FIGS. 10, 37, 38). Indeed, on cDNA sequencing, two of the anti-αvβ3 antibodies, EM22703 and EM22903, were found to be derived from a single clone. The specificities in ELISA and the apparent binding affinities expressed as $IC_{50}$ in ELISA were shown in Table 12.

TABLE 12

Recombinant RabMab $IC_{50}$ in ELISA on isolated integrins.

| Recombinant antibody identifier | Immunogen | avβ3 (ng/ml) | avβ5 (ng/ml) | avβ6 (ng/ml) | avβ8 (ng/ml) | Gpiibiiia (ng/ml) |
|---|---|---|---|---|---|---|
| EM22703 | Human αvβ3 ECD | 1.4 | >10000 | >>10000 | >>10000 | 0.85 |
| EM09902 | Human αvβ5 ECD | ~450 | 5.6 | >>10000 | >>10000 | ~400 |
| EM00212 | Human β3 ICD | >>10000 | >>10000 | >>10000 | >>10000 | >>10000 |
| EM005201 | Human αvβ6 ECD | >>10000 | >>10000 | 3.8 | >>10000 | >>10000 |
| EM013309 | Human αvβ8 ECD | >>10000 | >>10000 | >>10000 | 4.0 | >>10000 |
| EM001309 | Human αvβ3 ECD | 4.7 | 5.6 | 4.9 | 4.1 | >>10000 |

EXAMPLE 12

Recombinant RabMabs do not Affect Ligand Binding to their Receptors

Figure 39:
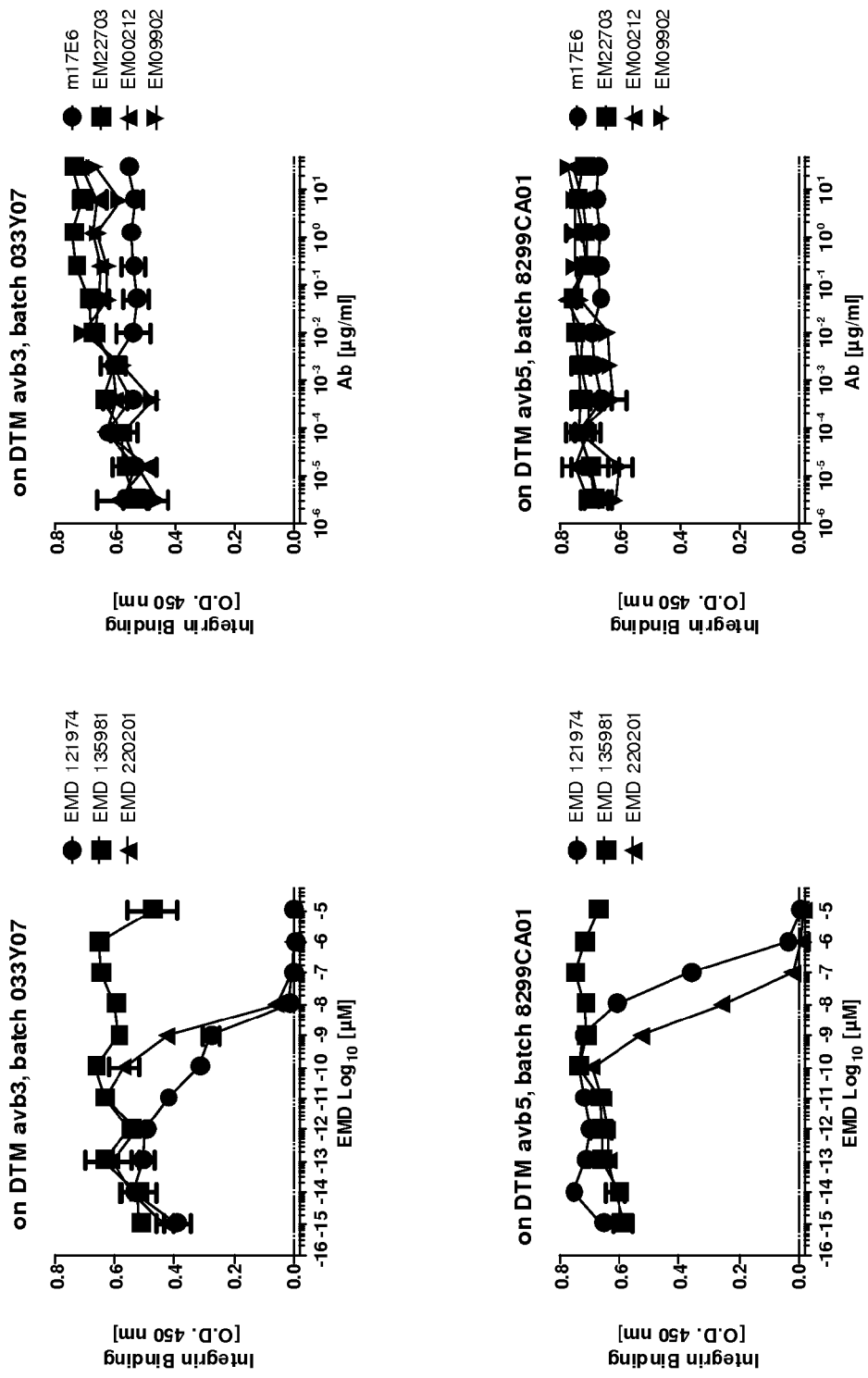
FIG. 39 shows the receptor inhibition assay for RabMab antibodies EM22703, EM09902, EM00212 using biotin vitronectin as ligand.
Figure 40:
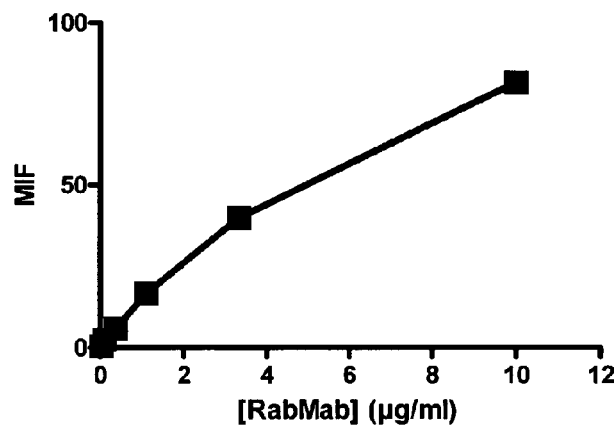
FIG. 40 shows the FACS titration of EM022703 on M21.
Figure 41:
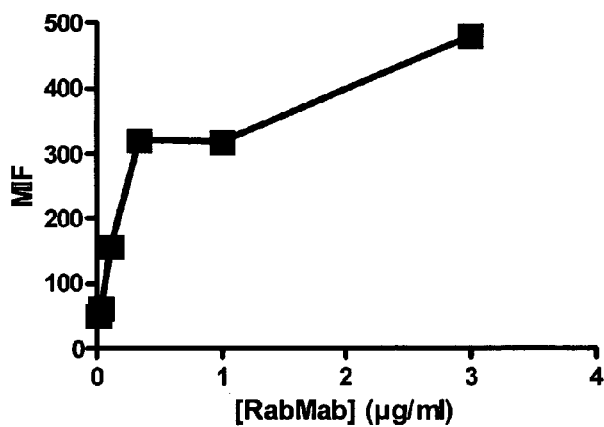
FIG. 41 shows the FACS titration of EM009902 on A549.
Figure 42:
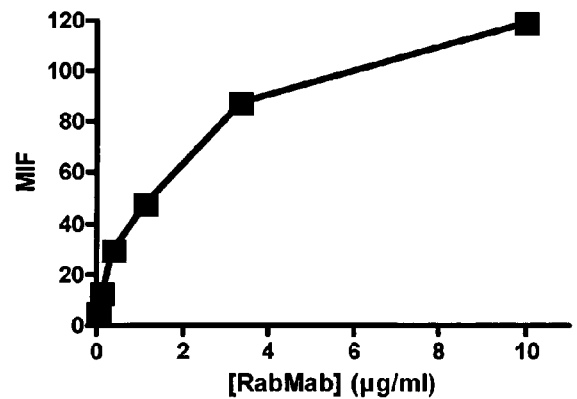
FIG. 42 shows the FACS titration of EM05202 on HT29.
Figure 43:
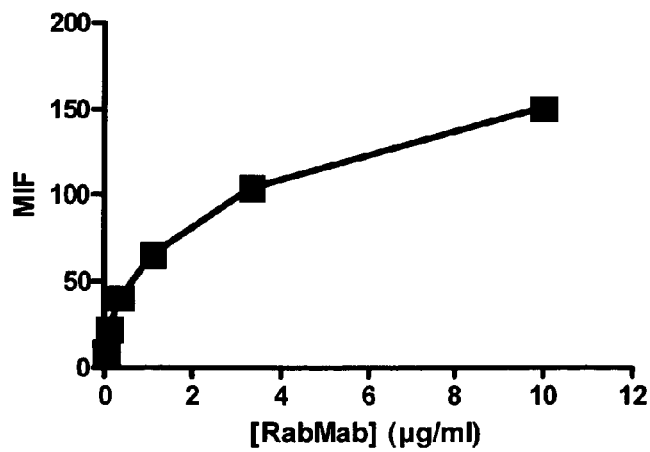
FIG. 43 shows the FACS titration of EM13309 on M24-met cells.

Both antibodies and small molecules can inhibit or enhance integrin activity, however the RabMabs selected here had no effect on ligand binding (FIG. 39). Inhibitors of αvβ3 and αvβ5, reacted as predicted, positive (cilengitide) and negative (c(RβA-DfV)).

EXAMPLE 13

Recombinant RabMabs in Live Cell Flow Cytometry ("FACS")

In FACS native integrins present their native glycosylation pattern in situ, so this represents a specificity "gold standard". The RabMabs were assessed in FACS compared to standard well characterized murine monoclonal antibodies. For αvβ8 no antibody is commercially available. The antibodies reacted in FACS in a cell type dependent fashion and the FACS profiles closely matched the ELISA profiles of the antibodies. The results were summarized as mean intensity of fluorescence normalized to second layer control antibodies (Table 13). Differences in the absolute levels of expression between RabMabs and mouse Mabs were likely due to the varying affinity of the second layer antibodies.

Live cell flow cytometry was unequivocal. The antibodies did not react above background with the αv-deficient M21-L cell line. As the normalized MIF attained with EM22703 and EM09902 approach 100, and with EM05201 and EM13309, this indicated the basic routinely attainable signal-to-noise of the antibodies, which was considerably above that attained with the standard LM609 and P1F6 reagents. It was not yet

TABLE 13

RabMab and comparator antibody activity in live cell flow cytometry using Alexa-488 labeled $2^{nd}$ layer antibody vs. rabbit Ig or FITC labeled anti-mouse. rMIF is peak mean intensity of fluorescence, relative to second layer alone.

| Antibody type | Antibody Identifier | Immunogen/target | HUVEC | HT-29 | A549 | M24Met | M21 | M21-L | M21-Gpiib |
|---|---|---|---|---|---|---|---|---|---|
| MoMab | 17E6 | Human αv | 9.9 | 7.3 | 6.8 | 7.8 | 9.3 | 1.0 | 1.1 |
| MoMab | LM609 | αvβ3 | 10.7 | 1.0 | 1.3 | 4.9 | 9.1 | 1.1 | 1.2 |
| MoMab | P1F6 | αvβ5 | 2.7 | 3.2 | 3.6 | 3.8 | 3.8 | 1.1 | 1.0 |
| MoMab | P4C10 | β1 | 38.9 | 14.5 | 7.5 | 14.0 | 7.2 | 12.1 | 10.8 |
| RabMab | EM22703 | Human αvβ3/ECD β3 | 12.4 | 1.7 | 1.7 | 8.1 | 17.6 | 1.7 | 56.0 |
| RabMab | EM09902 | Human αvβ5/ECD αvβ5 | 33.9 | 98.9 | 77.8 | 40.1 | 7.2 | 2.0 | 1.9 |
| RabMab | EM00212 | Human β3 cytoplasmic | 1.1 | 1.1 | 1.1 | 1.2 | 1.2 | 1.2 | 1.2 |
| RabMab | EM05201 | Human αvβ6/ECD αvβ6 | 1.6 | 8.0 | 1.3 | 1.0 | 1.1 | 1.1 | 1.0 |
| RabMab | EM013309 | Human αvβ8/ECD αvβ8 | 1.1 | 19.9 | 1.8 | 15.5 | 22.1 | 1.2 | 1.0 |
| RabMab | EM01309 | Human αvβ3/*ECD αv | 28.8 | 1.8 | 1.3 | 2.5 | 1.3 | 1.3 | 1.0 |

Murine antibodies showed the HUVEC cells to express high levels of αv, αvβ3 and αvβ5 and no αvβ6 or αvβ8. In these cells, the RabMab EM01309 reacted strongly, and at levels comparable to 17E6 the murine anti-αv comparator. Murine antibodies showed high levels of αv, no αvβ3, high levels of αvβ5 and some αvβ6 on the HT-29 CRC cells. The RabMabs confirmed this and also showed high expression of αvβ8 integrin. RabMab EM01309 reacted weakly. Murine antibodies showed high levels of αv, no αvβ3, high levels of αvβ5 and no αvβ6 on the A549 NSCLC cells. The RabMabs binding confirmed this, and also showed no expression of αvβ8 integrin. RabMab EM01309 did not react. Murine antibodies showed high levels of αv, αvβ3 and αvβ5 and no αvβ6, and strong expression of 11 on the M24 Met melanoma cells. The RabMabs confirmed this and also showed strong binding of EM13309, revealing expression of αvβ8 integrin. RabMab EM01309 did not react. Murine antibodies showed high levels of αv, αvβ3 and αvβ5, no αvβ6, and strong expression of 11 on the M21 melanoma cells. The RabMabs confirmed this and also showed high levels of EM13309 binding, showing αvβ8 expression. RabMab EM01309 did not react. Murine antibodies showed no αv, αvβ3, αvβ5 or αvβ6 on the M21-L melanoma cells, and strong expression of β1. None of the RabMabs bound significantly above background. Murine antibodies showed no αv, αvβ3, αvβ5 or αvβ6 on the M21-gpiib melanoma cells, but strong expression of β1 and β3. The RabMabs EM05201, EM13309 and EM01309 did not bind. However, both EM22703 and EM09902 reacted, EM22703 strongly. This supported the ELISA data (cf. Example 11) that EM22703 could cross react with aiibβ3, and that EM09902 could weakly cross react with both αvβ3 and aiibβ3.

clear whether this was a result of higher affinity second layer fluorescinated reagents, rather than the properties of the primary RabMabs themselves, whatever the reason, the RabMabs were excellent reagents for FACS.

EM22703 gave a parallel staining in FACS to LM609, confirming that it was recognizing the αvβ3 complex, but also reacted strongly with M21-gpiib, showing that it was the β3 chain in the integrin complex that was being recognized by EM22703.

EM09902 staining generally paralleled the P1F6 staining, but reacted weakly with β3 as well as β5 chains. This was visible in the FACS of M21-gpiib cells, which did not express αvβ5, the supposed target of EM09902. By titering the antibody, the optimal concentration of reagent could be selected to minimize αvβ3 cross reactivity, while retaining a potent αvβ5 signal, as predicted from the ELISA data, and for FACS this was 0.3-1 µg/ml.

EM00212, directed against the b3 cytoplasmic domain was negative in FACS and ELISA. As this is a species, isotype and target control, it is an excellent indicator of specificity, and suggests that an excellent signal to noise ratio of 100:1 is being achieved in FACS.

EM05201 was intensely specific for αvβ6 and revealed this protein only on HT29 cells, where it is known to be expressed.

EM13309 is the first reagent capable of live cell FACS of αvβ8 integrin, and provided the surprising information that αvβ8 is more widely expressed than αvβ6, on HT29 carcinoma, and M21 and M24 met melanomas. The staining of the neuroectodermal lineage was perhaps not surprising as αvβ8 was reported in the astrocyte neuronal lineage, however, staining of the carcinoma was unexpected, and may reflect biology: recent analysis of the αvβ8 showed that its expression in gut APCs controlled inflammatory response in this site. Conceivably, the CRC line HT29 also reflected such a mechanism.

EM01309, against the αv extracellular domain, was uniformly negative with the exception of HUVEC.

In summary, the RabMab antibodies were shown to function in live cell flow cytometry. This provides a valuable bridge between the biochemistry and tissue IHC for tumor validation and characterization. Especially the αvβ6 and αvβ8 reagents are an important resource for integrin studies, and the ability to make such antibodies with these reactivity profiles in RabMabs opens a door, finally on a rigorous analysis of integrin expression patterns in archival tissues.

EXAMPLE 14

Titration Experiments

Titration experiments in FACS were performed to investigate appropriate staining concentrations (FIGS. 40-43). The curve forms did not indicate saturation, but begun to flatten above 1 mg/ml. The rabbit monoclonal antibodies are strong binders in FACS. Especially EM09902 had high affinity, and strong binding was seen to 0.1 μg/ml antibody concentration and hence, it could be successfully used at <1 ug/ml staining concentration.

The invention claimed is:

1. A monoclonal rabbit anti-integrin antibody or an integrin-binding fragment thereof, having specificity for an immunogen comprising an extracellular integrin domain said domain comprising an insect-derived glycosylation pattern, wherein the antibody or the integrin-binding fragment thereof is additionally capable of binding integrin with a eukaryotic glycosylation pattern other than derived from insects, wherein the antibody binds the immunogen integrin with an $IC_{50} \leq 5.6$ ng/ml, wherein the $IC_{50}$ of binding to the immunogen integrin is on the order of at least 10,000 times lower compared to the most closely related integrin.

2. The antibody according to claim 1, wherein the extracellular integrin domain has a human primary structure.

3. The antibody according to claim 1, wherein the antibody has specificity for a non-occluded epitope.

4. The antibody according to claim 1, wherein the antibody binds the integrin in formalin fixed paraffin embedded material.

5. The antibody according to claim 1, wherein the antibody is capable of binding intact heterodimers of the immunogen integrin in formalin fixed paraffin embedded material and on viable cells with the substantially same specificity.

6. The antibody according to claim 1, wherein the antibody binds the immunogen integrin with mono-specificity.

7. The antibody according to claim 1, wherein the antibody binds the immunogen integrin with 20-fold affinity or more compared to its binding to another biomolecule.

8. A monoclonal rabbit anti-integrin antibody or an integrin-binding fragment thereof, having specificity for an immunogen comprising an extracellular integrin chain domain, said domain comprising an insect-derived glycosylation pattern, wherein the antibody or the integrin-binding fragment thereof is additionally capable of binding integrin with a eukaryotic glycosylation pattern other than derived from insects, wherein the antibody binds the immunogen integrin with an $IC_{50} \leq 5.6$ ng/ml, wherein the $IC_{50}$ of binding to the immunogen integrin is on the order of at least 10,000 times lower compared to the most closely related integrin, with the proviso that said antibody or said integrin-binding fragment thereof does not block integrin-ligand binding.

9. A polynucleotide encoding the antibody, or an integrin-binding fragment thereof, of claim 1.

10. A method for preparing a monoclonal antibody, comprising
immunizing a rabbit with an immunogen, which comprises an extracellular integrin domain with an insect-derived glycosylation pattern;
obtaining a polyclonal antiserum comprising polyclonal antibodies from said rabbit; and
preparing the monoclonal antibody.

11. The method according to claim 10, wherein the immunogen is coupled as delta-trans membrane form.

12. The method according to claim 10, wherein the immunogen is recombinantly expressed in insect cells and purified.

13. The method according to claim 10, wherein the immunogen has an amino acid sequence of SEQ ID NOs: 10, 90, 130, 170 or 210, or variants, mutants, parts of the amino acid sequence or at least 95% homologous sequences having the same function.

14. A method for the detection of an integrin in formalin fixed paraffin embedded material, comprising contacting said material with the antibody, or an integrin-binding fragment thereof, of claim 1 under conditions suitable for the binding of said integrin to said antibody or said integrin-binding fragment thereof; and detecting the bound antibody.

15. A rabbit monoclonal antibody or an antigen-binding fragment thereof selected from the group consisting of
(a) an antibody or an antigen-binding fragment thereof that binds to the extracellular domain of integrin αvβ3, comprising a light chain variable region ($V_L$) comprising an amino acid sequence of SEQ ID NO: 95 ($V_L$-αvβ3) and a heavy chain variable region ($V_H$) comprising an amino acid sequence of SEQ ID NO: 96 ($V_H$-αvβ3);
(b) an antibody or an antigen-binding fragment thereof that binds to the extracellular domain of integrin αvβ5, comprising a light chain variable region ($V_L$) comprising an amino acid sequence of SEQ ID NO: 15 ($V_L$-αvβ5) and a heavy chain variable region ($V_H$) comprising an amino acid sequence of SEQ ID NO: 16 ($V_H$-αvβ5);
(c) an antibody or an antigen-binding fragment thereof that binds to the extracellular domain of integrin αvβ6, comprising a light chain variable region ($V_L$) comprising an amino acid sequence of SEQ ID NO: 135 ($V_L$-αvβ6) and a heavy chain variable region ($V_H$) comprising an amino acid sequence of SEQ ID NO: 136 ($V_H$-αvβ6);
(d) an antibody or an antigen-binding fragment thereof that binds to the extracellular domain of integrin αvβ8, comprising a light chain variable region ($V_L$) comprising an amino acid sequence of SEQ ID NO: 175 ($V_L$-αvβ8) and a heavy chain variable region ($V_H$) comprising an amino acid sequence of SEQ ID NO: 176 ($V_H$-αvβ8); and
(e) an antibody or an antigen-binding fragment thereof that binds to the extracellular domain of integrin αv, comprising a light chain variable region ($V_L$) comprising an amino acid sequence of SEQ ID NO: 215 ($V_L$-αv) and a heavy chain variable region ($V_H$) comprising an amino acid sequence of SEQ ID NO: 216 ($V_H$-αv).

16. The rabbit monoclonal antibody or an antigen-binding fragment thereof according to claim 15, which binds to an immunogen comprising an amino acid sequence set forth in SEQ ID NO: 10, SEQ ID NO: 90, SEQ ID NO: 130, SEQ ID NO: 170 or SEQ ID NO: 210.

17. A hybridoma which secretes at least one antibody or an antigen-binding fragment thereof enumerated in (a)-(e) of claim 15.

18. A kit comprising at least one antibody or an antigen-binding fragment thereof enumerated in (a)-(e) of claim 15 and a reporter moiety or a reporter apparatus for detecting integrins in FFPE material.

19. A recombinant monoclonal rabbit anti-integrin antibody or an integrin-binding fragment thereof, having specificity for an immunogen comprising an extracellular integrin domain said domain comprising an insect-derived glycosylation pattern, wherein the antibody is additionally capable of binding integrin with a eukaryotic glycosylation pattern other than derived from insects with an $IC_{50} \leq 5.6$ ng/ml, wherein the $IC_{50}$ binding to the immunogen integrin is on the order of at least 10,000 times lower compared to the most closely related integrin.

20. The recombinant monoclonal rabbit anti-integrin antibody or the integrin-binding fragment thereof of claim 1, wherein the immunogen integrin and the most closely related integrin respectively are:
(a) the immunogen integrin is αvβ3 and the most closely related integrin is αvβ5, αvβ6 or αvβ8;
(b) the immunogen integrin is αvβ5 and the most closely related integrin is αvβ6 or αvβ8;
(c) the immunogen integrin is αvβ6 and the most closely related integrin is αvβ3, αvβ5, αvβ8 or Gp IIb/IIIa; or
(d) the immunogen integrin is αvβ8 and the most closely related integrin is αvβ3, αvβ5, αvβ6 or Gp IIb/IIIa.

21. The recombinant monoclonal rabbit anti-integrin antibody or the integrin-binding fragment thereof of claim 8, wherein the immunogen integrin and the most closely related integrin respectively are:
(a) the immunogen integrin is αvβ3 and the most closely related integrin is αvβ5, αvβ6 or αvβ8;
(b) the immunogen integrin is αvβ5 and the most closely related integrin is αvβ6 or αvβ8;
(c) the immunogen integrin is αvβ6 and the most closely related integrin is αvβ3, αvβ5, αvβ8 or Gp IIb/IIIa; or (d) the immunogen integrin is αvβ8 and the most closely related integrin is αvβ3, αvβ5, αvβ6 or Gp IIb/IIIa.

\* \* \* \* \*

SEQUENCE LISTING

```
<160> NUMBER OF SEQ ID NOS: 240

<210> SEQ ID NO 1
<211> LENGTH: 6
<212> TYPE: PRT
<213> ORGANISM: rabbit

<400> SEQUENCE: 1

Arg Cys Ala Leu Val Met
1               5

<210> SEQ ID NO 2
<211> LENGTH: 6
<212> TYPE: PRT
<213> ORGANISM: rabbit

<400> SEQUENCE: 2

Gln Asp Ile Gly Ser Asp
1               5

<210> SEQ ID NO 3
<211> LENGTH: 12
<212> TYPE: PRT
<213> ORGANISM: rabbit

<400> SEQUENCE: 3

Ala Gly Tyr Lys Ser Tyr Ser Asp Asp Gly His Gly
1               5                   10

<210> SEQ ID NO 4
<211> LENGTH: 8
<212> TYPE: PRT
<213> ORGANISM: rabbit

<400> SEQUENCE: 4

Pro Leu Arg Asn Val Trp Ile Ser
1               5

<210> SEQ ID NO 5
<211> LENGTH: 9
<212> TYPE: PRT
<213> ORGANISM: rabbit

<400> SEQUENCE: 5

Cys Ile Tyr Thr Gly Arg Asp Trp Pro
1               5

<210> SEQ ID NO 6
<211> LENGTH: 12
<212> TYPE: PRT
<213> ORGANISM: rabbit
```

```
<400> SEQUENCE: 6

Ala Arg Ile Val Tyr Gly Gly Ala Gly Tyr Arg Leu
1               5                   10

<210> SEQ ID NO 7
<211> LENGTH: 20
<212> TYPE: PRT
<213> ORGANISM: rabbit

<400> SEQUENCE: 7

Met Asp Thr Arg Ala Pro Thr Gln Leu Leu Gly Leu Leu Leu Leu Trp
1               5                   10                  15

Leu Pro Gly Ala
            20

<210> SEQ ID NO 8
<211> LENGTH: 22
<212> TYPE: PRT
<213> ORGANISM: rabbit

<400> SEQUENCE: 8

Thr Gln Thr Pro Pro Ser Val Glu Ala Ala Val Gly Gly Thr Val Thr
1               5                   10                  15

Ile Asn Cys Gln Ala Ser
            20

<210> SEQ ID NO 9
<211> LENGTH: 56
<212> TYPE: PRT
<213> ORGANISM: rabbit

<400> SEQUENCE: 9

Leu Ala Trp Tyr Gln Gln Lys Pro Gly Gln Pro Pro Lys Leu Leu Ile
1               5                   10                  15

Tyr Ser Ala Ser Ser Leu Ala Ser Gly Val Pro Ser Arg Phe Lys Ala
            20                  25                  30

Ser Gly Ser Gly Thr Gln Phe Thr Leu Thr Ile Ser Asp Val Gln Cys
        35                  40                  45

Asp Asp Ala Ala Thr Tyr Ser Cys
        50                  55

<210> SEQ ID NO 10
<211> LENGTH: 696
<212> TYPE: PRT
<213> ORGANISM: human

<400> SEQUENCE: 10

Gly Leu Asn Ile Cys Thr Ser Gly Ser Ala Thr Ser Cys Glu Glu Cys
1               5                   10                  15

Leu Leu Ile His Pro Lys Cys Ala Trp Cys Ser Lys Glu Asp Phe Gly
            20                  25                  30

Ser Pro Arg Ser Ile Thr Ser Arg Cys Asp Leu Arg Ala Asn Leu Val
        35                  40                  45

Lys Asn Gly Cys Gly Gly Glu Ile Glu Ser Pro Ala Ser Ser Phe His
    50                  55                  60

Val Leu Arg Ser Leu Pro Leu Ser Ser Lys Gly Ser Gly Ser Ala Gly
65                  70                  75                  80

Trp Asp Val Ile Gln Met Thr Pro Gln Glu Ile Ala Val Asn Leu Arg
                85                  90                  95
```

```
Pro Gly Asp Lys Thr Thr Phe Gln Leu Gln Val Arg Gln Val Glu Asp
            100                 105                 110

Tyr Pro Val Asp Leu Tyr Tyr Leu Met Asp Leu Ser Leu Ser Met Lys
            115                 120                 125

Asp Asp Leu Asp Asn Ile Arg Ser Leu Gly Thr Lys Leu Ala Glu Glu
130                 135                 140

Met Arg Lys Leu Thr Ser Asn Phe Arg Leu Gly Phe Gly Ser Phe Val
145                 150                 155                 160

Asp Lys Asp Ile Ser Pro Phe Ser Tyr Thr Ala Pro Arg Tyr Gln Thr
                165                 170                 175

Asn Pro Cys Ile Gly Tyr Lys Leu Phe Pro Asn Cys Val Pro Ser Phe
            180                 185                 190

Gly Phe Arg His Leu Leu Pro Leu Thr Asp Arg Val Asp Ser Phe Asn
            195                 200                 205

Glu Glu Val Arg Lys Gln Arg Val Ser Arg Asn Arg Asp Ala Pro Glu
210                 215                 220

Gly Gly Phe Asp Ala Val Leu Gln Ala Ala Val Cys Lys Glu Lys Ile
225                 230                 235                 240

Gly Trp Arg Lys Asp Ala Leu His Leu Leu Val Phe Thr Thr Asp Asp
                245                 250                 255

Val Pro His Ile Ala Leu Asp Gly Lys Leu Gly Gly Leu Val Gln Pro
            260                 265                 270

His Asp Gly Gln Cys His Leu Asn Glu Ala Asn Glu Tyr Thr Ala Ser
            275                 280                 285

Asn Gln Met Asp Tyr Pro Ser Leu Ala Leu Leu Gly Glu Lys Leu Ala
            290                 295                 300

Glu Asn Asn Ile Asn Leu Ile Phe Ala Val Thr Lys Asn His Tyr Met
305                 310                 315                 320

Leu Tyr Lys Asn Phe Thr Ala Leu Ile Pro Gly Thr Thr Val Glu Ile
                325                 330                 335

Leu Asp Gly Asp Ser Lys Asn Ile Ile Gln Leu Ile Ile Asn Ala Tyr
            340                 345                 350

Asn Ser Ile Arg Ser Lys Val Glu Leu Ser Val Trp Asp Gln Pro Glu
            355                 360                 365

Asp Leu Asn Leu Phe Phe Thr Ala Thr Cys Gln Asp Gly Val Ser Tyr
370                 375                 380

Pro Gly Gln Arg Lys Cys Glu Gly Leu Lys Ile Gly Asp Thr Ala Ser
385                 390                 395                 400

Phe Glu Val Ser Leu Glu Ala Arg Ser Cys Pro Ser Arg His Thr Glu
                405                 410                 415

His Val Phe Ala Leu Arg Pro Val Gly Phe Arg Asp Ser Leu Glu Val
            420                 425                 430

Gly Val Thr Tyr Asn Cys Thr Cys Gly Cys Ser Val Gly Leu Glu Pro
            435                 440                 445

Asn Ser Ala Arg Cys Asn Gly Ser Gly Thr Tyr Val Cys Gly Leu Cys
            450                 455                 460

Glu Cys Ser Pro Gly Tyr Leu Gly Thr Arg Cys Glu Cys Gln Asp Gly
465                 470                 475                 480

Glu Asn Gln Ser Val Tyr Gln Asn Leu Cys Arg Glu Ala Glu Gly Lys
                485                 490                 495

Pro Leu Cys Ser Gly Arg Gly Asp Cys Ser Cys Asn Gln Cys Ser Cys
            500                 505                 510
```

```
Phe Glu Ser Glu Phe Gly Lys Ile Tyr Gly Pro Phe Glu Cys Asp
        515                 520                 525
Asn Phe Ser Cys Ala Arg Asn Lys Gly Val Leu Cys Ser Gly His Gly
    530                 535                 540
Glu Cys His Cys Gly Glu Cys Lys Cys His Ala Gly Tyr Ile Gly Asp
545                 550                 555                 560
Asn Cys Asn Cys Ser Thr Asp Ile Ser Thr Cys Arg Gly Arg Asp Gly
                565                 570                 575
Gln Ile Cys Ser Glu Arg Gly His Cys Leu Cys Gly Gln Cys Gln Cys
            580                 585                 590
Thr Glu Pro Gly Ala Phe Gly Glu Met Cys Glu Lys Cys Pro Thr Cys
        595                 600                 605
Pro Asp Ala Cys Ser Thr Lys Arg Asp Cys Val Glu Cys Leu Leu Leu
    610                 615                 620
His Ser Gly Lys Pro Asp Asn Gln Thr Cys His Ser Leu Cys Arg Asp
625                 630                 635                 640
Glu Val Ile Thr Trp Val Asp Thr Ile Val Lys Asp Asp Gln Glu Ala
                645                 650                 655
Val Leu Cys Phe Tyr Lys Thr Ala Lys Asp Cys Val Met Met Phe Thr
            660                 665                 670
Tyr Val Glu Leu Pro Ser Gly Lys Ser Asn Leu Thr Val Leu Arg Glu
        675                 680                 685
Pro Glu Cys Gly Asn Thr Pro Asn
        690                 695

<210> SEQ ID NO 11
<211> LENGTH: 46
<212> TYPE: PRT
<213> ORGANISM: rabbit

<400> SEQUENCE: 11

Met Glu Thr Gly Leu Arg Trp Leu Leu Leu Val Ala Val Leu Lys Gly
1               5                   10                  15
Val Gln Cys Gln Glu Gln Leu Glu Glu Ser Gly Gly Gly Leu Val Gln
            20                  25                  30
Pro Glu Gly Ser Leu Thr Leu Thr Cys Thr Val Ser Gly Phe
        35                  40                  45

<210> SEQ ID NO 12
<211> LENGTH: 14
<212> TYPE: PRT
<213> ORGANISM: rabbit

<400> SEQUENCE: 12

Trp Val Arg Gln Ala Pro Gly Lys Gly Leu Glu Trp Ile Gly
1               5                   10

<210> SEQ ID NO 13
<211> LENGTH: 37
<212> TYPE: PRT
<213> ORGANISM: rabbit

<400> SEQUENCE: 13

Tyr Tyr Ala Ser Trp Ala Lys Gly Arg Phe Thr Ile Ser Lys Ser Ser
1               5                   10                  15
Ser Thr Thr Val Thr Leu Gln Met Thr Ser Leu Thr Ala Thr Asp Thr
            20                  25                  30
Ala Thr Tyr Phe Cys
```

<210> SEQ ID NO 14
<211> LENGTH: 11
<212> TYPE: PRT
<213> ORGANISM: rabbit

<400> SEQUENCE: 14

Trp Gly Pro Gly Thr Leu Val Thr Val Ser Ser
1               5                   10

<210> SEQ ID NO 15
<211> LENGTH: 122
<212> TYPE: PRT
<213> ORGANISM: rabbit

<400> SEQUENCE: 15

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Pro Ser
                20                  25                  30

Val Glu Ala Ala Val Gly Gly Thr Val Thr Ile Asn Cys Gln Ala Ser
            35                  40                  45

Gln Asp Ile Gly Ser Asp Leu Ala Trp Tyr Gln Gln Lys Pro Gly Gln
    50                  55                  60

Pro Pro Lys Leu Leu Ile Tyr Ser Ala Ser Leu Ala Ser Gly Val
65                  70                  75                  80

Pro Ser Arg Phe Lys Ala Ser Gly Ser Gly Thr Gln Phe Thr Leu Thr
                85                  90                  95

Ile Ser Asp Val Gln Cys Asp Asp Ala Ala Thr Tyr Ser Cys Ala Gly
                100                 105                 110

Tyr Lys Ser Tyr Ser Asp Asp Gly His Gly
            115                 120

<210> SEQ ID NO 16
<211> LENGTH: 137
<212> TYPE: PRT
<213> ORGANISM: rabbit

<400> SEQUENCE: 16

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Gln
                20                  25                  30

Pro Glu Gly Ser Leu Thr Leu Thr Cys Thr Val Ser Gly Phe Pro Leu
            35                  40                  45

Arg Asn Val Trp Ile Ser Trp Val Arg Gln Ala Pro Gly Lys Gly Leu
    50                  55                  60

Glu Trp Ile Gly Cys Ile Tyr Thr Gly Arg Asp Trp Pro Tyr Tyr Ala
65                  70                  75                  80

Ser Trp Ala Lys Gly Arg Phe Thr Ile Ser Lys Ser Ser Thr Thr
                85                  90                  95

Val Thr Leu Gln Met Thr Ser Leu Thr Ala Thr Asp Thr Ala Thr Tyr
                100                 105                 110

Phe Cys Ala Arg Ile Val Tyr Gly Gly Ala Gly Tyr Arg Leu Trp Gly
            115                 120                 125

Pro Gly Thr Leu Val Thr Val Ser Ser
        130                 135

<210> SEQ ID NO 17
<211> LENGTH: 114
<212> TYPE: PRT
<213> ORGANISM: rabbit

<400> SEQUENCE: 17

Phe Gly Gly Gly Thr Glu Val Val Lys Gly Asp Pro Val Ala Pro
1               5                   10                  15

Thr Val Leu Ile Phe Pro Pro Ala Ala Asp Gln Val Ala Thr Gly Thr
            20                  25                  30

Val Thr Ile Val Cys Val Ala Asn Lys Tyr Phe Pro Asp Val Thr Val
        35                  40                  45

Thr Trp Glu Val Asp Gly Thr Thr Gln Thr Thr Gly Ile Glu Asn Ser
    50                  55                  60

Lys Thr Pro Gln Asn Ser Ala Asp Cys Thr Tyr Asn Leu Ser Ser Thr
65                  70                  75                  80

Leu Thr Leu Thr Ser Thr Gln Tyr Asn Ser His Lys Glu Tyr Thr Cys
                85                  90                  95

Lys Val Thr Gln Gly Thr Thr Ser Val Val Gln Ser Phe Asn Arg Gly
            100                 105                 110

Asp Cys

<210> SEQ ID NO 18
<211> LENGTH: 323
<212> TYPE: PRT
<213> ORGANISM: rabbit

<400> SEQUENCE: 18

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

```
Glu Lys Thr Ile Ser Lys Ala Arg Gly Gln Pro Leu Glu Pro Lys Val
    210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
                260                 265                 270

Val Leu Asp Ser Asp Gly Ser Tyr Phe Leu Tyr Ser Lys Leu Ser Val
                275                 280                 285

Pro Thr Ser Glu Trp Gln Arg Gly Asp Val Phe Thr Cys Ser Val Met
290                 295                 300

His Glu Ala Leu His Asn His Tyr Thr Gln Lys Ser Ile Ser Arg Ser
305                 310                 315                 320

Pro Gly Lys

<210> SEQ ID NO 19
<211> LENGTH: 236
<212> TYPE: PRT
<213> ORGANISM: rabbit

<400> SEQUENCE: 19

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Pro Ser
                20                  25                  30

Val Glu Ala Ala Val Gly Gly Thr Val Thr Ile Asn Cys Gln Ala Ser
                35                  40                  45

Gln Asp Ile Gly Ser Asp Leu Ala Trp Tyr Gln Gln Lys Pro Gly Gln
    50                  55                  60

Pro Pro Lys Leu Leu Ile Tyr Ser Ala Ser Ser Leu Ala Ser Gly Val
65                  70                  75                  80

Pro Ser Arg Phe Lys Ala Ser Gly Ser Gly Thr Gln Phe Thr Leu Thr
                85                  90                  95

Ile Ser Asp Val Gln Cys Asp Asp Ala Ala Thr Tyr Ser Cys Ala Gly
                100                 105                 110

Tyr Lys Ser Tyr Ser Asp Asp Gly His Gly Phe Gly Gly Gly Thr Glu
            115                 120                 125

Val Val Val Lys Gly Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235

<210> SEQ ID NO 20
<211> LENGTH: 460
```

<212> TYPE: PRT
<213> ORGANISM: rabbit

<400> SEQUENCE: 20

```
Met Glu Thr Gly Leu Arg Trp Leu Leu Leu Val Ala Val Leu Lys Gly
1               5                   10                  15
Val Gln Cys Gln Glu Gln Leu Glu Glu Ser Gly Gly Gly Leu Val Gln
            20                  25                  30
Pro Glu Gly Ser Leu Thr Leu Thr Cys Thr Val Ser Gly Phe Pro Leu
        35                  40                  45
Arg Asn Val Trp Ile Ser Trp Val Arg Gln Ala Pro Gly Lys Gly Leu
    50                  55                  60
Glu Trp Ile Gly Cys Ile Tyr Thr Gly Arg Asp Trp Pro Tyr Tyr Ala
65                  70                  75                  80
Ser Trp Ala Lys Gly Arg Phe Thr Ile Ser Lys Ser Ser Thr Thr
                85                  90                  95
Val Thr Leu Gln Met Thr Ser Leu Thr Ala Thr Asp Thr Ala Thr Tyr
            100                 105                 110
Phe Cys Ala Arg Ile Val Tyr Gly Gly Ala Gly Tyr Arg Leu Trp Gly
        115                 120                 125
Pro Gly Thr Leu Val Thr Val Ser Ser Gly Gln Pro Lys Ala Pro Ser
    130                 135                 140
Val Phe Pro Leu Ala Pro Cys Cys Gly Asp Thr Pro Ser Ser Thr Val
145                 150                 155                 160
Thr Leu Gly Cys Leu Val Lys Gly Tyr Leu Pro Glu Pro Val Thr Val
                165                 170                 175
Thr Trp Asn Ser Gly Thr Leu Thr Asn Gly Val Arg Thr Phe Pro Ser
            180                 185                 190
Val Arg Gln Ser Ser Gly Leu Tyr Ser Leu Ser Ser Val Val Ser Val
        195                 200                 205
Thr Ser Ser Ser Gln Pro Val Thr Cys Asn Val Ala His Pro Ala Thr
    210                 215                 220
Asn Thr Lys Val Asp Lys Thr Val Ala Pro Ser Thr Cys Ser Lys Pro
225                 230                 235                 240
Thr Cys Pro Pro Pro Glu Leu Leu Gly Gly Pro Ser Val Phe Ile Phe
                245                 250                 255
Pro Pro Lys Pro Lys Asp Thr Leu Met Ile Ser Arg Thr Pro Glu Val
            260                 265                 270
Thr Cys Val Val Val Asp Val Ser Gln Asp Asp Pro Glu Val Gln Phe
        275                 280                 285
Thr Trp Tyr Ile Asn Asn Glu Gln Val Arg Thr Ala Arg Pro Pro Leu
    290                 295                 300
Arg Glu Gln Gln Phe Asn Ser Thr Ile Arg Val Val Ser Thr Leu Pro
305                 310                 315                 320
Ile Ala His Gln Asp Trp Leu Arg Gly Lys Glu Phe Lys Cys Lys Val
                325                 330                 335
His Asn Lys Ala Leu Pro Ala Pro Ile Glu Lys Thr Ile Ser Lys Ala
            340                 345                 350
Arg Gly Gln Pro Leu Glu Pro Lys Val Tyr Thr Met Gly Pro Pro Arg
        355                 360                 365
Glu Glu Leu Ser Ser Arg Ser Val Ser Leu Thr Cys Met Ile Asn Gly
    370                 375                 380
Phe Tyr Pro Ser Asp Ile Ser Val Glu Trp Glu Lys Asn Gly Lys Ala
385                 390                 395                 400
```

Glu Asp Asn Tyr Lys Thr Thr Pro Ala Val Leu Asp Ser Asp Gly Ser
            405                 410                 415

Tyr Phe Leu Tyr Ser Lys Leu Ser Val Pro Thr Ser Glu Trp Gln Arg
        420                 425                 430

Gly Asp Val Phe Thr Cys Ser Val Met His Glu Ala Leu His Asn His
            435                 440                 445

Tyr Thr Gln Lys Ser Ile Ser Arg Ser Pro Gly Lys
    450                 455                 460

<210> SEQ ID NO 21
<211> LENGTH: 18
<212> TYPE: DNA
<213> ORGANISM: rabbit

<400> SEQUENCE: 21
agatgtgcgc ttgtgatg                                              18

<210> SEQ ID NO 22
<211> LENGTH: 14
<212> TYPE: DNA
<213> ORGANISM: rabbit

<400> SEQUENCE: 22
acattggtag cgac                                                  14

<210> SEQ ID NO 23
<211> LENGTH: 35
<212> TYPE: DNA
<213> ORGANISM: rabbit

<400> SEQUENCE: 23
gcaggctata aaagttatag tgatgatggt catgg                           35

<210> SEQ ID NO 24
<211> LENGTH: 24
<212> TYPE: DNA
<213> ORGANISM: rabbit

<400> SEQUENCE: 24
cccctccgta atgtctggat atcc                                       24

<210> SEQ ID NO 25
<211> LENGTH: 24
<212> TYPE: DNA
<213> ORGANISM: rabbit

<400> SEQUENCE: 25
tgcatttata ctggtaggga ttgg                                       24

<210> SEQ ID NO 26
<211> LENGTH: 36
<212> TYPE: DNA
<213> ORGANISM: rabbit

<400> SEQUENCE: 26
gcgagaattg tttatggtgg tgctggttat agattg                          36

<210> SEQ ID NO 27
<211> LENGTH: 60
<212> TYPE: DNA
<213> ORGANISM: rabbit

<400> SEQUENCE: 27
atggacacga gggcccccac tcagctgctg gggctcctgc tgctctggct cccaggtgcc    60

<210> SEQ ID NO 28
<211> LENGTH: 70
<212> TYPE: DNA
<213> ORGANISM: rabbit

<400> SEQUENCE: 28
acccagactc caccctccgt ggaggcagct gtgggaggca cagtcaccat caattgccag    60
gccagtcagg                                                          70

<210> SEQ ID NO 29
<211> LENGTH: 168
<212> TYPE: DNA
<213> ORGANISM: rabbit

<400> SEQUENCE: 29
ttagcctggt atcagcagaa accagggcag cctcccaagc tcctgatcta ttctgcatcc    60
agtctggcat ctggggtccc atcgcgattc aaagccagtg gatctgggac acagttcact   120
ctcaccatca gcgacgtgca gtgtgacgat gctgccactt actcctgt                168

<210> SEQ ID NO 30
<211> LENGTH: 2157
<212> TYPE: DNA
<213> ORGANISM: human

<400> SEQUENCE: 30
atgccgcggg cccggcgcc gctgtacgcc tgcctcctgg ggctctgcgc gctcctgccc    60
cggctcgcag gtctcaacat atgcactagt ggaagtgcca cctcatgtga agaatgtctg   120
ctaatccacc caaaatgtgc ctggtgctcc aaagaggact tcggaagccc acggtccatc   180
acctctcggt gtgatctgag ggcaaacctt gtcaaaaatg ctgtggagg tgagatagag   240 agcccagcca gcagcttcca tgtcctgagg agcctgcccc tcagcagcaa gggttcgggc   300
tctgcaggct gggacgtcat tcagatgaca ccacaggaga ttgccgtgaa cctccggccc   360
ggtgacaaga ccaccttcca gctacaggtt cgccaggtgg aggactatcc tgtggacctg   420
tactacctga tggacctctc cctgtccatg aaggatgact ggacaatat ccggagcctg   480 ggcaccaaac tcgcggagga tgaggaag ctcaccagca acttccggtt gggatttggg    540
tcttttgttg ataaggacat ctctcctttc tcctacacgg caccgaggta ccagaccaat   600
ccgtgcattg gttacaagtt gttttccaaat tgcgtcccct cctttgggtt ccgccatctg   660
ctgcctctca cagacagagt ggacagcttc aatgaggaag ttcggaaaca gagggtgtcc   720
cggaaccgag atgcccctga ggggggcttt gatgcagtac tccaggcagc cgtctgcaag   780
gagaagattg ctggcgaaa ggatgcactg catttgctgg tgttcacaac agatgatgtg   840
ccccacatcg cattggatgg aaaattggga ggcctggtgc agccacacga tggccagtgc   900
cacctgaacg aggccaacga gtacacagca tccaaccaga tggactatcc atcccttgcc   960
ttgcttggag agaaattggc agagaacaac atcaacctca tctttgcagt gacaaaaaac  1020
cattatatgc tgtacaagaa ttttacagcc ctgatacctg aacaacggt ggagatttta  1080 gatggagact ccaaaaatat tattcaactg attattaatg catacaatag tatccggtct  1140
aaagtggagt tgtcagtctg ggatcagcct gaggatctta atctcttctt tactgctacc  1200
tgccaagatg gggtatccta tcctggtcag aggaagtgtg agggtctgaa gattggggac  1260

```
acggcatctt tgaagtatc attggaggcc cgaagctgtc ccagcagaca cacggagcat    1320
gtgtttgccc tgcggccggt gggattccgg gacagcctgg aggtgggggt cacctacaac    1380
tgcacgtgcg gctgcagcgt ggggctggaa cccaacagcg ccaggtgcaa cgggagcggg    1440
acctatgtct gcggcctgtg tgagtgcagc cccggctacc tgggcaccag gtgcgagtgc    1500
caggatgggg agaaccagag cgtgtaccag aacctgtgcc gggaggcaga gggcaagcca    1560
ctgtgcagcg gcgtgggga ctgcagctgc aaccagtgct cctgcttcga gagcgagttt    1620
ggcaagatct atgggccttt ctgtgagtgc gacaacttct cctgtgccag gaacaaggga    1680
gtcctctgct caggccatgg cgagtgtcac tgcggggaat gcaagtgcca tgcaggttac    1740
atcggggaca actgtaactg ctcgacagac atcagcacat gccggggcag agatggccag    1800
atctgcagcg agcgtgggca ctgtctctgt gggcagtgcc aatgcacgga gccggggcc    1860 tttggggaga tgtgtgagaa gtgccccacc tgcccggatg catgcagcac caagagagat    1920
tgcgtcgagt gcctgctgct ccactctggg aaacctgaca accagacctg ccacagccta    1980
tgcagggatg aggtgatcac atgggtggac accatcgtga agatgaccag ggaggctgtg    2040
ctatgtttct acaaaaccgc caaggactgc gtcatgatgt tcacctatgt ggagctcccc    2100
agtgggaagt ccaacctgac cgtcctcagg gagccagagt gtggaaacac ccccaac       2157

<210> SEQ ID NO 31
<211> LENGTH: 138
<212> TYPE: DNA
<213> ORGANISM: rabbit

<400> SEQUENCE: 31
atggagactg ggctgcgctg gcttctcctg gtcgctgtgc tcaaaggtgt ccagtgtcag     60
gagcagctgg aggagtccgg gggaggcctg gtccagcctg agggatccct gacactcacc    120
tgcacagtct ctggattc                                                  138

<210> SEQ ID NO 32
<211> LENGTH: 42
<212> TYPE: DNA
<213> ORGANISM: rabbit

<400> SEQUENCE: 32
tgggtccgcc aggctccagg gaaggggctg gagtggatcg ga                       42

<210> SEQ ID NO 33
<211> LENGTH: 114
<212> TYPE: DNA
<213> ORGANISM: rabbit

<400> SEQUENCE: 33
ccctactacg cgagctgggc gaaaggccga ttcaccattt ccaagtcctc gtcgaccacg     60
gtgactctcc aaatgaccag tctgacagcc acggacacgg ccacatattt ctgt          114

<210> SEQ ID NO 34
<211> LENGTH: 33
<212> TYPE: DNA
<213> ORGANISM: rabbit

<400> SEQUENCE: 34 tggggccag gcaccctggt caccgtttcc tca                                  33

<210> SEQ ID NO 35
```

<210> SEQ ID NO 35
<211> LENGTH: 365
<212> TYPE: DNA
<213> ORGANISM: rabbit

<400> SEQUENCE: 35

```
atggacacga gggcccccac tcagctgctg gggctcctgc tgctctggct cccaggtgcc      60
agatgtgcgc ttgtgatgac ccagactcca ccctccgtgg aggcagctgt gggaggcaca     120
gtcaccatca attgccaggc cagtcaggac attggtagcg acttagcctg gtatcagcag     180
aaaccagggc agcctcccaa gctcctgatc tattctgcat ccagtctggc atctggggtc     240
ccatcgcgat tcaaagccag tggatctggg acacagttca ctctcaccat cagcgacgtg     300
cagtgtgacg atgctgccac ttactcctgt gcaggctata aaagttatag tgatgatggt     360
catgg                                                                 365
```

<210> SEQ ID NO 36
<211> LENGTH: 411
<212> TYPE: DNA
<213> ORGANISM: rabbit

<400> SEQUENCE: 36

```
atggagactg ggctgcgctg gcttctcctg gtcgctgtgc tcaaaggtgt ccagtgtcag      60
gagcagctgg aggagtccgg ggaggcctg gtccagcctg agggatccct gacactcacc      120
tgcacagtct ctggattccc cctccgtaat gtctggatat cctgggtccg ccaggctcca    180
gggaaggggc tggagtggat cggatggcat tatactggta gggattggcc ctactacgcg    240
agctgggcga aggccgatt caccatttcc aagtcctcgt cgaccacggt gactctccaa     300
atgaccagtc tgacagccac ggacacggcc acatatttct gtgcgagaat tgtttatggt    360
ggtgctggtt atagattgtg gggcccaggc accctggtca ccgtttcctc a             411
```

<210> SEQ ID NO 37
<211> LENGTH: 346
<212> TYPE: DNA
<213> ORGANISM: rabbit

<400> SEQUENCE: 37

```
tttcggcgga gggaccgagg tggtggtcaa ggtgatcca gttgcaccta ctgtcctcat       60
cttcccacca gctgctgatc aggtggcaac tggaacagtc accatcgtgt gtgtggcgaa    120
taaatacttt cccgatgtca ccgtcacctg gaaggtggat ggcaccaccc aaacaactgg    180
catcgagaac agtaaaacac cgcagaattc tgcagattgt acctacaacc tcagcagcac    240
tctgacactg accagcacac agtacaacag ccacaaagag tacacctgca aggtgaccca    300
gggcacgacc tcagtcgtcc agagcttcaa tagggtgac tgttag                    346
```

<210> SEQ ID NO 38
<211> LENGTH: 972
<212> TYPE: DNA
<213> ORGANISM: rabbit

<400> SEQUENCE: 38

```
gggcaaccta aggctccatc agtcttccca ctggccccct gctgcgggga cacacccagc      60
tccacggtga ccctgggctg cctggtcaaa gggtacctcc cggagccagt gaccgtgacc    120
tggaactcgg gcaccctcac caatgggta cgcaccttcc cgtccgtccg gcagtcctca     180
ggcctctact cgctgagcag cgtggtgagc gtgacctcaa gcagccagcc cgtcacctgc    240
aacgtggccc acccagccac caacaccaaa gtggacaaga ccgttgcgcc ctcgacatgc    300
```

```
agcaagccca cgtgcccacc ccctgaactc ctggggggac cgtctgtctt catcttcccc    360
ccaaaaccca aggacaccct catgatctca cgcacccccg aggtcacatg cgtggtggtg    420
gacgtgagcc aggatgaccc cgaggtgcag ttcacatggt acataaacaa cgagcaggtg    480
cgcaccgccc ggccgccgct acgggagcag cagttcaaca gcacgatccg cgtggtcagc    540
accctcccca tcgcgcacca ggactggctg aggggcaagg agttcaagtg caaagtccac    600
aacaaggcac tcccggcccc catcgagaaa accatctcca aagccagagg cagcccctg     660 gagccgaagg tctacaccat ggcccctccc cgggaggagc tgagcagcag gtcggtcagc    720
ctgacctgca tgatcaacgg cttctaccct tccgacatct cggtggagtg ggagaagaac    780
gggaaggcag aggacaacta caagaccacg ccggccgtgc tggacagcga cggctcctac    840
ttcctctaca gcaagctctc agtgcccacg agtgagtggc agcggggcga cgtcttcacc    900
tgctccgtga tgcacgaggc cttgcacaac cactacacgc agaagtccat ctcccgctct    960
ccgggtaaat ga                                                        972

<210> SEQ ID NO 39
<211> LENGTH: 711
<212> TYPE: DNA
<213> ORGANISM: rabbit

<400> SEQUENCE: 39
atggacacga gggcccccac tcagctgctg ggctcctgc tgctctggct cccaggtgcc      60
agatgtgcgc ttgtgatgac ccagactcca ccctccgtgg aggcagctgt gggaggcaca    120
gtcaccatca attgccaggc cagtcaggac attggtagcg acttagcctg gtatcagcag    180
aaaccagggc agcctcccaa gctcctgatc tattctgcat ccagtctggc atctggggtc    240
ccatcgcgat tcaaagccag tggatctggg acacagttca ctctcaccat cagcgacgtg    300
cagtgtgacg atgctgccac ttactcctgt gcaggctata aaagttatag tgatgatggt    360
catggtttcg gcggagggac cgaggtggtg gtcaagggtg atccagttgc acctactgtc    420
ctcatcttcc caccagctgc tgatcaggtg gcaactggaa cagtcaccat cgtgtgtgtg    480
gcgaataaat actttcccga tgtcaccgtc acctgggagg tggatggcac cacccaaaca    540
actggcatcg agaacagtaa aaccaccgcag aattctgcag attgtaccta caacctcagc    600
agcactctga cactgaccag cacacagtac aacagccaca aagagtacac ctgcaaggtg    660
acccagggca cgacctcagt cgtccagagc ttcaataggg gtgactgtta g             711

<210> SEQ ID NO 40
<211> LENGTH: 1383
<212> TYPE: DNA
<213> ORGANISM: rabbit

<400> SEQUENCE: 40
atggagactg gctgcgctg gcttctcctg gtcgctgtgc tcaaaggtgt ccagtgtcag      60
gagcagctgg aggagtccgg gggaggcctg gtccagcctg agggatccct gacactcacc    120
tgcacagtct ctggattccc cctccgtaat gtctggatat cctgggtccg ccaggctcca    180 gggaagggggc tggagtggat cggatgcatt tatactggta gggattggcc ctactacgcg    240
agctgggcga aaggccgatt caccatttcc aagtcctcgt cgaccacggt gactctccaa    300
atgaccagtc tgacagccac ggacacggcc acatatttct gtgcgagaat tgtttatggt    360
ggtgctggtt atagattgtg gggcccaggc accctggtca ccgtttcctc agggcaacct    420
```

-continued

```
aaggctccat cagtcttccc actggccccc tgctgcgggg acacacccag ctccacggtg    480
accctgggct gcctggtcaa agggtacctc ccggagccag tgaccgtgac ctggaactcg    540
ggcaccctca ccaatggggt acgcaccttc ccgtccgtcc ggcagtcctc aggcctctac    600
tcgctgagca gcgtggtgag cgtgacctca agcagccagc ccgtcacctg caacgtggcc    660
cacccagcca ccaacaccaa agtggacaag accgttgcgc cctcgacatg cagcaagccc    720
acgtgcccac cccctgaact cctgggggga ccgtctgtct tcatcttccc cccaaaaccc    780
aaggacaccc tcatgatctc acgcaccccc gaggtcacat gcgtggtggt ggacgtgagc    840
caggatgacc ccgaggtgca gttcacatgg tacataaaca acgagcaggt gcgcaccgcc    900
cggccgccgc tacgggagca gcagttcaac agcacgatcc gcgtggtcag caccctcccc    960
atcgcgcacc aggactggct gagggggcaag gagttcaagt gcaaagtcca acaacaaggca   1020 ctcccggccc ccatcgagaa aaccatctcc aaagccagag gcagcccct ggagccgaag   1080 gtctacacca tgggccctcc ccgggaggag ctgagcagca ggtcggtcag cctgacctgc   1140
atgatcaacg gcttctaccc ttccgacatc tcggtggagt gggagaagaa cgggaaggca   1200
gaggacaact acaagaccac gccggccgtg ctggacagcg acggctccta cttcctctac   1260
agcaagctct cagtgcccac gagtgagtgg cagcggggcg acgtcttcac ctgctccgtg   1320
atgcacgagg ccttgcacaa ccactacacg cagaagtcca tctcccgctc tccgggtaaa   1380
tga                                                                 1383
```

<210> SEQ ID NO 41
<211> LENGTH: 7
<212> TYPE: PRT
<213> ORGANISM: rabbit

<400> SEQUENCE: 41

Arg Phe Ala Gln Ile Val Met
1               5

<210> SEQ ID NO 42
<211> LENGTH: 6
<212> TYPE: PRT
<213> ORGANISM: rabbit

<400> SEQUENCE: 42

Gln Ser Ile Tyr Ser Tyr
1               5

<210> SEQ ID NO 43
<211> LENGTH: 12
<212> TYPE: PRT
<213> ORGANISM: rabbit

<400> SEQUENCE: 43

Gln Ala Tyr Ser Asp Ser Tyr Ser Tyr Asp Asn Ser
1               5                   10

<210> SEQ ID NO 44
<211> LENGTH: 9
<212> TYPE: PRT
<213> ORGANISM: rabbit

<400> SEQUENCE: 44

Asp Phe Ser Ser Asp Tyr Trp Met Ser
1               5

```
<210> SEQ ID NO 45
<211> LENGTH: 8
<212> TYPE: PRT
<213> ORGANISM: rabbit

<400> SEQUENCE: 45

Tyr Ile Asn Val Gly Asp Gly Lys
1               5

<210> SEQ ID NO 46
<211> LENGTH: 6
<212> TYPE: PRT
<213> ORGANISM: rabbit

<400> SEQUENCE: 46

Gly Lys Asp Leu Gly Leu
1               5

<210> SEQ ID NO 47
<211> LENGTH: 20
<212> TYPE: PRT
<213> ORGANISM: rabbit

<400> SEQUENCE: 47

Met Asp Thr Arg Ala Pro Thr Gln Leu Leu Gly Leu Leu Leu Leu Trp
1               5                   10                  15

Leu Pro Gly Ala
            20

<210> SEQ ID NO 48
<211> LENGTH: 22
<212> TYPE: PRT
<213> ORGANISM: rabbit

<400> SEQUENCE: 48

Thr Gln Thr Pro Ala Ser Val Glu Ala Ala Val Gly Gly Thr Val Thr
1               5                   10                  15

Ile Lys Cys Gln Ala Ser
            20

<210> SEQ ID NO 49
<211> LENGTH: 58
<212> TYPE: PRT
<213> ORGANISM: rabbit

<400> SEQUENCE: 49

Leu Ser Trp Phe Gln Gln Lys Pro Gly Gln Pro Pro Asn Leu Leu Ile
1               5                   10                  15

Tyr Asp Ala Ser Lys Leu Ala Ser Gly Val Pro Ser Arg Phe Lys Gly
            20                  25                  30

Ser Gly Ser Gly Thr Glu Phe Thr Leu Thr Ile Ser Asp Leu Glu Cys
        35                  40                  45

Ala Asp Ala Ala Thr Phe Tyr Cys Gln Ser
        50                  55

<210> SEQ ID NO 50
<211> LENGTH: 292
<212> TYPE: PRT
<213> ORGANISM: artificial
<220> FEATURE:
<223> OTHER INFORMATION: Fusion protein of GST and BETA-3

<400> SEQUENCE: 50
```

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Arg
    210                 215                 220

Ser Thr Ser Leu Tyr Lys Lys Ala Gly Phe Gly Gly Gly Ser Glu
225                 230                 235                 240

Asn Leu Tyr Phe Gln Lys Leu Leu Ile Thr Ile His Asp Arg Lys Glu
                245                 250                 255

Phe Ala Lys Phe Glu Glu Glu Arg Ala Arg Ala Lys Trp Asp Thr Ala
            260                 265                 270

Asn Asn Pro Leu Tyr Lys Glu Ala Thr Ser Thr Phe Thr Asn Ile Thr
        275                 280                 285

Tyr Arg Gly Thr
    290

<210> SEQ ID NO 51
<211> LENGTH: 45
<212> TYPE: PRT
<213> ORGANISM: rabbit

<400> SEQUENCE: 51

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Lys Pro
            20                  25                  30

Gly Gly Thr Leu Thr Leu Thr Cys Lys Ala Ser Gly Phe
        35                  40                  45

<210> SEQ ID NO 52
<211> LENGTH: 14
<212> TYPE: PRT
<213> ORGANISM: rabbit
```

-continued

<400> SEQUENCE: 52

Trp Val Arg Gln Gly Pro Gly Lys Gly Leu Gln Trp Ile Ala
1               5                   10

<210> SEQ ID NO 53
<211> LENGTH: 38
<212> TYPE: PRT
<213> ORGANISM: rabbit

<400> SEQUENCE: 53

Thr Tyr Tyr Ala Ser Trp Ala Lys Gly Arg Phe Thr Ile Ser Lys Thr
1               5                   10                  15

Ser Ser Thr Thr Val Thr Leu Gln Met Thr Ser Leu Ala Ala Ala Asp
            20                  25                  30

Thr Ala Thr Tyr Phe Cys
        35

<210> SEQ ID NO 54
<211> LENGTH: 11
<212> TYPE: PRT
<213> ORGANISM: rabbit

<400> SEQUENCE: 54

Trp Gly Pro Gly Thr Leu Val Thr Val Ser Ser
1               5                   10

<210> SEQ ID NO 55
<211> LENGTH: 125
<212> TYPE: PRT
<213> ORGANISM: rabbit

<400> SEQUENCE: 55

Met Asp Thr Arg Ala Pro Thr Gln Leu Leu Gly Leu Leu Leu Leu Trp
1               5                   10                  15

Leu Pro Gly Ala Arg Phe Ala Gln Ile Val Met Thr Gln Thr Pro Ala
            20                  25                  30

Ser Val Glu Ala Ala Val Gly Gly Thr Val Thr Ile Lys Cys Gln Ala
        35                  40                  45

Ser Gln Ser Ile Tyr Ser Tyr Leu Ser Trp Phe Gln Gln Lys Pro Gly
    50                  55                  60

Gln Pro Pro Asn Leu Leu Ile Tyr Asp Ala Ser Lys Leu Ala Ser Gly
65                  70                  75                  80

Val Pro Ser Arg Phe Lys Gly Ser Gly Ser Gly Thr Glu Phe Thr Leu
                85                  90                  95

Thr Ile Ser Asp Leu Glu Cys Ala Asp Ala Ala Thr Phe Tyr Cys Gln
            100                 105                 110

Ser Gln Ala Tyr Ser Asp Ser Tyr Ser Tyr Asp Asn Ser
        115                 120                 125

<210> SEQ ID NO 56
<211> LENGTH: 131
<212> TYPE: PRT
<213> ORGANISM: rabbit

<400> SEQUENCE: 56

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Lys Pro
            20                  25                  30

```
Gly Gly Thr Leu Thr Leu Thr Cys Lys Ala Ser Gly Phe Asp Phe Ser
            35                  40                  45

Ser Asp Tyr Trp Met Ser Trp Val Arg Gln Gly Pro Gly Lys Gly Leu
    50                  55                  60

Gln Trp Ile Ala Tyr Ile Asn Val Gly Asp Gly Lys Thr Tyr Tyr Ala
65                  70                  75                  80

Ser Trp Ala Lys Gly Arg Phe Thr Ile Ser Lys Thr Ser Ser Thr Thr
                85                  90                  95

Val Thr Leu Gln Met Thr Ser Leu Ala Ala Ala Asp Thr Ala Thr Tyr
            100                 105                 110

Phe Cys Gly Lys Asp Leu Gly Leu Trp Gly Pro Gly Thr Leu Val Thr
            115                 120                 125

Val Ser Ser
    130

<210> SEQ ID NO 57
<211> LENGTH: 114
<212> TYPE: PRT
<213> ORGANISM: rabbit

<400> SEQUENCE: 57

Phe Gly Gly Gly Thr Glu Leu Val Val Glu Gly Asp Pro Val Ala Pro
1               5                   10                  15

Thr Val Leu Ile Phe Pro Pro Ala Ala Asp Gln Val Ala Thr Gly Thr
            20                  25                  30

Val Thr Ile Val Cys Val Ala Asn Lys Tyr Phe Pro Asp Val Thr Val
            35                  40                  45

Thr Trp Glu Val Asp Gly Thr Thr Gln Thr Thr Gly Ile Glu Asn Ser
        50                  55                  60

Lys Thr Pro Gln Asn Ser Ala Asp Cys Thr Tyr Asn Leu Ser Ser Thr
65                  70                  75                  80

Leu Thr Leu Thr Ser Thr Gln Tyr Asn Ser His Lys Glu Tyr Thr Cys
                85                  90                  95

Lys Val Thr Gln Gly Thr Thr Ser Val Val Gln Ser Phe Asn Arg Gly
            100                 105                 110

Asp Cys

<210> SEQ ID NO 58
<211> LENGTH: 323
<212> TYPE: PRT
<213> ORGANISM: rabbit

<400> SEQUENCE: 58

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
            35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95
```

```
Pro Ser Thr Cys Ser Lys Pro Thr Cys Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Val Asp Val Ser Gln
        130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
                180                 185                 190

Lys Glu Phe Lys Cys Lys Val His Asn Lys Ala Leu Pro Ala Pro Ile
            195                 200                 205

Glu Lys Thr Ile Ser Lys Ala Arg Gly Gln Pro Leu Glu Pro Lys Val
        210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
                260                 265                 270

Val Leu Asp Ser Asp Gly Ser Tyr Phe Leu Tyr Ser Lys Leu Ser Val
            275                 280                 285

Pro Thr Ser Glu Trp Gln Arg Gly Asp Val Phe Thr Cys Ser Val Met
        290                 295                 300

His Glu Ala Leu His Asn His Tyr Thr Gln Lys Ser Ile Ser Arg Ser
305                 310                 315                 320

Pro Gly Lys

<210> SEQ ID NO 59
<211> LENGTH: 239
<212> TYPE: PRT
<213> ORGANISM: rabbit

<400> SEQUENCE: 59

Met Asp Thr Arg Ala Pro Thr Gln Leu Leu Gly Leu Leu Leu Leu Trp
1               5                   10                  15

Leu Pro Gly Ala Arg Phe Ala Gln Ile Val Met Thr Gln Thr Pro Ala
            20                  25                  30

Ser Val Glu Ala Ala Val Gly Gly Thr Val Thr Ile Lys Cys Gln Ala
        35                  40                  45

Ser Gln Ser Ile Tyr Ser Tyr Leu Ser Trp Phe Gln Gln Lys Pro Gly
    50                  55                  60

Gln Pro Pro Asn Leu Leu Ile Tyr Asp Ala Ser Lys Leu Ala Ser Gly
65                  70                  75                  80

Val Pro Ser Arg Phe Lys Gly Ser Gly Ser Gly Thr Glu Phe Thr Leu
                85                  90                  95

Thr Ile Ser Asp Leu Glu Cys Ala Asp Ala Ala Thr Phe Tyr Cys Gln
            100                 105                 110

Ser Gln Ala Tyr Ser Asp Ser Tyr Ser Tyr Asp Asn Ser Phe Gly Gly
        115                 120                 125

Gly Thr Glu Leu Val Val Glu Gly Asp Pro Val Ala Pro Thr Val Leu
    130                 135                 140
```

-continued

```
Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 60
<211> LENGTH: 454
<212> TYPE: PRT
<213> ORGANISM: rabbit

<400> SEQUENCE: 60

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Lys Pro
            20                  25                  30

Gly Gly Thr Leu Thr Leu Thr Cys Lys Ala Ser Gly Phe Asp Phe Ser
        35                  40                  45

Ser Asp Tyr Trp Met Ser Trp Val Arg Gln Gly Pro Gly Lys Gly Leu
    50                  55                  60

Gln Trp Ile Ala Tyr Ile Asn Val Gly Asp Gly Lys Thr Tyr Tyr Ala
65                  70                  75                  80

Ser Trp Ala Lys Gly Arg Phe Thr Ile Ser Lys Thr Ser Ser Thr Thr
                85                  90                  95

Val Thr Leu Gln Met Thr Ser Leu Ala Ala Ala Asp Thr Ala Thr Tyr
            100                 105                 110

Phe Cys Gly Lys Asp Leu Gly Leu Trp Gly Pro Gly Thr Leu Val Thr
        115                 120                 125

Val Ser Ser Gly Gln Pro Lys Ala Pro Ser Val Phe Pro Leu Ala Pro
130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285
```

```
Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Ser Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450
```

<210> SEQ ID NO 61
<211> LENGTH: 21
<212> TYPE: DNA
<213> ORGANISM: rabbit

<400> SEQUENCE: 61
agatttgccc aaattgtgat g                                              21

<210> SEQ ID NO 62
<211> LENGTH: 14
<212> TYPE: DNA
<213> ORGANISM: rabbit

<400> SEQUENCE: 62
agcatttaca gcta                                                      14

<210> SEQ ID NO 63
<211> LENGTH: 41
<212> TYPE: DNA
<213> ORGANISM: rabbit

<400> SEQUENCE: 63
caaagccagg cttatagtga tagttatagt tatgataata g                        41

<210> SEQ ID NO 64
<211> LENGTH: 27
<212> TYPE: DNA
<213> ORGANISM: rabbit

<400> SEQUENCE: 64
gacttcagta gcgactactg gatgtcc                                        27

<210> SEQ ID NO 65
<211> LENGTH: 24
<212> TYPE: DNA
<213> ORGANISM: rabbit

```
<400> SEQUENCE: 65
tacattaatg ttggtgatgg taaa                                          24

<210> SEQ ID NO 66
<211> LENGTH: 18
<212> TYPE: DNA
<213> ORGANISM: rabbit

<400> SEQUENCE: 66
ggcaaagatt taggcttg                                                 18

<210> SEQ ID NO 67
<211> LENGTH: 60
<212> TYPE: DNA
<213> ORGANISM: rabbit

<400> SEQUENCE: 67
atggacacga gggcccccac tcagctgctg gggctcctac tgctctggct cccaggtgcc   60

<210> SEQ ID NO 68
<211> LENGTH: 69
<212> TYPE: DNA
<213> ORGANISM: rabbit

<400> SEQUENCE: 68
acccagactc cagcctccgt ggaggcagct gtgggaggca cagtcaccat caagtgccag   60
gccagtcag                                                           69

<210> SEQ ID NO 69
<211> LENGTH: 169
<212> TYPE: DNA
<213> ORGANISM: rabbit

<400> SEQUENCE: 69
cttatcctgg tttcagcaga aaccagggca gcctcccaac ctcctgatct acgatgcatc   60
caaactggcc tctggggtcc catcgcggtt caaaggcagt ggatctggga cagagttcac  120
tctcaccatc agcgacctgg agtgtgccga tgctgccact ttctactgt               169

<210> SEQ ID NO 70
<211> LENGTH: 126
<212> TYPE: DNA
<213> ORGANISM: human

<400> SEQUENCE: 70
cacgaccgaa aagaattcgc taaatttgag gaagaacgcg ccagagcaaa atgggacaca   60
gccaacaacc cactgtataa agaggccacg tctaccttca ccaatatcac gtaccggggc  120
acttaa                                                              126

<210> SEQ ID NO 71
<211> LENGTH: 135
<212> TYPE: DNA
<213> ORGANISM: rabbit

<400> SEQUENCE: 71
atggagactg gctgcgcctg cttctcctg gtcgctgtgc tcaaaggtgt ccagtgtcag    60
tcgttggagg agtccggggg aggcctggtc aagcctggag gaaccctgac actcacctgc  120
aaagcctctg gattc                                                    135
```

<210> SEQ ID NO 72
<211> LENGTH: 42
<212> TYPE: DNA
<213> ORGANISM: rabbit

<400> SEQUENCE: 72
tgggtccgcc agggtccagg gaagggctg cagtggatcg ca                42

<210> SEQ ID NO 73
<211> LENGTH: 114
<212> TYPE: DNA
<213> ORGANISM: rabbit

<400> SEQUENCE: 73
acttactacg cgagctgggc gaaaggccga ttcaccatct ccaaaacctc gtcgaccacg    60
gtgactctgc aaatgaccag tctggcagcc gcggacacgg ccacctattt ctgt         114

<210> SEQ ID NO 74
<211> LENGTH: 33
<212> TYPE: DNA
<213> ORGANISM: rabbit

<400> SEQUENCE: 74
tggggcccag gcaccctggt caccgtctcc tca                         33

<210> SEQ ID NO 75
<211> LENGTH: 374
<212> TYPE: DNA
<213> ORGANISM: rabbit

<400> SEQUENCE: 75
atggacacga gggcccccac tcagctgctg gggctcctac tgctctggct cccaggtgcc    60
agatttgccc aaattgtgat gacccagact ccagcctccg tggaggcagc tgtgggaggc   120
acagtcacca tcaagtgcca ggccagtcag agcatttaca gctacttatc ctggtttcag   180
cagaaaccag gcagcctcc caacctcctg atctacgatg catccaaact ggcctctggg    240
gtcccatcgc ggttcaaagg cagtggatct gggacagagt tcactctcac catcagcgac   300
ctggagtgtg ccgatgctgc cactttctac tgtcaaagcc aggcttatag tgatagttat   360
agttatgata atag                                             374

<210> SEQ ID NO 76
<211> LENGTH: 393
<212> TYPE: DNA
<213> ORGANISM: rabbit

<400> SEQUENCE: 76
atggagactg ggctgcgctg gcttctcctg gtcgctgtgc tcaaaggtgt ccagtgtcag    60
tcgttggagg agtccggggg aggcctggtc aagcctggag aaccctgac actcacctgc   120 aaagcctctg gattcgactt cagtagcgac tactggatgt cctgggtccg ccagggtcca   180
gggaaggggc tgcagtggat cgcatacatt aatgttggtg atggtaaaac ttactacgcg   240
agctgggcga aaggccgatt caccatctcc aaaacctcgt cgaccacggt gactctgcaa   300
atgaccagtc tggcagccgc ggacacggcc acctatttct gtgcaaaga tttaggcttg   360 tggggcccag gcaccctggt caccgtctcc tca                         393

<210> SEQ ID NO 77
<211> LENGTH: 346

<212> TYPE: DNA
<213> ORGANISM: rabbit

<400> SEQUENCE: 77

| | | | | | |
|---|---|---|---|---|---|
| tttcggcggg | gggaccgaac | tggtggtcga | aggtgatcca | gttgcaccta | ctgtcctcat | 60 |
| cttcccacca | gctgctgatc | aggtggcaac | tggaacagtc | accatcgtgt | gtgtggcgaa | 120 |
| taaatacttt | cccgatgtca | ccgtcacctg | ggaggtggat | ggcaccaccc | aaacaactgg | 180 |
| catcgagaac | agtaaaacac | cgcagaattc | tgcagattgt | acctacaacc | tcagcagcac | 240 |
| tctgacactg | accagcacac | agtacaacag | ccacaaagag | tacacctgca | aggtgaccca | 300 |
| gggcacgacc | tcagtcgtcc | agagcttcaa | taggggtgac | tgttag | | 346 |

<210> SEQ ID NO 78
<211> LENGTH: 967
<212> TYPE: DNA
<213> ORGANISM: rabbit

<400> SEQUENCE: 78

| | | | | | |
|---|---|---|---|---|---|
| gggcaaccta | aggctccatc | agtcttccca | ctggccccct | gctgcgggga | cacacccagc | 60 |
| tccacggtga | ccctgggctg | cctggtcaaa | gggtacctcc | cggagccagt | gaccgtgacc | 120 |
| tggaactcgg | gcaccctcac | caatggggta | cgcaccttcc | cgtccgtccg | gcagtcctca | 180 |
| ggcctctact | cgctgagcag | cgtggtgagc | gtgacctcaa | gcagccagcc | cgtcacctgc | 240 |
| aacgtggccc | acccagccac | caacaccaaa | gtggacaaga | ccgttgcgcc | ctcgacatgc | 300 |
| agcaagccca | cgtgcccacc | ccctgaactc | ctggggggac | cgtctgtctt | catcttcccc | 360 |
| ccaaaaccca | aggacaccct | catgatctca | cgcaccccg | aggtcacatg | cgtggtggtg | 420 |
| gacgtgagcc | aggatgaccc | cgaggtgcag | ttcacatggt | acataaacaa | cgagcaggtg | 480 |
| cgcaccgccc | ggccgccgct | acgggagcag | cagttcaaca | gcacgatccg | cgtggtcagc | 540 |
| accctcccca | tcgcgcacca | ggactggctg | aggggcaagg | agttcaagtg | caaagtccac | 600 |
| aacaaggcac | tcccggcccc | catcgagaaa | accatctcca | agccagagg | gcagcccctg | 660 |
| gagccgaagg | tctacaccat | gggccctccc | cgggaggagc | tgagcagcag | gtcggtcagc | 720 |
| ctgacctgca | tgatcaacgg | cttctaccct | tccgacatct | cggtggagtg | ggagaagaac | 780 |
| gggaaggcag | aggacaacta | caagaccacg | ccggccgtgc | tggacagcga | cggctcctac | 840 |
| ttcctctaca | gcaagctctc | agtgcccacg | agtgagtggc | agcggggcga | cgtcttcacc | 900 |
| tgctccgtga | tgcacgaggc | cttgcacaac | cactacacgc | agaagtccat | ctcccgctct | 960 |
| ccgggta | | | | | | 967 |

<210> SEQ ID NO 79
<211> LENGTH: 720
<212> TYPE: DNA
<213> ORGANISM: rabbit

<400> SEQUENCE: 79

| | | | | | |
|---|---|---|---|---|---|
| atggacacga | gggcccccac | tcagctgctg | gggctcctac | tgctctggct | cccaggtgcc | 60 |
| agatttgccc | aaattgtgat | gacccagact | ccagcctccg | tggaggcagc | tgtgggaggc | 120 |
| acagtcacca | tcagtgcca | ggccagtcag | agcatttaca | gctacttatc | ctggtttcag | 180 |
| cagaaaccag | gcagcctcc | caacctcctg | atctacgatg | catccaaact | ggcctctggg | 240 |
| gtcccatcgc | ggttcaaagg | cagtggatct | gggacagagt | tcactctcac | catcagcgac | 300 |
| ctggagtgtg | ccgatgctgc | cactttctac | tgtcaaagcc | aggcttatag | tgatagttat | 360 |

| | |
|---|---|
| agttatgata atagtttcgg cggggggacc gaactggtgg tcgaaggtga tccagttgca | 420 |
| cctactgtcc tcatcttccc accagctgct gatcaggtgg caactggaac agtcaccatc | 480 |
| gtgtgtgtgg cgaataaata ctttcccgat gtcaccgtca cctgggaggt ggatggcacc | 540 |
| acccaaacaa ctggcatcga gaacagtaaa acaccgcaga attctgcaga ttgtacctac | 600 |
| aacctcagca gcactctgac actgaccagc acacagtaca cagccacaa agagtacacc | 660 |
| tgcaaggtga cccagggcac gacctcagtc gtccagagct caataggggg tgactgttag | 720 |

<210> SEQ ID NO 80
<211> LENGTH: 1365
<212> TYPE: DNA
<213> ORGANISM: rabbit

<400> SEQUENCE: 80

| | |
|---|---|
| atggagactg ggctgcgctg gcttctcctg gtcgctgtgc tcaaaggtgt ccagtgtcag | 60 |
| tcgttggagg agtccggggg aggcctggtc aagcctggag aaccctgac actcacctgc | 120 |
| aaagcctctg gattcgactt cagtagcgac tactggatgt cctgggtccg ccagggtcca | 180 |
| gggaaggggc tgcagtggat cgcatacatt aatgttggtg atggtaaaac ttactacgcg | 240 |
| agctgggcga aaggccgatt caccatctcc aaaacctcgt cgaccacggt gactctgcaa | 300 |
| atgaccagtc tggcagccgc ggacacggcc acctatttct gtggcaaaga tttaggcttg | 360 |
| tggggcccag gcaccctggt caccgtctcc tcagggcaac taaggctcc atcagtcttc | 420 |
| ccactggccc cctgctgcgg ggacacaccc agctccacgg tgaccctggg ctgcctggtc | 480 |
| aaagggtacc tcccggagcc agtgaccgtg acctggaact cgggcaccct caccaatggg | 540 |
| gtacgcacct tcccgtccgt ccggcagtcc tcaggcctct actcgctgag cagcgtggtg | 600 |
| agcgtgacct caagcagcca gcccgtcacc tgcaacgtgg cccacccagc caccaacacc | 660 |
| aaagtggaca gaccgttgc gccctcgaca tgcagcaagc ccacgtgccc accccctgaa | 720 |
| ctcctggggg gaccgtctgt cttcatcttc cccccaaaac ccaaggacac cctcatgatc | 780 |
| tcacgcaccc ccgaggtcac atgcgtggtg gtggacgtga gccaggatga cccgaggtg | 840 |
| cagttcacat ggtacataaa caacgagcag gtgcgcaccg cccggccgcc gctacgggag | 900 |
| cagcagttca acagcacgat ccgcgtggtc agcacctcc ccatcgcgca ccaggactgg | 960 |
| ctgaggggca aggagttcaa gtgcaaagtc cacaacaagg cactcccggc ccccatcgag | 1020 |
| aaaaccatct ccaaagccag agggcagccc ctggagccga aggtctacac catgggccct | 1080 |
| cccgggagg agctgagcag caggtcggtc agcctgacct gcatgatcaa cggcttctac | 1140 |
| ccttccgaca tctcggtgga gtgggagaag aacgggaagg cagaggacaa ctacaagacc | 1200 |
| acgccggccg tgctggacag cgacggctcc tacttcctct acagcaagct ctcagtgccc | 1260 |
| acgagtgagt ggcagcgggg cgacgtcttc acctgctccg tgatgcacga ggccttgcac | 1320 |
| aaccactaca cgcagaagtc catctcccgc tctccgggta aatga | 1365 |

<210> SEQ ID NO 81
<211> LENGTH: 6
<212> TYPE: PRT
<213> ORGANISM: rabbit

<400> SEQUENCE: 81

Thr Phe Ala Gln Val Leu
1               5

<210> SEQ ID NO 82

```
<211> LENGTH: 8
<212> TYPE: PRT
<213> ORGANISM: rabbit

<400> SEQUENCE: 82

Glu Ser Val Tyr Ala Asp Ile Ala
1               5

<210> SEQ ID NO 83
<211> LENGTH: 12
<212> TYPE: PRT
<213> ORGANISM: rabbit

<400> SEQUENCE: 83

Ala Gly Asp Tyr Gly Ala Gly Thr Glu Pro Asn Leu
1               5                   10

<210> SEQ ID NO 84
<211> LENGTH: 8
<212> TYPE: PRT
<213> ORGANISM: rabbit

<400> SEQUENCE: 84

Ser Leu Ser Ser Tyr Gly Val Ser
1               5

<210> SEQ ID NO 85
<211> LENGTH: 7
<212> TYPE: PRT
<213> ORGANISM: rabbit

<400> SEQUENCE: 85

Ser Ile Ser Thr Thr Gly Ile
1               5

<210> SEQ ID NO 86
<211> LENGTH: 14
<212> TYPE: PRT
<213> ORGANISM: rabbit

<400> SEQUENCE: 86

Ala Arg Gly Phe Pro Gly His Leu Arg Lys Pro Ser Asp Ile
1               5                   10

<210> SEQ ID NO 87
<211> LENGTH: 20
<212> TYPE: PRT
<213> ORGANISM: rabbit

<400> SEQUENCE: 87

Met Asp Thr Arg Ala Pro Thr Gln Leu Leu Gly Leu Leu Leu Leu Trp
1               5                   10                  15

Leu Pro Gly Ala
            20

<210> SEQ ID NO 88
<211> LENGTH: 22
<212> TYPE: PRT
<213> ORGANISM: rabbit

<400> SEQUENCE: 88

Thr Gln Thr Pro Ser Ser Val Ser Ala Ala Val Gly Gly Thr Val Ser
1               5                   10                  15

Ile Ser Cys Gln Ser Ser
```

<210> SEQ ID NO 89
<211> LENGTH: 56
<212> TYPE: PRT
<213> ORGANISM: rabbit

<400> SEQUENCE: 89

Leu Ser Trp Phe Gln Gln Lys Pro Gly Gln Pro Pro Lys Leu Leu Ile
1               5                   10                  15

Tyr Gly Ala Ser Thr Leu Ala Ser Gly Val Pro Ser Arg Phe Ser Gly
            20                  25                  30

Ser Gly Ser Gly Thr Glu Phe Thr Leu Thr Ile Ser Asp Val Gln Cys
        35                  40                  45

Asp Ala Ala Ala Thr Tyr Tyr Cys
    50                  55

<210> SEQ ID NO 90
<211> LENGTH: 692
<212> TYPE: PRT
<213> ORGANISM: human

<400> SEQUENCE: 90

Gly Pro Asn Ile Cys Thr Thr Arg Gly Val Ser Ser Cys Gln Gln Cys
1               5                   10                  15

Leu Ala Val Ser Pro Met Cys Ala Trp Cys Ser Asp Glu Ala Leu Pro
            20                  25                  30

Leu Gly Ser Pro Arg Cys Asp Leu Lys Glu Asn Leu Leu Lys Asp Asn
        35                  40                  45

Cys Ala Pro Glu Ser Ile Glu Phe Pro Val Ser Glu Ala Arg Val Leu
    50                  55                  60

Glu Asp Arg Pro Leu Ser Asp Lys Gly Ser Gly Asp Ser Ser Gln Val
65                  70                  75                  80

Thr Gln Val Ser Pro Gln Arg Ile Ala Leu Arg Leu Arg Pro Asp Asp
                85                  90                  95

Ser Lys Asn Phe Ser Ile Gln Val Arg Gln Val Glu Asp Tyr Pro Val
            100                 105                 110

Asp Ile Tyr Tyr Leu Met Asp Leu Ser Tyr Ser Met Lys Asp Asp Leu
        115                 120                 125

Trp Ser Ile Gln Asn Leu Gly Thr Lys Leu Ala Thr Gln Met Arg Lys
    130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Glu Ala Leu Glu Asn Pro
                165                 170                 175

Cys Tyr Asp Met Lys Thr Thr Cys Leu Pro Met Phe Gly Tyr Lys His
            180                 185                 190

Val Leu Thr Leu Thr Asp Gln Val Thr Arg Phe Asn Glu Glu Val Lys
        195                 200                 205

Lys Gln Ser Val Ser Arg Asn Arg Asp Ala Pro Glu Gly Gly Phe Asp
    210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Gln Pro Asn Asp Gly Gln

```
                260                 265                 270
Cys His Val Gly Ser Asp Asn His Tyr Ser Ala Ser Thr Thr Met Asp
            275                 280                 285
Tyr Pro Ser Leu Gly Leu Met Thr Glu Lys Leu Ser Gln Lys Asn Ile
290                 295                 300
Asn Leu Ile Phe Ala Val Thr Glu Asn Val Val Asn Leu Tyr Gln Asn
305                 310                 315                 320
Tyr Ser Glu Leu Ile Pro Gly Thr Thr Val Gly Val Leu Ser Met Asp
            325                 330                 335
Ser Ser Asn Val Leu Gln Leu Ile Val Asp Ala Tyr Gly Lys Ile Arg
            340                 345                 350
Ser Lys Val Glu Leu Glu Val Arg Asp Leu Pro Glu Glu Leu Ser Leu
            355                 360                 365
Ser Phe Asn Ala Thr Cys Leu Asn Asn Glu Val Ile Pro Gly Leu Lys
            370                 375                 380
Ser Cys Met Gly Leu Lys Ile Gly Asp Thr Val Ser Phe Ser Ile Glu
385                 390                 395                 400
Ala Lys Val Arg Gly Cys Pro Gln Glu Lys Glu Lys Ser Phe Thr Ile
            405                 410                 415
Lys Pro Val Gly Phe Lys Asp Ser Leu Ile Val Gln Val Thr Phe Asp
            420                 425                 430
Cys Asp Cys Ala Cys Gln Ala Gln Ala Glu Pro Asn Ser His Arg Cys
            435                 440                 445
Asn Asn Gly Asn Gly Thr Phe Glu Cys Gly Val Cys Arg Cys Gly Pro
450                 455                 460
Gly Trp Leu Gly Ser Gln Cys Glu Cys Ser Glu Glu Asp Tyr Arg Pro
465                 470                 475                 480
Ser Gln Gln Asp Glu Cys Ser Pro Arg Glu Gly Gln Pro Val Cys Ser
            485                 490                 495
Gln Arg Gly Glu Cys Leu Cys Gly Gln Cys Val Cys His Ser Ser Asp
            500                 505                 510
Phe Gly Lys Ile Thr Gly Lys Tyr Cys Glu Cys Asp Asp Phe Ser Cys
            515                 520                 525
Val Arg Tyr Lys Gly Glu Met Cys Ser Gly His Gly Gln Cys Ser Cys
            530                 535                 540
Gly Asp Cys Leu Cys Asp Ser Asp Trp Thr Gly Tyr Tyr Cys Asn Cys
545                 550                 555                 560
Thr Thr Arg Thr Asp Thr Cys Met Ser Ser Asn Gly Leu Leu Cys Ser
            565                 570                 575
Gly Arg Gly Lys Cys Glu Cys Gly Ser Cys Val Cys Ile Gln Pro Gly
            580                 585                 590
Ser Tyr Gly Asp Thr Cys Glu Lys Cys Pro Thr Cys Pro Asp Ala Cys
            595                 600                 605
Thr Phe Lys Lys Glu Cys Val Glu Cys Lys Lys Phe Asp Arg Glu Pro
610                 615                 620
Tyr Met Thr Glu Asn Thr Cys Asn Arg Tyr Cys Arg Asp Glu Ile Glu
625                 630                 635                 640
Ser Val Lys Glu Leu Lys Asp Thr Gly Lys Asp Ala Val Asn Cys Thr
            645                 650                 655
Tyr Lys Asn Glu Asp Asp Cys Val Val Arg Phe Gln Tyr Tyr Glu Asp
            660                 665                 670
Ser Ser Gly Lys Ser Ile Leu Tyr Val Val Glu Glu Pro Glu Cys Pro
            675                 680                 685
```

Lys Gly Pro Asp
        690

<210> SEQ ID NO 91
<211> LENGTH: 45
<212> TYPE: PRT
<213> ORGANISM: rabbit

<400> SEQUENCE: 91

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Ile Leu Thr Cys Thr Val Ser Gly Phe
        35                  40                  45

<210> SEQ ID NO 92
<211> LENGTH: 14
<212> TYPE: PRT
<213> ORGANISM: rabbit

<400> SEQUENCE: 92

Trp Val Arg Gln Ala Pro Gly Asn Gly Leu Glu Tyr Ile Gly
1               5                   10

<210> SEQ ID NO 93
<211> LENGTH: 39
<212> TYPE: PRT
<213> ORGANISM: rabbit

<400> SEQUENCE: 93

Thr Tyr Tyr Ala Ser Trp Ala Lys Ser Arg Ser Thr Ile Thr Arg Asn
1               5                   10                  15

Thr Asn Leu Tyr Thr Val Thr Leu Lys Met Thr Gly Leu Thr Ala Ala
            20                  25                  30

Asp Thr Ala Thr Tyr Phe Cys
        35

<210> SEQ ID NO 94
<211> LENGTH: 11
<212> TYPE: PRT
<213> ORGANISM: rabbit

<400> SEQUENCE: 94

Trp Gly Pro Gly Thr Leu Val Thr Val Ser Ala
1               5                   10

<210> SEQ ID NO 95
<211> LENGTH: 124
<212> TYPE: PRT
<213> ORGANISM: rabbit

<400> SEQUENCE: 95

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Ser Ile Ser Cys Gln Ser Ser
        35                  40                  45

Glu Ser Val Tyr Ala Asp Ile Ala Leu Ser Trp Phe Gln Gln Lys Pro
    50                  55                  60

-continued

Gly Gln Pro Pro Lys Leu Leu Ile Tyr Gly Ala Ser Thr Leu Ala Ser
65                  70                  75                  80

Gly Val Pro Ser Arg Phe Ser Gly Ser Gly Ser Gly Thr Glu Phe Thr
            85                  90                  95

Leu Thr Ile Ser Asp Val Gln Cys Asp Ala Ala Thr Tyr Tyr Cys
            100                 105                 110

Ala Gly Asp Tyr Gly Ala Gly Thr Glu Pro Asn Leu
        115                 120

<210> SEQ ID NO 96
<211> LENGTH: 138
<212> TYPE: PRT
<213> ORGANISM: rabbit

<400> SEQUENCE: 96

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Ile Leu Thr Cys Thr Val Ser Gly Phe Ser Leu Ser
        35                  40                  45

Ser Tyr Gly Val Ser Trp Val Arg Gln Ala Pro Gly Asn Gly Leu Glu
    50                  55                  60

Tyr Ile Gly Ser Ile Ser Thr Thr Gly Ile Thr Tyr Tyr Ala Ser Trp
65                  70                  75                  80

Ala Lys Ser Arg Ser Thr Ile Thr Arg Asn Thr Asn Leu Tyr Thr Val
            85                  90                  95

Thr Leu Lys Met Thr Gly Leu Thr Ala Ala Asp Thr Ala Thr Tyr Phe
            100                 105                 110

Cys Ala Arg Gly Phe Pro Gly His Leu Arg Lys Pro Ser Asp Ile Trp
        115                 120                 125

Gly Pro Gly Thr Leu Val Thr Val Ser Ala
        130                 135

<210> SEQ ID NO 97
<211> LENGTH: 114
<212> TYPE: PRT
<213> ORGANISM: rabbit

<400> SEQUENCE: 97

Phe Gly Gly Gly Thr Glu Val Val Val Ser Gly Asp Pro Val Ala Pro
1               5                   10                  15

Thr Val Leu Ile Phe Pro Pro Ala Ala Asp Gln Val Ala Thr Gly Thr
            20                  25                  30

Val Thr Ile Val Cys Val Ala Asn Lys Tyr Phe Pro Asp Val Thr Val
        35                  40                  45

Thr Trp Glu Val Asp Gly Thr Thr Gln Thr Thr Gly Ile Glu Asn Ser
    50                  55                  60

Lys Thr Pro Gln Asn Ser Ala Asp Cys Thr Tyr Asn Leu Ser Ser Thr
65                  70                  75                  80

Leu Thr Leu Thr Ser Thr Gln Tyr Asn Ser His Lys Tyr Thr Cys
            85                  90                  95

Lys Val Thr Gln Gly Thr Thr Ser Val Val Gln Ser Phe Asn Arg Gly
            100                 105                 110

Asp Cys

<210> SEQ ID NO 98
<211> LENGTH: 323
<212> TYPE: PRT
<213> ORGANISM: rabbit

<400> SEQUENCE: 98

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
    210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
            260                 265                 270

Val Leu Asp Ser Asp Gly Ser Tyr Phe Leu Tyr Ser Lys Leu Ser Val
        275                 280                 285

Pro Thr Ser Glu Trp Gln Arg Gly Asp Val Phe Thr Cys Ser Val Met
    290                 295                 300

His Glu Ala Leu His Asn His Tyr Thr Gln Lys Ser Ile Ser Arg Ser
305                 310                 315                 320

Pro Gly Lys

<210> SEQ ID NO 99
<211> LENGTH: 238
<212> TYPE: PRT
<213> ORGANISM: rabbit

<400> SEQUENCE: 99

Met Asp Thr Arg Ala Pro Thr Gln Leu Leu Gly Leu Leu Leu Leu Trp

```
             1               5                  10                 15
            Leu Pro Gly Ala Thr Phe Ala Gln Val Leu Thr Gln Thr Pro Ser Ser
                            20                 25                 30

Val Ser Ala Ala Val Gly Gly Thr Val Ser Ile Ser Cys Gln Ser Ser
                        35                 40                 45

Glu Ser Val Tyr Ala Asp Ile Ala Leu Ser Trp Phe Gln Gln Lys Pro
                50                 55                 60

Gly Gln Pro Pro Lys Leu Leu Ile Tyr Gly Ala Ser Thr Leu Ala Ser
            65                 70                 75                 80

Gly Val Pro Ser Arg Phe Ser Gly Ser Gly Ser Gly Thr Glu Phe Thr
                            85                 90                 95

Leu Thr Ile Ser Asp Val Gln Cys Asp Ala Ala Thr Tyr Tyr Cys
                        100                105                110

Ala Gly Asp Tyr Gly Ala Gly Thr Glu Pro Asn Leu Phe Gly Gly Gly
                        115                120                125

Thr Glu Val Val Val Ser Gly Asp Pro Val Ala Pro Thr Val Leu Ile
                    130                135                140

Phe Pro Pro Ala Ala Asp Gln Val Ala Thr Gly Thr Val Thr Ile Val
            145                150                155                160

Cys Val Ala Asn Lys Tyr Phe Pro Asp Val Thr Val Thr Trp Glu Val
                            165                170                175

Asp Gly Thr Thr Gln Thr Thr Gly Ile Glu Asn Ser Lys Thr Pro Gln
                        180                185                190

Asn Ser Ala Asp Cys Thr Tyr Asn Leu Ser Ser Thr Leu Thr Leu Thr
                        195                200                205

Ser Thr Gln Tyr Asn Ser His Lys Glu Tyr Thr Cys Lys Val Thr Gln
                    210                215                220

Gly Thr Thr Ser Val Val Gln Ser Phe Asn Arg Gly Asp Cys
                    225                230                235

<210> SEQ ID NO 100
            <211> LENGTH: 461
            <212> TYPE: PRT
            <213> ORGANISM: rabbit

<400> SEQUENCE: 100

Met Glu Thr Gly Leu Arg Trp Leu Leu Leu Val Ala Val Leu Lys Gly
            1               5                   10                 15

Val Gln Cys Gln Ser Val Lys Glu Ser Glu Gly Gly Leu Phe Lys Pro
                            20                  25                 30

Thr Asp Thr Leu Ile Leu Thr Cys Thr Val Ser Gly Phe Ser Leu Ser
                        35                  40                 45

Ser Tyr Gly Val Ser Trp Val Arg Gln Ala Pro Gly Asn Gly Leu Glu
                50                  55                  60

Tyr Ile Gly Ser Ile Ser Thr Gly Ile Thr Tyr Tyr Ala Ser Trp
            65                  70                  75                 80

Ala Lys Ser Arg Ser Thr Ile Thr Arg Asn Thr Asn Leu Tyr Thr Val
                            85                  90                 95

Thr Leu Lys Met Thr Gly Leu Thr Ala Ala Asp Thr Ala Thr Tyr Phe
                        100                 105                110

Cys Ala Arg Gly Phe Pro Gly His Leu Arg Lys Pro Ser Asp Ile Trp
                        115                 120                125

Gly Pro Gly Thr Leu Val Thr Val Ser Ala Gly Gln Pro Lys Ala Pro
                    130                 135                 140
```

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
            165                 170                 175

Val Thr Trp Asn Ser Gly Thr Leu Thr Asn Gly Val Arg Thr Phe Pro
        180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
        210                 215                 220

Thr Asn Thr Lys Val Asp Lys Thr Val Ala Pro Ser Thr Cys Ser Lys
225                 230                 235                 240

Pro Thr Cys Pro Pro Pro Glu Leu Leu Gly Gly Pro Ser Val Phe Ile
            245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
            275                 280                 285

Phe Thr Trp Tyr Ile Asn Asn Glu Gln Val Arg Thr Ala Arg Pro Pro
        290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys
            325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
            355                 360                 365

Arg Glu Glu Leu Ser Ser Arg Ser Val Ser Leu Thr Cys Met Ile Asn
370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Ala Val Leu Asp Ser Asp Gly
            405                 410                 415

Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
            435                 440                 445

His Tyr Thr Gln Lys Ser Ile Ser Arg Ser Pro Gly Lys
    450                 455                 460

<210> SEQ ID NO 101
<211> LENGTH: 18
<212> TYPE: DNA
<213> ORGANISM: rabbit

<400> SEQUENCE: 101
acatttgccc aagtgctg                                                  18

<210> SEQ ID NO 102
<211> LENGTH: 20
<212> TYPE: DNA
<213> ORGANISM: rabbit

<400> SEQUENCE: 102
agtgtttatg ctgacatcgc                                                20

-continued

<210> SEQ ID NO 103
<211> LENGTH: 36
<212> TYPE: DNA
<213> ORGANISM: rabbit

<400> SEQUENCE: 103
gcaggcgatt atggggctgg tactgagcct aatctt                                36

<210> SEQ ID NO 104
<211> LENGTH: 24
<212> TYPE: DNA
<213> ORGANISM: rabbit

<400> SEQUENCE: 104
tccctcagta gctatggagt gagc                                             24

<210> SEQ ID NO 105
<211> LENGTH: 21
<212> TYPE: DNA
<213> ORGANISM: rabbit

<400> SEQUENCE: 105
tccattagta ctactggtat c                                                21

<210> SEQ ID NO 106
<211> LENGTH: 36
<212> TYPE: DNA
<213> ORGANISM: rabbit

<400> SEQUENCE: 106
gaggttttcc tggtcatctt cgtaagccgt cggaca                                36

<210> SEQ ID NO 107
<211> LENGTH: 60
<212> TYPE: DNA
<213> ORGANISM: rabbit

<400> SEQUENCE: 107
atggacacga gggcccccac tcagctgctg gggctcctgc tgctctggct cccaggtgcc      60

<210> SEQ ID NO 108
<211> LENGTH: 69
<212> TYPE: DNA
<213> ORGANISM: rabbit

<400> SEQUENCE: 108
acccagactc catcctccgt gtctgcagct gtgggaggca cagtcagcat cagttgccag      60
tccagtgag                                                              69

<210> SEQ ID NO 109
<211> LENGTH: 169
<212> TYPE: DNA
<213> ORGANISM: rabbit

<400> SEQUENCE: 109
cttatcctgg tttcagcaga aaccagggca gcctcccaag ctcctgatct atggtgcatc      60
cactctggca tctggggtcc catcgcggtt cagcggcagt ggatctggga cagaattcac     120
tctcaccatc agcgacgtgc agtgtgacgc tgctgccact tactattgt                 169

<210> SEQ ID NO 110

```
<211> LENGTH: 2154
<212> TYPE: DNA
<213> ORGANISM: human

<400> SEQUENCE: 110
atgcgagcgc ggccgcggcc ccggccgctc tgggtgactg tgctggcgct gggggcgctg      60
gcgggcgttg gcgtaggagg gcccaacatc tgtaccacgc gaggtgtgag ctcctgccag     120
cagtgcctgg ctgtgagccc catgtgtgcc tggtgctctg atgaggccct gcctctgggc     180
tcacctcgct gtgacctgaa ggagaatctg ctgaaggata actgtgcccc agaatccatc     240
gagttcccag tgagtgaggc ccagtactac gaggacaggc ccctcagcga caagggctct     300
ggagacagct cccaggtcac tcaagtcagt ccccagagga ttgcactccg gctccggcca     360
gatgattcga agaatttctc catccaagtc cggcaggtgg aggattaccc tgtggacatc     420
tactacttga tggacctgtc ttactccatg aaggatgatc tgtggagcat ccagaacctg     480
ggtaccaagc tggccaccca gatgcgaaag ctcaccagta acctgcggat tggcttcggg     540
gcatttgtgg acaagcctgt gtcaccatac atgtatatct ccccaccaga ggccctcgaa     600
aacccctgct atgatatgaa gaccacctgc ttgcccatgt ttggctacaa cacgtgctg     660
acgctaactg accaggtgac ccgcttcaat gaggaagtga agaagcagag tgtgtcacgg     720
aaccgagatg ccccagaggg tggctttgat gccatcatgc aggctacagt ctgtgatgaa     780
aagattggct ggaggaatga tgcatcccac ttgctggtgt ttaccactga tgccaagact     840
catatagcat tggacggaag gctggcaggc attgtccagc taatgacggg cagtgtcat      900
gttggtagtg acaatcatta ctctgcctcc actaccatgg attatccctc tttgggctg      960
atgactgaga agctatccca gaaaaacatc aatttgatct ttgcagtgac tgaaaatgta    1020
gtcaatctct atcagaacta tagtgagctc atcccaggga ccacagttgg ggttctgtcc    1080
atggattcca gcaatgtcct ccagctcatt gttgatgctt atgggaaaat ccgttctaaa    1140
gtcgagctgg aagtgcgtga cctccctgaa gagttgtctc tatccttcaa tgccacctgc    1200
ctcaacaatg aggtcatccc tggcctcaag tcttgtatgg gactcaagat tggagacacg    1260
gtgagcttca gcattgaggc caaggtgcga ggctgtcccc aggagaagga gaagtccttt    1320
accataaagc ccgtgggctt caaggacagc ctgatcgtcc aggtcacctt tgattgtgac    1380
tgtgcctgcc aggcccaagc tgaacctaat agccatcgct gcaacaatgg caatgggacc    1440
tttgagtgtg gggtatgccg ttgtgggcct ggctggctgg atcccagtg tgagtgctca    1500
gaggaggact atcgcccttc ccagcaggac gagtgcagcc cccgagaggg tcagcccgtc    1560
tgcagccagc ggggcgagtg cctctgtggt caatgtgtct gccacagcag tgactttggc    1620
aagatcacgg gcaagtactg cgagtgtgac gacttctcct gtgtccgcta caaggggag    1680
atgtgctcag ccatggcca gtgcagctgt ggggactgcc tgtgtgactc cgactggacc    1740
ggctactact gcaactgtac cacgcgtact gacacctgca tgtccagcaa tgggctgctg    1800
tgcagcggcc gcggcaagtg tgaatgtggc agctgtgtct gtatccagcc gggctcctat    1860
ggggacacct gtgagaagtg ccccacctgc ccagatgcct gcacctttaa gaaagaatgt    1920
gtggagtgta agaagtttga ccgggagccc tacatgaccg aaaataccctg caaccgttac    1980
tgccgtgacg agattgagtc agtgaaagag cttaaggaca ctggcaagga tgcagtgaat    2040
tgtacctata agaatgagga tgactgtgtc gtcagattcc agtactatga agattctagt    2100
ggaaagtcca tcctgtatgt ggtagaagag ccagagtgtc caagggccc tgac           2154
```

```
<210> SEQ ID NO 111
<211> LENGTH: 135
<212> TYPE: DNA
<213> ORGANISM: rabbit

<400> SEQUENCE: 111
atggagactg ggctgcgctg gcttctcctg gtcgctgtgc tcaaaggtgt ccagtgtcag      60
tcggtgaagg agtccgaggg aggtctcttc aagccaacgg ataccctgat actcacctgc    120
acagtctctg gattc                                                     135

<210> SEQ ID NO 112
<211> LENGTH: 42
<212> TYPE: DNA
<213> ORGANISM: rabbit

<400> SEQUENCE: 112
tgggtccgcc aggctccagg gaacgggctg gaatacatcg ga                        42

<210> SEQ ID NO 113
<211> LENGTH: 121
<212> TYPE: DNA
<213> ORGANISM: rabbit

<400> SEQUENCE: 113
acatactacg cgagctgggc gaaaagccga tccaccatca ccagaaacac caacctgtac     60
acggtgactc tgaaaatgac cggtctgaca gccgcggaca cggccaccta tttctgtgcg   120
a                                                                    121

<210> SEQ ID NO 114
<211> LENGTH: 35
<212> TYPE: DNA
<213> ORGANISM: rabbit

<400> SEQUENCE: 114
tttggggccc cggcaccctg gtcaccgtct ccgca                                35

<210> SEQ ID NO 115
<211> LENGTH: 372
<212> TYPE: DNA
<213> ORGANISM: rabbit

<400> SEQUENCE: 115
atggacacga gggcccccac tcagctgctg gggctcctgc tgctctggct cccaggtgcc     60
acatttgccc aagtgctgac ccagactcca tcctccgtgt ctgcagctgt gggaggcaca   120
gtcagcatca gttgccagtc cagtgagagt gtttatgctg acatcgcctt atcctggttt   180
cagcagaaac cagggcagcc tcccaagctc ctgatctatg gtgcatccac tctggcatct   240
ggggtcccat cgcggttcag cggcagtgga tctgggacag aattcactct caccatcagc   300
gacgtgcagt gtgacgctgc tgccacttac tattgtgcag gcgattatgg ggctggtact   360
gagcctaatc tt                                                        372

<210> SEQ ID NO 116
<211> LENGTH: 414
<212> TYPE: DNA
<213> ORGANISM: rabbit

<400> SEQUENCE: 116
atggagactg ggctgcgctg gcttctcctg gtcgctgtgc tcaaaggtgt ccagtgtcag     60
```

```
tcggtgaagg agtccgaggg aggtctcttc aagccaacgg ataccctgat actcacctgc      120
acagtctctg gattctccct cagtagctat ggagtgagct gggtccgcca ggctccaggg      180
aacgggctgg aatacatcgg atccattagt actactggta tcacatacta cgcgagctgg      240
gcgaaaagcc gatccaccat caccagaaac accaacctgt acacggtgac tctgaaaatg      300
accggtctga cagccgcgga cacggccacc tatttctgtg cgagaggttt tcctggtcat      360
cttcgtaagc cgtcggacat ttggggcccc ggcaccctgg tcaccgtctc cgca            414

<210> SEQ ID NO 117
<211> LENGTH: 345
<212> TYPE: DNA
<213> ORGANISM: rabbit

<400> SEQUENCE: 117
ttcggcggag ggaccgaggt ggtggtcagc ggtgatccag ttgcacctac tgtcctcatc       60
ttcccaccag ctgctgatca ggtggcaact ggaacagtca ccatcgtgtg tgtggcgaat      120
aaatactttc ccgatgtcac cgtcacctgg gaggtggatg gcaccaccca aacaactggc      180
atcgagaaca gtaaaacacc gcagaattct gcagattgta cctacaacct cagcagcact      240
ctgacactga ccagcacaca gtacaacagc acaaagagt acacctgcaa ggtgacccag       300
ggcacgacct cagtcgtcca gagcttcaat aggggtgact gttag                      345

<210> SEQ ID NO 118
<211> LENGTH: 972
<212> TYPE: DNA
<213> ORGANISM: rabbit

<400> SEQUENCE: 118
gggcaaccta aggctccatc agtcttccca ctggccccct gctgcgggga cacacccagc       60
tccacggtga ccctgggctg cctggtcaaa gggtacctcc ggagccagt gaccgtgacc       120 tggaactcgg gcaccctcac caatggggta cgcaccttcc cgtccgtccg gcagtcctca      180
ggcctctact cgctgagcag cgtggtgagc gtgacctcaa gcagccagcc cgtcacctgc      240
aacgtggccc acccagccac caacaccaaa gtggacaaga ccgttgcgcc ctcgacatgc      300
agcaagccca cgtgcccacc ccctgaactc ctgggggac cgtctgtctt catcttcccc       360
ccaaaaccca aggacaccct catgatctca cgcaccccg aggtcacatg cgtggtggtg       420
gacgtgagcc aggatgaccc cgaggtgcag ttcacatggt acataaacaa cgagcaggtg      480
cgcaccgccc ggccgccgct acgggagcag cagttcaaca gcacgatccg cgtggtcagc      540
accctcccca tcgcgcacca ggactggctg aggggcaagg agttcaagtg caaagtccac      600
aacaaggcac tcccggcccc catcgagaaa accatctcca aagccagagg gcagcccctg      660
gagccgaagg tctacaccat gggccctccc cgggaggagc tgagcagcag gtcggtcagc      720
ctgacctgca tgatcaacgg cttctaccct tccgacatct cggtggagtg ggagaagaac      780
gggaaggcag aggacaacta caagaccacg ccggccgtg tggacagcga cggctcctac      840
ttcctctaca gcaagctctc agtgcccacg agtgagtggc agcggggcga cgtcttcacc      900
tgctccgtga tgcacgaggc cttgcacaac cactacacgc agaagtccat ctcccgctct      960
ccgggtaaat ga                                                          972

<210> SEQ ID NO 119
<211> LENGTH: 717
<212> TYPE: DNA
<213> ORGANISM: rabbit
```

<400> SEQUENCE: 119

```
atggacacga gggcccccac tcagctgctg gggctcctgc tgctctggct cccaggtgcc      60
acatttgccc aagtgctgac ccagactcca tcctccgtgt ctgcagctgt gggaggcaca     120
gtcagcatca gttgccagtc cagtgagagt gtttatgctg acatcgcctt atcctggttt     180
cagcagaaac cagggcagcc tcccaagctc ctgatctatg gtgcatccac tctggcatct     240
ggggtcccat cgcggttcag cggcagtgga tctgggacag aattcactct caccatcagc     300
gacgtgcagt gtgacgctgc tgccacttac tattgtcag gcgattatgg ggctggtact     360
gagcctaatc ttttcggcgg agggaccgag gtggtggtca gcggtgatcc agttgcacct     420
actgtcctca tcttcccacc agctgctgat caggtggcaa ctggaacagt caccatcgtg     480
tgtgtggcga ataaatactt tcccgatgtc accgtcacct gggaggtgga tggcaccacc     540
caaacaactg gcatcgagaa cagtaaaaca ccgcagaatt ctgcagattg tacctacaac     600
ctcagcagca ctctgacact gaccagcaca cagtacaaca gccacaaaga gtacacctgc     660
aaggtgaccc agggcacgac ctcagtcgtc cagagcttca ataggggtga ctgttag      717
```

<210> SEQ ID NO 120
<211> LENGTH: 1386
<212> TYPE: DNA
<213> ORGANISM: rabbit

<400> SEQUENCE: 120

```
atggagactg ggctgcgctg gcttctcctg gtcgctgtgc tcaaaggtgt ccagtgtcag      60
tcggtgaagg agtccgaggg aggtctcttc aagccaacgg ataccctgat actcacctgc     120
acagtctctg gattctccct cagtagctat ggagtgagct gggtccgcca ggctccaggg     180
aacgggctgg aatacatcgg atccattagt actactggta tcacatacta cgcgagctgg     240
gcgaaaagcc gatccaccat caccagaaac accaacctgt acacggtgac tctgaaaatg     300
accggtctga gccgcggaa cacggccacc tatttctgtg cgagaggttt tcctggtcat     360
cttcgtaagc cgtcggacat ttggggcccc ggcaccctgg tcaccgtctc cgcagggcaa     420
cctaaggctc catcagtctt cccactggcc cctgctgcg gggacacacc cagctccacg     480
gtgaccctgg gctgcctggt caaagggtac ctcccggagc cagtgaccgt gacctggaac     540
tcgggcaccc tcaccaatgg ggtacgcacc ttcccgtccg tccggcagtc ctcaggcctc     600
tactcgctga gcagcgtggt gagcgtgacc tcaagcagcc agcccgtcac ctgcaacgtg     660
gcccacccag ccaccaacac caaagtggac aagaccgttg cgcctcgac atgcagcaag     720
cccacgtgcc cacccctga actcctgggg ggaccgtctg tcttcatctt cccccccaaa     780
cccaaggaca cctcatgat ctcacgcacc ccgaggtca catgcgtggt ggtggacgtg     840
agccaggatg accccgaggt gcagttcaca tggtacataa caacgagca ggtgcgcacc     900
gcccggccgc cgctacggga gcagcagttc aacagcacga tccgcgtggt cagcaccctc     960
cccatcgcgc accaggactg gctgaggggc aaggagttca gtgcaaagt ccacaacaag    1020
gcactcccgg ccccccatcga gaaaaccatc tccaaagcca gagggcagcc cctggagccg    1080
aaggtctaca ccatgggccc ctccccggag gagctgagca gcaggtcggt cagcctgacc    1140
tgcatgatca acggcttcta cccttccgac atctcggtgg agtgggagaa gaacgggaag    1200
gcagaggaca actacaagac cacgccggcc gtgctggaca cgacggctc ctacttcctc    1260
tacagcaagc tctcagtgcc cacgagtgag tggcagcggg gcgacgtctt cacctgctcc    1320
```

```
gtgatgcacg aggccttgca caaccactac acgcagaagt ccatctcccg ctctccgggt    1380
aaatga                                                                1386
```

<210> SEQ ID NO 121
<211> LENGTH: 16
<212> TYPE: PRT
<213> ORGANISM: rabbit

<400> SEQUENCE: 121

```
Arg Cys Ala Tyr Asp Met Thr Gln Thr Pro Ala Ser Val Glu Val Val
1               5                   10                  15
```

<210> SEQ ID NO 122
<211> LENGTH: 6
<212> TYPE: PRT
<213> ORGANISM: rabbit

<400> SEQUENCE: 122

```
Gln Ser Val Gly Ile Asn
1               5
```

<210> SEQ ID NO 123
<211> LENGTH: 11
<212> TYPE: PRT
<213> ORGANISM: rabbit

<400> SEQUENCE: 123

```
Gln Thr Tyr Ser Ser Gly Asn Val Asp Asn Val
1               5                   10
```

<210> SEQ ID NO 124
<211> LENGTH: 9
<212> TYPE: PRT
<213> ORGANISM: rabbit

<400> SEQUENCE: 124

```
Ile Asp Leu Ser Ser Ala Ala Ile Asn
1               5
```

<210> SEQ ID NO 125
<211> LENGTH: 9
<212> TYPE: PRT
<213> ORGANISM: rabbit

<400> SEQUENCE: 125

```
Val Ile Gly Gly Ser Thr Gly Pro Tyr
1               5
```

<210> SEQ ID NO 126
<211> LENGTH: 12
<212> TYPE: PRT
<213> ORGANISM: rabbit

<400> SEQUENCE: 126

```
Gly Leu Phe Gly Ile Asn Asn Asp Ile Ser Arg Ile
1               5                   10
```

<210> SEQ ID NO 127
<211> LENGTH: 20
<212> TYPE: PRT
<213> ORGANISM: rabbit

<400> SEQUENCE: 127

```
Met Asp Thr Arg Ala Pro Thr Gln Leu Leu Gly Leu Leu Leu Leu Trp
```

```
1               5                   10                  15
Leu Pro Gly Ala
            20

<210> SEQ ID NO 128
<211> LENGTH: 12
<212> TYPE: PRT
<213> ORGANISM: rabbit

<400> SEQUENCE: 128

Val Gly Gly Thr Val Thr Ile Lys Cys Gln Ala Ser
1               5                   10

<210> SEQ ID NO 129
<211> LENGTH: 57
<212> TYPE: PRT
<213> ORGANISM: rabbit

<400> SEQUENCE: 129

Leu Ala Trp Tyr Gln Lys Lys Ser Gly Gln Arg Pro Lys Leu Leu Ile
1               5                   10                  15

Tyr Ala Ala Ser Thr Leu Ala Ser Gly Val Ser Ser Arg Phe Lys Gly
            20                  25                  30

Ser Gly Ser Gly Thr Gln Phe Thr Leu Thr Ile Ser Asp Leu Glu Cys
        35                  40                  45

Ala Asp Ala Ala Thr Tyr Tyr Cys Gln
    50                  55

<210> SEQ ID NO 130
<211> LENGTH: 694
<212> TYPE: PRT
<213> ORGANISM: human

<400> SEQUENCE: 130

Gly Arg Asn Asp His Val Gln Gly Gly Cys Ala Val Gly Gly Ala Glu
1               5                   10                  15

Thr Cys Glu Asp Cys Leu Leu Ile Gly Pro Gln Cys Ala Trp Cys Ser
            20                  25                  30

Gln Glu Asn Phe Thr His Leu Ser Gly Val Gly Glu Arg Cys Asp Thr
        35                  40                  45

Pro Ala Asn Leu Leu Ala Lys Gly Cys Gln Leu Thr Phe Ile Glu Asn
    50                  55                  60

Pro Val Ser Gln Val Glu Ile Leu Thr Asn Lys Pro Leu Ser Ile Gly
65                  70                  75                  80

Arg Gln Lys Asn Ser Ser Asp Ile Val Gln Ile Ser Pro Gln Ser Leu
                85                  90                  95

Ala Leu Lys Leu Arg Pro Gly Leu Glu Gln Thr Leu Gln Val Gln Val
            100                 105                 110

Arg Gln Thr Glu Asp Tyr Pro Val Asp Leu Tyr Tyr Leu Met Asp Leu
        115                 120                 125

Ser Ala Ser Met Asp Asp Leu Asn Thr Ile Lys Glu Leu Gly Ser
    130                 135                 140

Leu Leu Ser Lys Glu Met Ser Lys Leu Thr Ser Asn Phe Arg Leu Gly
145                 150                 155                 160

Phe Gly Ser Phe Val Glu Lys Pro Ile Ser Pro Phe Met Lys Thr Thr
                165                 170                 175

Pro Glu Glu Ile Ala Asn Pro Cys Ser Ser Ile Pro Tyr Phe Cys Leu
            180                 185                 190
```

```
Pro Thr Phe Gly Phe Lys His Ile Leu Pro Leu Thr Asn Asp Ala Glu
        195                 200                 205

Arg Phe Asn Glu Ile Val Lys Asn Gln Lys Ile Ser Ala Asn Ile Asp
    210                 215                 220

Thr Pro Glu Gly Gly Phe Asp Ala Ile Met Gln Ala Ala Val Cys Lys
225                 230                 235                 240

Glu Lys Ile Gly Trp Arg Asn Asp Ser Leu His Leu Leu Val Phe Val
                245                 250                 255

Ser Asp Ala Asp Ser His Phe Gly Met Asp Ser Lys Leu Ala Gly Ile
                260                 265                 270

Val Ile Pro Asn Asp Gly Leu Cys His Leu Asp Ser Lys Asn Glu Tyr
            275                 280                 285

Ser Met Ser Thr Ile Leu Glu Tyr Pro Thr Ile Gly Gln Leu Ile Asp
        290                 295                 300

Lys Leu Val Gln Asn Asn Val Leu Leu Ile Phe Ala Val Thr Gln Glu
305                 310                 315                 320

Gln Val His Leu Tyr Glu Asn Tyr Ala Lys Leu Ile Pro Gly Ala Thr
                325                 330                 335

Val Gly Val Leu Gln Lys Asp Ser Gly Asn Ile Leu Gln Leu Ile Ile
            340                 345                 350

Ser Ala Tyr Glu Glu Leu Arg Ser Glu Val Glu Leu Glu Val Leu Gly
        355                 360                 365

Asp Thr Glu Gly Leu Asn Leu Ser Phe Thr Ala Ile Cys Asn Thr Gly
    370                 375                 380

Ile Pro Val Pro His Gln Lys Lys Cys Ser His Met Lys Val Gly Asp
385                 390                 395                 400

Thr Ala Ser Phe Asn Val Thr Val Ser Leu Pro Asn Cys Glu Arg Arg
                405                 410                 415

Ser Arg His Ile Ile Leu Lys Pro Val Gly Leu Gly Asp Ala Leu Glu
            420                 425                 430

Ile Leu Val Ser Pro Glu Cys Ser Cys Asp Cys Gln Lys Glu Val Glu
        435                 440                 445

Val Asn Ser Ser Lys Cys Asn Asn Gly Asn Gly Ser Phe Gln Cys Gly
    450                 455                 460

Val Cys Ala Cys His Pro Gly His Met Gly His His Cys Glu Cys Gly
465                 470                 475                 480

Glu Asp Thr Leu Ser Thr Glu Ser Cys Lys Glu Ala Pro Gly Arg Pro
                485                 490                 495

Ser Cys Ser Gly Arg Gly Asp Cys Tyr Cys Gly Gln Cys Val Cys His
            500                 505                 510

Leu Ser Pro Tyr Gly Asn Ile Tyr Gly Pro Tyr Cys Gln Cys Asp Asn
        515                 520                 525

Phe Ser Cys Val Arg His Lys Gly Leu Leu Cys Gly Asp Asn Gly Asp
    530                 535                 540

Cys Asp Cys Gly Glu Cys Val Cys Arg Ser Gly Trp Thr Gly Glu Tyr
545                 550                 555                 560

Cys Asn Cys Thr Thr Ser Thr Asp Pro Cys Val Ser Glu Asp Gly Ile
                565                 570                 575

Leu Cys Ser Gly Arg Gly Asp Cys Val Cys Gly Lys Cys Ile Cys Thr
            580                 585                 590

Asn Pro Gly Ala Ser Gly Pro Thr Cys Glu Arg Cys Pro Thr Cys Gly
        595                 600                 605
```

Asp Pro Cys Asn Ser Lys Arg Ser Cys Ile Glu Cys Tyr Leu Ser Ala
    610                 615                 620

Asp Gly Gln Ala Gln Glu Glu Cys Val Asp Lys Cys Lys Leu Ala Gly
625                 630                 635                 640

Ala Thr Ile Asn Glu Glu Glu Asp Phe Ser Lys Asp Ser Phe Val Ser
                645                 650                 655

Cys Ser Leu Gln Gly Glu Asn Glu Cys Leu Ile Thr Phe Leu Leu Thr
            660                 665                 670

Thr Asp Asn Glu Gly Lys Thr Val Ile His Ser Ile Asn Glu Lys Asp
        675                 680                 685

Cys Pro Lys Pro Pro Asn
    690

<210> SEQ ID NO 131
<211> LENGTH: 44
<212> TYPE: PRT
<213> ORGANISM: rabbit

<400> SEQUENCE: 131

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Lys Pro
            20                  25                  30

Gly Thr Pro Leu Thr Leu Thr Cys Thr Val Ser Gly
        35                  40

<210> SEQ ID NO 132
<211> LENGTH: 14
<212> TYPE: PRT
<213> ORGANISM: rabbit

<400> SEQUENCE: 132

Trp Val Arg Gln Ala Pro Gly Lys Gly Leu Glu Trp Ile Gly
1               5                   10

<210> SEQ ID NO 133
<211> LENGTH: 37
<212> TYPE: PRT
<213> ORGANISM: rabbit

<400> SEQUENCE: 133

Tyr Ala Ser Trp Val Asn Gly Arg Phe Thr Ile Ser Lys Thr Ser Thr
1               5                   10                  15

Thr Val Ala Leu Lys Ile Ala Gly Pro Thr Thr Glu Asp Thr Ala Thr
            20                  25                  30

Tyr Phe Cys Ala Arg
        35

<210> SEQ ID NO 134
<211> LENGTH: 11
<212> TYPE: PRT
<213> ORGANISM: rabbit

<400> SEQUENCE: 134

Trp Gly Pro Gly Thr Leu Val Thr Val Ser Leu
1               5                   10

<210> SEQ ID NO 135
<211> LENGTH: 122
<212> TYPE: PRT
<213> ORGANISM: rabbit

<400> SEQUENCE: 135

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Val Val Gly Gly Thr Val Thr Ile Lys Cys Gln Ala Ser
        35                  40                  45

Gln Ser Val Gly Ile Asn Leu Ala Trp Tyr Gln Lys Lys Ser Gly Gln
    50                  55                  60

Arg Pro Lys Leu Leu Ile Tyr Ala Ala Ser Thr Leu Ala Ser Gly Val
65                  70                  75                  80

Ser Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Thr Tyr Ser Ser Gly Asn Val Asp Asn Val
        115                 120

<210> SEQ ID NO 136
<211> LENGTH: 136
<212> TYPE: PRT
<213> ORGANISM: rabbit

<400> SEQUENCE: 136

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Lys Pro
            20                  25                  30

Gly Thr Pro Leu Thr Leu Thr Cys Thr Val Ser Gly Ile Asp Leu Ser
        35                  40                  45

Ser Ala Ala Ile Asn Trp Val Arg Gln Ala Pro Gly Lys Gly Leu Glu
    50                  55                  60

Trp Ile Gly Val Ile Gly Gly Ser Thr Gly Pro Tyr Tyr Ala Ser Trp
65                  70                  75                  80

Val Asn Gly Arg Phe Thr Ile Ser Lys Thr Ser Thr Thr Val Ala Leu
                85                  90                  95

Lys Ile Ala Gly Pro Thr Thr Glu Asp Thr Ala Thr Tyr Phe Cys Ala
            100                 105                 110

Arg Gly Leu Phe Gly Ile Asn Asn Asp Ile Ser Arg Ile Trp Gly Pro
        115                 120                 125

Gly Thr Leu Val Thr Val Ser Leu
    130                 135

<210> SEQ ID NO 137
<211> LENGTH: 114
<212> TYPE: PRT
<213> ORGANISM: rabbit
<220> FEATURE:
<221> NAME/KEY: misc_feature
<222> LOCATION: (100)..(100)
<223> OTHER INFORMATION: Xaa can be any naturally occurring amino acid

<400> SEQUENCE: 137

Phe Gly Gly Gly Thr Glu Val Val Lys Gly Asp Pro Val Ala Pro
1               5                   10                  15

Thr Val Leu Ile Phe Pro Pro Ala Ala Asp Gln Val Ala Thr Gly Thr
            20                  25                  30

```
Val Thr Ile Val Cys Val Ala Asn Lys Tyr Phe Pro Asp Val Thr Val
            35                  40                  45

Thr Trp Glu Val Asp Gly Thr Thr Gln Thr Thr Gly Ile Glu Asn Ser
 50                  55                  60

Lys Thr Pro Gln Asn Ser Ala Asp Cys Thr Tyr Asn Leu Ser Ser Thr
 65                  70                  75                  80

Leu Thr Leu Thr Ser Thr Gln Tyr Asn Ser His Lys Glu Tyr Thr Cys
                 85                  90                  95

Lys Val Thr Xaa Gly Thr Thr Ser Val Val Gln Ser Phe Asn Arg Gly
                100                 105                 110

Asp Cys

<210> SEQ ID NO 138
<211> LENGTH: 323
<212> TYPE: PRT
<213> ORGANISM: rabbit

<400> SEQUENCE: 138

Gly Gln Pro Lys Ala Pro Ser Val Phe Pro Leu Ala Pro Cys Cys Gly
 1               5                  10                  15

Asp Thr Pro Ser Ser Thr Val Thr Leu Gly Cys Leu Val Lys Gly Tyr
                 20                  25                  30

Leu Pro Glu Pro Val Thr Val Thr Trp Asn Ser Gly Thr Leu Thr Asn
             35                  40                  45

Gly Val Arg Thr Phe Pro Ser Val Arg Gln Ser Ser Gly Leu Tyr Ser
 50                  55                  60

Leu Ser Ser Val Val Ser Val Thr Ser Ser Ser Gln Pro Val Thr Cys
 65                  70                  75                  80

Asn Val Ala His Pro Ala Thr Asn Thr Lys Val Asp Lys Thr Val Ala
                 85                  90                  95

Pro Ser Thr Cys Ser Lys Pro Thr Cys Pro Pro Pro Glu Leu Leu Gly
                100                 105                 110

Gly Pro Ser Val Phe Ile Phe Pro Pro Lys Pro Lys Asp Thr Leu Met
             115                 120                 125

Ile Ser Arg Thr Pro Glu Val Thr Cys Val Val Val Asp Val Ser Gln
130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
                180                 185                 190

Lys Glu Phe Lys Cys Lys Val His Asn Lys Ala Leu Pro Ala Pro Ile
            195                 200                 205

Glu Lys Thr Ile Ser Lys Ala Arg Gly Gln Pro Leu Glu Pro Lys Val
 210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
            260                 265                 270

Val Leu Asp Ser Asp Gly Ser Tyr Phe Leu Tyr Ser Lys Leu Ser Val
         275                 280                 285
```

```
Pro Thr Ser Glu Trp Gln Arg Gly Asp Val Phe Thr Cys Ser Val Met
    290                 295                 300

His Glu Ala Leu His Asn His Tyr Thr Gln Lys Ser Ile Ser Arg Ser
305                 310                 315                 320

Pro Gly Lys

<210> SEQ ID NO 139
<211> LENGTH: 236
<212> TYPE: PRT
<213> ORGANISM: rabbit
<220> FEATURE:
<221> NAME/KEY: misc_feature
<222> LOCATION: (222)..(222)
<223> OTHER INFORMATION: Xaa can be any naturally occurring amino acid

<400> SEQUENCE: 139

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Val Gly Gly Thr Val Thr Ile Lys Cys Gln Ala Ser
        35                  40                  45

Gln Ser Val Gly Ile Asn Leu Ala Trp Tyr Gln Lys Lys Ser Gly Gln
    50                  55                  60

Arg Pro Lys Leu Leu Ile Tyr Ala Ala Ser Thr Leu Ala Ser Gly Val
65                  70                  75                  80

Ser Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Thr Tyr Ser Ser Gly Asn Val Asp Asn Val Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Xaa Gly Thr
    210                 215                 220

Thr Ser Val Val Gln Ser Phe Asn Arg Gly Asp Cys
225                 230                 235

<210> SEQ ID NO 140
<211> LENGTH: 459
<212> TYPE: PRT
<213> ORGANISM: rabbit

<400> SEQUENCE: 140

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Lys Pro
            20                  25                  30
```

```
Gly Thr Pro Leu Thr Leu Thr Cys Thr Val Ser Gly Ile Asp Leu Ser
            35                  40                  45

Ser Ala Ala Ile Asn Trp Val Arg Gln Ala Pro Gly Lys Gly Leu Glu
 50                  55                  60

Trp Ile Gly Val Ile Gly Gly Ser Thr Gly Pro Tyr Tyr Ala Ser Trp
 65                  70                  75                  80

Val Asn Gly Arg Phe Thr Ile Ser Lys Thr Thr Thr Val Ala Leu
                 85                  90                  95

Lys Ile Ala Gly Pro Thr Thr Glu Asp Thr Ala Thr Tyr Phe Cys Ala
                100                 105                 110

Arg Gly Leu Phe Gly Ile Asn Asn Asp Ile Ser Arg Ile Trp Gly Pro
                115                 120                 125

Gly Thr Leu Val Thr Val Ser Leu Gly Gln Pro Lys Ala Pro Ser Val
            130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
                180                 185                 190

Arg Gln Ser Ser Gly Leu Tyr Ser Leu Ser Ser Val Val Ser Val Thr
                195                 200                 205

Ser Ser Ser Gln Pro Val Thr Cys Asn Val Ala His Pro Ala Thr Asn
            210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
            275                 280                 285

Trp Tyr Ile Asn Asn Glu Gln Val Arg Thr Ala Arg Pro Pro Leu Arg
            290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
                340                 345                 350

Gly Gln Pro Leu Glu Pro Lys Val Tyr Thr Met Gly Pro Pro Arg Glu
            355                 360                 365

Glu Leu Ser Ser Arg Ser Val Ser Leu Thr Cys Met Ile Asn Gly Phe
370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Ser Lys Leu Ser Val Pro Thr Ser Glu Trp Gln Arg Gly
                420                 425                 430

Asp Val Phe Thr Cys Ser Val Met His Glu Ala Leu His Asn His Tyr
                435                 440                 445
```

Thr Gln Lys Ser Ile Ser Arg Ser Pro Gly Lys
    450                 455

<210> SEQ ID NO 141
<211> LENGTH: 48
<212> TYPE: DNA
<213> ORGANISM: rabbit

<400> SEQUENCE: 141
agatgtgcct atgatatgac ccagactcca gcctctgtgg aggtagtt                48

<210> SEQ ID NO 142
<211> LENGTH: 18
<212> TYPE: DNA
<213> ORGANISM: rabbit

<400> SEQUENCE: 142
cagagcgttg gtattaat                                                 18

<210> SEQ ID NO 143
<211> LENGTH: 33
<212> TYPE: DNA
<213> ORGANISM: rabbit

<400> SEQUENCE: 143
cagacttata gtagtggtaa tgttgataat gtg                                33

<210> SEQ ID NO 144
<211> LENGTH: 26
<212> TYPE: DNA
<213> ORGANISM: rabbit

<400> SEQUENCE: 144
tcgacctcag tagcgctgca ataaac                                        26

<210> SEQ ID NO 145
<211> LENGTH: 27
<212> TYPE: DNA
<213> ORGANISM: rabbit

<400> SEQUENCE: 145
gtcattggtg gtagtaccgg tccatac                                       27

<210> SEQ ID NO 146
<211> LENGTH: 36
<212> TYPE: DNA
<213> ORGANISM: rabbit

<400> SEQUENCE: 146
ggcttgtttg gtataaataa tgatattagt aggatc                             36

<210> SEQ ID NO 147
<211> LENGTH: 60
<212> TYPE: DNA
<213> ORGANISM: rabbit

<400> SEQUENCE: 147
atggacacga gggcccccac tcagctgctg gggctcctgc tgctctggct cccaggtgcc    60

<210> SEQ ID NO 148
<211> LENGTH: 36
<212> TYPE: DNA
<213> ORGANISM: rabbit

<400> SEQUENCE: 148
gtgggaggca cagtcaccat caagtgccag gccagt          36

<210> SEQ ID NO 149
<211> LENGTH: 171
<212> TYPE: DNA
<213> ORGANISM: rabbit

<400> SEQUENCE: 149
ttagcctggt atcaaaaaaa atcagggcag cgtcccaaac tcctgatcta tgctgcatcc     60
actctggcat ctggggtctc atcgcggttc aaaggcagtg gatctgggac acagttcact    120
ctcaccatca gcgacctgga gtgtgccgat gctgccactt actattgtca g             171

<210> SEQ ID NO 150
<211> LENGTH: 2121
<212> TYPE: DNA
<213> ORGANISM: human

<400> SEQUENCE: 150
atggggattg aactgctttg cctgttcttt ctatttctag gaaggaatga tcacgtacaa     60
ggtggctgtg ccctggggag tgcagaaacc tgtgaagact gcctgcttat ggacctcag    120
tgtgcctggt gtgctcagga gaattttact catccatctg gagttggcga aggtgtgat    180
acccagcaa accttttagc taaaggatgt caattaaact tcatcgaaaa ccctgtctcc    240
caagtagaaa tacttaaaaa taagcctctc agtgtaggca gacagaaaaa tagttctgac    300
attgttcaga ttgcgcctca agcttgatc cttaagttga gaccaggtgg tgcgcagact    360
ctgcaggtgc atgtccgcca gactgaggac tacccggtgg atttgtatta cctcatggac    420
ctctccgcct ccatggatga cgacctcaac acaataaagg agctgggctc ccggcttttcc    480
aaagagatgt ctaaattaac cagcaacttt agactgggct tcggatcttt tgtggaaaaa    540
cctgtatccc ctttcgtgaa aacaacacca gaagaaattg ccaacccttg cagtagtatt    600
ccatacttct gtttacctac atttggattc aagcacattt tgccattgac aaatgatgct    660
gaaagattca atgaaattgt gaagaatcag aaaatttctg ctaatattga cacacccgaa    720
ggtggatttg atgcaattat gcaagctgct gtgtgtaagg aaaaaattgg ctggcggaat    780
gactcccctcc acctcctggt cttttgtgagt gatgctgatt ctcatttttgg aatgacagc    840
aaactagcag gcatcgtcat tcctaatgac gggctctgtc acttggacag caagaatgaa    900
tactccatgt caactgtctt ggaatatcca acaattggac aactcattga taaactggta    960
caaaacaacg tgttattgat cttcgctgta acccaagaac aagttcattt atatgagaat   1020
tacgcaaaac ttattcctgg agctacagta ggtctacttc agaaggactc cggaaacatt   1080
ctccagctga tcatctcagc ttatgaagaa ctgcggtctg aggtggaact ggaagtatta   1140
ggagacactg aaggactcaa cttgtcattt acagccatct gtaacaacgg taccctcttc   1200
caacaccaaa agaaatgctc tcacatgaaa gtgggagaca cagcttcctt cagcgtgact   1260
gtgaatatcc cacactgcga gagaagaagc aggcacatta tcataaagcc tgtggggctg   1320
ggggatgccc tggaattact tgtcagccca gaatgcaact cgactgtca gaaagaagtg   1380
gaagtgaaca gctccaaatg tcaccacggg aacggctctt ccagtgtgg ggtgtgtgcc   1440
tgccacctg ccacatgggg gcctcgctgt gagtgtggcg aggacatgct gagcacagat   1500
tcctgcaagg aggccccaga tcatcccctcc tgcagcggaa ggggtgactg ctactgtggg   1560
cagtgtatct gccactgtc tccctatgga aacatttatg ggcctattg ccagtgtgac   1620

```
aatttctcct gcgtgagaca caaagggctg ctctgcggag gtaacggcga ctgtgactgt    1680
ggtgaatgtg tgtgcaggag cggctggact ggcgagtact gcaactgcac caccagcacg    1740
gactcctgcg tctctgaaga tggagtgctc tgcgcgggc gcggggactg tgtttgtggc     1800
aagtgtgttt gcacaaaccc tggagcctca ggaccaacct gtgaacgatg tcctacctgt    1860
ggtgacccct gtaactctaa acggagctgc attgagtgcc acctgtcagc agctggccaa    1920
gcccgagaag aatgtgtgga caagtgcaaa ctagctggtg cgaccatcag tgaagaagaa    1980
gatttctcaa aggatggttc tgtttcctgc tctctgcaag gagaaaatga atgtcttatt    2040
acattcctaa taactacaga taatgagggg aaaaccatca ttcacagcat caatgaaaaa    2100
gattgtccga agcctccaaa c                                              2121

<210> SEQ ID NO 151
<211> LENGTH: 133
<212> TYPE: DNA
<213> ORGANISM: rabbit

<400> SEQUENCE: 151
atggagactg ggctgcgctg gcttctcctg gtcgctgtgc tcaaaggtgt ccagtgtcag     60
tcgctggagg agtccggggg tcgcctggtc aagcctggga cacccctgac actcacctgc    120
acagtctctg gaa                                                       133

<210> SEQ ID NO 152
<211> LENGTH: 42
<212> TYPE: DNA
<213> ORGANISM: rabbit

<400> SEQUENCE: 152
tgggtccgcc aggctccagg gaaggggctg gaatggatcg gg                       42

<210> SEQ ID NO 153
<211> LENGTH: 111
<212> TYPE: DNA
<213> ORGANISM: rabbit

<400> SEQUENCE: 153
tacgcgagct gggtgaatgg ccgattcacc atctccaaaa cctcgaccac ggtggctctg     60
aaaatcgccg gccgacaac cgaggacacg gccacctatt tctgtgccag a              111

<210> SEQ ID NO 154
<211> LENGTH: 33
<212> TYPE: DNA
<213> ORGANISM: rabbit

<400> SEQUENCE: 154
tggggcccag gcaccctggt caccgtctcc tta                                 33

<210> SEQ ID NO 155
<211> LENGTH: 366
<212> TYPE: DNA
<213> ORGANISM: rabbit

<400> SEQUENCE: 155
atggacacga gggcccccac tcagctgctg gggctcctgc tgctctggct cccaggtgcc     60
agatgtgcct atgatatgac ccagactcca gcctctgtgg aggtagttgt gggaggcaca    120
gtcaccatca agtgccaggc cagtcagagc gttggtatta atttagcctg gtatcaaaaa    180
```

| aaatcagggc agcgtcccaa actcctgatc tatgctgcat ccactctggc atctggggtc | 240 |
| tcatcgcggt tcaaaggcag tggatctggg acacagttca ctctcaccat cagcgacctg | 300 |
| gagtgtgccg atgctgccac ttactattgt cagcagactt atagtagtgg taatgttgat | 360 |
| aatgtg | 366 |

<210> SEQ ID NO 156
<211> LENGTH: 408
<212> TYPE: DNA
<213> ORGANISM: rabbit

<400> SEQUENCE: 156

| atggagactg ggctgcgctg gcttctcctg gtcgctgtgc tcaaaggtgt ccagtgtcag | 60 |
| tcgctggagg agtccggggg tcgcctggtc aagcctggga caccctgac actcacctgc | 120 |
| acagtctctg gaatcgacct cagtagcgct gcaataaact gggtccgcca ggctccaggg | 180 |
| aaggggctgg aatggatcgg ggtcattggt ggtagtaccg gtccatacta cgcgagctgg | 240 |
| gtgaatggcc gattcaccat ctccaaaacc tcgaccacgt ggctctgaa atcgccggg | 300 |
| ccgacaaccg aggacacggc cacctatttc tgtgccagag gcttgtttgg tataaataat | 360 |
| gatattagta ggatctgggg cccaggcacc ctggtcaccg tctcctta | 408 |

<210> SEQ ID NO 157
<211> LENGTH: 360
<212> TYPE: DNA
<213> ORGANISM: rabbit
<220> FEATURE:
<221> NAME/KEY: misc_feature
<222> LOCATION: (297)..(298)
<223> OTHER INFORMATION: n is a, c, g, or t

<400> SEQUENCE: 157

| ttcggcggag ggaccgaggt ggtggtcaaa ggtgatccag ttgcacctac tgtcctcatc | 60 |
| ttcccaccag ctgctgatca ggtggcaact ggaacagtca ccatcgtgtg tgtggcgaat | 120 |
| aaatactttc ccgatgtcac cgtcacctgg gaggtggatg gcaccaccca acaactggc | 180 |
| atcgagaaca gtaaaacacc gcagaattct gcagattgta cctacaacct cagcagcact | 240 |
| ctgacactga ccagcacaca gtacaacagc cacaaagagt acacctgcaa ggtgacnnag | 300 |
| ggcacgacct cagtcgtcca gagcttcaat aggggtgact gttagagtga gagcggccgc | 360 |

<210> SEQ ID NO 158
<211> LENGTH: 998
<212> TYPE: DNA
<213> ORGANISM: rabbit

<400> SEQUENCE: 158

| gggcaaccta aggctccatc agtcttccca ctggcccct gctgcgggga cacacccagc | 60 |
| tccacggtga ccctgggctg cctggtcaaa gggtacctcc cggagccagt gaccgtgacc | 120 |
| tggaactcgg gcaccctcac caatggggta cgcaccttcc cgtccgtccg gcagtcctca | 180 |
| ggcctctact cgctgagcag cgtggtgagc gtgacctcaa gcagccagcc cgtcacctgc | 240 |
| aacgtggccc acccagccac caacaccaaa gtggacaaga ccgttgcgcc ctcgacatgc | 300 |
| agcaagccca cgtgcccacc cctgaactc ctgggggac cgtctgtctt catcttcccc | 360 |
| ccaaaaccca aggacaccct catgatctca cgcaccccg aggtcacatg cgtggtggtg | 420 |
| gacgtgagcc aggatgaccc cgaggtgcag ttcacatggt acataaacaa cgagcaggtg | 480 |
| cgcaccgccc ggccgccgct acgggagcag cagttcaaca gcacgatccg cgtggtcagc | 540 |

| | |
|---|---|
| accctcccca tcgcgcacca ggactggctg aggggcaagg agttcaagtg caaagtccac | 600 |
| aacaaggcac tcccggcccc catcgagaaa accatctcca aagccagagg gcagccctg | 660 |
| gagccgaagg tctacaccat gggccctccc cgggaggagc tgagcagcag gtcggtcagc | 720 |
| ctgacctgca tgatcaacgg cttctaccct tccgacatct cggtggagtg gagaagaac | 780 |
| gggaaggcag aggacaacta caagaccacg ccggccgtgc tggacagcga cggctcctac | 840 |
| ttcctctaca gcaagctctc agtgcccacg agtgagtggc agcggggcga cgtcttcacc | 900 |
| tgctccgtga tgcacgaggc cttgcacaac cactacacgc agaagtccat ctcccgctct | 960 |
| ccgggtaaat gagcgctgtg ccggcgagct gcggccgc | 998 |

<210> SEQ ID NO 159
<211> LENGTH: 726
<212> TYPE: DNA
<213> ORGANISM: rabbit
<220> FEATURE:
<221> NAME/KEY: misc_feature
<222> LOCATION: (663)..(664)
<223> OTHER INFORMATION: n is a, c, g, or t

<400> SEQUENCE: 159

| | |
|---|---|
| atggacacga gggcccccac tcagctgctg gggctcctgc tgctctggct cccaggtgcc | 60 |
| agatgtgcct atgatatgac ccagactcca gcctctgtgg aggtagttgt gggaggcaca | 120 |
| gtcaccatca agtgccaggc cagtcagagc gttggtatta atttagcctg gtatcaaaaa | 180 |
| aaatcagggc agcgtcccaa actcctgatc tatgctgcat ccactctggc atctggggtc | 240 |
| tcatcgcggt tcaaaggcag tggatctggg acacagttca ctctcaccat cagcgacctg | 300 |
| gagtgtgccg atgctgccac ttactattgt cagcagactt atagtagtgg taatgttgat | 360 |
| aatgtgttcg gcggagggac cgaggtggtg gtcaaaggtg atccagttgc acctactgtc | 420 |
| ctcatcttcc caccagctgc tgatcaggtg gcaactggaa cagtcaccat cgtgtgtgtg | 480 |
| gcgaataaat actttcccga tgtcaccgtc acctgggagg tggatggcac caccaaaca | 540 |
| actggcatcg agaacagtaa aacaccgcag aattctgcag attgtaccta caacctcagc | 600 |
| agcactctga cactgaccag cacacagtac aacagccaca aagagtacac ctgcaaggtg | 660 |
| acnnagggca cgacctcagt cgtccagagc ttcaataggg gtgactgtta gagtgagagc | 720 |
| ggccgc | 726 |

<210> SEQ ID NO 160
<211> LENGTH: 1406
<212> TYPE: DNA
<213> ORGANISM: rabbit

<400> SEQUENCE: 160

| | |
|---|---|
| atggagactg gctgcgctg cttctcctg gtcgctgtgc tcaaaggtgt ccagtgtcag | 60 |
| tcgctggagg agtccggggg tcgcctggtc aagcctggga cacccctgac actcacctgc | 120 |
| acagtctctg gaatcgacct cagtagcgct gcaataaact gggtccgcca ggctccaggg | 180 |
| aaggggctgg aatggatcgg ggtcattggt ggtagtaccg gtccatacta cgcgagctgg | 240 |
| gtgaatggcc gattcaccat ctccaaaacc tcgaccacgt ggctctgaa atcgccggg | 300 |
| ccgacaaccg aggacacggc cacctatttc tgtgccagag cttgtttgg tataaataat | 360 |
| gatattagta ggatctgggg cccaggcacc ctggtcaccg tctccttagg caacctaag | 420 |
| gctccatcag tcttcccact ggccccctgc tgcgggaca cacccagctc cacggtgacc | 480 |

```
ctgggctgcc tggtcaaagg gtacctcccg gagccagtga ccgtgacctg gaactcgggc    540
accctcacca atggggtacg caccttcccg tccgtccggc agtcctcagg cctctactcg    600
ctgagcagcg tggtgagcgt gacctcaagc agccagcccg tcacctgcaa cgtggcccac    660
ccagccacca acaccaaagt ggacaagacc gttgcgccct cgacatgcag caagcccacg    720
tgcccacccc ctgaactcct ggggggaccg tctgtcttca tcttcccccc aaaacccaag    780
gacaccctca tgatctcacg caccccccgag gtcacatgcg tggtggtgga cgtgagccag    840
gatgaccccg aggtgcagtt cacatggtac ataaacaacg agcaggtgcg caccgcccgg    900
ccgccgctac gggagcagca gttcaacagc acgatccgcg tggtcagcac cctcccccatc    960 gcgcaccagg actggctgag gggcaaggag ttcaagtgca aagtccacaa caaggcactc   1020
ccggccccca tcgagaaaac catctccaaa gccagagggc agcccctgga ccgaaggtc    1080 tacaccatgg gccctccccg ggaggagctg agcagcaggt cggtcagcct gacctgcatg   1140
atcaacggct ctaccccttc cgacatctcg gtggagtggg agaagaacgg gaaggcagag   1200
gacaactaca gaccacgcc ggccgtgctg acagcgacg gctcctactt cctctacagc     1260
aagctctcag tgcccacgag tgagtggcag cggggcgacg tcttcacctg ctccgtgatg   1320
cacgaggcct gcacaacca ctacacgcag aagtccatct cccgctctcc gggtaaatga    1380
gcgctgtgcc ggcgagctgc ggccgc                                        1406
```

<210> SEQ ID NO 161
<211> LENGTH: 16
<212> TYPE: PRT
<213> ORGANISM: rabbit

<400> SEQUENCE: 161

Arg Cys Asp Val Val Met Thr Gln Thr Pro Ser Ser Val Ser Glu Pro
1               5                   10                  15

<210> SEQ ID NO 162
<211> LENGTH: 6
<212> TYPE: PRT
<213> ORGANISM: rabbit

<400> SEQUENCE: 162

Glu Asn Ile Tyr Ser Ser
1               5

<210> SEQ ID NO 163
<211> LENGTH: 12
<212> TYPE: PRT
<213> ORGANISM: rabbit

<400> SEQUENCE: 163

Gln Cys Thr Gly Gly Ile Ile Ile Asp Gly Gly Ala
1               5                   10

<210> SEQ ID NO 164
<211> LENGTH: 9
<212> TYPE: PRT
<213> ORGANISM: rabbit

<400> SEQUENCE: 164

Phe Ser Leu Asn Ser Gly Asn Met Gln
1               5

<210> SEQ ID NO 165
<211> LENGTH: 9

-continued

```
<212> TYPE: PRT
<213> ORGANISM: rabbit

<400> SEQUENCE: 165

Tyr Ile Gly Ser Gly Gly Ser Thr Phe
1               5

<210> SEQ ID NO 166
<211> LENGTH: 9
<212> TYPE: PRT
<213> ORGANISM: rabbit

<400> SEQUENCE: 166

Gly Arg Tyr Gly Gly Ser Arg Gly Val
1               5

<210> SEQ ID NO 167
<211> LENGTH: 20
<212> TYPE: PRT
<213> ORGANISM: rabbit

<400> SEQUENCE: 167

Met Asp Thr Arg Ala Pro Thr Gln Leu Leu Gly Leu Leu Leu Leu Trp
1               5                   10                  15

Leu Pro Gly Ala
            20

<210> SEQ ID NO 168
<211> LENGTH: 12
<212> TYPE: PRT
<213> ORGANISM: rabbit

<400> SEQUENCE: 168

Val Gly Gly Thr Val Thr Ile Asn Cys Gln Ala Ser
1               5                   10

<210> SEQ ID NO 169
<211> LENGTH: 56
<212> TYPE: PRT
<213> ORGANISM: rabbit

<400> SEQUENCE: 169

Leu Ala Trp Tyr Gln Gln Lys Pro Gly Gln Pro Pro Lys Leu Leu Ile
1               5                   10                  15

Tyr Ala Ala Ser Asn Leu Ala Ser Gly Val Pro Ser Arg Phe Lys Gly
                20                  25                  30

Ser Gly Ser Gly Thr Glu Phe Thr Leu Thr Ile Ser Asp Leu Ala Cys
            35                  40                  45

Ala Asp Ala Ala Thr Tyr Tyr Cys
        50                  55

<210> SEQ ID NO 170
<211> LENGTH: 642
<212> TYPE: PRT
<213> ORGANISM: human

<400> SEQUENCE: 170

Glu Asp Asn Arg Cys Ala Ser Ser Asn Ala Ala Ser Cys Ala Arg Cys
1               5                   10                  15

Leu Ala Leu Gly Pro Glu Cys Gly Trp Cys Val Gln Glu Asp Phe Ile
                20                  25                  30

Ser Gly Gly Ser Arg Ser Glu Arg Cys Asp Ile Val Ser Asn Leu Ile
```

```
                 35                  40                  45
Ser Lys Gly Cys Ser Val Asp Ser Ile Glu Tyr Pro Ser Val His Val
 50                  55                  60
Ile Ile Pro Thr Glu Asn Glu Ile Asn Thr Gln Val Thr Pro Gly Glu
 65                  70                  75                  80
Val Ser Ile Gln Leu Arg Pro Gly Ala Glu Ala Asn Phe Met Leu Lys
                 85                  90                  95
Val His Pro Leu Lys Lys Tyr Pro Val Asp Leu Tyr Tyr Leu Val Asp
                100                 105                 110
Val Ser Ala Ser Met His Asn Ile Glu Lys Leu Asn Ser Val Gly
            115                 120                 125
Asn Asp Leu Ser Arg Lys Met Ala Phe Phe Ser Arg Asp Phe Arg Leu
            130                 135                 140
Gly Phe Gly Ser Tyr Val Asp Lys Thr Val Ser Pro Tyr Ile Ser Ile
145                 150                 155                 160
His Pro Glu Arg Ile His Asn Gln Cys Ser Asp Tyr Asn Leu Asp Cys
                    165                 170                 175
Met Pro Pro His Gly Tyr Ile His Val Leu Ser Leu Thr Glu Asn Ile
                180                 185                 190
Thr Glu Phe Glu Lys Ala Val His Arg Gln Lys Ile Ser Gly Asn Ile
            195                 200                 205
Asp Thr Pro Glu Gly Gly Phe Asp Ala Met Leu Gln Ala Ala Val Cys
210                 215                 220
Glu Ser His Ile Gly Trp Arg Lys Glu Ala Lys Arg Leu Leu Leu Val
225                 230                 235                 240
Met Thr Asp Gln Thr Ser His Leu Ala Leu Asp Ser Lys Leu Ala Gly
                    245                 250                 255
Ile Val Val Pro Asn Asp Gly Asn Cys His Leu Lys Asn Asn Val Tyr
                260                 265                 270
Val Lys Ser Thr Thr Met Glu His Pro Ser Leu Gly Gln Leu Ser Glu
            275                 280                 285
Lys Leu Ile Asp Asn Asn Ile Asn Val Ile Phe Ala Val Gln Gly Lys
            290                 295                 300
Gln Phe His Trp Tyr Lys Asp Leu Leu Pro Leu Leu Pro Gly Thr Ile
305                 310                 315                 320
Ala Gly Glu Ile Glu Ser Lys Ala Ala Asn Leu Asn Asn Leu Val Val
                    325                 330                 335
Glu Ala Tyr Gln Lys Leu Ile Ser Glu Val Lys Val Gln Val Glu Asn
                340                 345                 350
Gln Val Gln Gly Ile Tyr Phe Asn Ile Thr Ala Ile Cys Pro Asp Gly
            355                 360                 365
Ser Arg Lys Pro Gly Met Glu Gly Cys Arg Asn Val Thr Ser Asn Asp
            370                 375                 380
Glu Val Leu Phe Asn Val Thr Val Thr Met Lys Lys Cys Asp Val Thr
385                 390                 395                 400
Gly Gly Lys Asn Tyr Ala Ile Ile Lys Pro Ile Gly Phe Asn Glu Thr
                    405                 410                 415
Ala Lys Ile His Ile His Arg Asn Cys Ser Cys Gln Cys Glu Asp Asn
                420                 425                 430
Arg Gly Pro Lys Gly Lys Cys Val Asp Glu Thr Phe Leu Asp Ser Lys
            435                 440                 445
Cys Phe Gln Cys Asp Glu Asn Lys Cys His Phe Asp Glu Asp Gln Phe
            450                 455                 460
```

```
Ser Ser Glu Ser Cys Lys Ser His Lys Asp Gln Pro Val Cys Ser Gly
465                 470                 475                 480

Arg Gly Val Cys Val Cys Gly Lys Cys Ser Cys His Lys Ile Lys Leu
                485                 490                 495

Gly Lys Val Tyr Gly Lys Tyr Cys Glu Lys Asp Asp Phe Ser Cys Pro
            500                 505                 510

Tyr His His Gly Asn Leu Cys Ala Gly His Gly Glu Cys Glu Ala Gly
        515                 520                 525

Arg Cys Gln Cys Phe Ser Gly Trp Glu Gly Asp Arg Cys Gln Cys Pro
    530                 535                 540

Ser Ala Ala Gln His Cys Val Asn Ser Lys Gly Gln Val Cys Ser
545                 550                 555                 560

Gly Arg Gly Thr Cys Val Cys Gly Arg Cys Glu Cys Thr Asp Pro Arg
                565                 570                 575

Ser Ile Gly Arg Phe Cys Glu His Cys Pro Thr Cys Tyr Thr Ala Cys
            580                 585                 590

Lys Glu Asn Trp Asn Cys Met Gln Cys Leu His Pro His Asn Leu Ser
                595                 600                 605

Gln Ala Ile Leu Asp Gln Cys Lys Thr Ser Cys Ala Leu Met Glu Gln
            610                 615                 620

Gln His Tyr Val Asp Gln Thr Ser Glu Cys Phe Ser Ser Pro Ser Tyr
625                 630                 635                 640

Leu Arg

<210> SEQ ID NO 171
<211> LENGTH: 44
<212> TYPE: PRT
<213> ORGANISM: rabbit

<400> SEQUENCE: 171

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Ala Val Ser Gly
            35                  40

<210> SEQ ID NO 172
<211> LENGTH: 14
<212> TYPE: PRT
<213> ORGANISM: rabbit

<400> SEQUENCE: 172

Trp Val Arg Gln Ala Pro Gly Lys Gly Leu Glu Tyr Ile Gly
1               5                   10

<210> SEQ ID NO 173
<211> LENGTH: 35
<212> TYPE: PRT
<213> ORGANISM: rabbit

<400> SEQUENCE: 173

Tyr Ala Ser Trp Val Asn Gly Arg Phe Thr Ile Ser Lys Thr Ser Thr
1               5                   10                  15

Thr Val Asp Leu Lys Ile Thr Ser Pro Thr Thr Glu Asp Thr Ala Thr
            20                  25                  30

Tyr Phe Cys
```

<210> SEQ ID NO 174
<211> LENGTH: 11
<212> TYPE: PRT
<213> ORGANISM: rabbit

<400> SEQUENCE: 174

Trp Gly Pro Gly Thr Leu Val Thr Val Ser Leu
1               5                   10

<210> SEQ ID NO 175
<211> LENGTH: 122
<212> TYPE: PRT
<213> ORGANISM: rabbit

<400> SEQUENCE: 175

Met Asp Thr Arg Ala Pro Thr Gln Leu Gly Leu Leu Leu Leu Trp
1               5                   10                  15

Leu Pro Gly Ala Arg Cys Asp Val Val Met Thr Gln Thr Pro Ser Ser
                20                  25                  30

Val Ser Glu Pro Val Gly Gly Thr Val Thr Ile Asn Cys Gln Ala Ser
            35                  40                  45

Glu Asn Ile Tyr Ser Ser Leu Ala Trp Tyr Gln Gln Lys Pro Gly Gln
    50                  55                  60

Pro Pro Lys Leu Leu Ile Tyr Ala Ala Ser Asn Leu Ala Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Ala Cys Ala Asp Ala Ala Thr Tyr Tyr Cys Gln Cys
            100                 105                 110

Thr Gly Gly Ile Ile Ile Asp Gly Gly Ala
        115                 120

<210> SEQ ID NO 176
<211> LENGTH: 131
<212> TYPE: PRT
<213> ORGANISM: rabbit

<400> SEQUENCE: 176

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Ala Val Ser Gly Phe Ser Leu Asn
            35                  40                  45

Ser Gly Asn Met Gln Trp Val Arg Gln Ala Pro Gly Lys Gly Leu Glu
    50                  55                  60

Tyr Ile Gly Tyr Ile Gly Ser Gly Gly Ser Thr Phe Tyr Ala Ser Trp
65                  70                  75                  80

Val Asn Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Gly
            100                 105                 110

Arg Tyr Gly Gly Ser Arg Gly Val Trp Gly Pro Gly Thr Leu Val Thr
        115                 120                 125

Val Ser Leu
        130

```
<210> SEQ ID NO 177
<211> LENGTH: 116
<212> TYPE: PRT
<213> ORGANISM: rabbit
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 177

Phe Gly Gly Gly Thr Glu Val Val Lys Gly Asp Pro Val Ala Pro
1               5                   10                  15

Thr Val Leu Ile Phe Pro Ala Ala Asp Gln Val Ala Thr Gly Thr
            20                  25                  30

Val Thr Ile Val Cys Val Ala Asn Lys Tyr Phe Pro Asp Val Thr Val
            35                  40                  45

Thr Trp Glu Val Asp Gly Thr Thr Gln Thr Thr Gly Ile Glu Asn Ser
50                  55                  60

Lys Thr Pro His Asn Ser Ala Asp Cys Thr Tyr Asn Leu Ile Ser Thr
65                  70                  75                  80

Leu Thr Leu Thr Xaa Thr Gln Tyr Asn Ser His Lys Glu Tyr Thr Cys
                85                  90                  95

Lys Val Thr Gln Gly Thr Thr Ser Val Val Gln Xaa Phe Asn Arg Gly
            100                 105                 110

Asp Cys Leu Glu
        115

<210> SEQ ID NO 178
<211> LENGTH: 323
<212> TYPE: PRT
<213> ORGANISM: rabbit

<400> SEQUENCE: 178

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
            35                  40                  45

Gly Val Arg Thr Phe Pro Ser Val Arg Gln Ser Ser Gly Leu Tyr Ser
50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
            115                 120                 125

Ile Ser Arg Thr Pro Glu Val Thr Cys Val Val Val Asp Val Ser Gln
130                 135                 140

Asp Asp Pro Glu Val Gln Phe Thr Trp Tyr Ile Asn Asn Glu Gln Val
145                 150                 155                 160
```

```
Arg Thr Ala Arg Pro Pro Leu Arg Glu Gln Gln Phe Asn Ser Thr Ile
                165                 170                 175
Arg Val Val Ser Thr Leu Pro Ile Ala His Gln Asp Trp Leu Arg Gly
            180                 185                 190
Lys Glu Phe Lys Cys Lys Val His Asn Lys Ala Leu Pro Ala Pro Ile
        195                 200                 205
Glu Lys Thr Ile Ser Lys Ala Arg Gly Gln Pro Leu Glu Pro Lys Val
    210                 215                 220
Tyr Thr Met Gly Pro Pro Arg Glu Glu Leu Ser Ser Arg Ser Val Ser
225                 230                 235                 240
Leu Thr Cys Met Ile Asn Gly Phe Tyr Pro Ser Asp Ile Ser Val Glu
                245                 250                 255
Trp Glu Lys Asn Gly Lys Ala Glu Asp Asn Tyr Lys Thr Thr Pro Ala
            260                 265                 270
Val Leu Asp Ser Asp Gly Ser Tyr Phe Leu Tyr Ser Lys Leu Ser Val
        275                 280                 285
Pro Thr Ser Glu Trp Gln Arg Gly Asp Val Phe Thr Cys Ser Val Met
    290                 295                 300
His Glu Ala Leu His Asn His Tyr Thr Gln Lys Ser Ile Ser Arg Ser
305                 310                 315                 320
Pro Gly Lys

<210> SEQ ID NO 179
<211> LENGTH: 238
<212> TYPE: PRT
<213> ORGANISM: rabbit
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid

<400> SEQUENCE: 179

Met Asp Thr Arg Ala Pro Thr Gln Leu Leu Gly Leu Leu Leu Leu Trp
1               5                   10                  15
Leu Pro Gly Ala Arg Cys Asp Val Val Met Thr Gln Thr Pro Ser Ser
            20                  25                  30
Val Ser Glu Pro Val Gly Gly Thr Val Thr Ile Asn Cys Gln Ala Ser
        35                  40                  45
Glu Asn Ile Tyr Ser Ser Leu Ala Trp Tyr Gln Gln Lys Pro Gly Gln
    50                  55                  60
Pro Pro Lys Leu Leu Ile Tyr Ala Ala Ser Asn Leu Ala Ser Gly Val
65                  70                  75                  80
Pro Ser Arg Phe Lys Gly Ser Gly Ser Gly Thr Glu Phe Thr Leu Thr
                85                  90                  95
Ile Ser Asp Leu Ala Cys Ala Asp Ala Ala Thr Tyr Tyr Cys Gln Cys
            100                 105                 110
Thr Gly Gly Ile Ile Ile Asp Gly Gly Ala Phe Gly Gly Gly Thr Glu
        115                 120                 125
Val Val Val Lys Gly Asp Pro Val Ala Pro Thr Val Leu Ile Phe Pro
    130                 135                 140
Pro Ala Ala Asp Gln Val Ala Thr Gly Thr Val Thr Ile Val Cys Val
145                 150                 155                 160
Ala Asn Lys Tyr Phe Pro Asp Val Thr Val Thr Trp Glu Val Asp Gly
```

```
                        165                 170                 175
Thr Thr Gln Thr Thr Gly Ile Glu Asn Ser Lys Thr Pro His Asn Ser
            180                 185                 190

Ala Asp Cys Thr Tyr Asn Leu Ile Ser Thr Leu Thr Leu Thr Xaa Thr
            195                 200                 205

Gln Tyr Asn Ser His Lys Glu Tyr Thr Cys Lys Val Thr Gln Gly Thr
            210                 215                 220

Thr Ser Val Val Gln Xaa Phe Asn Arg Gly Asp Cys Leu Glu
225                 230                 235

<210> SEQ ID NO 180
<211> LENGTH: 454
<212> TYPE: PRT
<213> ORGANISM: rabbit

<400> SEQUENCE: 180

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Ala Val Ser Gly Phe Ser Leu Asn
            35                  40                  45

Ser Gly Asn Met Gln Trp Val Arg Gln Ala Pro Gly Lys Gly Leu Glu
        50                  55                  60

Tyr Ile Gly Tyr Ile Gly Ser Gly Gly Ser Thr Phe Tyr Ala Ser Trp
65                  70                  75                  80

Val Asn Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Gly
            100                 105                 110

Arg Tyr Gly Gly Ser Arg Gly Val Trp Gly Pro Gly Thr Leu Val Thr
        115                 120                 125

Val Ser Leu Gly Gln Pro Lys Ala Pro Ser Val Phe Pro Leu Ala Pro
130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300
```

```
Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
            325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
            355                 360                 365

Ser Val Ser Leu Thr Cys Met Ile Asn Gly Phe Tyr Pro Ser Asp Ile
370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Ser Lys
            405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
            435                 440                 445

Ser Arg Ser Pro Gly Lys
    450
```

```
<210> SEQ ID NO 181
<211> LENGTH: 48
<212> TYPE: DNA
<213> ORGANISM: rabbit

<400> SEQUENCE: 181
agatgtgatg ttgtgatgac ccagactcca tcctccgtgt ctgaacct          48

<210> SEQ ID NO 182
<211> LENGTH: 18
<212> TYPE: DNA
<213> ORGANISM: rabbit

<400> SEQUENCE: 182
gagaacattt acagttct                                            18

<210> SEQ ID NO 183
<211> LENGTH: 33
<212> TYPE: DNA
<213> ORGANISM: rabbit

<400> SEQUENCE: 183
tgtactggtg gtattattat tgatgggggt gct                           33

<210> SEQ ID NO 184
<211> LENGTH: 27
<212> TYPE: DNA
<213> ORGANISM: rabbit

<400> SEQUENCE: 184
ttctccctca atagtggcaa tatgcaa                                  27

<210> SEQ ID NO 185
<211> LENGTH: 27
<212> TYPE: DNA
<213> ORGANISM: rabbit

<400> SEQUENCE: 185
tacattggta gtggtggtag cacattc                                  27
```

<210> SEQ ID NO 186
<211> LENGTH: 27
<212> TYPE: DNA
<213> ORGANISM: rabbit

<400> SEQUENCE: 186
ggcagatatg gtggtagtag gggtgta                                27

<210> SEQ ID NO 187
<211> LENGTH: 60
<212> TYPE: DNA
<213> ORGANISM: rabbit

<400> SEQUENCE: 187
atggacacga gggcccccac tcagctgctg gggctcctgc tgctctggct cccaggtgcc    60

<210> SEQ ID NO 188
<211> LENGTH: 36
<212> TYPE: DNA
<213> ORGANISM: rabbit

<400> SEQUENCE: 188
gtgggaggca cagtcaccat caattgccag gccagt                              36

<210> SEQ ID NO 189
<211> LENGTH: 171
<212> TYPE: DNA
<213> ORGANISM: rabbit

<400> SEQUENCE: 189
ttagcctggt atcagcagaa accagggcag cctcccaagc tcctgatcta tgctgcatcc    60
aatctggcat ctggggtccc atcgcggttc aaaggcagtg gatctgggac agagttcact   120
ctcaccatca gcgacctggc gtgtgccgat gctgccactt actattgtca a            171

<210> SEQ ID NO 190
<211> LENGTH: 2052
<212> TYPE: DNA
<213> ORGANISM: human

<400> SEQUENCE: 190
atgtgcggct cggccctggc ttttttttacc gctgcatttg tctgcctgca aaacgaccgg    60
cgaggtcccg cctcgttcct ctgggcagcc tgggtgtttt cacttgttct ggactgggc   120 caaggtgaag acaatagatg tgcatcttca aatgcagcat cctgtgccag gtgccttgcg   180
ctgggtccag aatgtggatg gtgtgttcaa gaggatttca tttcaggtgg atcaagaagt   240
gaacgttgtg atattgtttc caatttaata agcaaaggct gctcagttga ttcaatagaa   300
tacccatctg tgcatgttat aataccccact gaaaatgaaa ttaataccca ggtgacacca   360
ggagaagtgt ctatccagct gcgtccagga gccgaagcta ttttatgct gaaagttcat   420 cctctgaaga aatatcctgt ggatctttat tatcttgttg atgtctcagc atcaatgcac   480
aataatatag aaaaattaaa ttccgttgga aacgatttat ctagaaaaat ggcattttc   540 tcccgtgact ttcgtcttgg atttggctca tacgttgata aaacagtttc accatacatt   600
agcatccacc ccgaaaggat tcataatcaa tgcagtgact acaatttaga ctgcatgcct   660
ccccatggat acatccatgt gctgtctttg acagagaaca tcactgagtt tgagaaagca   720
gttcatagac agaagatctc tggaaacata gataccagg aaggaggttt tgacgccatg   780

```
cttcaggcag ctgtctgtga aagtcatatc ggatggcgaa agaggctaaa agattgctg      840 ctggtgatga cagatcagac gtctcatctc gctcttgata gcaaattggc aggcatagtg     900
gtgcccaatg acggaaactg tcatctgaaa acaacgtct  atgtcaaatc gacaaccatg    960
gaacacccct cactaggcca actttcagag aaattaatag acaacaacat taatgtcatc    1020
tttgcagttc aaggaaaaca atttcattgg tataaggatc ttctacccct cttgccaggc    1080
accattgctg gtgaaataga atcaaaggct gcaaacctca ataatttggt agtgaaagcc    1140
tatcagaagc tcatttcaga agtgaaagtt caggtggaaa accaggtaca aggcatctat    1200
tttaacatta ccgccatctg tccagatggg tccagaaagc caggcatgga aggatgcaga    1260
aacgtgacga gcaatgatga agttcttttc aatgtaacag ttacaatgaa aaaatgtgat    1320
gtcacaggag gaaaaaacta tgcaataatc aaacctattg gttttaatga aaccgctaaa    1380
attcatatac acagaaactg cagctgtcag tgtgaggaca cagaggacc  taaaggaaag    1440 tgtgtagatg aaactttct  agattccaag tgtttccagt gtgatgagaa taatgtcat    1500 tttgatgaag atcagttttc ttctgagagt tgcaagtcac acaaggatca gcctgtttgc    1560
agtggtcgag gagtttgtgt ttgtgggaaa tgttcatgtc acaaaattaa gcttggaaaa    1620
gtgtatggaa aatactgtga aaaggatgac ttttcttgtc catatcacca tggaaatctg    1680
tgtgctgggc atggagagtg tgaagcaggc agatgccaat gcttcagtgg ctgggaaggt    1740
gatcgatgcc agtgccttc  agcagcagcc cagcactgtg tcaattcaaa gggccaagtg    1800
tgcagtggaa gaggcacgtg tgtgtgtgga aggtgtgagt gcaccgatcc caggagcatc    1860
ggccgcttct gtgaacactg ccccacctgt tatacagcct gcaaggaaaa ctggaattgt    1920
atgcaatgcc ttcaccctca caatttgtct caggctatac ttgatcagtg caaaacctca    1980
tgtgctctca tggaacaaca gcattatgtc gaccaaactt cagaatgttt ctccagccca    2040
agctacttga ga                                                        2052

<210> SEQ ID NO 191
<211> LENGTH: 132
<212> TYPE: DNA
<213> ORGANISM: rabbit

<400> SEQUENCE: 191
atggagactg ggctgcgctg gcttctcctg gtcgctgtgc tcaaaggtgt ccagtgtcag     60
tcggtggagg agtccggggg tcgcctggtc acgcctggga caccctgac  actcacctgc    120 gcagtctctg ga                                                        132

<210> SEQ ID NO 192
<211> LENGTH: 42
<212> TYPE: DNA
<213> ORGANISM: rabbit

<400> SEQUENCE: 192
tgggtccgcc aggctccagg gaaggggctg gaatacatcg ga                       42

<210> SEQ ID NO 193
<211> LENGTH: 105
<212> TYPE: DNA
<213> ORGANISM: rabbit

<400> SEQUENCE: 193
tacgcgagct gggtgaatgg ccgattcacc atctccaaaa cctcgaccac ggtggatctg    60
aagatcacca gtccgacaac cgaggacacg gccacctatt tttgt                    105
```

<210> SEQ ID NO 194
<211> LENGTH: 18
<212> TYPE: DNA
<213> ORGANISM: rabbit

<400> SEQUENCE: 194
tggggcccag gcaccctg                                                   18

<210> SEQ ID NO 195
<211> LENGTH: 366
<212> TYPE: DNA
<213> ORGANISM: rabbit

<400> SEQUENCE: 195
atggacacga gggcccccac tcagctgctg gggctcctgc tgctctggct cccaggtgcc     60
agatgtgatg ttgtgatgac ccagactcca tcctccgtgt ctgaacctgt gggaggcaca    120
gtcaccatca attgccaggc cagtgagaac atttacagtt ctttagcctg gtatcagcag    180
aaaccagggc agcctcccaa gctcctgatc tatgctgcat ccaatctggc atctggggtc    240
ccatcgcggt tcaaaggcag tggatctggg acagagttca ctctcaccat cagcgacctg    300
gcgtgtgccg atgctgccac ttactattgt caatgtactg gtggtattat tattgatggg    360
ggtgct                                                              366

<210> SEQ ID NO 196
<211> LENGTH: 378
<212> TYPE: DNA
<213> ORGANISM: rabbit

<400> SEQUENCE: 196
atggagactg ggctgcgctg gcttctcctg gtcgctgtgc tcaaaggtgt ccagtgtcag     60
tcggtggagg agtccggggg tcgcctggtc acgcctggga caccctgac actcacctgc    120 gcagtctctg gattctccct caatagtggc aatatgcaat gggtccgcca ggctccaggg    180
aaggggctgg aatacatcgg atacattggt agtggtggta gcacattcta cgcgagctgg    240
gtgaatggcc gattccacat ctccaaaacc tcgaccacgg tggatctgaa gatcaccagt    300
ccgacaaccg aggacacggc cacctatttt tgtggcagat atggtggtag taggggtgta    360
tggggcccag gcaccctg                                                 378

<210> SEQ ID NO 197
<211> LENGTH: 361
<212> TYPE: DNA
<213> ORGANISM: rabbit
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t

<400> SEQUENCE: 197
ttcggcggag ggaccgaggt ggtggtcaaa ggtgatccag ttgcacctac tgtcctcatc     60
ttcccaccag ctgctgatca ggtggcaact ggaacagtca ccatcgtgtg tgtggcgaat    120
aaatactttc ccgatgtcac cgtcacctgg gaggtggatg gcaccaccca aacaactggc    180
atcgagaaca gtaaaacacc gcataattct gcagattgta cctacaacct catcagcact    240

```
ctgacactga ccancacaca gtacaacagc cacaaagagt acacctgcaa ggtgacccag    300
ggcacgacct cagtcgtcca gancttcaat aggggtgact gtttagagtg agagcggccg    360
c                                                                   361
```

```
<210> SEQ ID NO 198
<211> LENGTH: 1013
<212> TYPE: DNA
<213> ORGANISM: rabbit

<400> SEQUENCE: 198
```

```
gtcaccgtct ccttagggca acctaaggct ccatcagtct tcccactggc cccctgctgc     60
ggggacacac ccagctccac ggtgaccctg ggctgcctgg tcaaagggta cctcccggag    120
ccagtgaccg tgacctggaa ctcgggcacc ctcaccaatg gggtacgcac cttcccgtcc    180
gtccggcagt cctcaggcct ctactcgctg agcagcgtgt gagcgtgac ctcaagcagc     240 cagcccgtca cctgcaacgt ggcccaccca gccaccaaca ccaaagtgga caagaccgtt    300
gcgccctcga catgcagcaa gcccacgtgc ccaccccctg aactcctggg gggaccgtct    360
gtcttcatct tccccccaaa acccaaggac accctcatga tctcacgcac ccccgaggtc    420
acatgcgtgg tggtggacgt gagccaggat gaccccgagg tgcagttcac atggtacata    480
aacaacgagc aggtgcgcac cgcccggccg ccgctacggg agcagcagtt caacagcacg    540
atccgcgtgg tcagcaccct ccccatcgcg caccaggact ggctgagggg caaggagttc    600
aagtgcaaag tccacaacaa ggcactcccg gcccccatcg agaaaaccat ctccaaagcc    660
agagggcagc cctggagcc gaaggtctac accatgggcc ctccccggga ggagctgagc     720
agcaggtcgg tcagcctgac ctgcatgatc aacggcttct acccttccga catctcggtg    780
gagtgggaga gaacgggaa ggcagaggac aactacaaga ccacgccggc cgtgctggac     840
agcgacggct cctacttcct ctacagcaag ctctcagtgc ccacgagtga gtggcagcgg    900
ggcgacgtct tcacctgctc cgtgatgcac gaggccttgc acaaccacta cacgcagaag    960
tccatctccc gctctccggg taaatgagcg ctgtgccggc gagctgcggc cgc          1013
```

```
<210> SEQ ID NO 199
<211> LENGTH: 727
<212> TYPE: DNA
<213> ORGANISM: rabbit
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t

<400> SEQUENCE: 199
```

```
atggacacga gggcccccac tcagctgctg gggctcctgc tgctctggct cccaggtgcc     60
agatgtgatg ttgtgatgac ccagactcca tcctccgtgt ctgaacctgt gggaggcaca    120
gtcaccatca attgccaggc cagtgagaac atttacagtt ctttagcctg gtatcagcag    180
aaaccagggc agcctcccaa gctcctgatc tatgctgcat ccaatctggc atctggggtc    240
ccatcgcggt tcaaaggcag tggatctggg acagagttca ctctcaccat cagcgacctg    300
gcgtgtgccg atgctgccac ttactattgt caatgtactg gtggtattat tattgatggg    360
ggtgctttcg gcgagggac cgaggtggtg gtcaaaggtg atccagttgc acctactgtc    420
ctcatcttcc caccagctgc tgatcaggtg gcaactggaa cagtcaccat cgtgtgtgtg    480
```

```
gcgaataaat actttcccga tgtcaccgtc acctgggagg tggatggcac cacccaaaca    540
actggcatcg agaacagtaa aacaccgcat aattctgcag attgtaccta caacctcatc    600
agcactctga cactgaccan cacacagtac aacagccaca aagagtacac ctgcaaggtg    660
acccagggca cgacctcagt cgtccaganc ttcaataggg gtgactgttt agagtgagag    720
cggccgc                                                              727

<210> SEQ ID NO 200
<211> LENGTH: 1391
<212> TYPE: DNA
<213> ORGANISM: rabbit

<400> SEQUENCE: 200
atggagactg ggctgcgctg gcttctcctg gtcgctgtgc tcaaaggtgt ccagtgtcag     60
tcggtggagg agtccggggg tcgcctggtc acgcctggga cacccctgac actcacctgc    120
gcagtctctg gattctccct caatagtggc aatatgcaat gggtccgcca ggctccaggg    180
aaggggctgg aatacatcgg atacattggt agtggtggta gcacattcta cgcgagctgg    240
gtgaatggcc gattcaccat ctccaaaacc tcgaccacgg tggatctgaa gatcaccagt    300
ccgacaaccg aggacacggc cacctatttt tgtggcagat atggtggtag tagggggtgta    360 tggggcccag gcaccctggt caccgtctcc ttagggcaac taaggctcc atcagtcttc    420 ccactggccc cctgctgcgg ggacacaccc agctccacgg tgaccctggg ctgcctggtc    480
aaagggtacc tcccggagcc agtgaccgtg acctggaact cgggcaccct caccaatggg    540
gtacgcacct tcccgtccgt ccggcagtcc tcaggcctct actcgctgag cagcgtggtg    600
agcgtgacct caagcagcca gcccgtcacc tgcaacgtgg cccacccagc caccaacacc    660
aaagtggaca agaccgttgc gccctcgaca tgcagcaagc ccacgtgccc accccctgaa    720
ctcctggggg gaccgtctgt cttcatcttc ccccccaaaac ccaaggacac cctcatgatc    780
tcacgcaccc ccgaggtcac atgcgtggtg gtggacgtga gccaggatga ccccgaggtg    840
cagttcacat ggtacataaa caacgagcag gtgcgcaccg cccggccgcc gctacgggag    900
cagcagttca acagcacgat ccgcgtggtc agcaccctcc ccatcgcgca ccaggactgg    960
ctgaggggca aggagttcaa gtgcaaagtc cacaacaagg cactcccggc ccccatcgag   1020
aaaaccatct ccaaagccag agggcagccc ctggagccga ggtctacac catgggccct   1080 ccccgggagg agctgagcag caggtcggtc agcctgacct gcatgatcaa cggcttctac   1140
ccttccgaca tctcggtgga gtgggagaag aacgggaagg cagaggacaa ctacaagacc   1200
acgccggccg tgctggacag cgacggctcc tacttcctct acagcaagct ctcagtgccc   1260
acgagtgagt ggcagcgggg cgacgtcttc acctgctccg tgatgcacga ggccttgcac   1320
aaccactaca cgcagaagtc catctcccgc tctccgggta atgagcgct gtgccggcga   1380 gctgcggccg c                                                        1391

<210> SEQ ID NO 201
<211> LENGTH: 16
<212> TYPE: PRT
<213> ORGANISM: rabbit

<400> SEQUENCE: 201

Thr Phe Ala Gln Val Leu Thr Gln Thr Pro Ser Ser Val Ser Ala Ala
1               5                   10                  15
```

```
<210> SEQ ID NO 202
<211> LENGTH: 8
<212> TYPE: PRT
<213> ORGANISM: rabbit

<400> SEQUENCE: 202

Gln Ser Val Ala Ser Asn Asn Ala
1               5

<210> SEQ ID NO 203
<211> LENGTH: 13
<212> TYPE: PRT
<213> ORGANISM: rabbit

<400> SEQUENCE: 203

Leu Gly Gly Tyr Asp Cys Arg Gly Thr Asp Cys Asn Val
1               5                   10

<210> SEQ ID NO 204
<211> LENGTH: 9
<212> TYPE: PRT
<213> ORGANISM: rabbit

<400> SEQUENCE: 204

Ile Asp Leu Thr Ser Asn Ser Leu Ser
1               5

<210> SEQ ID NO 205
<211> LENGTH: 9
<212> TYPE: PRT
<213> ORGANISM: rabbit

<400> SEQUENCE: 205

Ala Ile Ser Ser Arg Ala Thr Thr Tyr
1               5

<210> SEQ ID NO 206
<211> LENGTH: 5
<212> TYPE: PRT
<213> ORGANISM: rabbit

<400> SEQUENCE: 206

Gly Lys Phe Asn Leu
1               5

<210> SEQ ID NO 207
<211> LENGTH: 20
<212> TYPE: PRT
<213> ORGANISM: rabbit

<400> SEQUENCE: 207

Met Asp Thr Arg Ala Pro Thr Gln Leu Leu Gly Leu Leu Leu Leu Trp
1               5                   10                  15

Leu Pro Gly Ala
            20

<210> SEQ ID NO 208
<211> LENGTH: 12
<212> TYPE: PRT
<213> ORGANISM: rabbit

<400> SEQUENCE: 208

Val Gly Gly Thr Val Thr Ile Asn Cys Gln Ala Ser
1               5                   10
```

<210> SEQ ID NO 209
<211> LENGTH: 56
<212> TYPE: PRT
<213> ORGANISM: rabbit

<400> SEQUENCE: 209

Leu Ala Trp Phe Gln Gln Lys Pro Gly Gln Pro Pro Lys Leu Leu Ile
1               5                   10                  15

Tyr Tyr Ala Ser Thr Leu Ala Ser Gly Val Pro Ser Arg Phe Lys Gly
            20                  25                  30

Ser Gly Ser Gly Thr Gln Phe Thr Leu Thr Ile Ser Asp Leu Glu Cys
        35                  40                  45

Ala Asp Ala Ala Thr Tyr Tyr Cys
    50                  55

<210> SEQ ID NO 210
<211> LENGTH: 957
<212> TYPE: PRT
<213> ORGANISM: human

<400> SEQUENCE: 210

Phe Asn Leu Asp Val Asp Ser Pro Ala Glu Tyr Ser Gly Pro Glu Gly
1               5                   10                  15

Ser Tyr Phe Gly Phe Ala Val Asp Phe Phe Val Pro Ser Ala Ser Ser
            20                  25                  30

Arg Met Phe Leu Leu Val Gly Ala Pro Lys Ala Asn Thr Thr Gln Pro
        35                  40                  45

Gly Ile Val Glu Gly Gly Gln Val Leu Lys Cys Asp Trp Ser Ser Thr
    50                  55                  60

Arg Arg Cys Gln Pro Ile Glu Phe Asp Ala Thr Gly Asn Arg Asp Tyr
65                  70                  75                  80

Ala Lys Asp Asp Pro Leu Glu Phe Lys Ser His Gln Trp Phe Gly Ala
                85                  90                  95

Ser Val Arg Ser Lys Gln Asp Lys Ile Leu Ala Cys Ala Pro Leu Tyr
            100                 105                 110

His Trp Arg Thr Glu Met Lys Gln Glu Arg Glu Pro Val Gly Thr Cys
        115                 120                 125

Phe Leu Gln Asp Gly Thr Lys Thr Val Glu Tyr Ala Pro Cys Arg Ser
130                 135                 140

Gln Asp Ile Asp Ala Asp Gly Gln Gly Phe Cys Gln Gly Gly Phe Ser
145                 150                 155                 160

Ile Asp Phe Thr Lys Ala Asp Arg Val Leu Leu Gly Gly Pro Gly Ser
                165                 170                 175

Phe Tyr Trp Gln Gly Gln Leu Ile Ser Asp Gln Val Ala Glu Ile Val
            180                 185                 190

Ser Lys Tyr Asp Pro Asn Val Tyr Ser Ile Lys Tyr Asn Asn Gln Leu
        195                 200                 205

Ala Thr Arg Thr Ala Gln Ala Ile Phe Asp Asp Ser Tyr Leu Gly Tyr
    210                 215                 220

Ser Val Ala Val Gly Asp Phe Asn Gly Asp Gly Ile Asp Asp Phe Val
225                 230                 235                 240

Ser Gly Val Pro Arg Ala Ala Arg Thr Leu Gly Met Val Tyr Ile Tyr
                245                 250                 255

Asp Gly Lys Asn Met Ser Ser Leu Tyr Asn Phe Thr Gly Glu Gln Met
            260                 265                 270

```
Ala Ala Tyr Phe Gly Phe Ser Val Ala Ala Thr Asp Ile Asn Gly Asp
            275                 280                 285

Asp Tyr Ala Asp Val Phe Ile Gly Ala Pro Leu Phe Met Asp Arg Gly
        290                 295                 300

Ser Asp Gly Lys Leu Gln Glu Val Gly Gln Val Ser Val Ser Leu Gln
305                 310                 315                 320

Arg Ala Ser Gly Asp Phe Gln Thr Thr Lys Leu Asn Gly Phe Glu Val
                325                 330                 335

Phe Ala Arg Phe Gly Ser Ala Ile Ala Pro Leu Gly Asp Leu Asp Gln
            340                 345                 350

Asp Gly Phe Asn Asp Ile Ala Ile Ala Ala Pro Tyr Gly Gly Glu Asp
        355                 360                 365

Lys Lys Gly Ile Val Tyr Ile Phe Asn Gly Arg Ser Thr Gly Leu Asn
370                 375                 380

Ala Val Pro Ser Gln Ile Leu Glu Gly Gln Trp Ala Ala Arg Ser Met
385                 390                 395                 400

Pro Pro Ser Phe Gly Tyr Ser Met Lys Gly Ala Thr Asp Ile Asp Lys
                405                 410                 415

Asn Gly Tyr Pro Asp Leu Ile Val Gly Ala Phe Gly Val Asp Arg Ala
            420                 425                 430

Ile Leu Tyr Arg Ala Arg Pro Val Ile Thr Val Asn Ala Gly Leu Glu
        435                 440                 445

Val Tyr Pro Ser Ile Leu Asn Gln Asp Asn Lys Thr Cys Ser Leu Pro
450                 455                 460

Gly Thr Ala Leu Lys Val Ser Cys Phe Asn Val Arg Phe Cys Leu Lys
465                 470                 475                 480

Ala Asp Gly Lys Gly Val Leu Pro Arg Lys Leu Asn Phe Gln Val Glu
                485                 490                 495

Leu Leu Leu Asp Lys Leu Lys Gln Lys Gly Ala Ile Arg Arg Ala Leu
            500                 505                 510

Phe Leu Tyr Ser Arg Ser Pro Ser His Ser Lys Asn Met Thr Ile Ser
        515                 520                 525

Arg Gly Gly Leu Met Gln Cys Glu Glu Leu Ile Ala Tyr Leu Arg Asp
530                 535                 540

Glu Ser Glu Phe Arg Asp Lys Leu Thr Pro Ile Thr Ile Phe Met Glu
545                 550                 555                 560

Tyr Arg Leu Asp Tyr Arg Thr Ala Ala Asp Thr Thr Gly Leu Gln Pro
                565                 570                 575

Ile Leu Asn Gln Phe Thr Pro Ala Asn Ile Ser Arg Gln Ala His Ile
            580                 585                 590

Leu Leu Asp Cys Gly Glu Asp Asn Val Cys Lys Pro Lys Leu Glu Val
        595                 600                 605

Ser Val Asp Ser Asp Gln Lys Lys Ile Tyr Ile Gly Asp Asp Asn Pro
610                 615                 620

Leu Thr Leu Ile Val Lys Ala Gln Asn Gln Gly Glu Gly Ala Tyr Glu
625                 630                 635                 640

Ala Glu Leu Ile Val Ser Ile Pro Leu Gln Ala Asp Phe Ile Gly Val
                645                 650                 655

Val Arg Asn Asn Glu Ala Leu Ala Arg Leu Ser Cys Ala Phe Lys Thr
            660                 665                 670

Glu Asn Gln Thr Arg Gln Val Val Cys Asp Leu Gly Asn Pro Met Lys
        675                 680                 685

Ala Gly Thr Gln Leu Leu Ala Gly Leu Arg Phe Ser Val His Gln Gln
```

```
                690                 695                 700
Ser Glu Met Asp Thr Ser Val Lys Phe Asp Leu Gln Ile Gln Ser Ser
705                 710                 715                 720

Asn Leu Phe Asp Lys Val Ser Pro Val Val Ser His Lys Val Asp Leu
                725                 730                 735

Ala Val Leu Ala Ala Val Glu Ile Arg Gly Val Ser Ser Pro Asp His
                740                 745                 750

Ile Phe Leu Pro Ile Pro Asn Trp Glu His Lys Glu Asn Pro Glu Thr
                755                 760                 765

Glu Glu Asp Val Gly Pro Val Val Gln His Ile Tyr Glu Leu Arg Asn
                770                 775                 780

Asn Gly Pro Ser Ser Phe Ser Lys Ala Met Leu His Leu Gln Trp Pro
785                 790                 795                 800

Tyr Lys Tyr Asn Asn Thr Leu Leu Tyr Ile Leu His Tyr Asp Ile
                805                 810                 815

Asp Gly Pro Met Asn Cys Thr Ser Asp Met Glu Ile Asn Pro Leu Arg
                820                 825                 830

Ile Lys Ile Ser Ser Leu Gln Thr Thr Glu Lys Asn Asp Thr Val Ala
                835                 840                 845

Gly Gln Gly Glu Arg Asp His Leu Ile Thr Lys Arg Asp Leu Ala Leu
                850                 855                 860

Ser Glu Gly Asp Ile His Thr Leu Gly Cys Gly Val Ala Gln Cys Leu
865                 870                 875                 880

Lys Ile Val Cys Gln Val Gly Arg Leu Asp Arg Gly Lys Ser Ala Ile
                885                 890                 895

Leu Tyr Val Lys Ser Leu Leu Trp Thr Glu Thr Phe Met Asn Lys Glu
                900                 905                 910

Asn Gln Asn His Ser Tyr Ser Leu Lys Ser Ser Ala Ser Phe Asn Val
                915                 920                 925

Ile Glu Phe Pro Tyr Lys Asn Leu Pro Ile Glu Asp Ile Thr Asn Ser
                930                 935                 940

Thr Leu Val Thr Thr Asn Val Thr Trp Gly Ile Gln Pro
945                 950                 955

<210> SEQ ID NO 211
<211> LENGTH: 44
<212> TYPE: PRT
<213> ORGANISM: rabbit

<400> SEQUENCE: 211

Met Glu Thr Gly Leu Arg Trp Leu Leu Leu Val Ala Val Leu Lys Gly
1               5                   10                  15

Ala Gln Cys Gln Ser Val Glu Glu Ser Gly Gly Arg Leu Val Thr Pro
                20                  25                  30

Gly Thr Ser Leu Thr Leu Thr Cys Thr Val Ser Gly
            35                  40

<210> SEQ ID NO 212
<211> LENGTH: 14
<212> TYPE: PRT
<213> ORGANISM: rabbit

<400> SEQUENCE: 212

Trp Val Arg Gln Ala Pro Gly Lys Gly Leu Glu Trp Ile Gly
1               5                   10
```

<210> SEQ ID NO 213
<211> LENGTH: 35
<212> TYPE: PRT
<213> ORGANISM: rabbit

<400> SEQUENCE: 213

Phe Ala Ala Trp Ala Lys Gly Arg Phe Thr Ile Ser Arg Thr Ser Thr
1               5                   10                  15

Thr Val Asp Leu Arg Ile Thr Ser Leu Thr Ala Ser Asp Thr Ala Thr
            20                  25                  30

Tyr Phe Cys
        35

<210> SEQ ID NO 214
<211> LENGTH: 11
<212> TYPE: PRT
<213> ORGANISM: rabbit

<400> SEQUENCE: 214

Trp Gly Gln Gly Thr Leu Val Thr Val Ser Ser
1               5                   10

<210> SEQ ID NO 215
<211> LENGTH: 125
<212> TYPE: PRT
<213> ORGANISM: rabbit

<400> SEQUENCE: 215

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Asn Cys Gln Ala Ser
        35                  40                  45

Gln Ser Val Ala Ser Asn Asn Ala Leu Ala Trp Phe Gln Gln Lys Pro
    50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Ala Asp Ala Ala Thr Tyr Tyr Cys
            100                 105                 110

Leu Gly Gly Tyr Asp Cys Arg Gly Thr Asp Cys Asn Val
        115                 120                 125

<210> SEQ ID NO 216
<211> LENGTH: 127
<212> TYPE: PRT
<213> ORGANISM: rabbit

<400> SEQUENCE: 216

Met Glu Thr Gly Leu Arg Trp Leu Leu Leu Val Ala Val Leu Lys Gly
1               5                   10                  15

Ala Gln Cys Gln Ser Val Glu Glu Ser Gly Gly Arg Leu Val Thr Pro
            20                  25                  30

Gly Thr Ser Leu Thr Leu Thr Cys Thr Val Ser Gly Ile Asp Leu Thr
        35                  40                  45

Ser Asn Ser Leu Ser Trp Val Arg Gln Ala Pro Gly Lys Gly Leu Glu
    50                  55                  60

```
Trp Ile Gly Ala Ile Ser Ser Arg Ala Thr Thr Tyr Phe Ala Ala Trp
 65                  70                  75                  80

Ala Lys Gly Arg Phe Thr Ile Ser Arg Thr Ser Thr Val Asp Leu
                 85                  90                  95

Arg Ile Thr Ser Leu Thr Ala Ser Asp Thr Ala Thr Tyr Phe Cys Gly
            100                 105                 110

Lys Phe Asn Leu Trp Gly Gln Gly Thr Leu Val Thr Val Ser Ser
            115                 120                 125

<210> SEQ ID NO 217
<211> LENGTH: 114
<212> TYPE: PRT
<213> ORGANISM: rabbit

<400> SEQUENCE: 217

Phe Gly Gly Gly Thr Glu Val Val Lys Gly Asp Pro Val Ala Pro
 1               5                  10                  15

Thr Val Leu Ile Phe Pro Pro Ala Ala Asp Gln Val Ala Thr Gly Thr
             20                  25                  30

Val Thr Ile Val Cys Val Ala Asn Lys Tyr Phe Pro Asp Val Thr Val
             35                  40                  45

Thr Trp Glu Val Asp Gly Thr Thr Gln Thr Thr Gly Ile Glu Asn Ser
 50                  55                  60

Lys Thr Pro Gln Asn Ser Ala Asp Cys Thr Tyr Asn Leu Ser Ser Thr
 65                  70                  75                  80

Leu Thr Leu Thr Ser Thr Gln Tyr Asn Ser His Lys Glu Tyr Thr Cys
                 85                  90                  95

Lys Val Thr Gln Gly Thr Thr Ser Val Val Gln Ser Phe Asn Arg Gly
            100                 105                 110

Asp Cys

<210> SEQ ID NO 218
<211> LENGTH: 323
<212> TYPE: PRT
<213> ORGANISM: rabbit

<400> SEQUENCE: 218

Gly Gln Pro Lys Ala Pro Ser Val Phe Pro Leu Ala Pro Cys Cys Gly
 1               5                  10                  15

Asp Thr Pro Ser Ser Thr Val Thr Leu Gly Cys Leu Val Lys Gly Tyr
             20                  25                  30

Leu Pro Glu Pro Val Thr Val Thr Trp Asn Ser Gly Thr Leu Thr Asn
             35                  40                  45

Gly Val Arg Thr Phe Pro Ser Val Arg Gln Ser Ser Gly Leu Tyr Ser
 50                  55                  60

Leu Ser Ser Val Val Ser Val Thr Ser Ser Ser Gln Pro Val Thr Cys
 65                  70                  75                  80

Asn Val Ala His Pro Ala Thr Asn Thr Lys Val Asp Lys Thr Val Ala
                 85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
            115                 120                 125

Ile Ser Arg Thr Pro Glu Val Thr Cys Val Val Val Asp Val Ser Gln
            130                 135                 140

Asp Asp Pro Glu Val Gln Phe Thr Trp Tyr Ile Asn Asn Glu Gln Val
```

```
                145                 150                 155                 160
Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
                180                 185                 190

Lys Glu Phe Lys Cys Lys Val His Asn Lys Ala Leu Pro Ala Pro Ile
                195                 200                 205

Glu Lys Thr Ile Ser Lys Ala Arg Gly Gln Pro Leu Glu Pro Lys Val
                210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
                260                 265                 270

Val Leu Asp Ser Asp Gly Ser Tyr Phe Leu Tyr Ser Lys Leu Ser Val
                275                 280                 285

Pro Thr Ser Glu Trp Gln Arg Gly Asp Val Phe Thr Cys Ser Val Met
                290                 295                 300

His Glu Ala Leu His Asn His Tyr Thr Gln Lys Ser Ile Ser Arg Ser
305                 310                 315                 320

Pro Gly Lys

<210> SEQ ID NO 219
<211> LENGTH: 239
<212> TYPE: PRT
<213> ORGANISM: rabbit

<400> SEQUENCE: 219

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
                20                  25                  30

Val Ser Ala Ala Val Gly Gly Thr Val Thr Ile Asn Cys Gln Ala Ser
                35                  40                  45

Gln Ser Val Ala Ser Asn Asn Ala Leu Ala Trp Phe Gln Gln Lys Pro
                50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Ala Asp Ala Ala Thr Tyr Tyr Cys
                100                 105                 110

Leu Gly Gly Tyr Asp Cys Arg Gly Thr Asp Cys Asn Val Phe Gly Gly
                115                 120                 125

Gly Thr Glu Val Val Val Lys Gly Asp Pro Val Ala Pro Thr Val Leu
                130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
                180                 185                 190

Gln Asn Ser Ala Asp Cys Thr Tyr Asn Leu Ser Ser Thr Leu Thr Leu
```

```
            195                 200                 205
Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 220
<211> LENGTH: 450
<212> TYPE: PRT
<213> ORGANISM: rabbit

<400> SEQUENCE: 220

```
Met Glu Thr Gly Leu Arg Trp Leu Leu Leu Val Ala Val Leu Lys Gly
1               5                   10                  15

Ala Gln Cys Gln Ser Val Glu Glu Ser Gly Gly Arg Leu Val Thr Pro
            20                  25                  30

Gly Thr Ser Leu Thr Leu Thr Cys Thr Val Ser Gly Ile Asp Leu Thr
        35                  40                  45

Ser Asn Ser Leu Ser Trp Val Arg Gln Ala Pro Gly Lys Gly Leu Glu
    50                  55                  60

Trp Ile Gly Ala Ile Ser Ser Arg Ala Thr Thr Tyr Phe Ala Ala Trp
65                  70                  75                  80

Ala Lys Gly Arg Phe Thr Ile Ser Arg Thr Ser Thr Thr Val Asp Leu
                85                  90                  95

Arg Ile Thr Ser Leu Thr Ala Ser Asp Thr Ala Thr Tyr Phe Cys Gly
            100                 105                 110

Lys Phe Asn Leu Trp Gly Gln Gly Thr Leu Val Thr Val Ser Ser Gly
            115                 120                 125

Gln Pro Lys Ala Pro Ser Val Phe Pro Leu Ala Pro Cys Cys Gly Asp
        130                 135                 140

Thr Pro Ser Ser Thr Val Thr Leu Gly Cys Leu Val Lys Gly Tyr Leu
145                 150                 155                 160

Pro Glu Pro Val Thr Val Thr Trp Asn Ser Gly Thr Leu Thr Asn Gly
                165                 170                 175

Val Arg Thr Phe Pro Ser Val Arg Gln Ser Ser Gly Leu Tyr Ser Leu
            180                 185                 190

Ser Ser Val Val Ser Val Thr Ser Ser Ser Gln Pro Val Thr Cys Asn
        195                 200                 205

Val Ala His Pro Ala Thr Asn Thr Lys Val Asp Lys Thr Val Ala Pro
    210                 215                 220

Ser Thr Cys Ser Lys Pro Thr Cys Pro Pro Glu Leu Leu Gly Gly
225                 230                 235                 240

Pro Ser Val Phe Ile Phe Pro Pro Lys Pro Lys Asp Thr Leu Met Ile
                245                 250                 255

Ser Arg Thr Pro Glu Val Thr Cys Val Val Val Asp Val Ser Gln Asp
            260                 265                 270

Asp Pro Glu Val Gln Phe Thr Trp Tyr Ile Asn Asn Glu Gln Val Arg
        275                 280                 285

Thr Ala Arg Pro Pro Leu Arg Glu Gln Gln Phe Asn Ser Thr Ile Arg
    290                 295                 300

Val Val Ser Thr Leu Pro Ile Ala His Gln Asp Trp Leu Arg Gly Lys
305                 310                 315                 320

Glu Phe Lys Cys Lys Val His Asn Lys Ala Leu Pro Ala Pro Ile Glu
                325                 330                 335
```

```
Lys Thr Ile Ser Lys Ala Arg Gly Gln Pro Leu Glu Pro Lys Val Tyr
            340                 345                 350

Thr Met Gly Pro Pro Arg Glu Glu Leu Ser Ser Arg Ser Val Ser Leu
        355                 360                 365

Thr Cys Met Ile Asn Gly Phe Tyr Pro Ser Asp Ile Ser Val Glu Trp
    370                 375                 380

Glu Lys Asn Gly Lys Ala Glu Asp Asn Tyr Lys Thr Thr Pro Ala Val
385                 390                 395                 400

Leu Asp Ser Asp Gly Ser Tyr Phe Leu Tyr Ser Lys Leu Ser Val Pro
                405                 410                 415

Thr Ser Glu Trp Gln Arg Gly Asp Val Phe Thr Cys Ser Val Met His
            420                 425                 430

Glu Ala Leu His Asn His Tyr Thr Gln Lys Ser Ile Ser Arg Ser Pro
        435                 440                 445

Gly Lys
    450

<210> SEQ ID NO 221
<211> LENGTH: 46
<212> TYPE: DNA
<213> ORGANISM: rabbit

<400> SEQUENCE: 221
catttgccca agtgctgacc cagactccat cctccgtgtc tgcagc        46

<210> SEQ ID NO 222
<211> LENGTH: 24
<212> TYPE: DNA
<213> ORGANISM: rabbit

<400> SEQUENCE: 222
cagagtgttg ctagtaacaa tgcc        24

<210> SEQ ID NO 223
<211> LENGTH: 36
<212> TYPE: DNA
<213> ORGANISM: rabbit

<400> SEQUENCE: 223
ggcggttatg attgtagggg tactgattgt aatgtt        36

<210> SEQ ID NO 224
<211> LENGTH: 27
<212> TYPE: DNA
<213> ORGANISM: rabbit

<400> SEQUENCE: 224
atcgacctca ctagcaattc gctgagc        27

<210> SEQ ID NO 225
<211> LENGTH: 27
<212> TYPE: DNA
<213> ORGANISM: rabbit

<400> SEQUENCE: 225
gccattagta gtcgtgctac cacatat        27

<210> SEQ ID NO 226
<211> LENGTH: 15
<212> TYPE: DNA
<213> ORGANISM: rabbit
```

<400> SEQUENCE: 226
gggaaattta atttg                                                      15

<210> SEQ ID NO 227
<211> LENGTH: 61
<212> TYPE: DNA
<213> ORGANISM: rabbit

<400> SEQUENCE: 227
atggacacga gggcccccac tcagctgctg gggctcctgc tgctctggct cccaggtgcc     60
a                                                                     61

<210> SEQ ID NO 228
<211> LENGTH: 37
<212> TYPE: DNA
<213> ORGANISM: rabbit

<400> SEQUENCE: 228 tgtgggggc acagtcacca tcaattgcca ggccagt                               37

<210> SEQ ID NO 229
<211> LENGTH: 171
<212> TYPE: DNA
<213> ORGANISM: rabbit

<400> SEQUENCE: 229
ttagcctggt tcagcagaa accagggcag cctcccaaac tcctgatcta ttatgcgtcc     60
actctggcat ctggggtccc atcgcgattc aaaggcagtg gatctgggac acagttcact    120
ctcaccatca gcgacctgga gtgtgccgat gctgccactt actactgtct a             171

<210> SEQ ID NO 230
<211> LENGTH: 2961
<212> TYPE: DNA
<213> ORGANISM: human

<400> SEQUENCE: 230
atggcttttc cgccgcggcg acggctgcgc ctcggtcccc gcggcctccc gcttcttctc     60
tcgggactcc tgctacctct gtgccgcgcc ttcaacctag acgtggacag tcctgccgag    120
tactctggcc ccgagggaag ttacttcggc ttcgccgtgg attcttcgt gcccagcgcg     180 tcttcccgga tgtttcttct cgtgggagct cccaaagcaa acaccaccca gcctgggatt    240
gtggaaggag gcaggtcct caaatgtgac tggtcttcta cccgccggtg ccagccaatt    300
gaatttgatg caacaggcaa tagagattat gccaaggatg atccattgga atttaagtcc    360
catcagtggt ttggagcatc tgtgaggtcg aaacaggata aaattttggc ctgtgcccca    420
ttgtaccatt ggagaactga gatgaaacag gagcgagagc tgttggaaac atgctttctt    480
caagatggaa caaagactgt tgagtatgct ccatgtagat cacaagatat tgatgctgat    540
ggacagggat tttgtcaagg aggattcagc attgatttta ctaaagctga cagagtactt    600
cttggtggtc ctggtagctt ttattggcaa ggtcagctta tttcggatca agtggcagaa    660
atcgtatcta atacgaccc caatgtttac agcatcaagt ataataacca attagcaact    720
cggactgcac aagctatttt tgatgacagc tatttgggtt attctgtggc tgtcggagat    780
ttcaatggtg atggcataga tgactttgtt tcaggagttc caagagcagc aaggactttg    840
ggaatggttt atatttatga tgggaagaac atgtcctcct tatacaattt tactggcgag    900

| | | |
|---|---|---|
| cagatggctg catatttcgg attttctgta gctgccactg acattaatgg agatgattat | 960 | |
| gcagatgtgt ttattggagc acctctcttc atggatcgtg gctctgatgg caaactccaa | 1020 | |
| gaggtggggc aggtctcagt gtctctacag agagcttcag gagacttcca gacgacaaag | 1080 | |
| ctgaatggat ttgaggtctt tgcacggttt ggcagtgcca tagctccttt gggagatctg | 1140 | |
| gaccaggatg gtttcaatga tattgcaatt gctgctccat atggggtga agataaaaaa | 1200 | |
| ggaattgttt atatcttcaa tggaagatca acaggcttga acgcagtccc atctcaaatc | 1260 | |
| cttgaagggc agtgggctgc tcgaagcatg ccaccaagct ttggctattc aatgaaagga | 1320 | |
| gccacagata tagacaaaaa tggatatcca gacttaattg taggagcttt tggtgtagat | 1380 | |
| cgagctatct tatacagggc cagaccagtt atcactgtaa atgctggtct tgaagtgtac | 1440 | |
| cctagcattt taaatcaaga caataaaacc tgctcactgc ctggaacagc tctcaaagtt | 1500 | |
| tcctgtttta atgttaggtt ctgcttaaag gcagatggca aggagtact tcccaggaaa | 1560 | |
| cttaatttcc aggtggaact tcttttggat aaactcaagc aaaagggagc aattcgacga | 1620 | |
| gcactgtttc tctacagcag gtccccaagt cactccaaga acatgactat ttcaggggg | 1680 | |
| ggactgatgc agtgtgagga attgatagcg tatctgcggg atgaatctga atttagagac | 1740 | |
| aaactcactc caattactat ttttatggaa tatcggttgg attatagaac agctgctgat | 1800 | |
| acaacaggct tgcaacccat tcttaaccag ttcacgcctg ctaacattag tcgacaggct | 1860 | |
| cacattctac ttgactgtgg tgaagacaat gtctgtaaac ccaagctgga agtttctgta | 1920 | |
| gatagtgatc aaaagaagat ctatattggg gatgacaacc ctctgacatt gattgttaag | 1980 | |
| gctcagaatc aaggagaagg tgcctacgaa gctgagctca tcgtttccat tccactgcag | 2040 | |
| gctgatttca tcggggttgt ccgaaacaat gaagccttag caagactttc ctgtgcattt | 2100 | |
| aagacagaaa accaaactcg ccaggtggta tgtgaccttg gaaacccaat gaaggctgga | 2160 | |
| actcaactct tagctggtct tcgtttcagt gtgcaccagc agtcagagat ggatacttct | 2220 | |
| gtgaaatttg acttacaaat ccaaagctca aatctatttg acaaagtaag cccagttgta | 2280 | |
| tctcacaaag ttgatcttgc tgttttagct gcagttgaga taagaggagt ctcgagtcct | 2340 | |
| gatcatatct ttcttccgat tccaaactgg gagcacaagg agaaccctga gactgaagaa | 2400 | |
| gatgttgggc cagttgttca gcacatctat gagctgagaa acaatggtcc aagttcattc | 2460 | |
| agcaaggcaa tgctccatct tcagtggcct tacaaatata ataataacac tctgttgtat | 2520 | |
| atccttcatt atgatattga tggaccaatg aactgcactt cagatatgga gatcaaccct | 2580 | |
| ttgagaatta agatctcatc tttgcaaaca actgaaaaga atgacacggt tgccgggcaa | 2640 | |
| ggtgagcggg accatctcat cactaagcgg gatcttgccc tcagtgaagg agatattcac | 2700 | |
| actttgggtt gtggagttgc tcagtgcttg aagattgtct gccaagttgg gagattagac | 2760 | |
| agaggaaaga gtgcaatctt gtacgtaaag tcattactgt ggactgagac ttttatgaat | 2820 | |
| aaagaaaatc agaatcattc ctattctctg aagtcgtctg cttcatttaa tgtcatagag | 2880 | |
| tttccttata agaatcttcc aattgaggat atcaccaact ccacattggt taccactaat | 2940 | |
| gtcacctggg gcattcagcc a | 2961 | |

<210> SEQ ID NO 231
<211> LENGTH: 132
<212> TYPE: DNA
<213> ORGANISM: rabbit

<400> SEQUENCE: 231

| | | |
|---|---|---|
| atggagactg ggctgcgctg gcttctcctg gtcgctgtgc tcaaaggtgc ccagtgtcag | 60 | | tcggtggagg agtccggggg tcgcctggtc acgcctggga catccctgac actcacctgc    120 acggtctctg ga    132

<210> SEQ ID NO 232
<211> LENGTH: 42
<212> TYPE: DNA
<213> ORGANISM: rabbit

<400> SEQUENCE: 232
tgggtccgcc aggctccagg gaagggctg gaatggatcg gg    42

<210> SEQ ID NO 233
<211> LENGTH: 105
<212> TYPE: DNA
<213> ORGANISM: rabbit

<400> SEQUENCE: 233
ttcgcggctt gggcgaaggg ccgattcacc atctccagaa cctcgaccac ggtggatctc    60
agaatcacca gtctgacagc ttcagacacg gccacctatt tctgt    105

<210> SEQ ID NO 234
<211> LENGTH: 33
<212> TYPE: DNA
<213> ORGANISM: rabbit

<400> SEQUENCE: 234
tggggccaag gcaccctggt caccgtctcc tca    33

<210> SEQ ID NO 235
<211> LENGTH: 375
<212> TYPE: DNA
<213> ORGANISM: rabbit

<400> SEQUENCE: 235
atggacacga gggcccccac tcagctgctg gggctcctgc tgctctggct cccaggtgcc    60
acatttgccc aagtgctgac ccagactcca tcctccgtgt ctgcagctgt gggggggcaca    120 gtcaccatca attgccaggc cagtcagagt gttgctagta caatgccttt agcctggttt    180
cagcagaaac cagggcagcc tcccaaactc ctgatctatt atgcgtccac tctggcatct    240 gggtcccat cgcgattcaa aggcagtgga tctgggacag agttcactct caccatcagc    300
gacctggagt gtgccgatgc tgccacttac tactgtctag gcggttatga ttgtaggggt    360
actgattgta atgtt    375

<210> SEQ ID NO 236
<211> LENGTH: 381
<212> TYPE: DNA
<213> ORGANISM: rabbit

<400> SEQUENCE: 236
atggagactg ggctgcgctg gcttctcctg gtcgctgtgc tcaaaggtgc ccagtgtcag    60
tcggtggagg agtccggggg tcgcctggtc acgcctggga catccctgac actcacctgc    120
acggtctctg gaatcgacct cactagcaat tcgctgagct gggtccgcca ggctccaggg    180
aaggggctgg aatggatcgg ggccattagt agtcgtgcta ccacatattt cgcggcttgg    240
gcgaagggcc gattcaccat ctccagaacc tcgaccacgg tggatctcag aatcaccagt    300
ctgacagctt cagacacggc cacctatttc tgtgggaaat taatttgtg gggccaaggc    360

```
accctggtca ccgtctcctc a                                              381

<210> SEQ ID NO 237
<211> LENGTH: 360
<212> TYPE: DNA
<213> ORGANISM: rabbit

<400> SEQUENCE: 237
ttcggcggag ggaccgaggt ggtggtcaaa ggtgatccag ttgcacctac tgtcctcatc    60
ttcccaccag ctgctgatca ggtggcaact ggaacagtca ccatcgtgtg tgtggcgaat   120
aaatactttc ccgatgtcac cgtcacctgg gaggtggatg gcaccaccca aacaactggc   180
atcgagaaca gtaaaacacc gcagaattct gcagattgta cctacaacct cagcagcact   240
ctgacactga ccagcacaca gtacaacagc cacaaagagt acacctgcaa ggtgacccag   300
ggcacgacct cagtcgtcca gagcttcaat aggggtgact gttagagtga gagcggccgc   360

<210> SEQ ID NO 238
<211> LENGTH: 998
<212> TYPE: DNA
<213> ORGANISM: rabbit

<400> SEQUENCE: 238
gggcaaccta aggctccatc agtcttccca ctggcccccct gctgcgggga cacacccagc    60
tccacggtga ccctgggctg cctggtcaaa gggtacctcc cggagccagt gaccgtgacc   120
tggaactcgg gcaccctcac caatgggta cgcaccttcc cgtccgtccg gcagtcctca   180
ggcctctact cgctgagcag cgtggtgagc gtgacctcaa gcagccagcc cgtcacctgc   240
aacgtggccc acccagccac caacaccaaa gtggacaaga ccgttgcgcc ctcgacatgc   300
agcaagccca cgtgcccacc ccctgaactc tggggggac cgtctgtctt catcttcccc   360
ccaaaaccca aggacaccct catgatctca cgcaccccg aggtcacatg cgtggtggtg   420
gacgtgagcc aggatgaccc cgaggtgcag ttcacatggt acataaacaa cgagcaggtg   480
cgcaccgccc ggccgccgct acgggagcag cagttcaaca gcacgatccg cgtggtcagc   540 accctccccca tcgcgcacca ggactggctg aggggcaagg agttcaagtg caaagtccac   600
aacaaggcac tcccggcccc catcgagaaa accatctcca agccagagg gcagcccctg   660 gagccgaagg tctacaccat gggccctccc cgggaggagc tgagcagcag gtcggtcagc   720
ctgacctgca tgatcaacgg cttctaccct tccgacatct cggtggagtg ggagaagaac   780
gggaaggcag aggacaacta caagaccacg cggccgtgc tggacagcga cggctcctac   840
ttcctctaca gcaagctctc agtgcccacg agtgagtggc agcggggcga cgtcttcacc   900
tgctccgtga tgcacgaggc cttgcacaac cactacacgc agaagtccat ctcccgctct   960
ccgggtaaat gagcgctgtg ccggcgagct gcggccgc                          998

<210> SEQ ID NO 239
<211> LENGTH: 735
<212> TYPE: DNA
<213> ORGANISM: rabbit

<400> SEQUENCE: 239
atggacacga gggcccccac tcagctgctg ggctcctgc tgctctggct cccaggtgcc    60
acatttgccc aagtgctgac ccagactcca tcctccgtgt ctgcagctgt ggggggcaca   120
gtcaccatca attgccaggc cagtcagagt gttgctagta caatgccttt agcctggttt   180
cagcagaaac cagggcagcc tcccaaactc ctgatctatt atgcgtccac tctggcatct   240
```

```
gggtcccat cgcgattcaa aggcagtgga tctgggacac agttcactct caccatcagc    300
gacctggagt gtgccgatgc tgccacttac tactgtctag gcggttatga ttgtaggggt    360
actgattgta atgttttcgg cggagggacc gaggtggtgg tcaaaggtga tccagttgca    420
cctactgtcc tcatcttccc accagctgct gatcaggtgg caactggaac agtcaccatc    480
gtgtgtgtgg cgaataaata ctttcccgat gtcaccgtca cctgggaggt ggatggcacc    540
acccaaacaa ctggcatcga aacagtaaa acaccgcaga attctgcaga ttgtacctac    600
aacctcagca gcactctgac actgaccagc acacagtaca cagccacaa agagtacacc    660 tgcaaggtga cccagggcac gacctcagtc gtccagagct tcaataggggg tgactgttag    720 agtgagagcg gccgc                                                    735

<210> SEQ ID NO 240
<211> LENGTH: 1379
<212> TYPE: DNA
<213> ORGANISM: rabbit

<400> SEQUENCE: 240
atggagactg gctgcgctg gcttctcctg gtcgctgtgc tcaaaggtgc ccagtgtcag     60
tcggtggagg agtccggggg tcgcctggtc acgcctggga catccctgac actcacctgc    120
acggtctctg gaatcgacct cactagcaat tcgctgagct gggtccgcca ggctccaggg    180
aaggggctgg aatggatcgg ggccattagt agtcgtgcta ccacatattt cgcggcttgg    240
gcgaagggcc gattcaccat ctccagaacc tcgaccacgg tggatctcag aatcaccagt    300
ctgacagctt cagacacggc cacctatttc tgtgggaaat ttaatttgtg gggccaaggc    360
accctggtca ccgtctcctc agggcaacct aaggctccat cagtcttccc actggccccc    420
tgctgcgggg acacacccag ctccacggtg acctgggct gcctggtcaa agggtacctc    480
ccggagccag tgaccgtgac ctggaactcg gcacccctca ccaatggggt acgcaccttc    540
ccgtccgtcc ggcagtcctc aggcctctac tcgctgagca gcgtggtgag cgtgacctca    600
agcagccagc ccgtcacctg caacgtggcc cacccagcca ccaacaccaa agtggacaag    660
accgttgcgc cctcgacatg cagcaagccc acgtgcccac cccctgaact cctggggga    720 ccgtctgtct tcatcttccc cccaaaaccc aaggacaccc tcatgatctc acgcacccc    780 gaggtcacat gcgtggtggt ggacgtgagc caggatgacc ccgaggtgca gttcacatgg    840
tacataaaca acgagcaggt gcgcaccgcc cggccgccgc tacgggagca gcagttcaac    900
agcacgatcc gcgtggtcag cacctccc atcgcgcacc aggactggct gaggggcaag    960
gagttcaagt gcaaagtcca caacaaggca ctcccggccc catcgagaa aaccatctcc    1020 aaagccagag ggcagccccct ggagccgaag gtctacacca tgggccctcc ccgggaggag    1080
ctgagcagca ggtcggtcag cctgacctgc atgatcaacg gcttctaccc ttccgacatc    1140
tcggtggagt gggagaagaa cgggaaggca gaggacaact acaagaccac gccggccgtg    1200
ctggacagcg acggctccta cttcctctac agcaagctct cagtgccac gagtgagtgg    1260 cagcggggcg acgtcttcac ctgctccgtg atgcacgagg ccttgcacaa ccactacacg    1320
cagaagtcca tctcccgctc tccgggtaaa tgagcgctgt gccggcgagc tgcggccgc    1379
```